US007807387B2

(12) United States Patent
Gatanaga et al.

(10) Patent No.: US 7,807,387 B2
(45) Date of Patent: Oct. 5, 2010

(54) BIOLOGICAL AGENT THAT CAUSES IL-6 RECEPTOR RELEASE

(75) Inventors: Tetsuya Gatanaga, Irvine, CA (US); Ronald L. Niece, Irvine, CA (US); Sheldon Broedel, Baltimore, MD (US)

(73) Assignee: Meyer Pharmaceuticals LLC, Newport Beach, CA (US)

( * ) Notice: Subject to any disclaimer, the term of this patent is extended or adjusted under 35 U.S.C. 154(b) by 490 days.

(21) Appl. No.: 11/389,352

(22) Filed: Mar. 23, 2006

(65) Prior Publication Data

US 2007/0149453 A1 Jun. 28, 2007

Related U.S. Application Data

(63) Continuation of application No. PCT/US2004/031377, filed on Sep. 23, 2004.

(60) Provisional application No. 60/505,336, filed on Sep. 23, 2003.

(51) Int. Cl.

| | |
|---|---|
| ***G01N 33/53*** | (2006.01) |
| ***G01N 33/567*** | (2006.01) |
| ***C07K 1/00*** | (2006.01) |
| ***C07K 14/00*** | (2006.01) |
| ***C07K 17/00*** | (2006.01) |

(52) U.S. Cl. ........................................ 435/7.2; 530/350

(58) Field of Classification Search ........................ None
See application file for complete search history.

(56) References Cited

FOREIGN PATENT DOCUMENTS

WO WO0153312 * 7/2001

OTHER PUBLICATIONS

Chen J, et al. Biochem. Biophys. Res, Commun, 294, 161-166, 2002.*

Terry C, et al. J. Biol. Chem. 275(24):18138-18144, 2000.*

* cited by examiner

*Primary Examiner*—Robert Landsman
(74) *Attorney, Agent, or Firm*—Michael Schiff

(57) ABSTRACT

This disclosure describes inventions related to the use of biological agents that cause cytokine receptors to be released from the surface of cells. One aspect of this invention is based on the unexpected finding that extending the length of an exemplary agent at the N-terminus enhances expression and production of the product by at least 10-fold. The extended protein can be used to prepare pharmaceutical compositions for treating inflammatory conditions such as rheumatoid arthritis. Another aspect of this invention is based on the identification of biological agents that cause release of cytokine receptors not previously known as natural enzyme targets, such as the IL-1 Type I receptor, IL-1 Type II receptor and the IL-6 receptor. This disclosure provides products, assays, expression systems, purification methods, and production protocols useful for developing cytokine receptor releasing proteins as therapeutic agents.

5 Claims, 25 Drawing Sheets

Figure 1(A)
DEAE Sephadex® Chromatography
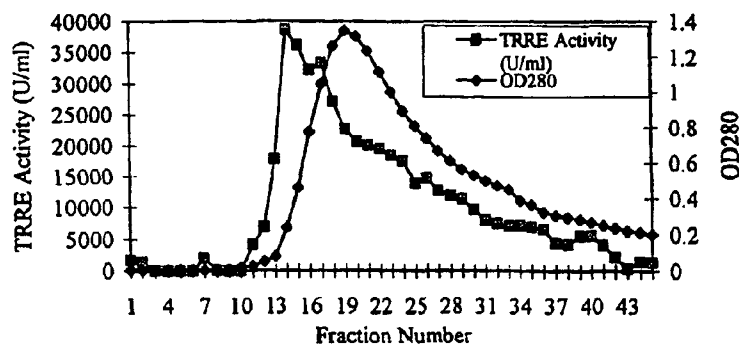
Preparative Native Polyacrylamide Gel
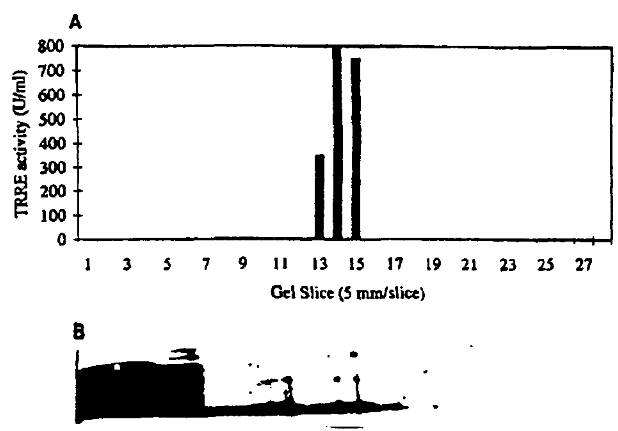
Figure 1(B)
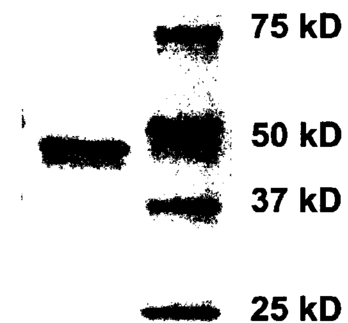

Figure 2(A)

```
Human                                           MEDHQH VPIDIQTSKLLDWLV DRRHCSLKWQSLVLT IREKINAAIQDMP E SEEIAQLLSGSYIHY   65
Rat                                             .Q.... ............... .....N......... ......T...... . .Q.............   65
Mouse                                           .Q.... ............... .....N......... ......T...... . .Q.............   65
Danio                                           ..NI.N L.............. .....T.....A.M. ............. . N...K.........H   65
Tetraodon                                       ..NI.N L.............L .....NMR..NAFKE ............. . N...K......H...   65
Xenopus                                         .Q.V.N L......GR...... .....T.....K..Q ......Q.L.... . HD..RS....T..N.   65
Anopheles      TLFCFCIHIPFTDQQ RTSVWPVTNNMNEAE I....AAG......I S..IVDKN.HLHIRN ..N..SN..T... . HD.LL.....AH.N.   89
Drosophila                                       MNESE I....H.L..Q...I S..IVPKNV.QELRE .HR..SN.L.... S N.QLIK..ARTN.N.   64
Caenorhabditis                                    MSDD L....HS........ S....NKD..KS..A .....KH..L... . .QK.VE..Q.A..N.   63
Arabidopsis                                  MPSQD.V.N L....TF.R.GE... ..KRIPAD.RKR.AV ..V..LKEFSSL.K. IDPFF.T.DPEV.G.   69

Vertebrates                                     MxxxQx xPIDIQTxxLLDWLx DRRHCxxxWQxxxxx IREKINxAxQDMP x xxEIxQLLSGxxxxx
Mammals                                         MxDHQH xPIDIQTSKLLDWLV DRRHCxLKWQSLVLT IREKINxAIQDMP E SxEIAQLLSGSYIHY
Motifs                                            PIDIQT  LLDWL  DRRHC           IREKIN                QLLSG


Human          FHCLRILDLLKGTEA STKNIFGRYSSQRMK DWQEIIALYEKDNTY LVELSSLLVRNVNYE IPSLKKQIAKCQQLQ QEYSRKEEECQAGAA  155
Rat            ......V........ ............... ......S........ ............... ............... .D.......G.....  155
Mouse          ......V........ ............... .....VS........ ....C......S... ............... .........G.....  155
Danio          ....Q.IEV...... ............... .....VSM.....V. .A.MA.I.....S.. G.A.R..VS.A.... ..L..R.L...S.S.  155
Tetraodon      ......VEI..R... .S............. ...D.VS...A..V. .A..AG..I...T.. G.A.RR.L..A.... ..L..R.V...SS..  155
Xenopus        ....K.VEI...... A.R.L.......... ....VVS..QA.... .G.SA..FM.S.S.. ..A....MTR.E..S L.SE.RA...LH...  155
Anopheles      ......V.I..T... DS..V....G..... .....VKM.....L. .A.AAQI....I... ..GIR...KHLE..S E.ADK.V.DLERSEK  179
Drosophila     Y.VKE.IEI..Q..K D..SV..T.G..... .....SR....NA.. .A.TAQIF....... ..GVR..M.RLE.QA D.TQKRAHDLNKPES  154
Caenorhabditis ...CQ.IEV.RD..K D...FL.F....... .....EGM.K...V. .A.AAQT.Q.LAQ.. ..G.....T.ND.VV SDAIK.FADYGKQSE  153
Arabidopsis    LEVKKVYEI.LK.TP ESR.....L.G ASG V.EA.VRAF...HI. .G.AAQIIIQ..... ..Y....VQ.V..QM T.LD...ADIKRSV.  158

Vertetrates    FHCLxIxxxLKxTEA xxxxxFGRYSSQRMK DWQxxxxxYxxDNxY LxExxxxxxxxxxYE xxxxxxQxxxxxxxx xxxxxxxxxxxxxxx
Mammals        FHCLRIxDLLKGTEA STKNIFGRYSSQRMK DWQEIxxLYEKDNTY LVELxSLLVRNVxYE IPSLKKQIAKCQQLQ QxYSRKEEExQAGAA
Motifs         FHCL                 FGRYSSQRMK DWQ
```

Figure 2(B)

```
Human          EMREQFYHSCKQYGI TGENVRGELLALVK  DLPSQLAEIGAAAQQ S LGEAIDVYQASVG FVCES     PTEQVLP MLRFVQKR          233
Rat            ............... ..D...R.......  ...........G..S   ......L...C.E ...D.     ....... ...Y...K          232
Mouse          ............... ..D...R.......  ...........G..S   ......L...C.E ...D.     ....... ...Y...K          232
Danio          D...RY.AA...... K....AR..Q.Q..  ...VV.E.T.KK.AC   .KD..EF.T.FTK ..SD      WS.E... L......K          231
Tetraodon      D...RY.AA.R.... R.DS.TR..Q....  ...VV.EGV.KDSAK   .EKQ.QL.S.FTD ...G      WS.A... ..T.....          231
Xenopus        QQ...Y.N...N... S..DI.K..V...C  .V..V.RQ...D.AG   .LS..QL...C.T ...D.     SP.EA.. I..H...C          232
Anopheles      VVMAEYQNM...L.V ..T.L.Q..VDK.FN ...GM.TKVASSVAP         LKKTVEL YASFM     NDAEC.T L.KH.LAK          251
Drosophila     QILADHSALLE.L.V K.D.LHA.FVQVLS  G..ELYDKSLVGIAN         IQPGIDL YAEV.     GNK.... I.NHLVEF          225
Caenorhabditis DAKK..EKNVQKM.L K.VSL.A.....AA  ...AFFEQTSKDI..   .SP.R.YFK.FRS YMHQNS A.ESSI.. L.ALICD.G          233
Arabidopsis    LSATKYEDA.REL.L Q.N...R...ETAS  S...TFSK.LEVINS DSVTG.MEY.S.Y.Q D.HTEKDK.LRI..Q N.KYIRENPPSLSVF  247

Vertebrates    xxRExxYxxxxxYGI xGxxxxxELxxxxx  DxPxxxxxxxxxxxx xxLxxxxxxYxxxxx FVxxxxxxxxxxxLP xxxxVQKx
Mammals        EMREQFYHSCKQYGI TGxNVRxELLALVK  DLPSQLAEIGAxAQx x LGEAIDxYQAxVx FVCxSxxxPTEQVLP MLRxVQKx
Motifs


                               |---------MP8 core protein----------------------------------------------------->

Human                          GNSTVYEWRTGTEP SVVERPHLEELPE   QVAEDAIDWGDFGVE AVSEGTDSG ISAEA AG IDWGIFPESDSK     303
Rat                            .............. ......Q..DP..   ..Q..E.......L. ...DSGNI  ....T P: .....SL..E..     301
Mouse                          .............. ......Q...P..   ..Q..E......... ...DSG    .V..T P. .....SL..EA.     299
Danio                          ..T....RK..NV. K.....VM..A.PD  V.T.ET.....L.SG .GTGSEEVN FGISV EDGV....GL..GTE     303
Tetraodon                      ..T.F......KT. T.....VV.AA.AG  GIT..T.......KS .GTS  .IP AAITV EDG.....SL.PVAE     301
Xenopus                        .DT.I....V.EA. RR....DK.KQETPQ CPE.GE.N....E.Q PSTAAETEAGLDSL. T.E.....SV.PEAA     306
Anopheles                      ..T....FVY.EP. LSI.E.PVKFVT.QQ .E.A.DGGAI...DD DGGAIDFGDGSGLDL DAPVELE.GDIDWGA     325
Drosophila                     ..T...QYIHKEA. LA..E.PIRLNLSEG NASK.DNAVAEIDFG TDDN.GT.STV...I IDYG.F.SGDLPE.D     299
Caenorhabditis                 VDV.T...KYHQK. DRI.Q.NF.L.LKDD KKGS.E..F..DIDF GDDD            .G..F.ADSVEIDI     295
Arabidopsis    GDSEGLDADNIQSSE NA.G.DAAADSIDWD IT..T.EIDWDVSMV EEVDSGN.L.SYEIV NA.DIPENSPFKV.E SQGLEVDVSEI.WDV  337

Vertebrates                    GxxTxYExxxGxxx xxVExPxxExxxxxx xxxxxxxxWGDxxxx xxxxxxxxxxxxxxx xxxxDWGIxxExxxx
Mammals                        GNSTVYEWRTGTEP SVVERPxLExxPExx QVxEDxIDWGDFGxE AVSxxxxxx IxAEx xx IDWGIxxESxxK
Motifs                                                                                             DWGI
```

Figure 2(C)

```
                >---------MP8 core protein------------------------------------------------------------>

Human           DPGGDG          I DWGDDAVAL QITVL EAGTQAPEGVARGPD ALTLLEYTETRNQFL DELMELEIFLAQRAV ELSEEADVLSVSQ F   383
Rat             .A.A.K          . ....N...S E.... .T..E........S. .......P......I ..........S.... .M.....I..... .   381
Mouse           .A.A.K          . ......A.ASE.... .T..E........S. .......P......I ..........S.... .M.....I..... .   380
Danio           ETS.G.          . N...SES.PLE.E.V DV..DC.D.....E. ..S...NSQ..S..I N..K...M..C..LS .MR..G.LVAM.. .   384
Tetraodon       .TSVS.          . ....AEAPPVE.E.V D...DC.......E. ...V..KPTS.S..I .......A..R..LS .MG..G..IAM.. .   382
Xenopus         EVD.            . N.DAGEEPTAV.... .T.SNVLP.....S. ..SV..N.D.....V .......L..C.WQQ SMECDT.IVT.T. .   385
Anopheles       ADE.ADPALAGANDG NVI.FNIS.EESGIV VEEDGNLG...K.DE .F.V.DAQQY.DR.V ND.L..QS..KM.LH Q.G S..KAQ.LA .   413
Drosophila      GGNI.WGIESAPTDA VEINFDIPVEEYGIV VE..GMDG.T.K.DQ .Y...DSPNY.DR.. ..IY...S..RM.IY ..K QLESS.DIM .   387
Caenorhabditis  VADDS.                                AVG.K..S.Q. ..S...NS.AQKALK L..N..LA..SM.LD DETR.TGADILIRGA   357
Arabidopsis     SVETP       QVE EI..S.LLE   SNQ TQL.DSTTQ.LGSGG ERSQ.LE..Y..KI. .D.Y.VKA..N..LI ..RN.DTLSLQHHVQ   417

Vertebrates                 (i dwgd)xxxxxxxxVx xxGxxxxxGVARGxD ALxxLExxxxRxQFx xELxELExFLxxxxx xxxxxxDxxxxxQ F
Mammals                         I DWGDxAxAxxxITVL ExGTxAPEGVARGxD ALTLLEYxETRNQFx DELMELEIFLxQRAV ExSEEADxLSVSQ F
Motifs                          I DWG                  GVARGxD AL

                >---------MP8 core protein------------------------------------------------------------>

Human           QLAPAILQGQTKEKM VTMVSVLEDLIGKLT SLQLQHLFMILASPR YVDRVTEFLQQKLKQ SQLLALKKELMVQKQ QEALEEQAALEPKLD   473
Rat             ............... LSL..T.QH...Q.. ..RM........... .......L....... ........D...E.. ....Q..........   471
Mouse           ............... LSL..T.QQ...R.. ..RM........... ............... ............E.. ....Q..........   470
Danio           ....SVI.A..PQRV QV.LADVRE.LNG.. .VRM......Q.... ..E..S.L.R..... ADIMV..RGTLAE.R ........K...RI.   474
Tetraodon       ....P.I.D.SC..V RQ.L.EVR.IL.R.. ...M.Q....Q.... ..E..SDV.R..M.. ADI.VV.GAR.IE.R ........R...RI.   472
Xenopus         .T..S......QG.V LA.I..VRG..SR.. DTRMRQ..L...... ......DH.G.R.R. A...EK.SVSW.ERG RA.Q..RQS...R.S   475
Anopheles       AIMDNFKDHD EKTV AS.LAEV.VVYAGV. DEL....LQ.KH..V ...IL.SNVK...TS IDKMKETALMKRE.S VSFKQQSVE.K.TQT   502
Drosophila      S.MDN.ATHD G.SI WKILVSV.KI.QQTS DK.T....QLKH..K .ANMLATK...MT.A VEK.RATR.ALK.LT I.LR.QRQD.N.V.E   476
Caenorhabditis  EKR.DDVAKV.DKDL KAWIAEI.RVLKEFE NP.KI...K.RGC.Q ..EQ.V.Q.EK.RDM E.RYKRLQS..TDN. EA.RVAVSKANAE.K   447
Arabidopsis     AVS.MV..QYSP.TI EP..VDISMA.SL.. NKKSRD.I...N.K. FL..LVSE.EE.KHR EVK.RESLKDVGRRR M.LQNSLS.IW..QE   507

Vertebrates     QxQPxxxQxQxxxxx xxxxxxxxxxxxxxx xxxxxxLFxIxASPR YVxRVxxxLxxxxxQ xxxxxxxxxxxxxxx xxxxxExxxLEPxxx
Mammals         QLAPAILQGQTKEKM xxxVSxLxxLIGxLT SLxxQHLFMILASPR YVDRVTExLQQKLKQ SQLLALKKxLMVxKQ QEALxEQAALEPKLD
Motifs                                                    ASPR YVxRV
```

Figure 2(D)

```
                >---------MP8 core protein--------|

Human           LLLEKTKELQKLIEA DISKRYSGRPVNLMG TSL           506
Rat             ......R........ ......N........ ..V           504
Mouse           ......R........ ............... ...           503
Danio           ..AAR.......... ......NN....... VHV           507
Tetraodon       ..AGH.R........ .......K....... VNV           505
Xenopus         ..Q.RSR..K.Q... .L....NN.....I. .G.           508
Anopheles       KIV.Q..T..GQ..K ......KN.....Y. .N.           535
Drosophila      E.IAQ.RT..SH..K ......KN.V..... GVN           509
Caenorhabditis  TIV.S.RL...QV.. E...K.N..R..... GINQALGGV     486
Arabidopsis     AA.S..R..KE.C.T SL.SMFD.....IR. EINTLLNAGVSA  549

Vertebrates     LLxxxxxELxKxIEA DxSKRYxxRPVNLxG xxx
Mammals         LLLEKTxELQKLIEA DISKRYxGRPVNLMG TSx
Motifs                      IEA DxSKRY  RPVNL
```

Figure 6
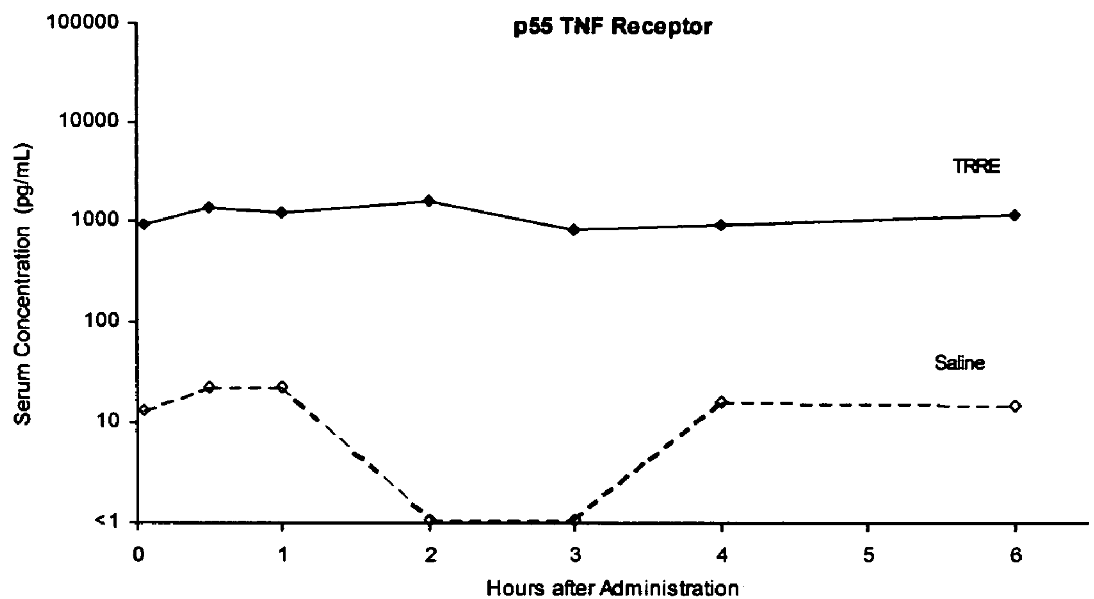
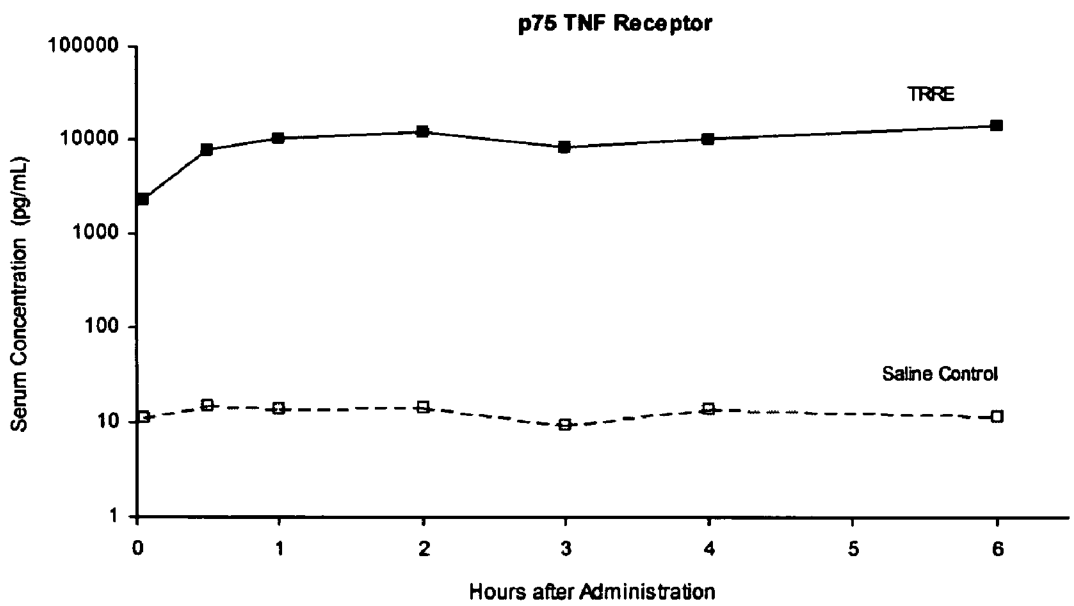

Figure 14
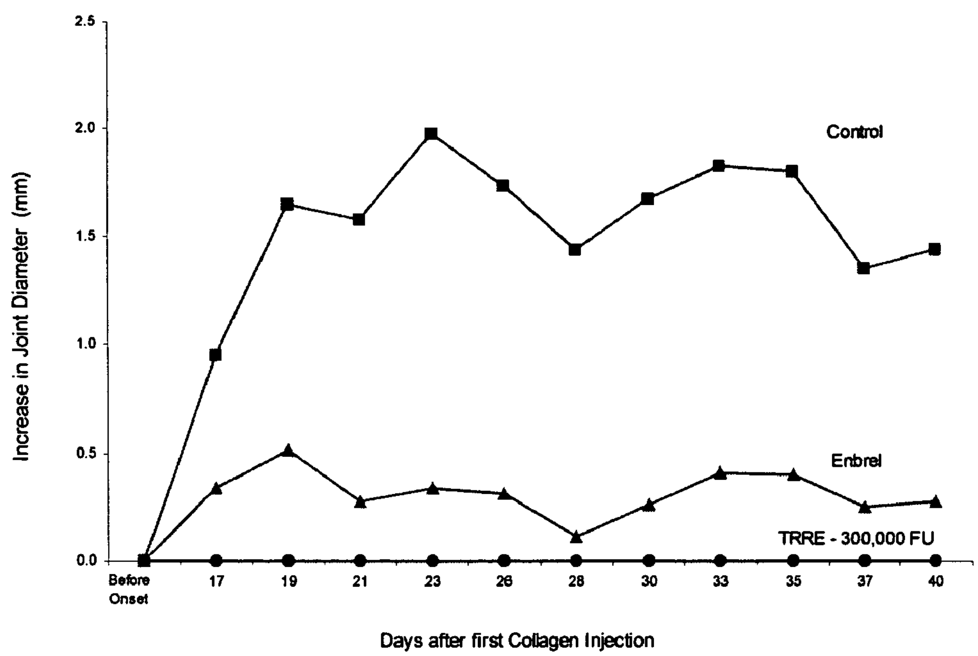
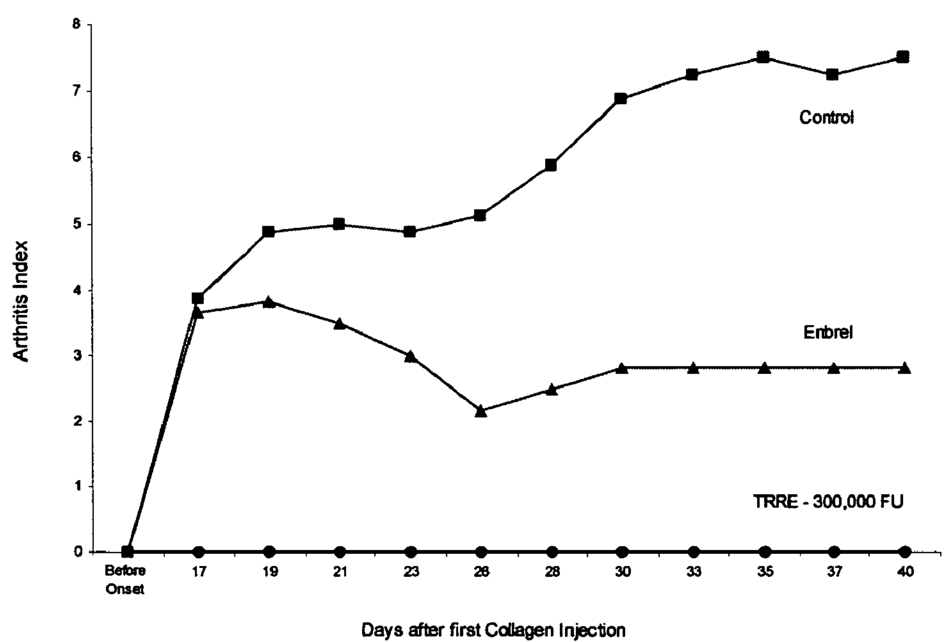

Figure 18
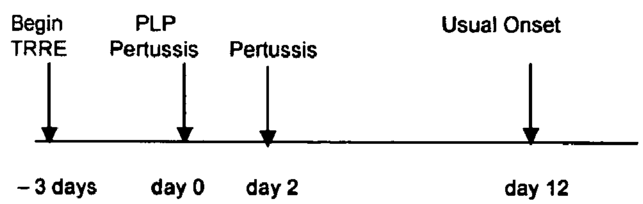
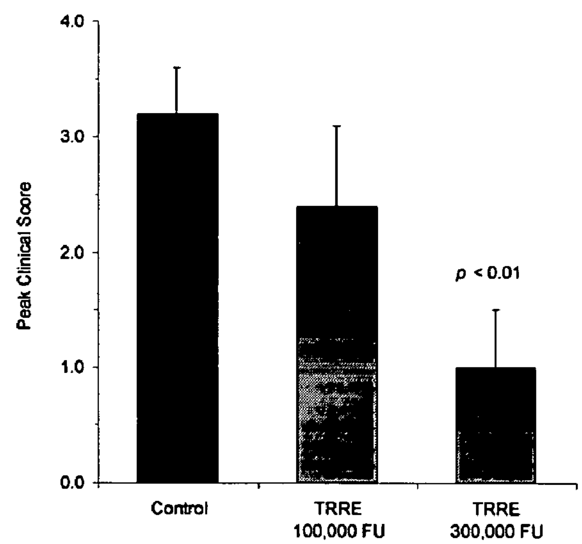
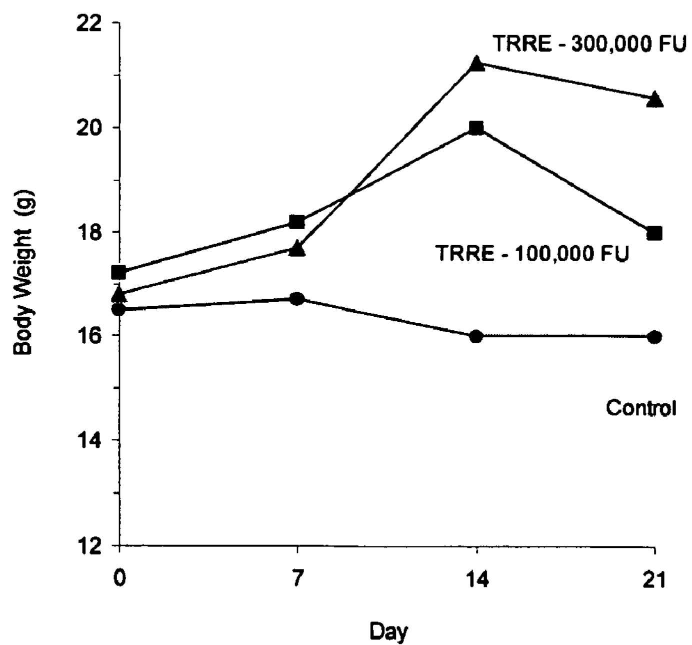

Figure 20
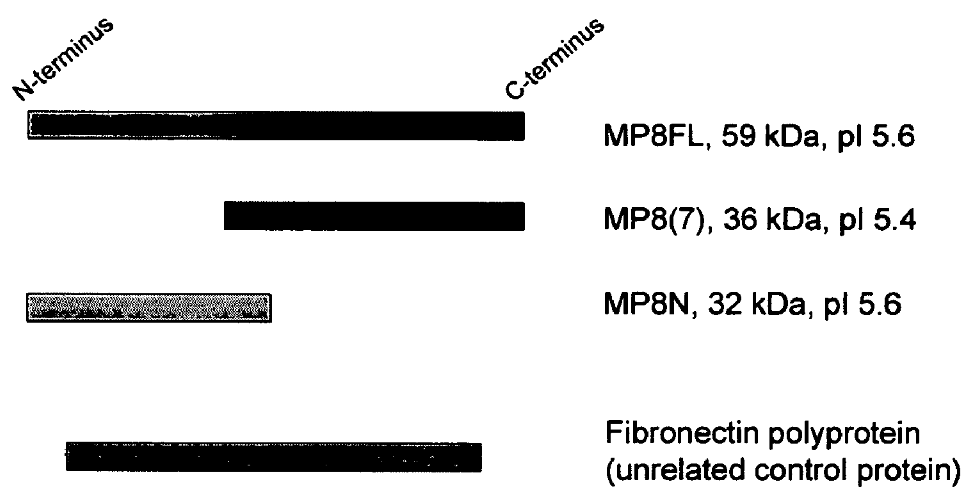
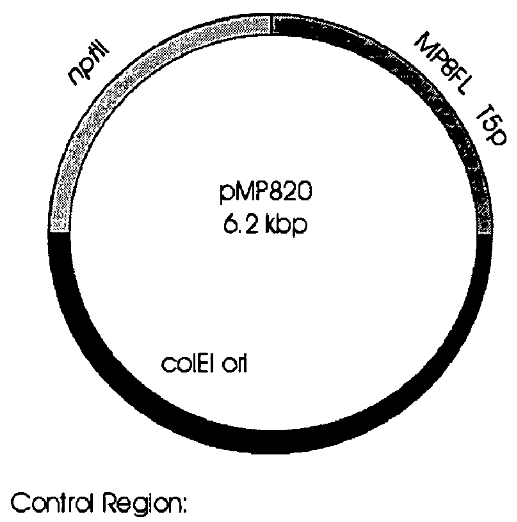
Control Region:
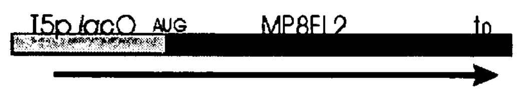

Figure 23
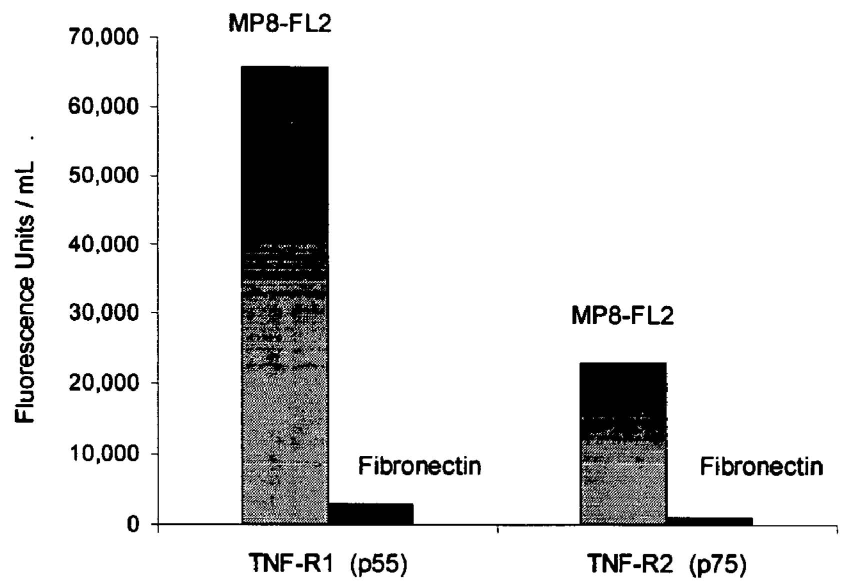
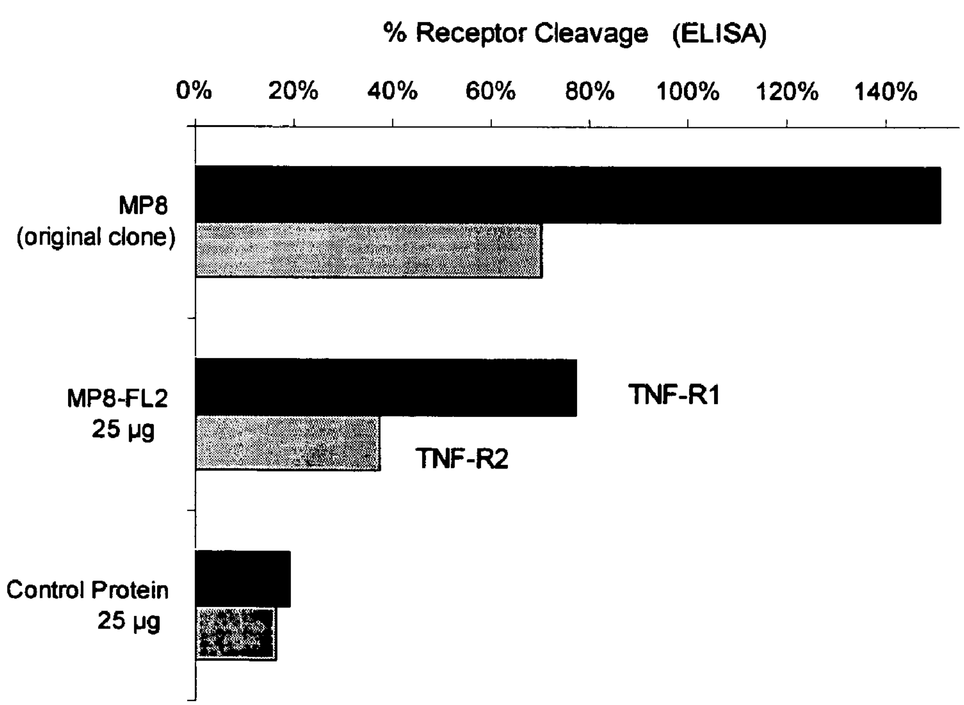

BIOLOGICAL AGENT THAT CAUSES IL-6 RECEPTOR RELEASE

RELATED APPLICATIONS

This application is a continuation of International Patent Application PCT/US2004/031377, filed Sep. 23, 2004 (pending), designating the U.S., and published as WO 2005/050241 on Apr. 7, 2005; through which it claims the priority benefit of U.S. provisional application 60/505,336, filed Sep. 23, 2003.

The two priority applications, and issued U.S. Pat. Nos. 6,569,664 and 6,593,456, are all incorporated herein by reference in their entirety with respect to treating inflammation using cytokine receptor releasing factors.

BACKGROUND

Inflammatory events play a central role in the pathology of disease conditions that adversely affect a considerable proportion of the population in developed countries. This process is mediated by cytokines, a system of polypeptides that enable one cell to signal to initiate events in another cell that initiate inflammatory sequelae. Normally, the system acts as part of a defensive reaction against infectious agents, harmful environmental agents, or malignantly transformed cells. But when inflammation exceeds the requirements of its defensive role, it can initiate adverse clinical effects, such as arthritis, septic shock, inflammatory bowel disease, and a range of other human disease conditions.

Small-molecule antirheumatic drugs such as methotrexate and sulfasalazine are insufficient to control inflammation in about two-thirds of arthritis patients. New biological agents developed in the last decade have proved to be effective for a majority of patients unresponsive to traditional drugs. The target for such agents is often one of the cytokine pathways—either capturing the ligand conveying the signal from one cell to another, or blocking the receptor at the surface of the effector cell, preventing transduction of the cytokine signal, thereby forestalling the inflammatory events.

A leading biological agent for treating inflammatory conditions is Enbrel® (Etanercept), marketed by Amgen Corp. It is a chimeric molecule comprising the extracellular portion of the human TNF receptor linked as a dimer to the IgG Fc region. The compound interferes with the binding of TNF to cell-surface TNF receptors—showing the importance of modulating the TNF pathway for clinical therapy of inflammatory conditions.

Enbrel® is licensed in the U.S. for treatment of patients with moderate to severe rheumatoid arthritis, juvenile rheumatoid arthritis, and psoriatic arthritis. Approval is expected in 2003 for treating ankylosing spondylitis. Sales of Enbrel® were $750 million in 2001. Scaling up production to meet growing demand has been a challenge. The projected sales in the U.S. market for current indication is expected to reach at least $4 billion by 2005, just for current indications.

Other biological agents currently licensed in the U.S. for treating arthritis are Remicade® (Infliximab), a chimeric antibody that binds the TNF-$\alpha$ ligand; Humira™, a humanized anti-TNF-$\alpha$ antibody, and Kineret™ (Anakinra), a recombinant form of IL-1Ra, an antagonist of the interleukin-1 receptor.

As it happens, cytokine ligands are not the only component of the cytokine pathway released from cells involved in inflammation. Receptors for the cytokines on the target effector cell are also released in certain inflammatory conditions (Gatanaga et al., *Proc. Natl. Acad. Sci. USA* 87:8781-8784, 1990; Brakebusch et al., J. Biol. Chem. 269:32488, 1994).

By 1997, Gatanaga and Granger had isolated a polypeptide that causes the human TNF receptor (both the p55 and p75 isoforms) to be cleaved from the cell surface (U.S. Pat. No. 6,569,664). They demonstrated that the enzyme can be used as an anti-inflammatory agent for treatment of septic shock, and proposed that it be used to treat other inflammatory conditions, such as arthritis, cachexia, and inflammatory heart disease. Subsequently, Gatanaga and Granger isolated nine recombinant cDNA clones that encoded proteins implicated in TNF receptor release (U.S. Pat. No. 6,593,456).

Some subjects having inflammatory conditions do not respond to the medicaments currently available, and the consumer cost of existing biological agents can be over $10,000 per year. There is a need for new biological agents that inhibit multiple cytokine pathways and which can be produced for more modest cost.

SUMMARY

This disclosure provides inventions related to the use of biological agents that cause cytokine receptors to be released from the surface of cells.

One aspect of this invention is based on the unexpected finding that making exemplary biological agent MP8 longer, rather than shorter, improves the scale by which it can be produced by at least 10-fold.

This discovery enables the use of extended versions of MP8 (or nucleic acids encoding such proteins) for a number of new purposes: preparing a pharmaceutical composition, causing a cytokine receptor to be released from the surface of a cell, inhibiting signal transduction from a cytokine receptor into a cell, screening a substance for its ability to inhibit release of a cytokine receptor, producing a protein that causes a cytokine receptor to be released from the surface of a cell, or treating inflammation in a subject by administering the extended MP8 or a nucleic acid that encodes it.

A preferred embodiment of the extended MP8 in this context is a polypeptide comprising SEQ. ID NO:53, or a fragment or variant thereof not contained in SEQ. ID NO:41. Fragments and variants can be defined as having a degree of sequence identity (as defined below) with SEQ. ID NO:53 not shared with SEQ. ID NO:41. Fragments and variants of the native sequence, and nucleic acids encoding them, are also an aspect of the invention as compositions of matter, with the proviso that previously known sequences and products are not included.

Also contemplated are immunoassays, hybridization assays, and PCR assays using the extended form of MP8; and the use of extended MP8 and nucleic acids related thereto for medical use, or the preparation of medicaments for treating inflammatory disease.

Another aspect of this invention is based on the identification of biological agents that cause release of cytokine receptors not previously known as natural enzyme targets, such as the IL-1 Type I receptor, IL-1 Type II receptor and the IL-6 receptor.

One embodiment of this aspect of the invention involves contacting one of these receptors (or a peptide taken therefrom) with a composition comprising either a protein expressed from an encoding sequence selected from SEQ. ID NOs:1 to 29, a recombinantly produced protein containing an amino acid sequence that is at least 90% identical to any one of SEQ. ID NOs:30 to 59 and 80, or fragment thereof, optionally extended beyond SEQ. ID NOs:30 to 42.

A related embodiment a method for reducing inflammation, comprising contacting an inflammatory cell with an IL-6 receptor protease or an IL-1 receptor protease (or metalloprotease) generally, which can be referred to as a means for causing specific release of the IL-6 or IL-1 receptor. Another embodiment is the use of such proteases for preparation of medicaments for treating inflammatory conditions such as rheumatoid arthritis, ankylosing spondylitis, psoriasis, psoriatic arthritis, osteoarthritis, cardiac insufficiency, arteriosclerosis, asthma, myasthenia gravis, septic shock, ulcerative colitis, or Crohn's disease.

Another aspect of this invention is an assay method for determining cytokine receptor releasing enzyme activity in a solution. The solution is combined with a peptide-consisting essentially of 8 to 20 consecutive amino acids of a human cytokine receptor, selected from p55 TNF receptor, p75 TNF receptor, IL-6 receptor, IL-1 type I receptor or IL-1 type II receptor, under conditions where the enzyme (if present in the solution) cleaves the peptide; cleavage of the peptide is measured, and enzyme activity is thereby determined. In a preferred embodiment, the peptide is labeled with a fluorescence emitter and a fluorescence quencher, and cleavage is measured by measuring change in fluorescence of the labeled peptide.

Other aspects of the invention will be apparent to the skilled reader from the description that follows, and the appended claims.

DRAWINGS

FIG. 1(A) shows isolation of cytokine receptor cleaving activity from human THP-1 cells. Total protein and cleaving activity was followed through purification on DEAE-Sepharose® (Top Panel) and native gels (Middle and Lower Panels) by measuring the ability of the fractions to cause receptor release from the surface of transfected cells.

FIG. 1(B) is a Western analysis of MP8, one of nine different cDNA clones that are associated with receptor releasing activity. The single MP8 band is shown beside molecular weight standards.

FIGS. 2(A), 2(B), 2(C) and 2(D) provide an alignment of full-length human MP8 protein sequence (SEQ. ID NO:53), compared with species orthologs (rat SEQ. ID NO:81, mouse SEQ. ID NO:57, and other species, top to bottom SEQ. ID NOs:82-88). Dots indicate residues that are identical with the human sequence on the top line. The orthologs are remarkably similar, sharing a good deal of identity especially between vertebrates (SEQ. ID NO:89) and mammals (SEQ. ID NO:90). Motifs shared throughout the family (SEQ. ID NOs:91-102) are shown below the mammalian consensus sequence.

Figure 3:
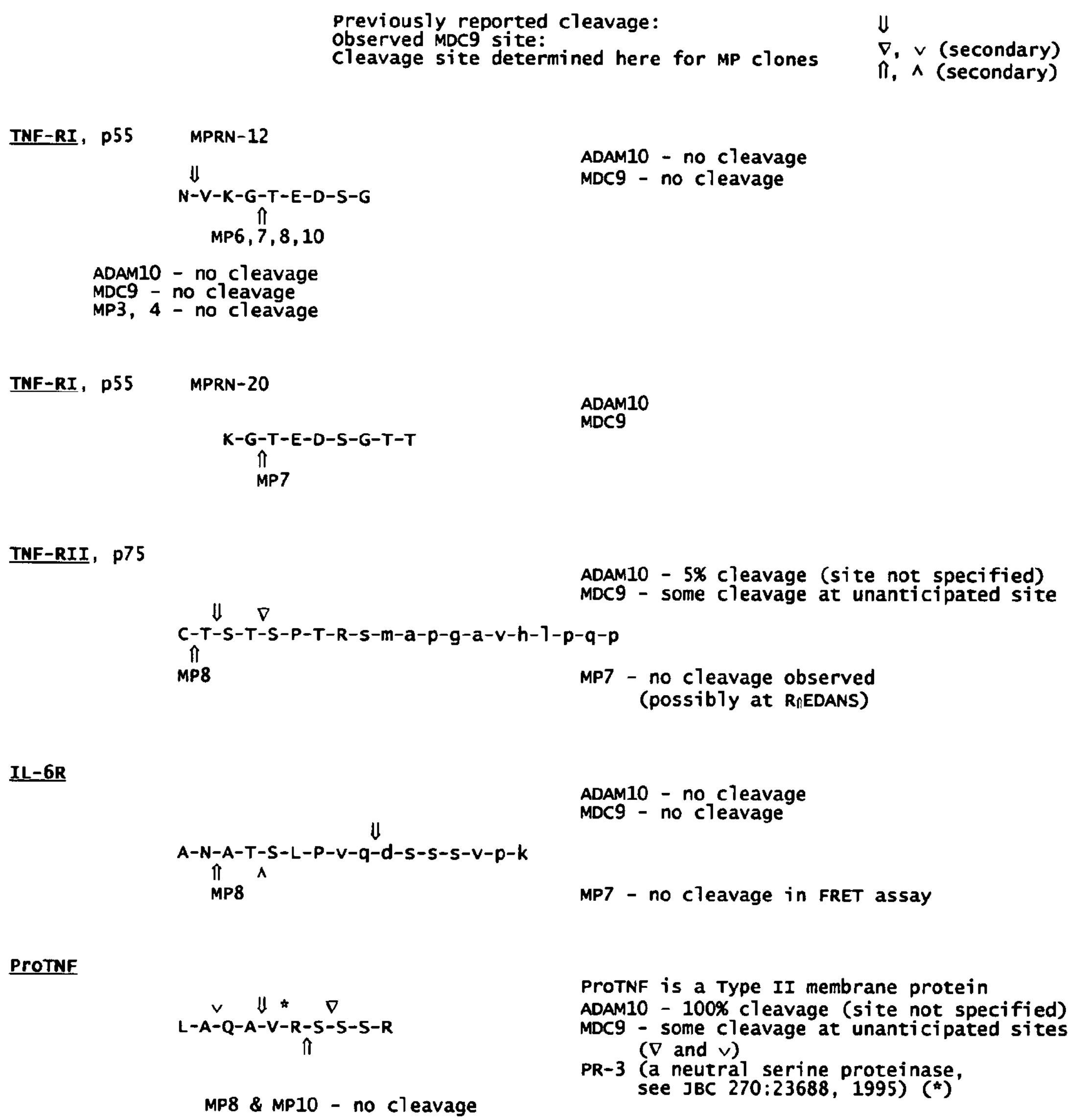

FIG. 3 shows receptor cleavage sites determined by mass spectrometry and peptide sequencing of cleaved peptide substrates (top to bottom, SEQ. ID NO:71-74 and 77).

Figure 4A:
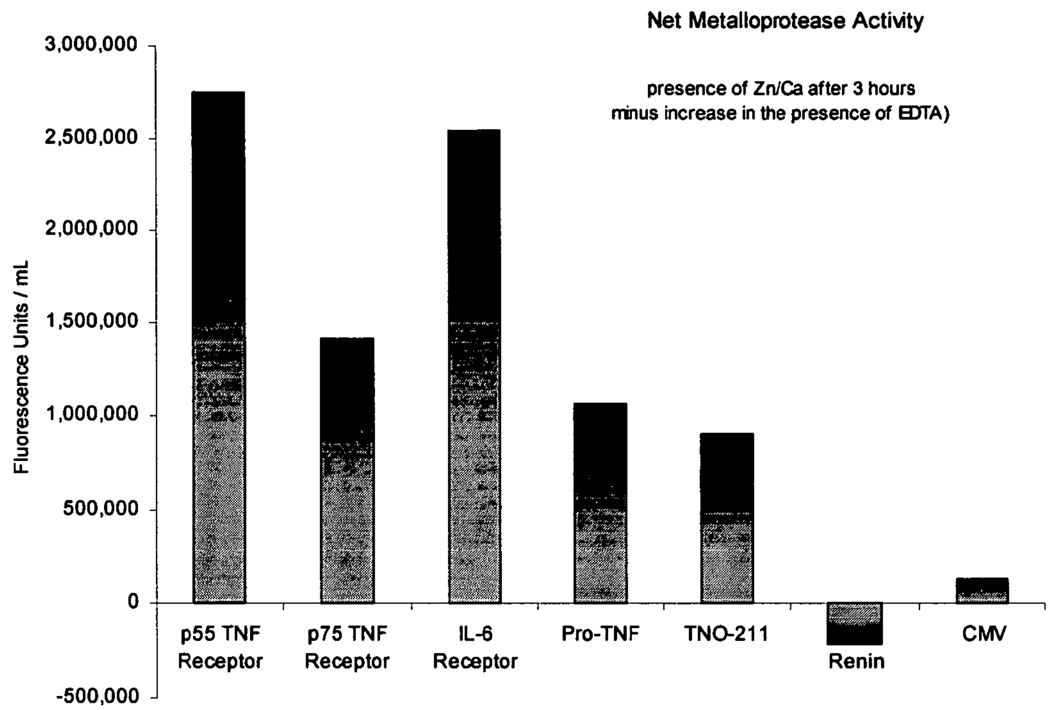
Figure 4B:
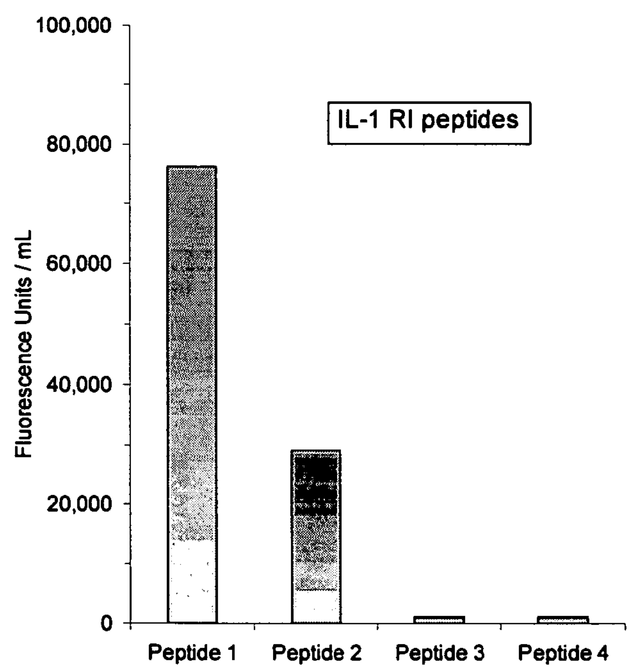
Figure 4C:
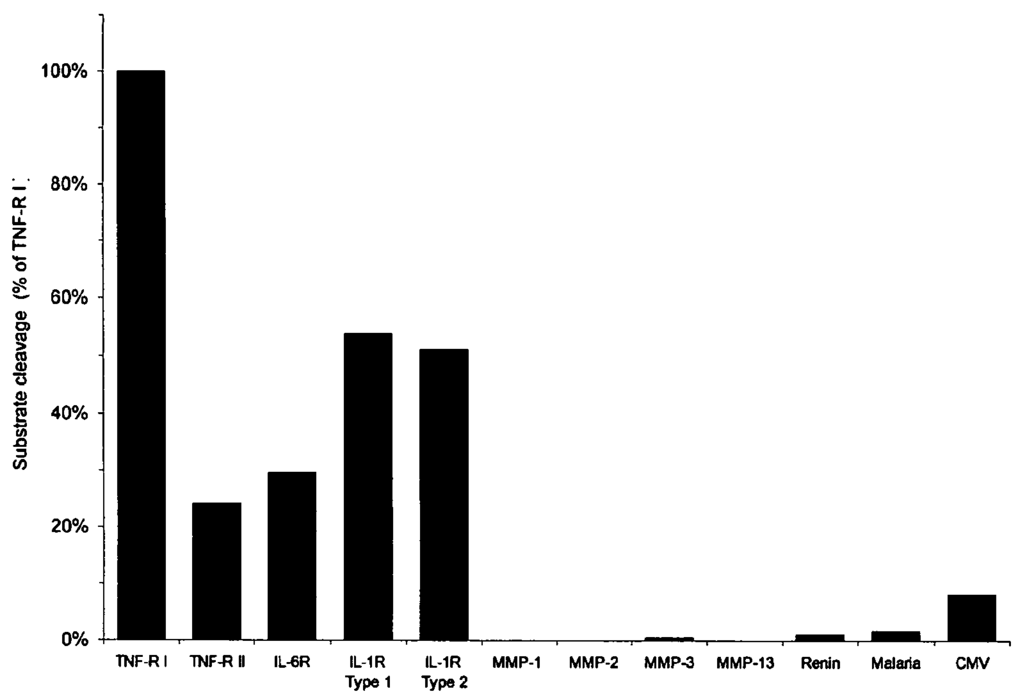
Figure 4D:
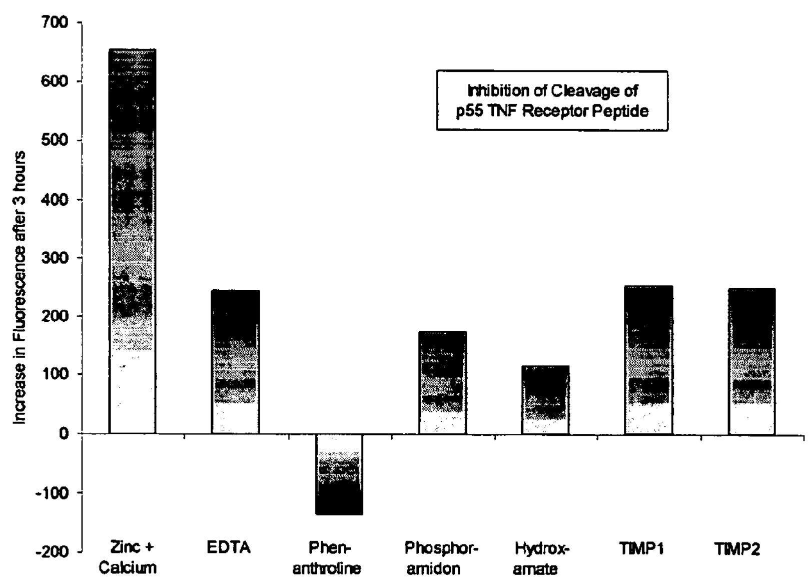

FIGS. 4(A), 4(B), and 4(C) shows receptor releasing activity measured in a peptide cleavage assay by fluorescence resonance energy transfer. Peptides having the sequence of the receptor cleavage site are labeled on opposite ends with a fluorescence emitter and fluorescence quencher, and metalloprotease activity is measured in the presence and absence of $Zn^{++}$ and $Ca^{++}$. Receptor cleaving enzyme clone MP8 shows specificity for several receptors involved in the inflammatory pathway (TNF-R p55 and p75 isoforms, IL-6 receptor and IL-1 receptors) in comparison with control substrates spanning known cleavage sites of other proteases. FIGS. 4(B) 4(D) illustrates the use of the FRET assay to assess potential inhibitors or activators of cytokine receptor cleavage activity. In this example, metal chelators have a strong inhibitory effect.

Figure 5A:
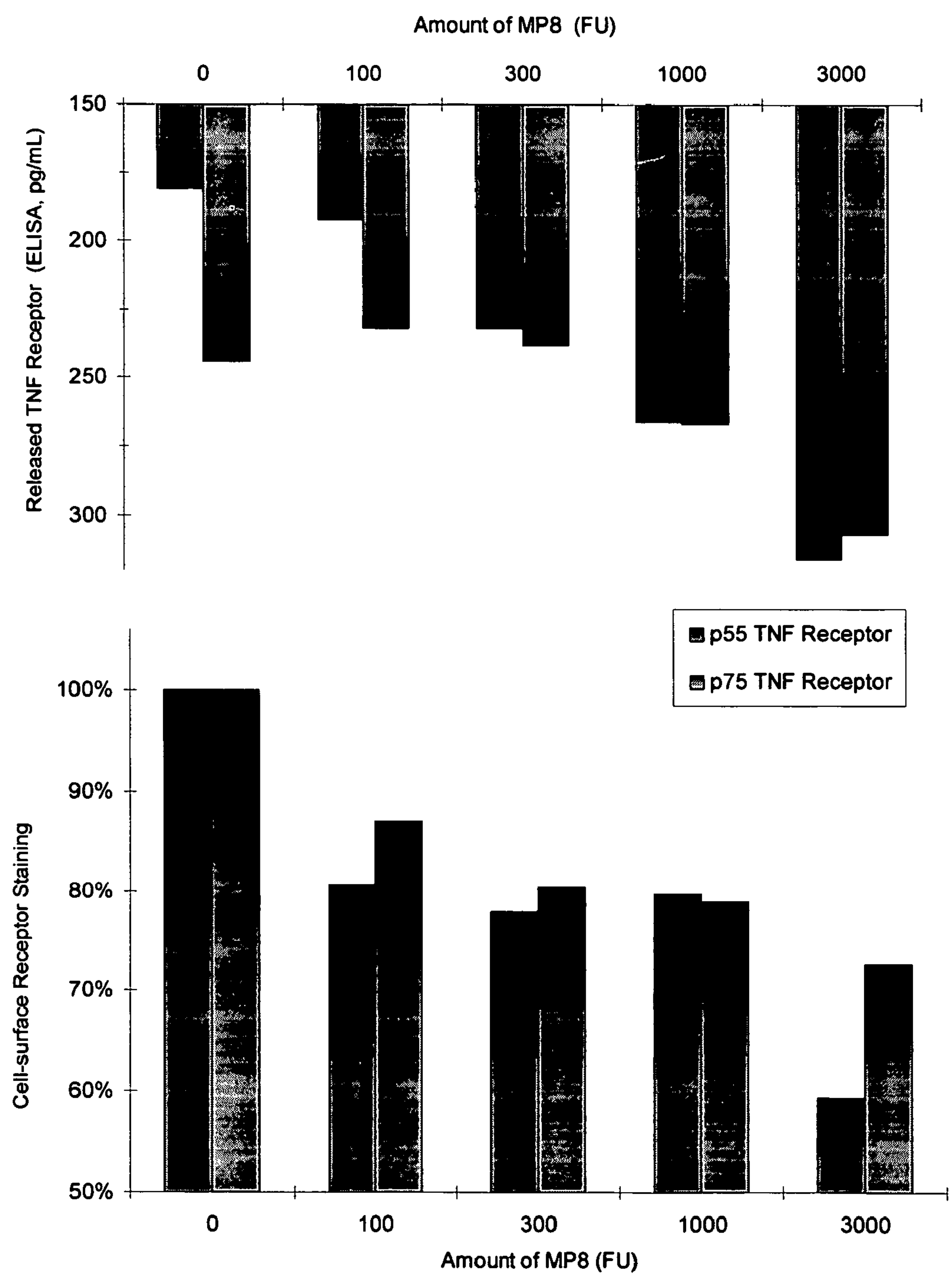
Figure 5B:
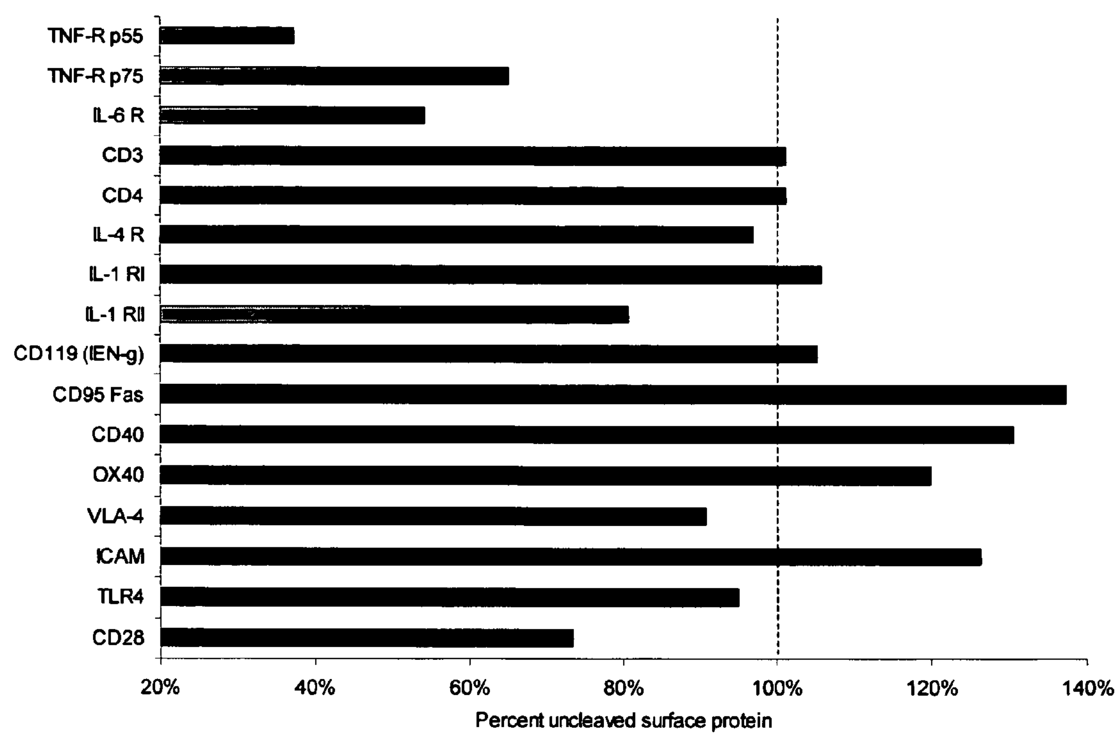

FIG. 5 shows cleavage of both the p55 and p75 isoforms of the TNF receptor by clone MP8 in vitro. As the receptor is cleaved from the cell surface, it accumulates in the culture supernatant where it can be measured by ELISA.

FIG. 6 shows cleavage of both isoforms of the TNF receptor by clone MP8 in vivo. Following subcutaneous injection into Balb/c mice, both isoforms accumulate in serum to a level that is over 100-fold above normal (saline control).

Figure 7:
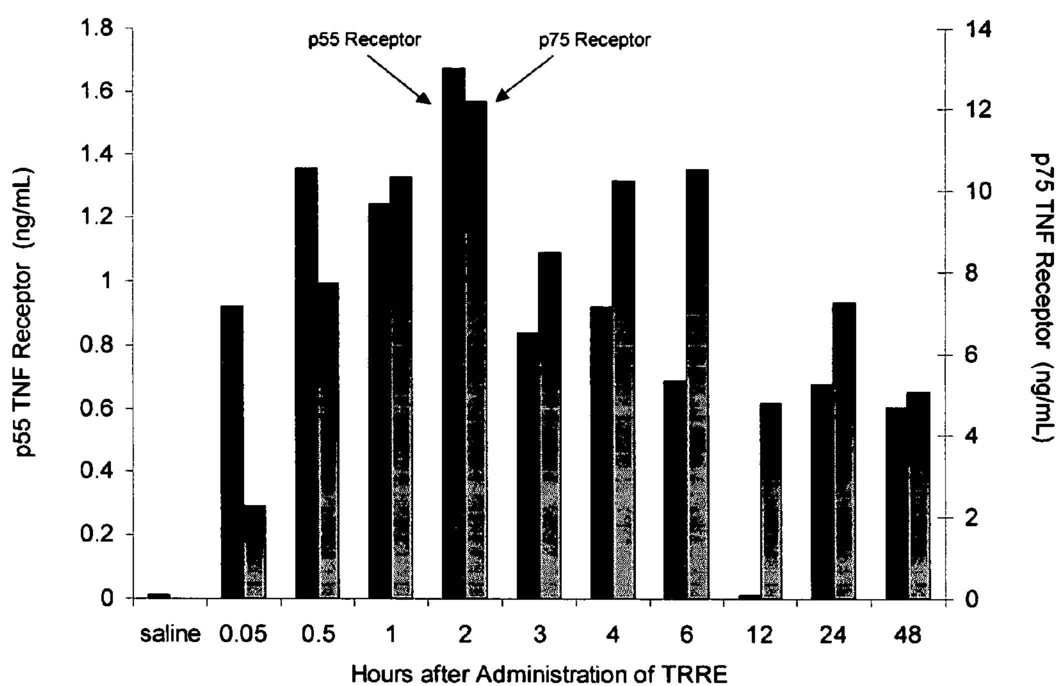

FIG. 7 is a compilation of data from two experiments, showing the kinetics of receptor release over a 48 hour period. In other experiments, released receptors persisted in the circulation for at least 6 days.

Figure 8:
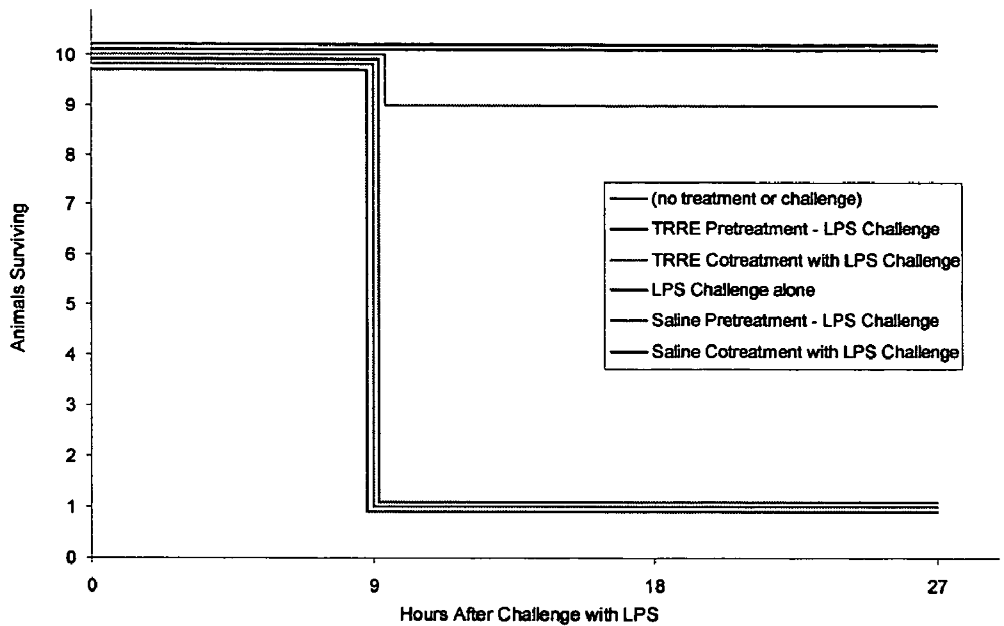

FIG. 8 shows results of a septic shock experiment. Sepsis was induced by injecting 10 μg LPS and 7 mg galactosamine intravenously into Balb/c mice. MP8 is fully protective against LPS-induced septic shock, whether given simultaneously with the LPS challenge, or 3 hours in advance.

Figure 9:
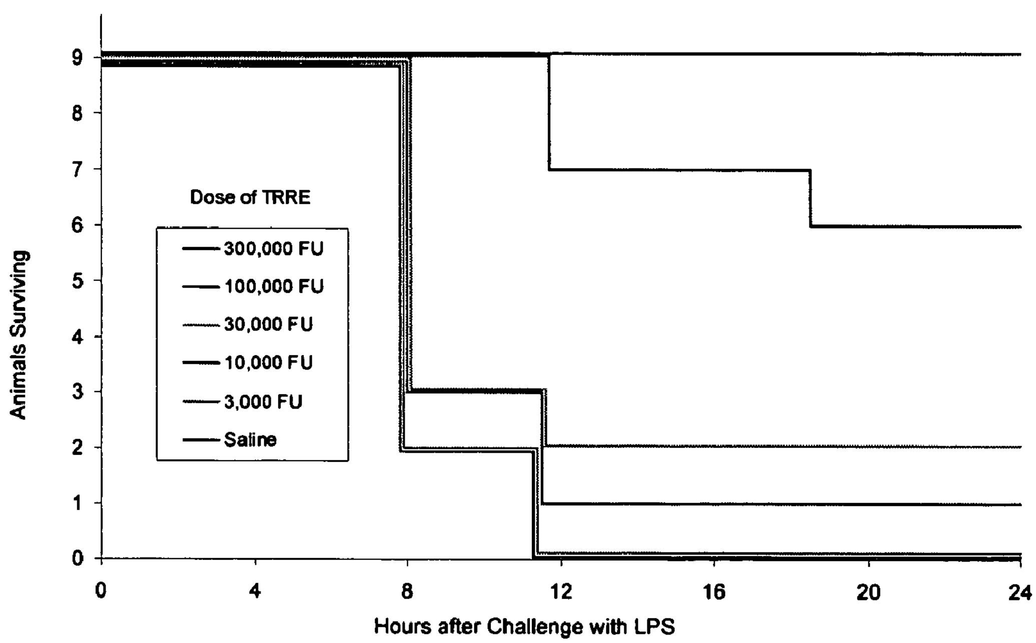

FIG. 9 shows that the anti-inflammatory effect of MP8 is dose-dependent, showing partial protection at 30,000 FU, and complete protection at 300,000 FU.

Figure 10:
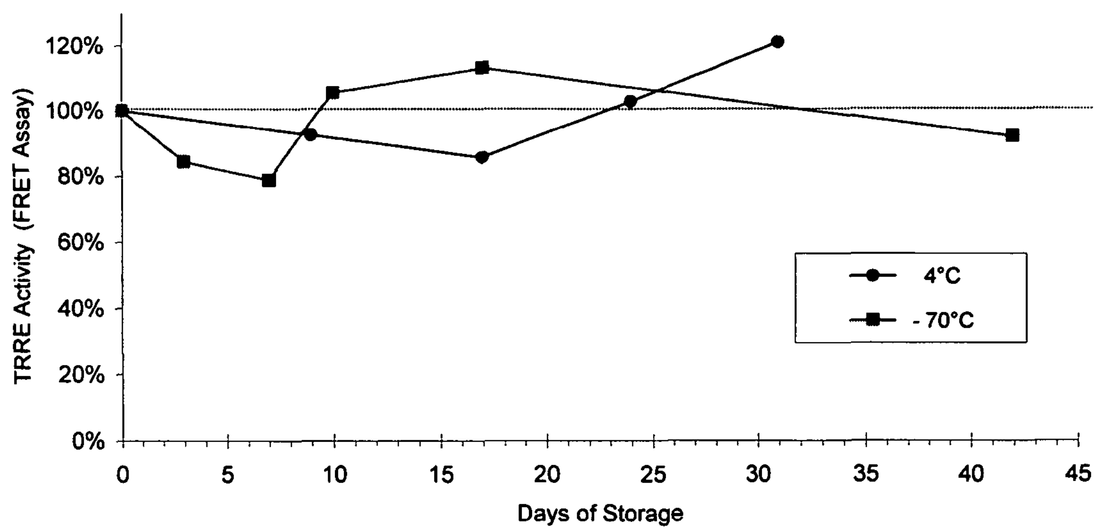

FIG. 10 shows the receptor cleaving activity of purified MP8 (as measured in the peptide cleavage assay) when stored for an extended period at 4° C. or −70° C.

Figure 11:
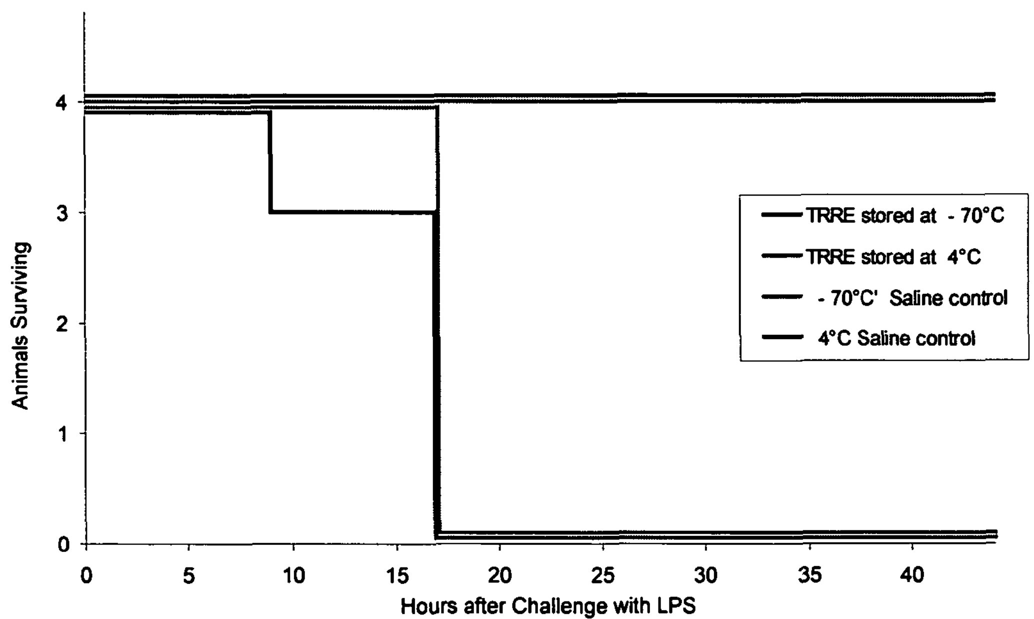

FIG. 11 shows the therapeutic benefit of MP8 is also stable. After storage at 4° C. or −70° C., the purified enzyme was still protective in the septic shock model.

Figure 12A:
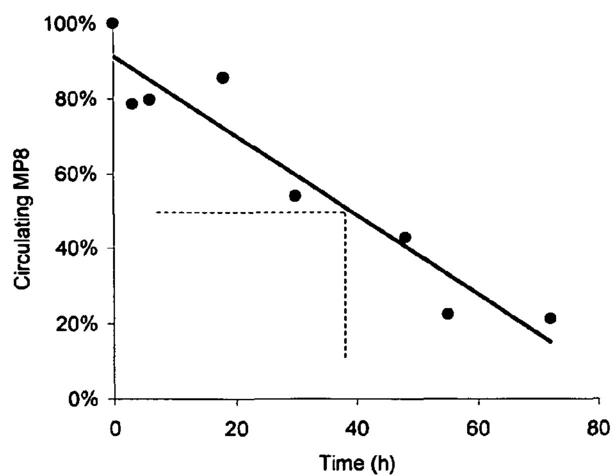
Figure 12B:
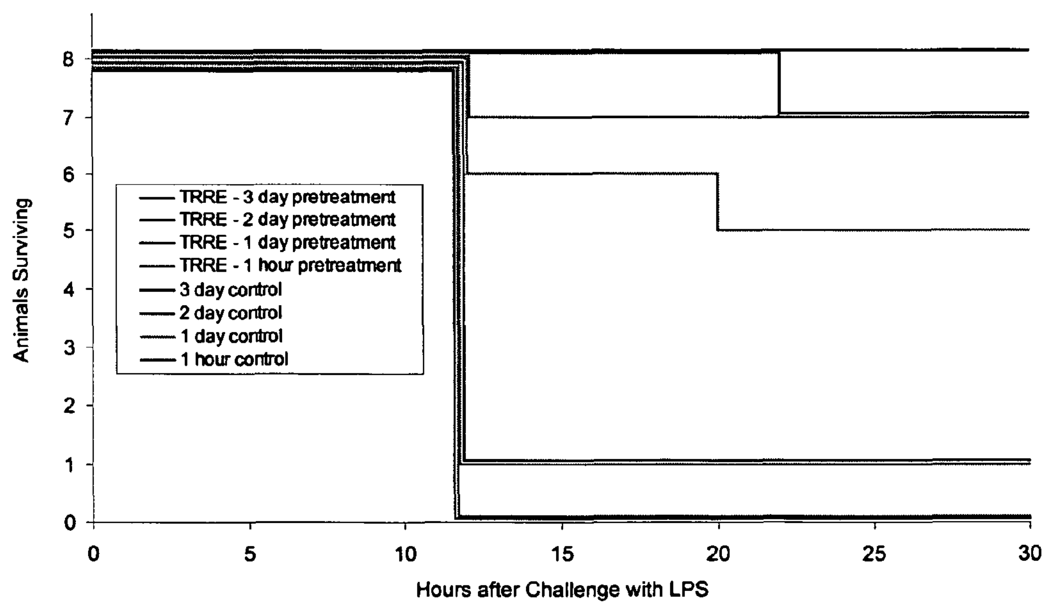

FIG. 12(A) shows that MP8 clears from the circulation in ~39 hours. FIG. 12(B) shows the therapeutic benefit of MP8 is long-lived. It was protective when administered up to three days before the septic shock challenge—either because the remaining receptor cleaving activity is sufficient to cause ongoing cleavage, or because released receptor blocks signal transduction for several days.

Figure 13:
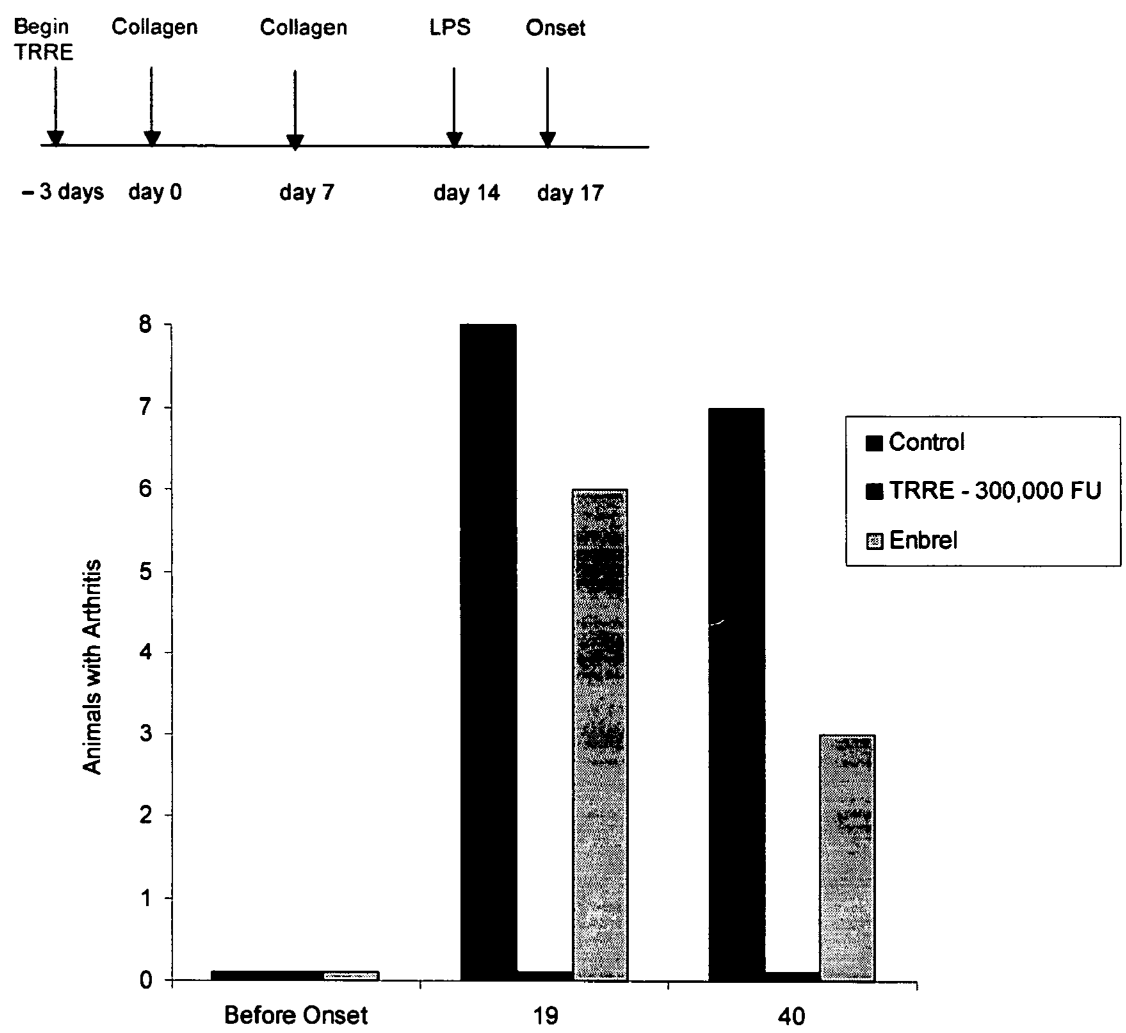

FIG. 13 is taken from an experiment in which MP8 was tested in a model for collagen-induced arthritis (CIA). DBA/1LacJ mice were treated daily beginning 3 days before the disease-inducing agent. Eight out of 9 control mice were affected, but MP8 treated mice showed no joint swelling or other signs of arthritis. The treatment was at least as effective as a scaled dose of Enbrel® (etanercept).

FIG. 14 shows the average increase in joint swelling and arthritis index in each group. MP8 prevented the animals from showing any measurable signs of the disease.

Figure 15:
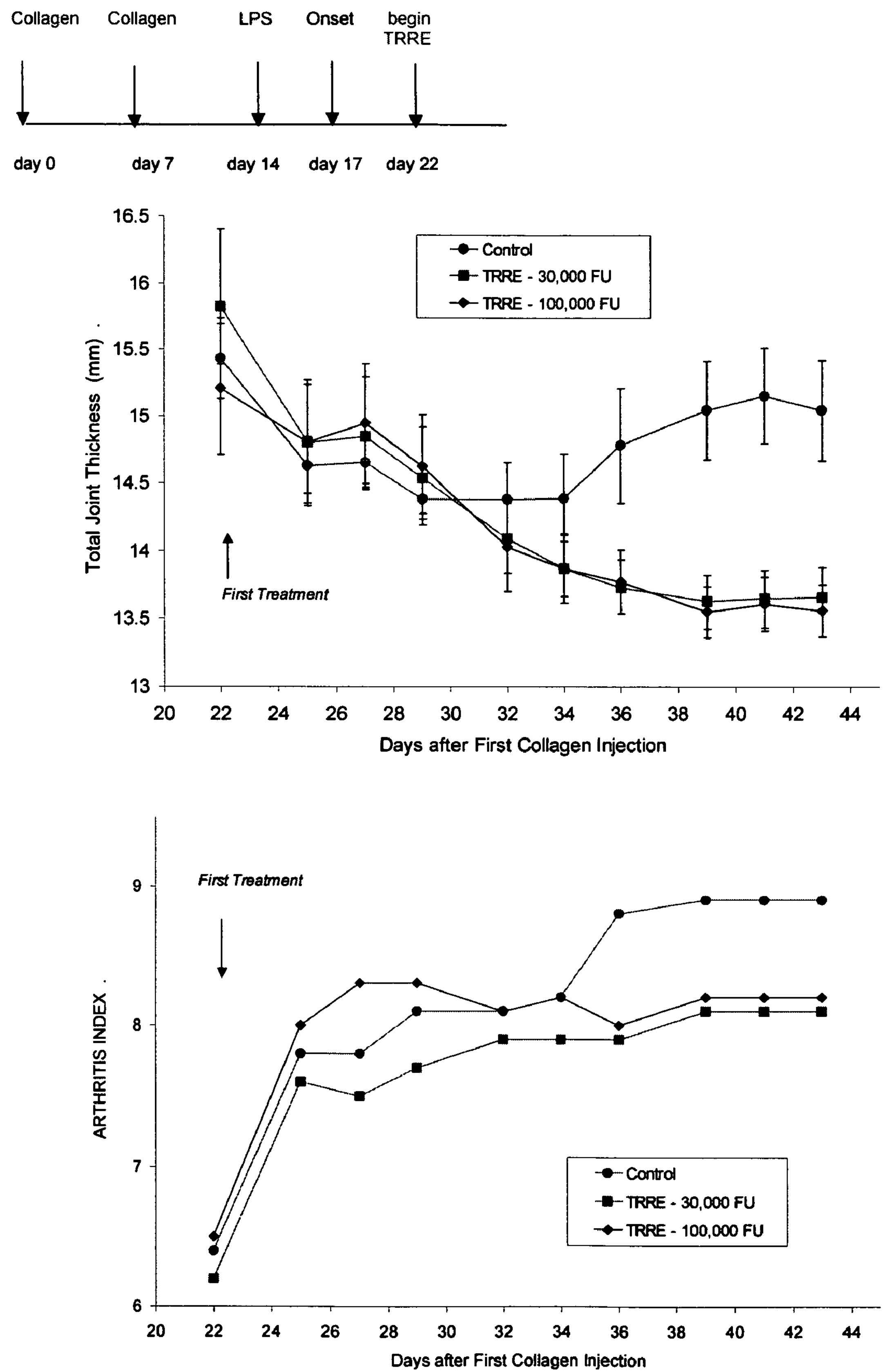

FIG. 15 is taken from an experiment in which MP8 was tested for its ability to treat established disease. Animals with arthritis were randomized on day 22, and treated daily with MP8 or saline control. There was a highly significant reduction in swelling in the affected joints of the two MP8-treated groups compared with control ($p<0.001$).

Figure 16:
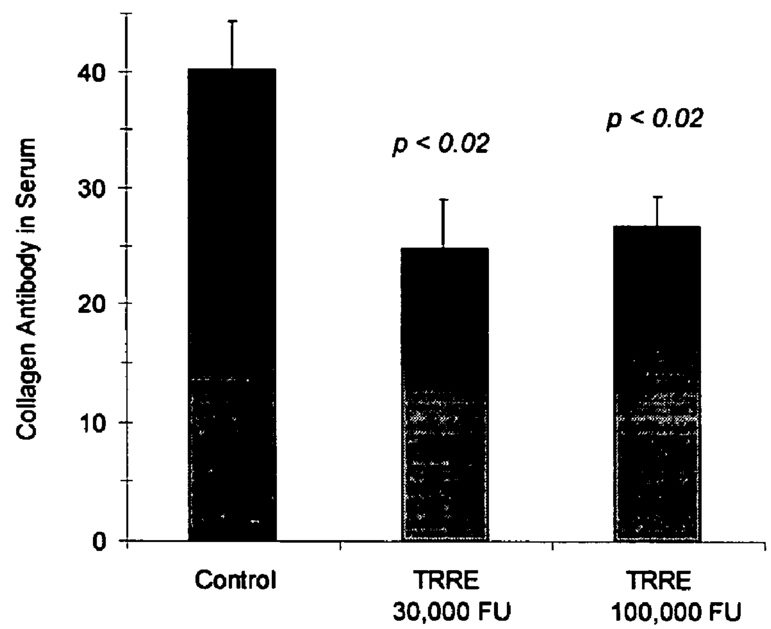

FIG. 16 shows the level of antibodies to type II collagen in the serum of the mice. The groups treated with MP8 had levels of pathogenic antibody that were almost half the control.

Figure 17:
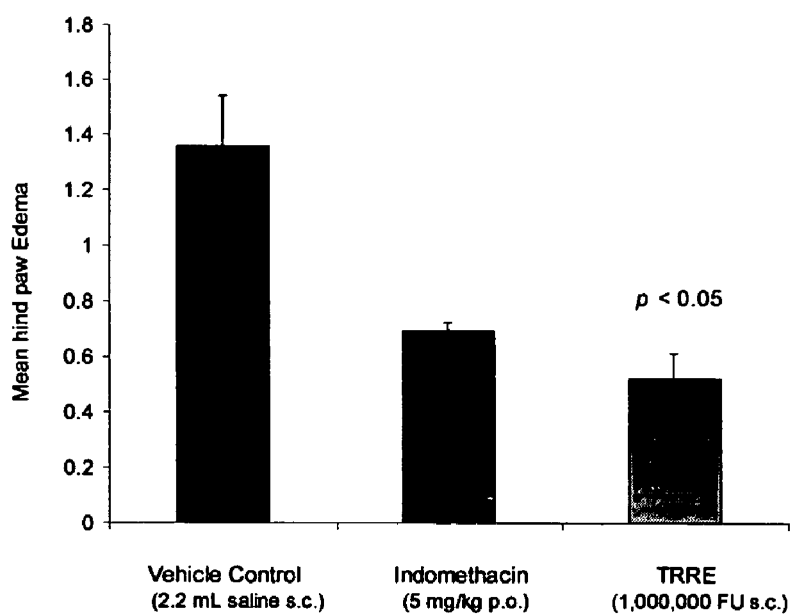

FIG. 17 is taken from an experiment where MP8 was found to inhibit paw edema in rats induced by injection of carrageenan. The effect was better than indomethacin, a small-molecule nonsteroidal anti-inflammatory agent.

FIG. 18 is taken from an experiment where MP8 was found to prevent development of Experimental Autoimmune Encephalomyelitis (EAE), an animal model for Multiple Sclerosis. The cloned enzyme delayed emergence of symptoms, and lowered disease severity by about 3-fold.

Figure 19:
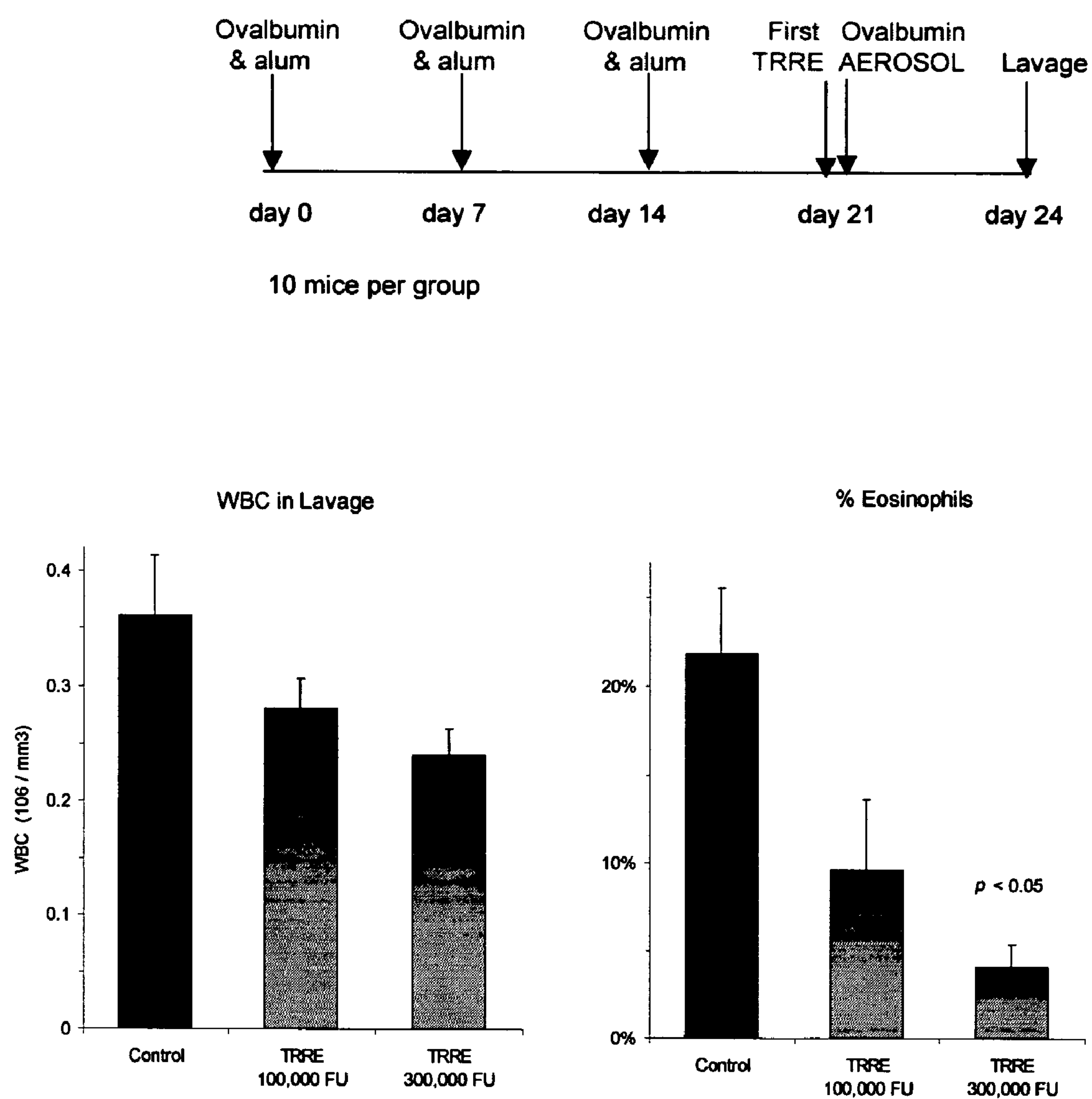

FIG. 19 was obtained from an animal model for experimentally-induced Asthma. Mice were sensitized by immunizing with ovalbumin, and then challenged with the allergen in aerosol form. MP8 reduced the inflammatory sequelae, shown by fewer white blood cells migrating into the alveolar fluid, and a reduced proportion of eosinophils.

FIG. 20 compares full-length MP8 with the originally isolated clone and various control proteins. The bottom panel is a map of the vector used to express MP8-FL in *E. coli.*

Figure 21:
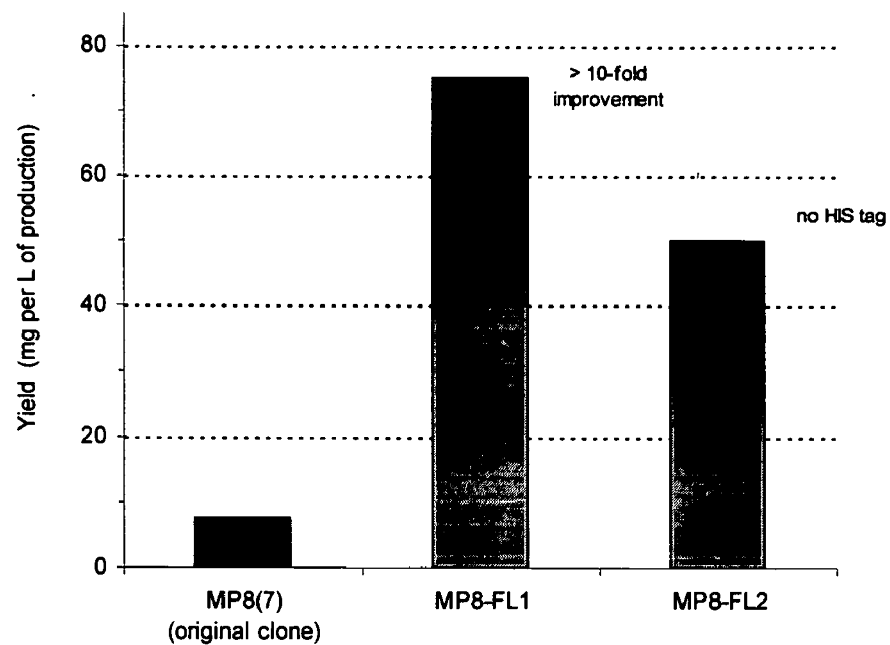

FIG. 21 shows the remarkable degree of improvement in going to the full length protein for commercial production. *E. coli* express most of the shorter protein in inclusion bodies, allowing only a small yield, even after extraction from the inclusion bodies and refolding. In contrast, the full length protein is produced in soluble form, and so can be produced 10 times more efficiently.

Figure 22:
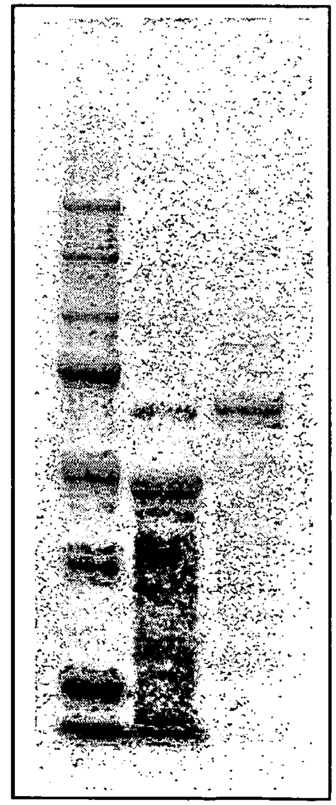

FIG. 22 is an SDS polyacrylamide gel stained with Coomassie Blue, comparing purified preparations of MP8 core protein, and full-length MP8.

FIG. 23 compares the activity of full-length MP8 with control protein in the peptide cleavage assay and cell surface cleavage assay. Full length MP8 retains the activity of the core protein.

Figure 24:
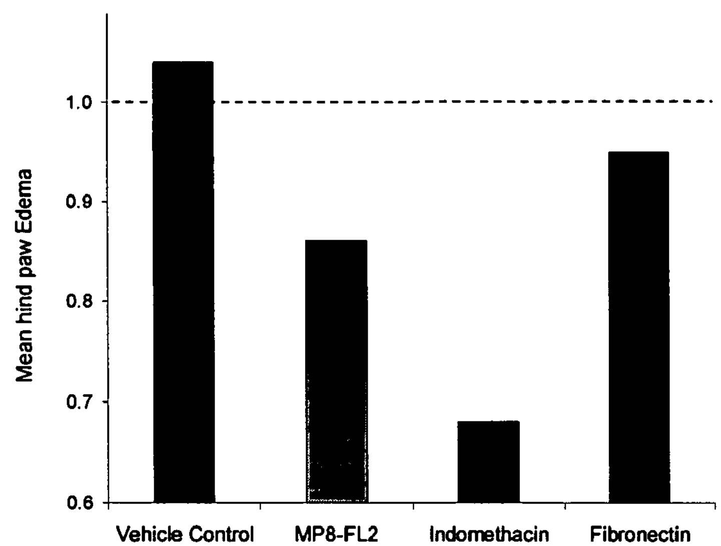

FIG. 24 shows that full length MP8 is effective as an anti-inflammatory agent in the animal model for edema.

Figure 25:
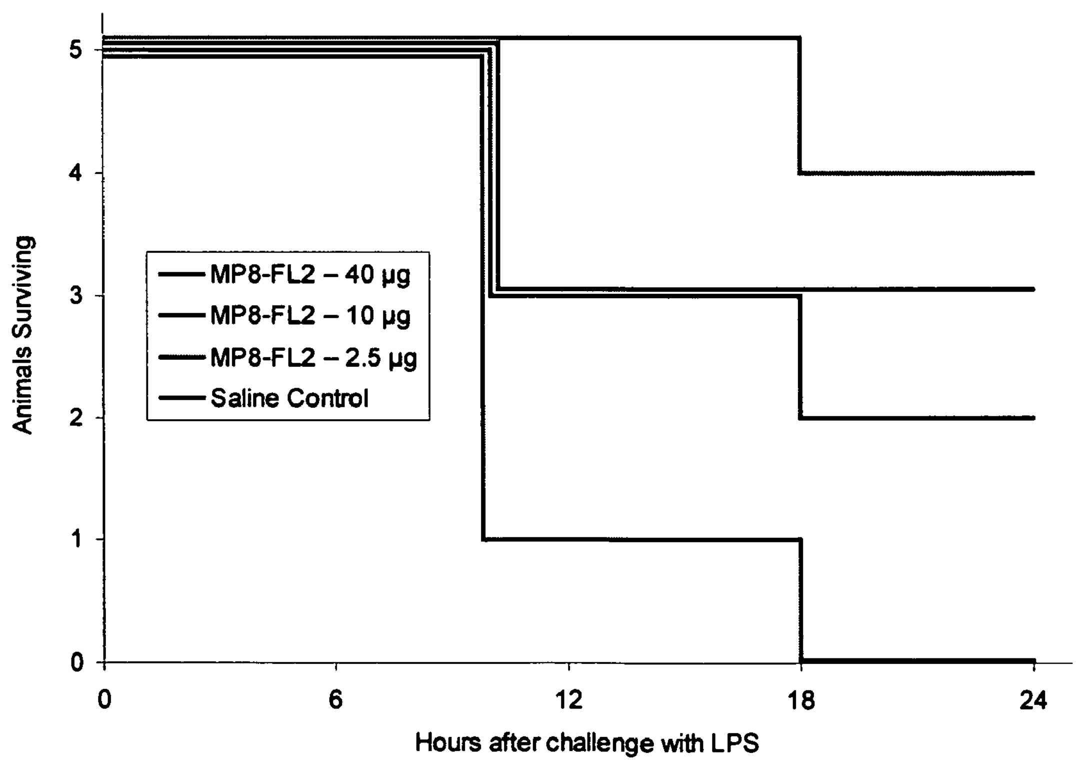

FIG. 25 shows that full length MP8 protects mice in a dose-dependent fashion against a lethal challenge with LPS in the septic shock model.

DETAILED DESCRIPTION

The commercial potential for receptor cleaving enzymes and the proteins that regulate them has been described previously (U.S. Pat. Nos. 6,569,664 and 6,593,456). This disclosure provides a number of milestone improvements that will serve to promote receptor cleavage as a clinically and commercially viable therapeutic strategy.

One of the discoveries of this invention ensued from development of the original exemplary clone MP8 (SEQ. ID NO:9). For research purposes, it was expressed in *E. coli*, and an amount suitable for in vitro and small animal testing was obtained. However, attempts to scale up the production for human clinical trials brought to light the fact that most of the expressed protein was produced in inclusion bodies, adversely affecting the yield. An extensive attempt to recover the protein from the inclusion bodies and refold it into active protein was disappointing—the protein was unstable, and only small amounts of biological activity were recovered. An alternative attempt to make MP8 in yeast was fruitless, as the protein was apparently degraded as fast as it was synthesized. At this point, the problem of how to scale up production was a considerable obstacle to commercialization of the product.

The solution came from quite an unexpected source. The original MP8 clone was the C-terminal portion of a longer reading frame (FIG. 20). It turns out that when the full reading frame was expressed in *E. coli*, more than half of the protein was produced in the soluble fraction—allowing for straightforward purification and scale-up. Accordingly, this disclosure provides full length MP8 and other variants extended beyond the core MP8 sequence at the N-terminal end, in order to enhance expression, production, and purification.

The finding that active full-length protein is considerably easier to produce than the truncated MP8 protein was quite unexpected. Smaller proteins are almost always easier to express and are more soluble, and so the usual prediction would be that full-length MP8 would be even harder to express and purify than the original MP8 clone. Furthermore, the otherwise unrecoverable MP8 core is still a component of the full-length molecule, so to the extent that self-catalysis contributed to the problem, there is no reason to believe that the full-length protein would be any more stable. Using currently available expression systems, the switch from the original MP8 clone to the full-length sequence was a key turning point in the development of the product for clinical testing and use.

Another discovery of this invention ensued from further refinement of the specificity testing of the family of TNF receptor releasing proteins. In particular, it was found that MP8 cleaves not only the TNF receptor, but also the IL-6 receptor, and one or both isoforms of the IL-1 receptor.

This has several important implications. For example, it indicates that MP8 (SEQ. ID NO:41 or 53), and some of the other members of this family of proteins, can be developed for the treatment of conditions where the TNF pathway is not a critical part of the pathology. IL-6 has been implicated as playing a central role in multiple sclerosis and osteoarthritis. Thus, a biological agent such as MP8 that inhibit IL-6 signal transduction may be therapeutic agents for these conditions, and for other conditions that are refractory for therapy such as Remicade® and Enbrel® directed at the TNF therapy (or where the patient's condition has become refractory to such therapy). Indeed, MP8 has shown to be effective in Experimental Autoimmune Encephalomyelitis (EAE), an animal model for multiple sclerosis (Example 13, FIG. 18).

Another implication is that the biological agents of this invention may effectively synergize with existing biological agents, by affecting cytokine pathways in addition to TNF. Other studies have demonstrated that Enbrel® (inhibiting the TNF pathway) and Kineret® (inhibiting the IL-1 pathway) are more effective together in certain biological and clinical situations than they are together. By combining MP8 with a TNF inhibitor, the clinician may be able to modulate a disease condition by affecting TNF, IL-1, IL-6, and perhaps other signaling pathways at the same time, for a more global approach to the underlying pathology.

Accordingly, this invention contemplates pharmaceutical compositions, kits, or methods of treatment in which a cytokine receptor releasing protein such as MP8 is used simultaneously or sequentially with TNF blocking agents, such as TNF-specific antibodies like Remicade®, TNF binding proteins having a soluble TNF component (such as Enbrel®), dominant negative mutants of TNF ligand, and other TNF inhibition means as may be known in the art or subsequently developed.

A further aspect of this invention that ensued from the commercial development of these biological agents is a peptide assay for measuring enzymatic activity causing cytokine receptor cleavage (Example 4). This allows the activity of certain receptor cleaving enzymes to be followed through purification, standardized by dose, and used for screening enzyme inhibitors.

This disclosure provides extensive animal model data demonstrating that biological agents mediating cytokine receptor cleavage have therapeutic and commercial potential for a number of different conditions. The data show that the biological agents of this invention have important advantages over the therapeutic products that are currently available to the general public for treatment of inflammatory diseases of various kinds. Some of the advantages are the following:

- Cleavage of cytokine receptors inhibits the TNF pathway in two ways: First, the receptor is removed from the membrane of the effector cell, so that it cannot participate in signal transduction. Second, the released ligand binding portion of the receptor neutralizes any incoming TNF ligand in a manner comparable with Enbrel® and Remicade®.
- Since receptor release is caused by enzyme cleavage, the biological agents of this invention have the potential to accomplish in catalytic amounts what receptor antagonists like Enbrel® accomplish in stochiometric amounts. This means that a single molecule of enzyme should inactivate many TNF ligands and receptors, resulting in greater effect per molecule of administered drug.

The biological agents of this invention can be formulated as naturally occurring human proteins that normally acts to regulate inflammation. This means they should not be immunogenic. Furthermore, the receptor that is released from the cell is an endogenous (non-recombinant) compound that neutralizes incoming cytokines in a physiologically natural way.

The molecules of this invention share with other specific biological agents the potential for a low side effect profile. No safety issues have arisen in five different animal disease models. Specificity of biological agents facilitates rapid completion of clinical trials.

Exemplary clone MP8-FL is a relatively small protein, causing greater effect per mass, while retaining the specificity and clinical benefit of other biological agents. The small size also provides a range of options for clinical formulation, including intradermal delivery, which would allow administration close to an inflamed joint.

Data in this report indicate that the cytokine receptor released by the proteases of this invention persist for days after administration. This means that administration of the enzyme just once a week (or less) may be sufficient for a full therapeutic effect.

Since the products of this invention work by different mechanisms than currently established drugs, it has potential not just as an alternative—it may also improve the effect of other therapeutic agents, increasing the number of indications and thereby expanding market size.

All of the clones tested so far retain functional activity when produced by bacterial expression. The proteins apparently do not require glycosylation in mammalian cells like antibody products such as Remicade®, or immunoglobulin derivatives such as Enbrel®. The modest cost of production per dose will be an important competitive advantage.

Based on the summary of the invention and the appended claims, and guided by the illustrations in the example section, one skilled in the art will readily know what techniques to employ in the practice of the invention. The following detailed description is provided for the additional convenience of the reader.

Definitions and Basic Techniques

Agents of this invention that act to reduce inflammation are referred to variously in this disclosure as cytokine receptor cleaving or releasing enzymes or proteins. The terms are interchangeable, and not meant to require any particular biochemical or biological activity, except where explicitly required. For example, cloned proteins of this invention (such as MP8-FL2 and its derivatives) may themselves have proteolytic activity, or they may cause release of one or more unspecified cytokine receptors from an inflammatory cell in a less direct fashion (such as by causing expression or activation of another protein). Demonstration of apparent proteolytic activity may be attributable directly to an enzymatic function of the protein, or may be due to a copurifying product that acts as a proxy to determine the relative concentration of the active biologic agent. The terms used to refer to the principal product are not meant to limit the therapeutic use of the compounds of this invention where not explicitly indicated, since the therapeutic benefit may be determined empirically without understanding the mechanism by which a compound is effective.

Designations used in general description of the invention are meant to include all functionally equivalent fragments, variants, and homologs, unless otherwise explicitly stated or implied. For example, reference to "core MP8" in specific working illustrations means a polypeptide having the sequence of SEQ. ID NO:41 (usually with a HIS tag); Otherwise it generally refers to fragments and homologs having a degree of identity with SEQ. ID NO:41 and an appropriate biological function. Reference to "full length MP8" or "MP8-FL" in specific working illustrations means a polypeptide having the sequence of SEQ. ID NO:53 (optionally with a HIS tag). Otherwise it generally refers to any fragment of SEQ. ID NO:53 that has sequence extending beyond that of SEQ. ID NO:41 by any length, up to the complete SEQ. ID NO:53, and homologs having a degree of identity therewith and an appropriate biological function. Reference to "MP8" outside the working illustrations refers interchangeably to full length MP8 and core MP8 (including fragments and variants thereof), unless otherwise explicitly stated or implied.

The term "polynucleotide" refers to a polymeric form of nucleotides of any length, either deoxyribonucleotides or ribonucleotides, or analogs thereof. Non-limiting examples include: a gene or gene fragment, mRNA, cDNA, other forms of recombinant or synthetic polynucleotides, plasmids, vectors, nucleic acid probes, and primers. The term refers interchangeably to double- and single-stranded molecules. Unless otherwise specified or required, any embodiment of the invention described herein that is a polynucleotide encompasses both the double-stranded form, and each of two complementary single-stranded forms known or predicted to make up the double-stranded form "Hybridization" refers to a reaction in which one or more polynucleotides react to form a complex that is stabilized via hydrogen bonding between the bases of the nucleotide residues. Hybridization reactions can be performed under conditions of different "stringency". Relevant conditions include temperature, ionic strength, and the presence of additional solutes in the reaction mixture such as formamide. Conditions of increasing stringency are 30° C. in 10×SSC (0.15 M NaC1, 15 mM citrate buffer); 40° C. in 6×SSC; 50° C. in 6×SSC, 60° C. in 6×SSC, or at about 40° C. in 0.5×SSC, or at about 30° C. in 6×SSC containing 50% formamide.

The percentage of sequence identity for polynucleotides or polypeptides is calculated by aligning the sequences being compared, and then counting the number of shared residues at each aligned position. No penalty is imposed for the presence of insertions or deletions, but are permitted only where required to accommodate an obviously increased number of amino acid residues in one of the sequences being aligned. When one of the sequences being compared is indicated as being "consecutive", then no gaps are permitted in that sequence during the comparison. The percentage identity is given in terms of residues in the test sequence that are identical to residues in the comparison or reference sequence.

As used herein, "expression" of a polynucleotide refers to the production of an RNA transcript. Subsequent translation into protein or other effector compounds may also occur, but is not required unless specified. "Genetic alteration" refers to a process wherein a genetic element is artificially introduced into a cell, which may result in expression or replication of the genetic element, or inheritance of the element by progeny of the cell.

The terms "polypeptide", "peptide" and "protein" are used interchangeably to refer to polymers of amino acids of any length, and their homologs and derivatives. They may be isolated from natural sources, or produced by recombinant expression or chemical synthesis.

It is understood that the folding and the biological function of proteins can accommodate insertions, deletions, and substitutions in the amino acid sequence. Some amino acid substitutions are more easily tolerated. For example, substitution of an amino acid with hydrophobic side chains, aromatic side chains, polar side chains, side chains with a positive or negative charge, or side chains comprising two or fewer carbon atoms, by another amino acid with a side chain of like properties can occur without disturbing the essential identity of the two sequences. Methods for determining homologous regions and scoring the degree of homology are described in Altschul et al. *Bull. Math. Bio.* 48:603-616, 1986; and Henikoff et al. *Proc. Natl. Acad. Sci. USA* 89:10915-10919, 1992. Substitutions that preserve the functionality of the polypeptide, or confer a new and beneficial property (such as enhanced activity, stability, or decreased immunogenicity) are especially preferred.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also antibody fragments, chimeras, and equivalents that include at least one antigen combining site of the desired specificity.

An "isolated" polynucleotide, polypeptide; protein, antibody, or other substance refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. A substance can also be provided in an isolated state by a process of artificial assembly, such as by chemical synthesis or recombinant expression.

The term "clinical sample" encompasses a variety of sample types obtained from a subject and useful in an in vitro procedure, such as a diagnostic test. The definition encompasses solid tissue samples obtained as a surgical removal, a pathology specimen, or a biopsy specimen, cells obtained from a clinical subject or their progeny obtained from culture, liquid samples such as blood, serum, plasma, spinal fluid, synovial fluid and urine, and any fractions or extracts of such samples that contain a potential indication of the disease.

Unless otherwise indicated, the practice of the invention will employ conventional techniques of molecular biology, microbiology, recombinant DNA, and immunology.

Polynucleotides

Polynucleotides of this invention can be prepared by any suitable technique, including but not limited to chemical synthesis or recombinant expression.

Using the data provided in this disclosure, sequences of less than ~50 base pairs are conveniently prepared by chemical synthesis, either through a commercial service or by a known synthetic method, such as the triester method or the phosphite method. A suitable method is solid phase synthesis using mononucleoside phosphoramidite coupling units (U.S. Pat. No. 4,415,732). For use in antisense therapy, polynucleotides can be prepared by chemistry that produce more stable in pharmaceutical preparations. Non-limiting examples include thiol-derivatized nucleosides (U.S. Pat. No. 5,578,718), and oligonucleotides with modified backbones (U.S. Pat. Nos. 5,541,307 and 5,378,825).

Polynucleotides of this invention can also be obtained by PCR amplification of a template with the desired sequence. Oligonucleotide primers spanning the desired sequence are annealed to the template, elongated by a DNA polymerase, and then melted at higher temperature so that the template and elongated oligonucleotides dissociate. The cycle is repeated until the desired amount of amplified polynucleotide is obtained (U.S. Pat. Nos. 4,683,195 and 4,683,202). Suitable templates include the Jurkat T cell library and other human or animal expression libraries that contain genes that cause release of cytokine receptors. The Jurkat T cell library is available from the American Type Culture Collection, 10801 University Blvd., Manassas Va. 20110, U.S.A. (ATCC #TIB-152). Production scale amounts of large polynucleotides are most conveniently obtained by inserting the desired sequence into a suitable cloning vector and reproducing the clone. Exemplary cloning and expression methods are illustrated in Example 2.

Preferred polynucleotide sequences are 50%, 70%, 80%, 90%, or 100% identical to one of the sequences exemplified in this disclosure; in order if increasing preference. The length of consecutive residues in the identical or homologous sequence compared with the exemplary sequence can be about 15, 30, 50, 75, 100, 200, 500 or 1000 residues in order of increasing preference, up to the length of the entire clone. Nucleotide changes that cause a conservative substitution or retain the function of the encoded polypeptide (in terms of hybridization properties or what is encoded) are especially preferred substitutions.

The polynucleotides of this invention can be used to measure altered receptor releasing activity in a cell or tissue sample. This involves contacting the sample with the polynucleotide under conditions that permit the polynucleotide to hybridize specifically with nucleic acid that affects receptor release, if present in the sample, and determining polynucleotide that has hybridized as a result of step a). Specificity of the test can be provided in one of several ways. One method involves the use of a specific probe—a polynucleotide of this invention with a sequence long enough and of sufficient identity to the sequence being detected, so that it binds the target and not other nucleic acid that might be present in the sample. The probe is typically labeled (either directly or through a secondary reagent) so that it can be subsequently detected. Suitable labels include $^{32}P$ and $^{33}P$, chemiluminescent and fluorescent reagents. After the hybridization reaction, unreacted probe is washed away so that the amount of hybridized probe can be determined. Signal can be amplified using branched probes (U.S. Pat. No. 5,124,246). In another method, the polynucleotide is a primer for a PCR reaction. Specificity is provided by the ability of the paired probes to amplify the sequence of interest. After a suitable number of PCR cycles, the amount of amplification product present correlates with the amount of target sequence originally present in the sample.

Such tests are useful both in research, and in the diagnosis or assessment of a disease condition. For example, cytokine signaling plays a role in eliminating tumor cells, and a cancer may evade the elimination process by activating cytokine receptor release in the diseased tissue. Hence, under some conditions, high expression of molecules that affect receptor release may correlate with progression of cancer. Diagnostic tests are also of use in monitoring therapy, such as when gene therapy is performed to increase receptor releasing activity.

Polynucleotides of this invention can also be expressed in a eukaryotic or prokaryotic expression system for production of polypeptides; or used for the preparation of medicaments, as explained below.

Polypeptides

Short polypeptides of this invention can be prepared by solid-phase chemical synthesis. The principles of solid phase chemical synthesis can be found in Dugas & Penney, Bioorganic Chemistry, Springer-Verlag N.Y. pp 54-92 (1981), and U.S. Pat. No. 4,493,795. Automated solid-phase peptide synthesis can be performed using devices such as a PE-Applied Biosystems 430A peptide synthesizer (commercially available from Applied Biosystems, Foster City Calif.).

Longer polypeptides are conveniently obtained by expression cloning. A polynucleotide encoding the desired polypeptide is operatively linked to control elements for transcription and translation, and then transfected into a suitable host cell. Expression may be effected in prokaryotes such as *E. coli* (ATCC Accession No. 31446 or 27325), eukaryotic microorganisms such as *Pichia pastoris* yeast, or higher eukaryotes, such as insect or mammalian cells. A number of expression systems are described in U.S. Pat. No. 5,552,524. Expression cloning is available from such commercial services as Lark Technologies, Houston Tex. The protein is purified from the producing host cell by standard methods in protein chemistry, such as affinity chromatography and HPLC. Expression products are optionally produced with a sequence tag to facilitate affinity purification, which can subsequently be removed.

Preferred sequences are 40%, 60%, 80, 90%, or 100% identical to one of the sequences exemplified in this disclosure; in order if increasing preference. The length of the identical or homologous sequence compared with the native human polynucleotide can be about 7, 10, 15, 20, 30, 50, 100, or 200 residues in order of increasing preference, up to the length of the entire encoding region.

Polypeptides can be tested for an ability to modulate release of cytokine receptors in a peptide cleavage assay. The polypeptide is contacted with the receptor (preferably expressed on the surface of a cell, such as a C75 or THP1 cell), and the ability of the polypeptide to increase or decrease receptor cleavage and release is determined.

Polypeptides of this invention can be used as immunogens for raising antibody. Large proteins will raise a cocktail of antibodies, while short peptide fragments will raise antibodies against small region of the intact protein. Antibody clones can be mapped for protein binding site by producing short overlapping peptides of about 10 amino acids in length. Overlapping peptides can be prepared on a nylon membrane support by standard F-Moc chemistry, using a SPOTS™ kit from Genosys according to manufacturer's directions.

Polypeptides of this invention can also be used to affect cytokine signal transduction in a therapeutic context, as explained below.

Variants

The user may decide to make fragments, variants, or other homologs of the prototype sequences provided in this disclosure in order to improve the activity to mass ratio, to alter glycosylation sites, improve production efficiency, or for any other worthwhile purpose.

Fragments of proteins disclosed in this invention (e.g., SEQ. ID NOs:41 and 53) that cause TNF receptor release can readily be identified by employing standard methodology for mapping function. Recombinant protein which is trimmed at the N- or C-terminus, and then test it for function using a suitable assay: such as the peptide cleavage assay or receptor release assay illustrated in Examples 4 and 5, respectively, which can be run in a high throughput manner. Trimming would continue until activity is lost, at which point the minimum functional unit of the protein would be identified. Fragments containing any portion of the protein down to the identified size would probably be functional, as would be fusion constructs containing at least the functional core of the protein.

To generate variants that incorporate one or more amino acid changes in the encoding sequence, the skilled reader can change particular nucleotides or codons and retest for activity. Optionally, the user may be guided in her site-specific mutagenesis by known homology data. For example, to make variants of MP8, the user may wish to avoid making mutations in regions conserved amongst vertebrates (SEQ. ID NO:89) or amongst mammals (SEQ. ID NO:90). Regions that show considerable variation (a plurality of x's in SEQ. ID NOs:89 or 90) may more likely accommodate deletions or additions. Adopting this strategy, the user would obtain a homolog identifiable by a degree of sequence identity (or an ability of the gene sequence to hybridize with the prototype sequence). A functional MP8 variant may contain one or several of the conserved motifs (SEQ. ID NOs:91-102); particularly those in the core protein (SEQ. ID NOs:97-102), which this region of the molecule is associated with receptor releasing activity.

Unless particular changes are desired, there is no need to target the mutations to particular positions in the sequence. An effective way to generate a large collection of functional variants is to use a random mutation strategy. The standard texts Protocols in Molecular Biology (Ausubel et al. eds.) and Molecular Cloning: A Laboratory Manual (Sambrook et al. eds.) describe techniques employing chemical mutagenesis, cassette mutagenesis, degenerate oligonucleotides, mutually priming oligonucleotides, linker-scanning mutagenesis, alanine-scanning mutagenesis, and error-prone PCR. Other efficient methods include the *E. coli* mutator strains of Stratagene (Greener et al., Methods Mol. Biol. 57:375, 1996) and the DNA shuffling technique of Maxygen (Patten et al., Curr. Opin. Biotechnol. 8:724, 1997; Harayama, Trends Biotechnol. 16:76, 1998; U.S. Pat. Nos. 5,605,793 and 6,132,970). To the extent that the user may wish to test variants near the outer limit of variability in the claims (i.e., only ~90% identical to SEQ ID NO:2), they may subject the representative sequence to successive cycles of mutation and functional testing—or choose a mutation strategy that generate more abrupt changes, such as the DNA shuffling technique.

There are several commercially available services and kits available to the skilled reader to use in obtaining variants of the claimed proteins. By way of illustration, enclosed with this Amendment is information regarding for several marketed systems specifically designed for mutagenesis projects of this kind (Exhibit 1): the GeneTailor™ Site-Directed Mutagenesis System sold by InVitrogen™ Life Technologies (Exhibit 1); the BD Diversify™ PCR Random Mutagenesis Kit™, sold by BD Biosciences/Clontech; the Template Generation System™, sold by MJ Research Inc., the XL1-Red™ mutator strain of *E. coli*, sold by Stratagene; and the GeneMorph® Random Mutagenesis Kit, also sold by Stratagene. By employing any of these types of systems in conjunction with a suitable functional assay such as those described in Examples 1 and 4, variants can be generated and tested in a high throughput manner.

After each iteration of mutagenesis, the user can screen the resultant variants for biological activity as already described, selecting the clones retaining the ability to cause cytokine receptor release. Optionally, the selected clones can be subject to further rounds of mutagenesis, until the desired degree of variation from the original sequence has been achieved.

Extended Sequences

One of the important discoveries of this disclosure is the finding that extending the sequence of MP8 beyond the core protein can improve production and recovery of the protein as much as 10-fold (Example 15). Thus, one aspect of the invention is the use of the full length sequence (SEQ. ID NO:53) for purposes previously contemplated only for the core sequence (SEQ. ID NO:41, and functional subfragments thereof. The user may readily make intermediate sized fragments and variants of the full-length MP8 sequence that are longer than the core fragment, but less than the complete open reading frame. Many of these will share with SEQ. ID NO:53 the property of being much easier to produce than the core protein.

To find such useful intermediate sized fragments, two tests would be involved. First, a candidate recombinant fragment would be tested to determine whether it retained the ability to cause cytokine receptor release. The user would also determine whether the candidate fragment was suitable for large-scale production in *E. coli, Pichia pastoris*, and other expression systems according to the strategy outlined in Example 15. It is generally not necessary to do a complete purification protocol to determine what recombinant proteins are suitable: more simply, the encoding sequence is cloned into the system, expression is induced, and a soluble extract is prepared as appropriate for the system being used. The extract can then immediately be immunoassayed for the amount of target protein in the extract using an appropriately specific antibody.

Similarly, variants of SEQ. ID NO:53 extending beyond the core protein can be generated using the mutation strategies described in the previous section, and tested for both biological activity and ease of expression. The variant proteins would contain or consist of an amino acid sequence having a degree of identity with SEQ. ID NO:53 (e.g., 70%, 80%, or 90% identical), but be longer (one, 10, or 50 amino acids or more) and not have the same degree of identity with SEQ. ID NO:41.

Alternatively or in addition, the variant may be constructed as a fusion protein, for example, containing the sequence of another protein towards the N-terminal end of SEQ. ID NO:41. The second sequence could take the place of the N-terminal 100 residues in SEQ. ID NO:53, promoting production of the protein as a soluble and recoverable protein in a suitable expression system. Candidate second sequences can be taken from innocuous human proteins known to be soluble, easily producible in common expression systems, and unlikely to interfere with the biological activity of MP8: for example, albumin, or other serum proteins. Other candidate sequences may promote accumulation of the fusion protein near the target tissue: for example, TNF ligand, ligand for a neighboring cell surface receptor, or a single chain antibody. Suitable protein sequences for inclusion in the fusion protein can be determined empirically using the testing systems already described.

Antibodies

Polyclonal antibodies can be prepared against the proteins of this invention by injecting a vertebrate with a polypeptide of this invention in an immunogenic form. Immunogenicity of a polypeptide can be enhanced by linking to a carrier such as KLH, or combining with an adjuvant, such as Freund's adjuvant. If desired, the specific antibody activity can be further purified by a combination of techniques, which may include protein A chromatography, ion exchange chromatography, and immunoaffinity chromatography.

Monoclonal antibodies can be prepared according to such standard references as Harrow & Lane (1988), U.S. Pat. Nos. 4,491,632, 4,472,500 and 4,444,887, and *Methods in Enzymology* 73B:3 (1981). Briefly, a mammal is immunized, and antibody-producing cells (usually splenocytes) are harvested. Cells are immortalized by fusion with a non-producing myeloma, transfecting with Epstein Barr Virus, or transforming with oncogenic DNA. The treated cells are cloned and cultured, and the clones are selected that produce antibody of the desired specificity.

Antibody can be produced for particular regions of a molecule by using fragment, and if necessary, selecting against or absorbing out unwanted activity. For example, antibody against core MP8 can be raised by using a protein consisting of SEQ. ID NO:41 or a portion thereof as immunogen. Antibody against full-length can be raised by immunizing with the portion of SEQ. ID NO:53 that does not contain SEQ. ID NO:41; or else by immunizing with the complete SEQ. ID NO:53 and selecting against or absorbing unwanted activity with SEQ. ID NO:41.

Other methods of obtaining specific antibody molecules (optimally in the form of single-chain variable regions) involve contacting a library of immunocompetent cells or viral particles with the target antigen, and growing out positively selected clones. Immunocompetent phage can be constructed to express immunoglobulin variable region segments on their surface. See Marks et al., *New Eng. J. Med.* 335:730, 1996, International Patent Applications WO 9413804, WO 9201047, WO 90 02809, and McGuiness et al., *Nature Biotechnol.* 14:1449, 1996.

The antibodies of this invention are can be used in immunoassays for proteins believed to cause receptor release. General techniques of immunoassay can be found in "The Immunoassay Handbook", Stockton Press NY, 1994; and "Methods of Immunological Analysis", Weinheim: VCH Verlags gesellschaft mbH, 1993). The antibody is combined with a test sample under conditions where the antibody will bind specifically to any modulator that might be present, but not any other proteins liable to be in the sample. The complex formed can be measured in situ (U.S. Pat. Nos. 4,208,479 and 4,708,929), or by physically separating it from unreacted reagents (U.S. Pat. No. 3,646,346). Separation assays typically involve labeled target reagent (competition assay), or labeled antibody (sandwich assay) to facilitate detection and quantitation of the complex. Suitable labels are radioisotopes such as $^{125}I$, enzymes such as β-galactosidase, and fluorescent labels such as fluorescein. Antibodies of this invention can also be used to detect molecules that cause receptor release in fixed tissue sections by immunohistology. The antibody is contacted with the tissue, unreacted antibody is washed away, and then bound antibody is detected—typically using a labeled anti-immunoglobulin reagent. Immunohistology will show not only whether the modulator is present, but where it is located in the tissue.

Detection of molecules that cause release of cytokine receptors is of interest for research purposes, and for clinical use. High expression of receptor cleaving enzymes may correlate with progression of cancer. Diagnostic tests are also of use in monitoring substances causing receptor release that are administered in the course of therapy.

Antibodies of this invention can also be used for preparation of medicaments. Antibodies with therapeutic potential include those that affect receptor releasing activity—either by promoting clearance of a receptor protease, or by blocking its physiological action. Antibodies can be screened for desirable activity according to assays described in the next section.

Screening Assays

This invention provides screening methods for selecting and developing products that modulate the activity of receptor releasing compounds of this invention, and thus affect cytokine signaling.

A screening method embodied in this invention is a method for screening substances that interfere with the action of a receptor protease at the protein level. The method involves incubating cells expressing cytokine receptor (such as C75R or THP cells) with a polypeptide of this invention having receptor releasing activity. There are two options for supplying the molecule with receptor releasing activity in this assay. In one option, the polypeptide is added to the medium of the cells as a reagent, along with the substance to be tested. In another option, the cells are genetically altered to express the molecule at a high level, and the assay requires only that the test substance be contacted with the cells. This option allows for high throughput screening of a number of test compounds.

Either way, the rate of receptor release is compared in the presence and absence of the test substance, to identify compounds that enhance or diminish receptor releasing activity. Parallel experiments should be conducted in which the activity of the substance on receptor shedding is tested in the absence of added polypeptide (using cells that don't express the polypeptide). This will determine whether the activity of the test substance occurs via an effect on the receptor releasing molecule being added, or through some other mechanism.

Another screening method of this invention involves an assay in which a cytokine receptor cleaving enzyme is combined with a short peptide spanning the receptor cleavage site. Enzyme activity can be measured, for example, by change in molecular weight of the peptide (detectable by mass spectroscopy), or labeling the peptide with a fluorescent quench pair. The test compound is then added to this system to determine whether it inhibits the rate of cleavage of the peptide by the enzyme. An illustration of such an assay is provided below in Example 4.

Screening assays are useful for high throughput screening of small molecule compounds that have the ability to affect the level of cytokine receptors on a cell, by way of its influence on receptor release. Small molecule compounds that have the desired activity have beneficial properties in the making pharmaceutical compositions, such as being more stable and less expensive to produce.

Medicaments and Their Use

As described earlier, a utility of certain products embodied in this invention is to affect signal transduction from cytokines. Products that promote receptor release have the effect of decreasing cytokine receptors on the surface of cells, which decrease signal transduction. Conversely, products that inhibit receptor release prevent cleavage of cytokine receptors, increasing signal transduction.

The ability to affect signal transduction is of considerable interest in the management of clinical conditions in which cytokine signaling contributes to the pathology of the condition. Such conditions include:

Heart failure. IL-1β and TNF are believed to be central mediators for perpetuating the inflammatory process, recruiting and activating inflammatory cells. The inflammation depress cardiac function in congestive heart failure, transplant rejection, myocarditis, sepsis, and burn shock.

Cachexia. The general weight loss and wasting occurring in the course of chronic diseases, such as cancer. Cytokines are believed to affect appetite, energy expenditure, and metabolic rate.

Crohn's disease. The inflammatory process mediated by multiple cytokines leads to thickening of the intestinal wall, ensuing from lymphedema and lymphocytic infiltration.

Endotoxic shock. The shock induced by release of endotoxins from gram-negative bacteria, such as *E. coli*, involves cytokine mediated inflammation Arthritis. TNF, IL-6, IL-1 and other cytokines promote expression of nitric oxide synthetase, believed to be involved in disease pathogenesis of rheumatoid arthritis and other arthritis sub-types.

Other conditions of interest include those conditions where part of the pathology is caused by inflammation, or a crossover between inflammation and other biological systems. Non-limiting examples are multiple sclerosis, ankylosing spondylitis, psoriasis, psoriatic arthritis, osteoarthritis, arteriosclerosis, sepsis, ulcerative colitis, arteriosclerosis, inflammation brought on by microbial infection, and diseases that have an autoimmune etiology, such as Type I Diabetes, myasthenia gravis, and systemic lupus erythematosis.

Polypeptides of this invention that promote receptor cleavage activity can be administered with the objective of decreasing or normalizing cytokine signal transduction. For example, in congestive heart failure or Crohn's disease, the polypeptide is given at regular intervals to lessen the inflammatory sequelae. The treatment is optionally in combination with small-molecule anti-inflammatory agents (such as methyltrexate), or with other agents that affect signal transduction (such as cytokine blockers like Enbrel®, or receptor antagonists like Kineret®) or that lessen the extent of inflammation in other ways.

Polynucleotides of this invention can also be used to promote cytokine receptor cleavage by gene therapy. The encoding sequence is operatively linked to control elements for transcription and translation in human cells. It is then provided in a form that will promote entry and expression of the encoding sequence in cells at the disease site. Forms suitable for local injection include naked DNA, polynucleotides packaged with cationic lipids, and polynucleotides in the form of viral vectors (such as adenovirus and MV constructs). Methods of gene therapy known to the practitioner skilled in the art will include those outlined in U.S. Pat. Nos. 5,399,346, 5,827,703, and 5,866,696.

The ability to affect cytokine signal transduction is also of interest where a cytokine is thought to play a beneficial role in resolving the disease. In particular, TNF and other cytokines play a beneficial role in the necrotizing of solid tumors. Accordingly, products of this invention can be administered to cancer patients to inhibit receptor release, thereby increasing cytokine signal transduction and improve the beneficial effect.

Embodiments of the invention that inhibit receptor release include antisense polynucleotides. A method of conferring long-standing inhibitory activity is to administer antisense gene therapy. A genetic construct is designed that will express RNA inside the cell which in turn will decrease the transcription of the target gene (U.S. Pat. No. 5,759,829). In humans, a more frequent form of antisense therapy is to administer the effector antisense molecule directly, in the form of a short stable polynucleotide fragment that is complementary to a segment of the target mRNA (U.S. Pat. Nos. 5,135,917 and 5,789,573)—in this case, the transcript that encodes the receptor releasing molecule. Another embodiment of the invention that inhibits receptor release are ribozymes, constructed as described in an earlier section. The function of ribozymes in inhibiting mRNA translation is described in U.S. Pat. Nos. 4,987,071 and 5,591,610.

Once a product of this invention is found to have suitable receptor releasing activity in the in vitro assays described in this disclosure, it is preferable to also test its effectiveness in an animal model of a cytokine mediated disease process. The Examples below provide animal models for sepsis, arthritis, multiple sclerosis, edema, and asthma. Those skilled in the art will know of other animal models for testing effects on cytokine signal transduction or inflammation: for example, the cardiac ischemia reperfusion models of Weyrich et al. (*J. Clin. Invest.* 91:2620, 1993) and Garcia-Criado et al. (*J. Am. Coll. Surg.* 181:327, 1995); the pulmonary ischemia reperfusion model of Steinberg et al. (*J. Heart Lung Transplant.* 13:306, 1994), the lung inflammation model of International Patent Application WO 9635418; the bacterial peritonitis model of Sharar et al. (*J. Immunol.* 151:4982, 1993), and the colitis model of Meenan et al. (*Scand. J. Gastroenterol.* 31:786, 1996).

For use as an active ingredient in a pharmaceutical preparation, a polypeptide, polynucleotide, or antibody of this invention is generally purified away from other reactive or potentially immunogenic components present in the mixture in which they are prepared. Typically, each active ingredient is provided in at least about 90% homogeneity, and more preferably 95% or 99% homogeneity, as determined by functional assay, chromatography, or SDS polyacrylamide gel electrophoresis. The active ingredient is then compounded into a medicament in accordance with generally accepted procedures for the preparation of pharmaceutical preparations, as described in standard textbooks on the subject. Steps in the compounding or formulating of the medicament depend in part on the intended use and mode of administration, and may include sterilizing, mixing with appropriate non-toxic and non-interfering excipients, buffers and other carriers, lyophilizing or freezing, dividing into dose units, and enclosing in a delivery device. The medicament will typically be packaged in a suitable container accompanied by or associated with written information about its intended use, such as the inflammatory disease to be treated, and aspects of dosing and administration.

Mode of administration will depend on the nature of the condition being treated. For conditions that are expected to require moderate dosing and that are at well perfused sites (such as cardiac failure), systemic administration is acceptable. For example, the medicament may be formulated for intravenous administration, intramuscular injection, or absorption sublingually or intranasally. Sometimes it is possible to administer the active ingredient locally to the disease site (such as near an inflamed joint), in order to enhance the concentration of the active ingredient, and minimize effects on cytokine receptors on other tissues not involved in the disease process. Alternatively, the pharmaceutical composition may be formulated to enhance accumulation of the active ingredient at the disease site. For example, the active ingredient can be encapsulated in a liposome or other matrix structure that displays an antibody or ligand capable of binding a cell surface protein on the target cell. Suitable targeting agents include antibodies or ligands for tissue-specific receptors (e.g., serotonin for pulmonary targeting). For compositions that decrease cytokine signaling, an appropriate targeting molecule may be the cytokine itself, since the target tissue may likely display an unusually high density of the corresponding receptor.

Effective amounts of the compositions of the present invention are those that alter receptor releasing activity by at least about 10%, typically by at least about 25%, more preferably by about 50%, 75%, or even 90%. Where increase of receptor release is desirable, preferred compositions increase receptor release by at least 2-fold. A minimum effective amount of the active compound will depend on the disease being treated, which of the effector molecules is selected for use, and whether the administration will be systemic or local. Effective doses can be estimated from the animal test results indicated below, scaling appropriately for the subject being treated.

The following examples provided as a further guide to the reader, and are not intended to limit the invention.

EXAMPLES

Example 1

Isolation of Naturally Occurring Receptor Cleaving Enzyme Activity

Receptor cleaving activity present in inflammatory cells was first isolated using an assay system using cells transfected to express cytokine receptors on their surface.

cDNA of human p75 TNF receptor was cloned from a λgt10 cDNA library from human monocytic U-937 cells, covering positions 58-2380 of the reported p75 TNF-R sequence, which encompasses the full length of the p75 TNF-R-coding sequence from positions 90-1475. The 2.3 kb p75 TNF-R cDNA was then subcloned into the pcDNA3 eukaryotic expression vector, and verified by restriction endonuclease mapping. The transfected cell line was designated C75R. The level of p75 TNF-R expression was assessed using $^{125}$I-labeled human recombinant TNF, and estimated to be 60,000-70,000 receptors per cell with an affinity of $5.6\times10^{-10}$ M.

Receptor cleaving activity was obtained from THP-1 cells (ATCC 45503) as follows. $1\times10^{6}$ cells/mL in RPMI-1640 plus 1% FCS were stimulated with $10^{-6}$ M phorbol myristal acetate (PMA) for 30 min at 37° C. Other stimulating agents can be used as an alternative, such as IL-10 and epinephrine. The cells were washed, and cultured in fresh medium for 2 h, and the cell-free supernatant was collected. Specific binding of $^{125}$I-TNF to the C75R cells was decreased by 87% after preincubating with the THP-1 supernatant. Soluble p75 TNF-R released into the supernatant was measured by ELISA. One unit of receptor cleaving activity was defined as 1 pg of net soluble p75 TNF-R release. The protease was found to release both p55 and p75 receptors from the surface of THP-1 cells.

Native receptor cleaving activity harvested from stimulated THP-1 cells was purified as follows. First, protein from the medium was concentrated by 100% saturated ammonium sulfate precipitation, resuspended in PBS, and dialyzed into 10 mM Tris-HCl, 60 mM NaCl, pH 7.0. This sample was loaded on an anion-exchange chromatography, DEAE-Sephadex® A-25 column. Receptor cleaving activity was eluted with a linear gradient of 60 to 250 mM NaCl in 50 mM Tris-HCl, pH 8.0.

DEAE fractions showing activity in the C75R cleavage assay can be purified further (WO 98/02140). The fractions were concentrated to 500 μL, and applied to electrophoresis on 6% polyacrylamide gels under non-denaturing conditions. The gel was sliced horizontally into 5 mm strips, which were each eluted into PBS.

FIG. 1(A) shows the results. In the top panel, receptor cleaving activity (measured using C75R cells) eluted from the DEAE column at lower ionic strength than the bulk of the protein in the extract (A280), consistent with a relatively electropositive pl. In the lower two panels, receptor activity had a defined mobility on native gels. The purified preparations were then analyzed for physicochemical and functional characteristics of the receptor cleaving enzyme.

FIG. 1(B) is a Western analysis of MP8, one of nine different cDNA clones that are associated with receptor releasing activity. The single MP8 band is shown beside molecular weight standards.

Example 2

Gene Cloning of Receptor Cleaving Activity

Different inflammatory cells have been found to express high levels of receptor cleaving activity, including the cell lines designated THP-1, U-937, HL60, ME-180, MRC-5, Raji, K-562. Jurkat cells have cleaving activity of 850 U/mL following stimulation with $10^{-2}$ M PMA). In this example, the expression library of the Jurkat T cell (ATCC #TIB-152) was obtained and used to clone out genes involved in regulating cytokine receptor release.

Sequences were selected from the library by repeated cycles of transfection into COS-1 cells, followed by assaying of the supernatant for proteolytic activity as in Example 1. Briefly, the DNA of $10^6$ Jurkat cells was extracted using an InVitrogen™ plasmid extraction kit according to manufacturer's directions. cDNA was inserted in the ZAP Express™/EcoR/vector (cat. no. 938201, Stratagene, LaJolla Calif. The library was divided into 48 groups of DNA and transformed into COS-1 cells using the CaCl transfection method. Once the cells were grown out, the C75R assay was performed, and five positive groups were selected. DNA from each of these five groups was obtained, and transfected into *E. coli*, with 15 plates per group. DNA was prepared from these cells and then transfected into COS-1 cells once more. The cells were grown out, and cleavage activity was tested again. Two positive groups were selected and transfected into *E. coli*, yielding 98 colonies. DNA was prepared from 96 of these colonies and transfected into COS-1 cells. The C75R assay was performed again, and nine clones were found to substantially increase receptor cleavage activity in the assay. These clones were designated MP1 to MP9, and then sequenced by DyeDeoxy sequencing techniques.

TABLE 1

Cloned Genes Associated with Cytokine Receptor Releasing Activity

| Clone designation | Length (bp) | Nucleotide SEQ. ID NO: | Open reading frame | Protein SEQ. ID NO: |
|---|---|---|---|---|
| MP1 | 4,047 | 1 | 482 amino acids | 30 |
| " | | 1 | 163 amino acids | 31 |
| MP2 | 739 | 2 | (partial sequence) | |
| " | 233 | 3 | (partial sequence) | |
| MP3 | 2,998 | 4 | 482 amino acids | 32 |
| " | | 4 | 368 amino acids | 33 |
| " | | 4 | 363 amino acids | 34 |
| " | | 4 | 254 amino acids | 35 |
| MP4 | 4,152 | 5 | 1022 amino acids | 36 |
| MP5 | 3,117 | 6 | 1028 amino acids | 37 |
| MP6 | 3,306 | 7 | 849 amino acids | 38 |
| " | | 7 | 208 amino acids | 39 |
| MP7 | 4,218 | 8 | 869 amino acids | 40 |
| MP8 | 1,187 | 9 | 281 amino acids | 41 |
| MP9 | 3,306 | 10 | 768 amino acids | 42 |

Example 3

Characterization of the Cloned Sequences

The sequences have been compared with the UniGene compilation of expressed human genes. SEQ. ID NOs:11 to 25 were analyzed in March of 2003, using UniGene *homo sapiens* build #159, dated Jan. 25, 2003. The database contained 4056423 sequences in 108944 assemblies.

TABLE 2

UniGene Match of Clone Sequences

| Clone | No. of Amino acids in open reading frame | GenBank Accession | Description | Nucleotide SEQ. ID NO: | Protein SEQ. ID NO: |
|---|---|---|---|---|---|
| MP1 | 482 | | delangin isoform B | 79 | 80 |
| " | 163 | NM_058189 | EST | 11 | 43 |
| MP2 | | | (no match) | | |
| MP3 | 482 | | (no match) | | |
| " | 368 | NM_002819 | Polypyrimidine Tract Binding Protein | 12 | 44 |
| " | 363 | NM_012402 | Carboxylase Protein | 13 | 45 |
| " | 254 | NM_006452 | RAC-1 binding protein (Arfaptin) | 14 | 46 |
| MP4 | 1022 | NM_014718 | Calsyntenin3 | 15 | 47 |
| " | | | Eukaryotic Initiation Factor 5A | 16 | 48 |
| MP5 | 1038 | NM_001970 | image clone 4328688 | 17 | 49 |
| MP6 | 849 | NM_000876 | IGF2 Receptor (Mannose-6-phosphate receptor) | 18 | 50 |
| " | 208 | NM_007006 | pre-mRNA cleavage factor "lm" | 19 | 51 |
| MP7 | 869 | AK091534 | EST1 | 20 | 52 |
| " | | AK074035 | EST2 | 21 | |
| MP8 | 281 | AF110322 | CDK5 Associated Protein | 22 | 53 |
| MP9 | 768 | NM_007040 | E1B-55 kDa-associated protein 5 isoform a | 23 | 54 |
| " | | AB075864 | EST1 | 24 | 55 |
| " | | AF318367 | EST2 | 25 | 56 |

The following species orthologs and full-length image clones have been identified (percent identity and conserved residues calculated by the blastp BLOSUM62 algorithm at the NCBI Blast website, with a gap cost of 11 (Extenstion 1).

TABLE 3

MP8 Related Sequences

| Species | GenBank | % Identical | % Conserved | Nucleotide SEQ. ID NO: | Protein SEQ. ID NO: |
|---|---|---|---|---|---|
| Human | AF110322 | (100%) | (100%) | 22 | 53 |
| Mouse | BC002318 | 87% | 93% | 26 | 57 |
| Rat | AAH81793 | 87% | 94% | | 81 |
| *Danio rerio* (zebrafish) | AAH71504 | 62% | 81% | | 82 |
| *Tetraodon nigroviridis* (Spotted Green Pufferfish) | CAG00652 | 61 | 78 | | 83 |
| Xenopus laevis (African clawed frog) | AAH77996 | 57 | 76 | | 84 |
| Anopheles gambiae (mosquito) | XP_318917 | 39% | 59% | | 85 |
| *Caenorhabditis* briggsae (soil nematode) | CAE67421 | 38 | 56 | | 86 |
| Drosophila melanogaster (fruit fly) | AAL28291 | 36 | 54 | | 87 |
| *Arabidopsis thaliana* (thale cress) | NP_196301 | 29% | 47% | | 88 |
| Human MP8 | Image clone 4130677 | | | 28 | 59 |
| Mouse MP8 | Image clone 3593792 | | | 29 | 60 |

FIGS. 2(A), 2(B), 2(C) and 2(D) provide an alignment of full-length human MP8 protein sequence (SEQ. ID NO:53), compared with species orthologs: rat (SEQ. ID NO:81), mouse (SEQ. ID NO:57). *Danio rerio* (zebrafish)(SEQ. ID NO:82), *Tetraodon nigroviridis* (Spotted Green Pufferfish) (SEQ. ID NO:83), *Xenopus laevis* (African clawed frog) (SEQ. ID NO:84), *Anopheles gambiae* (mosquito) (SEQ. ID NO:85), *Caenorhabditis briggsae* (soil nematode)(SEQ. ID NO:86), *Drosophila melanogaster* (fruit fly)(SEQ. ID NO:87), and *Arabidopsis thaliana* (thale cress)(SEQ. ID NO:88). As reflected in Table 3, the orthologs are remarkably similar, sharing a good deal of identity especially between vertebrates (SEQ. ID NO:89) and mammals (SEQ. ID NO:90) —particularly towards the N- and C-terminals. Motifs shared throughout the family (SEQ. ID NOs:91-102) are shown below the mammalian consensus sequence.

Example 4

Measuring Receptor Cleaving Activity by Fluorescence Resonance Energy Transfer Cytokine-specific proteolytic activity can rapidly be quantified by Fluorescence Resonance Energy Transfer (FRET). Peptides having the amino acid sequence of the TNF Receptor or other protein substrates are labeled at opposite ends with a fluorescence emitter and a fluorescence quencher. The peptide is then incubated with a source of receptor cleaving enzyme, and fluorescence is measured. The quenching group normally absorbs fluorescence from the emitter. But enzymatic cleavage of the peptide decouples the quenching group, and fluorescence emission increases proportionally.

For Examples 4 through 14, MP8 was produced under research conditions on a small scale. The MP8 cDNA sequence (SEQ. ID NO:9) was cloned into an expression vector behind an N-terminal His Tag sequence followed by a thrombin site. The protein extract was chromatographed on Q-Sepharose®, the peak was purified by fast-flow chromatography on Ni-NTA, and endotoxin levels was reduced on a Q-Sepharose® (HiTrap) column. Endotoxin level was measured using a chromogenic LAL assay.

FIG. 2 shows Western analysis of a typical MP8 preparation. Using either anti-His or anti-MP8, the product had an apparent molecular weight in the 45-50 kDa range.

The peptides used as substrates in the cleavage assay were taken from the known sites of proteolytic cleavage of the whole protein. The peptides were labeled with the fluorescence emitter (Edans-●) at the C-terminal, and the quenching hapten (Dabcyl-▲) at the N-terminal.

The assay is conducted in the presence of the metal cations $Zn^{++}$ (0.1 mM) and $Ca^{++}$ (2 mM), and corrected for cleavage in the presence of EDTA (20 mM). Dependence on divalent cations confirms that the enzyme activity measured in this assay is a metalloprotease. The assay mixture also contains a cocktail of protease inhibitors and bovine albumin. Cleavage is measured as the net change in fluorescence emission after incubating the enzyme with the peptide at 37° C. for 3 hours.

| | | SEQ. ID NO: |
|---|---|---|
| Cytokine receptor peptides: | | |
| p55 TNF Receptor | ▲-N-V-K-G-T-E-D-S-G-● | 71 |
| p55 TNF Receptor (peptide 2) | ▲-K-G-T-E-D-S-G-T-T-● | 72 |
| p75 TNF Receptor | ▲-C-T-S-T-S-P-T-R-● | 73 |
| IL-6 Receptor | ▲A-N-A-T-S-L-P-● | 74 |
| IL-1 Type I Receptor | ▲T-H-G-I-D-A-A-Y-I-Q-● | 75 |
| IL-1 Type II Receptor | ▲-Q-T-K-R-T-T-V-K-E-A-● | 76 |
| Other substrate peptides: | | |
| pro TNF (TACE substrate) | ▲-L-A-Q-A-V-R-S-S-S-R-● | 77 |
| TNO-211 (matrix metalloprotease substrate) | ▲-γ-Abu-P-Q-G-L-E(●)-A-K-$NH_2$ | 78 |

FIG. 4(A) shows results of a typical FRET assay for the purified clone MP8. Enzyme activity is calculated as Fluorescence Units per mL, the activity that causes increase in fluorescence at 460 nm in the presence of $Zn^{++}$ and $Ca^{++}$, corrected for the activity measured in the presence of EDTA.

MP8 cleaves the peptides from both the p55 and p75 TNF receptors (TNF-R1 and TNF-R2). These peptides span the extracellular region believed to be cleaved when TNF receptor is released from cells in vivo. MP8 also cleaves the IL-6 receptor peptide with high activity. Data published elsewhere indicate that metalloproteases ADAM-10 and MDC-9 do not efficiently cleave either the p55 or p75 TNF receptor.

This is the standard assay method used in the following Examples for quantitation of receptor cleaving activity.

FIG. 4(B) is taken from an experiment measuring cleavage of peptides to determine the ability of MP8 to cause release of human IL-1 type 1 and type 2 receptors.

FIG. 4(C) is a compilation of data from experiments with different peptide substrates, showing relative cleavage activity standardized to the p55 TNF receptor peptide. Clone MP8 shows specificity for several receptors involved in the inflammatory pathway (TNF-R p55 and p75 isoforms, IL-6 receptor and IL-1 receptors) in comparison with control substrates spanning known cleavage sites of other proteases. MMP-1 is fibroblast collagenase, MMP-2 is stromalysin, MMP-3 is gelatinase A, MMP-11 is collagenase III, renin is an aspartate protease; malaria is a cysteine protease, and CMV is a serine protease.

FIG. 4(D) is taken from an experiment illustrating the use of the FRET assay to assess potential inhibitors or activators. The MP8 protein was combined with the inhibitor, added to the FRET peptide, and cleavage (increased fluorescence) was measured after 3 hours.

Inhibitors were as follows: 1,10 phenanthroline at 40 mM; phospharamidon at 500 μM; hydroxamate (Pharmingen) at 2 mM; TIMP-1 (Chemicon) at 2.5 μg/mL; TIMP-2 (Chemicon) at 2.5 μg/mL. Hydroxamate is a small molecule metalloprotease inhibitor. The TIMPs are naturally occurring tissue metalloprotease inhibitors.

Example 5

MP8 Causes TNF Receptor Release in vivo

To demonstrate that clone MP8 is a protease capable of cleaving receptors from cell surfaces, MP8 was incubated with THP-1 cells. This cell line expresses both the p55 TNF receptor and the p75 TNF receptor. After incubating for 45 minutes at 37° C., the cells were washed, immunostained for cell surface receptor, and counted by flow cytometry.

FIG. 5 shows that MP8 cleaves both the p55 and p75 TNF receptors when presented on the surface of cells.

To determine if the enzyme cleaves TNF receptors in vivo, 100,000 FU of purified MP8 was injected subcutaneously as a 500 μL bolus into female Balb/c mice. Control mice were injected with saline. Serum was sampled periodically, and tested for cytokine levels using ELISA kits from R&D System.

FIG. 6 shows that the cloned enzyme causes shedding of TNF receptor to an extent that causes it to accumulate in the circulation.

FIG. 7 is a compilation of data from two experiments, showing the kinetics of receptor release over a 48 hour period. These data have several important implications:

- Both the p55 and p75 TNF receptors are cleaved in vivo—meaning that signal transduction through either receptor will be affected.
- Cloned MP8 causes an increase in the level of circulating TNF receptor by about 100-fold. The enzyme should affect TNF signal transduction in two ways—by removing TNF receptor from the surface of inflammatory cells at the affected site, and creating an extracellular sink .for TNF ligand.
- The effect of MP8 persists for 48 hours after administration—meaning that frequent dosing is not required.
- Human receptor cleaving enzyme is evidently capable of cleaving TNF receptors of other species. This validates use of the mouse as a model for studying the effects of this enzyme family as therapeutic agents.

Example 6

MP8 Protects Against Septic Shock

A classic model for determining effectiveness of agents against cytokine-mediated inflammation is endotoxin-induced septic shock (Morrison et al., J Infect Dis 162:1063, 1990). When tested in this model, the cloned MP8 enzyme was found to be completely protective against septic shock in a dose-dependent fashion, whether given simultaneously with the LPS challenge, or 3 hours in advance.

In order to test effectiveness in the septic shock model, MP8 enzyme was prepared under contract by Alliance Protein Laboratories from source material produced at Biosource International. The enzyme was purified using Nickel NTA column chromatography and Q-Sepharose® analytical column chromatography. Endotoxin level was reduced using Q-Sepharose®. Enzymatic activity was determined in the FRET assay, and endotoxin contamination was determined in a chromogenic LAL assay. Endotoxin was 0.16 μg per 300,000 fluorescence units of enzyme activity.

The septic shock experiment was conducted as follows. Female Balb/c mice were randomized by weight into 6 treatment groups. Sepsis was induced by injecting 10 μg LPS and 7 mg galactosamine in the lateral or dorsal caudal vein. Some of the groups were pretreated with 50,000 FU of MP8 simultaneously or 3 hours in advance of the LPS challenge to determine whether there was a protective effect.

FIG. 8 is a Kaplan-Meier survival curve, showing the mortality in each of the treatment groups in the study. Without any treatment or challenge, there is no effect on the animals, and the line stays at the top. Life-compromising challenge causes the line to fall to the bottom of the graph in a step-wise fashion as each animal succumbs. Treatment that is protective against the challenge maintains the line near the top of the graph.

The results of this experiment show that MP8 is fully protective against LPS-induced septic shock at a dose of 50,000—whether it is given simultaneously with the LPS challenge, or 3 hours in advance.

FIG. 9 shows an experiment in which the amount of MP8 was titrated out to determine the minimum effective dose. The enzyme was administered in a volume of 110 μL at one hour before the LPS challenge.

The data show that the protective effect of MP8 is dose-dependent. The LPS/galactosamine challenge was invariably fatal in mice treated only with saline control. At a single dose of 30,000 FU, MP8 was able to protect a proportion of the challenged subjects. At 300,000 FU, MP8 was completely protective.

Example 7

Stability of Receptor Cleaving Activity Upon Storage

The data provided in this example show that MP8 retains its full activity for more than a month's storage both in terms of its proteolytic activity in the FRET assay, and its protective effect in the septic shock model. It is able to protect mice against LPS challenge at least 3 days after administration—indicating that frequent dosing with receptor releasing enzyme is not required for it to have a therapeutically important effect.

The stability of MP8 was determined by storing aliquots of MP8 at 4° C. or −70°. Aliquots were taken out periodically to determine enzyme cleaving activity in the fluorescence resonance energy transfer peptide cleavage assay.

FIG. 10 shows that in its purified form, MP8 is as stable in a standard refrigerator as it is in deep freeze. There was no detectable loss of activity after a month of storage. Stability of the clinical effect of MP8 was determined in the septic shock model. Female Balb/c mice were injected with 300,000 FU of MP8 that had been stored for 4 days at −70° C., or 7 days at 4° C. One hour later, the mice were challenged with 10 μg LPS and 7 mg galactosamine as before.

FIG. 11 shows the results. The purified enzyme has a stable shelf life, and can be frozen without causing a loss in clinical efficacy.

Example 8

Persistence of Receptor Release in vivo

In this example, durability of receptor cleavage in vivo was determined by treating animals subcutaneously up to three days in advance with 300,000 FU of MP8. The mice were then challenged with 10 μl LPS and 7 mg galactosamine in the usual fashion.

FIG. 12(A) shows the clearance of MP8 protein from the circulation of mice, determined by dot-blot analysis. The first clearance half-time is ~39 hours.

FIG. 12(B) shows that the cloned enzyme is able to protect most mice up to 3 days after administration. This is either because the enzyme continues to cleave TNF receptor for at least this long, or because an effect of the treatment (such as release of TNF receptor) persists in such a manner that TNF signal transduction is modulated for several days. Either way, this result means that frequent dosing with the enzyme is not required for clinical efficacy.

Tissue distribution of MP8 expression was determined by Northern analysis. mRNA preparations from various human tissues were probed using labeled oligonucleotides based on the MP8 sequence.

Substantial expression was observed in peripheral blood, and in other tissues relatively rich in macrophage-like cells and other leukocytes (liver, spleen, small intestine). There is a degree of MP8 expression in all tissues, which is consistent with the view that the enzyme acts as a down-regulator of inflammation on an ongoing basis.

Example 10

MP8 Treats Experimentally Induced Arthritis

The potential clinical effectiveness of receptor cleaving enzyme was assessed in collagen-induced arthritis, an animal model for rheumatoid arthritis. In this example, the animals were treated daily with 300,000 FU of MP8, simultaneously with administration of the disease agent. Eight out of 9 control mice were affected, but MP8 treated mice showed no joint swelling or other signs of arthritis. The treatment was at least as effective as a scaled dose of Enbrel® (etanercept).

Collagen-induced arthritis is a standard model for evaluating potential therapeutic agents for rheumatoid arthritis (Courtenay et al., Nature 283:666, 1980; Williams et al., Proc Natl Acad Sci USA 89:9784, 1992; Gerlag et al., J Immunol 165:1652, 2000). Arthritis was induced in 7-9 week old female DBA/1 LacJ mice by immunization with collagen. On day 0, the mice were injected at the base of the tail with 100 μg bovine type II collagen in complete Freund's adjuvant. On day 7, mice were boosted with an intraperitoneal injection of 100 μg collagen. To enhance and synchronize synovitis, the mice were injected subcutaneously on day 14 with 100 μg of lipopolysaccharide (LPS). Joint swelling was monitored in a blinded fashion by measuring the diameter in all 4 paws and both ankles using a constant pressure gauge. Arthritis Index was also determined on the following scale, and summed for all extremities. 0≡normal; 1≡one digit swollen; 2≡more than one digit swollen; 3≡joint distortion; 4≡ankylosis. The arthritis experiments were conducted under contract by Calvert Preclinical Services, Inc., Olyphant Pa.

FIG. 13 shows results of an experiment in which mice were treated with a daily dose of 300,000 FU of MP8, a scaled dose of Enbrel®, or saline control, starting 3 days before the first collagen injection. As is typical in this model, not all animals respond to the collagen challenge. In this experiment, 8 out of the 9 control animals showed signs of arthritis. However, none of the animals treated with MP8 were affected.

FIG. 14 shows the average increase in joint swelling and arthritis index measured for the animals in each group. When MP8 was given prophylactically, it prevented the animals from showing any measurable signs of the disease.

Example 11

MP8 Prevents Progression of Established Arthritis

In this example, clone MP8 was tested for its ability to treat established disease. This protocol is closer to the clinical situation in rheumatoid arthritis, where patients are treated after the onset of inflammatory synovitis.

Mice were immunized with collagen on days 0, and 7, and then boosted with LPS on day 14. Treatment with MP8 was initiated on day 22 when arthritis was well established. At that time, animals with arthritis were randomized into three groups, and unaffected animals were excluded. The three affected groups were then treated for 18 consecutive days with saline control, or with MP8 at either of two different doses.

FIG. 15 shows the results. The results show a highly significant reduction in swelling in the affected joints of the two MP8-treated groups compared with control (n=10 in each group; $p<0.001$ at the end of the experiment, 1-tailed Student's t-test). The control animals had little change in joint swelling after daily treatment was commenced at day 22. In contrast, the animals treated with MP8 at either dose showed substantial regression of disease.

FIG. 16 shows the level of antibodies to type II collagen in the serum of the mice, as determined by ELISA. The groups treated with low or high doses of MP8 had levels of pathogenic antibody that were almost half the control (both $p<0.02$). The group treated at the higher dose of MP8 also had lower severity of inflammatory synovitis as determined by histopathology at the end of the experiment. No toxicity was detected in the MP8 treated groups.

These experiments show that systemic administration of receptor cleaving enzyme is both safe and effective in the treatment of experimentally induced arthritis—even in established disease. MP8 reduces the level of circulating autoantibody, and prevents or reverses joint swelling.

Example 12

MP8 Inhibits Carrageenan-induced Edema

Further experiments were performed to determine whether the beneficial effects of cytokine receptor releasing enzyme extend beyond arthritis. In the carrageenan-induced paw edema model, systemically administered MP8 was at least as effective as orally administered indomethacin in protecting against cytokine-mediated fluid accumulation.

Based on the standard model (Winter et al., Proc Soc Exp Biol Med 111:544, 1962; Hansra et al., Inflammation 24:141, 2000), the experiment was performed as follows. Male Sprague Dawley rats were randomized by weight into three treatment groups. The animals were administered MP8 or control solution subcutaneously, or indomethacin by mouth. One hour later, they were injected in the left hind paw with a sterile solution of 1% carrageenan suspension in water, in order to induce swelling. Three hours later, the volume of the injected paw was measured by water displacement in a water plethysmograph (mean±SEM; 10 animals per group).

FIG. 17 shows the results. MP8 inhibited edema formation by 62% ($p\leqq 0.05$). In comparison, indomethacin (a small-molecule nonsteroidal anti-inflammatory agent) inhibited edema formation by only 49%.

Example 13

MP8 Prevents Development of Multiple Sclerosis

In Experimental Autoimmune Encephalomyelitis, an animal model for Multiple Sclerosis, cytokine receptor releasing enzyme was found to delay emergence of symptoms from 12 days to 18 days, and lowered disease severity by about 3-fold.

The EAE model (Brown et al., Lab. Invest. 45:278, 1981) was conducted as follows. Female SJL/J mice (6 weeks old) were randomized into 3 groups of 10. 2 mL of Myelin Proteolipid Peptide (PLP) was emulsified in 3 mL of Complete Freund's Adjuvant containing an additional 20 mg of *M. tuberculosis* H37Ra. On day 0, mice were immunized subcutaneously in the base of the tail and footpad with a total of 60 μg PLP. They were also given 400 mg pertussis toxin i.p. on days 0 and 2. MP8 or saline control was administered s.c. every day from day −3 to day 20. Progression of the disease was measured up to day 21 on the following scale: 0≡normal; 1≡limp tail or hind limb weakness; 2≡both limp tail and hind limb weakness; 3≡partial hind limb paralysis; 4≡complete hind limb paralysis; 5≡moribund or sacrificed. FIG. 18 shows the results. MP8 had four clinically important effects.

- It completely prevented the disease from appearing in a proportion of animals
- In the animals that were affected, MP8 substantially delayed the onset of symptoms
- It reduced the severity of the disease by over 3-fold
- Treated animals continued to show normal weight gain

TABLE 4

Effect of MP8 on Experimental Autoimmune Encephalomyelitis

| Treatment | Incidence of Disease | Day of Onset (±SEM) | Peak Clinical Score (±SEM) |
|---|---|---|---|
| Saline Control | 7 out of 7 | 12.7 ± 0.6 | 3.2 ± 0.4 |
| MP8 - 100,000 FU | 5 out of 7 | 18.0 ± 0.8 [a] | 2.4 ± 0.7 |
| MP8 - 300,000 FU | 3 out of 7 | 18.0 ± 2.5 [a] | 1.0 ± 0.5 [b] |

[a] $p < 0.001$
[b] $p < 0.01$

Example 14

MP8 Limits Cellular Involvement in Experimentally-induced Asthma

In a further animal model for inflammation, clone MP8 was tested for its ability to modulate the pathology associated with experimentally induced Asthma.

Mice were sensitized on Days 0, 7, and 14 with 10 μg ovalbumin in 1% aluminum hydroxide. On Day 21, the mice were challenged with the allergen in aerosol form (5% wt/vol in saline). Treatment with MP8 or control was administered 1 h before the aerosol challenge, and 24 h and 48 h afterwards. On Day 24 (72 h after the challenge), lungs were ravaged under anesthesia with 2×0.5 mL buffer to recover cells in the alveolar fluid. FIG. 19 shows the results. MP8 reduced the number of the white blood cells migrating into the alveolar fluid. The proportion of eosinophils was also substantially reduced. These results indicate that MP8 reduced inflammatory and allergenic sequelae of an intrabronchial assault.

Example 15

Unexpected Improvement in Yield Using Full-length MP8

Process development was undertaken to scale up the production of MP8 for clinical testing. MP8 was produced in *E. coli* strain MP87 (HMS174(DE3)/pMP87). Only a small amount of the protein is expressed in a soluble form; the rest accumulated as inclusion bodies. While the amount of soluble protein produced in this manner may be adequate for research use, it is inadequate for clinical or commercial scale production.

Accordingly, a process was developed to refold the MP8 in the inclusion bodies. MP8 was recovered from the insoluble fraction obtained after centrifugation of crude extracts by dissolving the protein in buffered 8 M urea. The denatured product was fractionated by Ni affinity chromatography to separate the protein by way of an N-terminal poly-His sequence (HIS tag). After the affinity purification step, 1.8-2.5 mg of MP8 was recovered per gram of cells (65 to 90 mg per L of culture). The affinity purified protein was diluted in 50 mM sodium phosphate buffer at pH 8.0 supplemented with 1 mM EDTA. The protein was added to chilled (4° C.) buffer at the rate of 1 ml/min and held for 1 to 2 hours on ice with gentle stirring. The MP8 was then captured on a Q-Sepharose™ anion exchange column and eluted with a linear salt gradient. One preparation of MP8 made using this procedure, designated MP87-086-20, was active in the murine sepsis model. However, this and subsequent preparations gave poor recoveries and in most cases showed evidence of extensive degradation. There was negligible improvement obtained by adding a cocktail of protease inhibitors to the buffers, or by any other strategies employed in an extensive series of experiments. After considerable process development, a typical recovery from the soluble and insoluble fractions combined was ~7.5 mg MP8 (3.3 g total protein) per liter of fermentation. The product was designated MP8(7), and would be equivalent in terms of the active agent to the material used in previous testing.

As an alternative production process, the MP8 encoding sequence was cloned into the yeast *Pichia pastoris*. However, virtually no MP8 protein was recovered using expression systems which accumulate the protein in the cytoplasm or extracellularly. The evidence to date suggested that the protein was being degraded as fast as it was being synthesized.

The story turned out to be completely different for expression of the full-length protein. The human Image™ clone 4130677 (Table 3) was obtained, and ligated into plasmid pQE81 behind the T5 promoter and a HIS tag. At least 50% of the synthesized full-length protein (MP8-FL1) was produced as soluble protein, and could be purified in a straight forward manner. The supernatant of a crude extract was bound and eluted from a nickel affinity column followed by an anion exchange column, and then concentrated by diafiltration. The product was ~90% pure, and 75 mg MP8-FL1 was recovered per liter of fermentation.

Because of this remarkable improvement in yield, the decision was made to switch to full length MP8 for clinical testing. To produce MP8FL for clinical purposes, the His tag was removed, the bla gene replaced with nptII, and the resulting plasmid introduced into *E. coli* strain HMS174 to create strain MP820 (HMS174/pMP820)(FIG. 20). Current production protocol is as follows: One mL working stock is inoculated into 50 mL Turbo Prime Broth™ supplemented with 50 μg/mL kanamycin and incubated for 8 hours at 37° C. The 50 mL culture is used to inoculate 500 mL Turbo Prime Broth™ supplemented with 50 μg/mL kanamycin which is incubated overnight at 37° C. When the culture density reaches 2.3-2.8 $OD_{600}$, the temperature is lowered to 30° C. and expression is induced by adding IPTG to 1 mM. Maximum accumulation of soluble protein occurs at 3 h after induction.

The current purification protocol begins by extracting the cells in a buffer containing Triton X-100™ and guanidine HCl at pH 7.8 on ice for 2 h. The clarified extract is subject to anion exchange chromatography using StreamLine™ QXL or Q-Sepharose™ FF resin. The bound MP8-FL is eluted, further purified hydrophobic interaction chromatography on a Toyopearl™ Phenyl 650M column, and subject to final polishing (e.g., another anion exchange step). The protein produced from strain MP820 by this process has been designated MP8-FL2. Even though purification of the protein without the HIS tag takes more steps to purify, the yield is still considerably higher than the original MP8 clone (FIG. 21). About 50 mg of MP8-FL2 is recovered per liter of fermentation, at a purity level of ~85 to 90% (FIG. 22). Other properties of MP8-FL2 are shown in Table 5:

TABLE 5

Properties of MP8-FL2

| | | |
|---|---|---|
| Apparent Mass - | Calculated from amino acid sequence: | 57,305 |
| | SDS-PAGE: | 64,000 |
| | TOF mass spectroscopy: | 57,005 |
| | Native SEC-HPLC: | 120,000 |
| Isoelectric Point - | Theoretical: | 4.68 |
| | By isoelectric focusing: | 5.6 |

Other products have also been produced as control proteins for MP8 biological activity. One is the N-terminal fragment of the full length protein (SEQ. ID NO:53), purified by way of a HIS tag. Another is fibronectin polyprotein, the 127 domain of human fibronectin duplicated 8 times to produce a protein of 92,000 mol. wt. The synthetic fibronectin polyprotein is also purified by Nickel affinity chromatography followed by anion exchange chromatography. A third control preparation is an extract from the isogenic parent of the MP8-FL2 *E. coli* construct, subject to anion exchange chromatography in a similar manner to MP8-FL2.

Example 16

Full Length MP8 is an Effective Anti-inflammatory Agent

MP8-FL2 has been tested both in vitro and in vivo to determine whether it has biological activity suitable for treating inflammation.

FIG. 23 shows that MP8-FL2 causes release of cytokines from the cell surface. To determine cell surface cleavage activity, 25 μg of MP8-FL2 was combined with $2.5\times10^6$ cells. Release of both TNF receptor isoforms was determined by enzyme immunoassay as (treated—untreated)/untreated. The Bottom Panel shows that both the original MP8 core protein [I believe the MP8 in this picture is from the material made before Athena's involvement and is not MP87. Dropping the MP87 reference in the beginning would clarify this.] and MP8-FL2 both cause cleavage and release of TNF receptor, with preference for the R1 (p55) isoform. The same preparation of MP8-FL2 caused cleavage of both R1 (Dabcyl-N-V-K-G-T-E-D-S-G-Edans; SEQ. ID NO:71) and R2 (Dabcyl-C-T-S-T-S-P-T-R-Edans; SEQ. ID NO:73), whereas the matched synthetic fibronectin polyprotein control protein expressed and purified in the same manner had no activity.

FIG. 24 shows that MP8-FL2 reduces carrageenan-induced edema in an animal model. Male Sprague Dawley rats were administered with test protein or indomethacin (anti-inflammatory control), and then challenged in a hind footpad with carrageenan, as in Example 12. MP8-FL2 significantly prevented paw swelling, whereas the synthetic fibronectin polyprotein control protein did not.

FIG. 25 shows that MP8-FL2 is prophylactic against septic shock. Sepsis was induced in Balb/c mice by administering 10 μg LPS and 15 mg galactosamine, as in Example 3. Randomized groups were pretreated with up to 40 μg MP8-FL2 one hours in advance of the LPS challenge. The data show that MP8-FL2 protected the mice in a dose-dependent fashion.

These experiments demonstrate that MP8-FL2 has anti-inflammatory activity, and is suitable for use as a therapeutic agent for clinical use.

SEQUENCE INFORMATION

TABLE 6

| Sequences Listed in this Disclosure | | | |
|---|---|---|---|
| SEQ. ID NO: | Description | | Reference |
| 1 to 10 | Cloned genes that increase cytokine receptor releasing activity | DNA | This invention |
| 11 to 25 | UniGene match of cloned genes | DNA | Table 2 |
| 26 & 27 | MP8 species orthologs | DNA | Table 3 |
| 28 | Full length MP8 image clone (human) | DNA | Table 3 |
| 29 | Full length MP8 image clone (mouse) | DNA | Table 3 |
| 30 to 42 | Selected open reading frames of cloned genes | amino acid | This invention |
| 43 to 56 | UniGene match of cloned genes | amino acid | Table 2 |
| 26 & 27 | MP8 species orthologs | DNA | Table 3 |
| 28 | Full length MP8 image clone (human) | DNA | Table 3 |
| 29 | Full length MP8 image clone (mouse) | DNA | Table 3 |
| 57 & 58 | MP8 species orthologs | amino acid | Table 3; FIG. 3 |
| 59 | Full length MP8 image clone (human) | amino acid | Table 3 |
| 60 | Full length MP8 image clone (mouse) | amino acid | Table 3 |
| 61 | human p55 TNF receptor | DNA | GenBank M58286 |
| 62 | | amino acid | |
| 63 | human p75 TNF receptor | DNA | GenBank NM_001066 |
| 64 | | amino acid | |
| 65 | human IL-6 receptor | DNA | GenBank NM_000565 |
| 66 | | amino acid | |
| 67 | human IL-1 type I receptor | DNA | GenBank AAH67508 |
| 68 | | amino acid | |
| 69 | human IL-1 type II receptor | DNA | GenBank NM_173343 |
| 70 | | amino acid | |
| 71 to 78 | receptor cleavage assay peptides | amino acid | This invention |
| 79 | GenBank match of MP1 | DNA | Table 2 |
| 80 | GenBank match of MP1 | amino acid | Table 2 |
| 81-88 | More MP8 species orthologs | amino acid | Table 3; FIG. 3 |
| 89 | Vertebrate consensus sequence | amino acid | FIG. 3 |
| 90 | Mammal consensus sequence | amino acid | FIG. 3 |
| 91-102 | Motifs | amino acid | FIG. 3 |

Implementation of the invention in a particular context may entail further optimization, which the skilled reader can accomplish as a matter of routine experimentation, without departing from the claimed invention and its equivalents

The invention claimed is:

1. A method for causing IL-6 receptor to be released from the surface of a cell, comprising-contacting the cell with a polypeptide containing an amino acid sequence that is at least 90% identical to SEQ. ID NO:41, 53, or 59, or fragment thereof.

2. The method of claim 1, wherein said polypeptide contains SEQ. ID NO:41, 53, or 59, or fragment thereof.

3. The method of claim 1, wherein said polypeptide contains an amino acid sequence that is at least 90% identical to SEQ. ID NO:41.

4. The method of claim 1, wherein the cell is contacted with said polypeptide in tissue culture, thereby inhibiting signal transduction into the cell by IL-6.

5. The method of claim 1, wherein the cell is contacted with said polypeptide in vivo, thereby inhibiting pro-inflammatory effects of IL-6 on the cell.

* * * * *

SEQUENCE LISTING

```
<160> NUMBER OF SEQ ID NOS: 102

<210> SEQ ID NO 1
<211> LENGTH: 4047
<212> TYPE: DNA
<213> ORGANISM: Homo sapiens

<400> SEQUENCE: 1

aagcttttg ctttccttcc ccgggaaagg ccggggccag agacccgcac tcggaccagg      60

cgggggctgc ggggccagag tgggctgggg agggctggga gggcgtctgg ggccggctcc    120
```

-continued

```
tccaggctgg gggccgccag ctccgggaag gcagtcctgg cctgcggatg gggccgcgcg    180
tggggcccgg cggggcggcc tcgggaggcg tccaggctgc gggagcggga ggagcggccg    240
tgcgggcgcc agcgccgtgg gtggaggtcg ccgtccctcc tgaggggcag ccagtgcgtt    300
tgggacccgg gagcagagcc cgcgcctccc cagcggcctc cccgggggtc tcaccgggtc    360
acccgagagc ggaggccccg gctccgcaga aacccggggc ggccgcgggg aagcagcgcc    420
ctcaggcgtc ggaggagccc ccagaaggac ctcgcgcctt cccgccgggc tccgaccgcc    480
tgggttcggt gcgggacggc ccaggccgcc aggaccccca agcgcagctc agtctgcggg    540
gcacgaccca gaggccagca gcagaggacg gggccggggc cgggagaggg cggggagggc    600
gctcctggga ggtcaaggcc agggctagac tttcagggtc atggcctggc ccctcatccc    660
cagggaggtg agggggctct gtgagcagag gggccccgg  tggagaaggc gctgctagcc    720
aggggcgggg caggagccca ggtggggact taagggtggc tgaagggacc ctcaggctgc    780
agggataggg agggaagcta ggggtgtggc ttggggaggt gctgggggac cgcgggcgcc    840
ctttattctg aagccgaatg tgctgccgga gtccccagtg acctagaaat ccatttcaag    900
attttcagga gtttcaggtg gagacaaagg ccaggcccag gtgaaaatgt ggcagtgaca    960
gagtatgggg tgagaaccac ggagagagga agtccccgag gcggatgatg ggacagagag   1020
cggggaccag aattttttaa aacgcatctg agatgcgttt ggcagactca tagttgtttt   1080
cctttcacgg agaaagtgtg ggcagaagcc agctctaaag cccaggctgc ccagcctgca   1140
ctggcagagc tgacggaagg ccagggcaga gccttccctc cctgtcacag acatgagccc   1200
tggagatctg gaatgaggca gatgtgccca gggaaagctg atccgccccg acccagggcc   1260
ccccgggtgc ccctttgagc gtggaatcgt tgccaggtca tggctccctg ctatcgaaca   1320
ccggacacgg gtcgtgtgct gcacctggca gttgcaggac cgacacccac aatgccttaa   1380
gaggtgatga ctgccttcca ggggcctggc tggctgacac tttgcatggc tcctggagaa   1440
gagggattga gtggagtcca cgggtcatgg ccacgtcctg ggtgctgcct ctgaggcagg   1500
gcccggctgg ggtgagaagg ggctggagac aggttcctgc cagttcagcc tctaaccggt   1560
ggtcttcatg cctaggaacc cactgggggc ttatgaaact gcaggtggct gagtccttgc   1620
catggggtct ctccttcagg aggtctgggt ggggccggag actgtacccc acaaagggtc   1680
ccaggtgagg cggatgtggc ctggcgctgt gtggctctgg acctagtcct tgggcttggg   1740
ctggcgccca gggcctgggc ttgagacagc tgtgacgcag gcaagccatt taccccgttt   1800
gtggggacat tacatcttcc tagcttggaa cacacaggca gccagggttg ttatccacat   1860
tcctcctcca tgttcttctc ttgagaactt ttaccaggta tgtcaggagc tgggctccac   1920
cagggagact caagtggaaa gccctcatcc ttgtcctcca ggagacagga aaacctatgg   1980
ttacaattcc agggacaaga gcgatgcatg tgaggtgtgg caaatctcac tgttcaactg   2040
gagaaatcag agacagcttc ctggaggcag tgacacctgg acaggcttct ccacaggagg   2100
aagcgagtga gagaagccaa ctgggatgga cccatcatgt agggggaaca gtgcgcgcag   2160
aaccaacaac cacccccacc ctaggcccag agctcacgga gagagctggg cctctcgggg   2220
tgactacata gttccctgct ggatcttagg tcttgtcctt gggcagctct gctgagacct   2280
ctatgcctgt tccaggctgc accaaggttt tgtgactatt ggtctggggt tgttttgcag   2340
caactgaagt gttctgttgt aaaacaggca cttgatttgc tggaaggaat gctgtttgtt   2400
cttgctgcga caaacattga gcagcattta gtgggcggtt tatatcttgt ggagtaatgg   2460
```

-continued

```
gtgtttttga agtctgtcct gggtactgca cattaaaagg aatatcattt tctgaaacat   2520

tgctattttc cacaccagaa atcatatcct cttgctggtc catgtctgaa gaccttacac   2580

gagaaagtct taatgtaagt ttagtagagt ccttggatgg agaactaatt atatcataca   2640

ttgccgcttt ctcactctgc tctttttcat ccttgcctaa tttcattttc ttctgcttct   2700

tttgttttct ttctggagaa tctagcaaga tatctggtgg aacatctcga ggtgatgaac   2760

aaggtagaga ctgagattgt aggattaaag gtggtcttga gcctttagga gttccttcac   2820

ttccagcagg ggagcatact ggctgtggag atctcaaggg aaaagatgca gcattcctca   2880

ttgttgaaga atctccatcg tcactactta gcctgtgcac catgtgtagg tagtcctcac   2940

ttgaaccatg tctaggatta tcagcatgat gattagctga attgccagac aacggaccag   3000

aaactttatt atcatgtatg tttctcaaac cacctgcaac aatgggactt gataccgatg   3060

cttgttgcat ctgtggatgt gttgtgtaac ttgaaggatg ggaatatggc atgtatcctg   3120

cagggctttg tggggcgtat ggactaggca ctgggctatt ttgctgtggc ataaatctgt   3180

tcccagagct tgtctgtggt ggcacaaacc ggctggaggg gctatgtgag atagtggttt   3240

gttgataatt ggaagatgca ggactactgt gcatggaatt ctgagaaagt ttatactgag   3300

acatcatcat tccactttgt acatatctgt tctgcatgct tttctccctg aaaacattag   3360

gactccttgc caggacggcc tgcaacaaga ctggtatgtc accttctggg tcatcactgc   3420

caaggttatc tttcaactct atgtgatctg ttgatacctg gttgaggcta tggacaagct   3480

gtgaaaccaa attgtcatcc ctacaagcca aaaggcagtt cacctcttct gctattcgtg   3540

cattaaagag aaggctcttt gtagttgtag caggtaaagg agatggaaga ggcagctggt   3600

tcaggaggtc tgtgagacta gcaatccccg caagagtagt aatggggaca tggggcatat   3660

ccccattcat cctgaatttc tggaatggtg ttgcctataa aagtacttag ttcaggtgcc   3720

agctgtcatt acttcccatt tcccaaacac tgggcgaatc ggcgtctgaa tccaagggga   3780

ggccgaggcc gctgtggcga gagactataa tccgggccgg gagggggggc ggctacggct   3840

cctcttccgt ctcctcagtg cggggaacat gtagagccgg ggggagacca gccgagaaga   3900

caaatcgttg cttcttcttc ctcctcctcc tccttctccc acatagaaac actcacaaac   3960

acccgaccac gggcccgagc taccgggggg gcatcgccgc gggcccggga accaattctc   4020

ctgtcggcgg gggcgtcctt tggatcc                                       4047
```

<210> SEQ ID NO 2
<211> LENGTH: 739
<212> TYPE: DNA
<213> ORGANISM: Homo sapiens

<400> SEQUENCE: 2

```
ggatccaaag gtcaaactcc ccacctggca ctgtccccgg agcgggtcgc gcccggccgg     60

cgcgcggccg ggcgcttggc gccagaagcg agagcccctc ggggctcgcc cccccgcctc    120

accgggtcag tgaaaaaacg atcagagtag tggtatttca ccggcggccc gcagggccgg    180

cggaccccgc cccgggcccc tcgcggggac accggggggg cgccgggggc ctcccactta    240

ttctacacct ctcatgtctc ttcaccgtgc cagactagag tcaagctcaa cagggtcttc    300

tttccccgct gattccgcca agcccgttcc cttggctgtg gtttcgctgg atagtaggta    360

gggacagtgg gaatctcgtt catccattca tgcgcgtcac taattagatg acgaggcatt    420

tggctacctt aagagagtca tagttactcc cgccgtttac ccgcgcttca ttgaatttct    480

tcactttgac attcagagca ctgggcagaa atcacatcgc gtcaacaccc gccgcgggcc    540
```

-continued

```
ttcgcgatgc tttgttttaa ttaaacagtc ggattcccct ggtccgcacc agttctaagt    600

cggctgctag gcgccggccg aagcgaggcg ccgcgcggaa ccgcggcccc cggggcggac    660

ccgcgggggg gaccgggccg cggcccctcc gccgcctgcc gccgccgccg ccgccgcgcg    720

ccgaagaaga agggggaaa                                                 739
```

<210> SEQ ID NO 3
<211> LENGTH: 233
<212> TYPE: DNA
<213> ORGANISM: Homo sapiens

<400> SEQUENCE: 3

```
caagagtggc ggccgcagca ggccccccgg gtgcccgggc cccccctcgag ggggacagtg     60

cccccgccgc gggggccccg cggcgggccg ccgccggccc ctgccgcccc gacccttctc    120

cccccgccgc cgcccccacg cggcgctccc ccggggaggg gggaggacgg ggagcggggg    180

agagagagag agagagaggg cgcggggtgg ctcgtgccga attcaaaaag ctt           233
```

<210> SEQ ID NO 4
<211> LENGTH: 2998
<212> TYPE: DNA
<213> ORGANISM: Homo sapiens

<400> SEQUENCE: 4

```
ggatccaaag aattcggcac gaggtagtca cggctcttgt cattgttgta cttgacgttg     60

aggctggtga gcttggaaaa gtcgatgcgc agcgtgcagc aggcgttgta gatgttctgc    120

ccgtccagcg acagcttggc gtgctgggcg ctcacggggt ccgcatactg cagcagggcc    180

tggaactggt tgttcttggt gaaggtgatg atcttcaaca ctgtgccgaa cttggagaaa    240

atctggtgca gcacatccag ggtcacaggg tagaagaggt tctccacgat gatcctgagc    300

acggggctct gcccggccat cgccatccct gcatccacgg ccgccgccga ggcagccaag    360

gccaggttcc ccgactggac cgagttcacc gcctgcaggg ccgcctgggc ccgcgcctgg    420

ttgggagagc tgtcggtctt cagctccttg tggttggaga actggatgta gatgggctgg    480

ccgcgcagca caggggtcac cgaggtgtag tagttcacca tggtattggc agcctcctcc    540

gtgttcatct cgatgaaggc ctggtttttc cccttcagca tcaggaggtt ggtgaccttc    600

ccaaagggca gccccaggga gatgacttcc ccctccgtga cgtcgatggg gagcttccgg    660

atgtggatca ctctagaggg gacgcctgca cttcggctgt caccttttgaa cttcttgctg    720

tcatttccgt ttgctgcaga agccgagttg ctgctcatga taaacggtcc gttagtgaca    780

caagtagaga aaagctcgtc agatccccgc tttgtaccaa cggctatatc tgggacaatg    840

ccgtccatgg cacacagagc agacccgcgg gggacggagt ggaggcgccg gaatcctgga    900

gctagagctg cagattgagt tgctgcgtga gacgaagcgc aagtatgaga gtgtcctgca    960

gctgggccgg gcactgacag cccacctcta cagcctgctg cagacccagc atgcactggg   1020

tgatgccttt gctgacctca gccagaagtc cccagagctt caggaggaat ttggctacaa   1080

tgcagagaca cagaaactac tatgcaagaa tggggaaacg ctgctaggag ccgtgaactt   1140

ctttgtctct agcatcaaca cattggtcac caagaccatg gaagacacgc tcatgactgt   1200

gaaacagtat gaggctgcca ggctggaata tgatgcctac cgaacagact tagaggagct   1260

gagtctaggc cccccgggatg cagggacacg tggtcgactt gagagtgccc aggccacttt   1320

ccaggcccat cgggacaagt atgagaagct gcggggagat gtggccatca agctcaagtt   1380
```

-continued

```
cctggaagaa aacaagatca aggtgatgca caagcagctg ctgctcttcc acaatgctgt   1440

gtccgcctac tttgctggga accagaaaca gctggagcag accctgcagc agttcaacat   1500

caagctgcgg cctccaggag ctgagaaacc ctcctggcta gaggagcagt gagctgctcc   1560

cagcccaact tggctatcaa gaaagacatt gggaagggca gccccagggt gtgggagatt   1620

ggacatggta catcctttgt cacttgccct ctggcttggg ctccttttc tggctggggc    1680

ctgacaccag ttttgcccac attgctatgg tgggaagagg gcctggaggc ccagaagttg   1740

ctgccctgtc tatcttcctg gccacagggc ttcattccca gatcttttcc ttccacttca   1800

cagccaacgg ctatgacaaa accactccct ggccaatggc atcactcttc aggctggggt   1860

gtgctccctg accaatgaca gagcctgaaa atgccctgtc agccaatggc agctcttctc   1920

ggactcccct gggccaatga tgttgcgtct aataccettt gtctctcctc tatgcgtgcc   1980

cattgcagag aaggggactg ggaccaaagg ggtggggata atggggagcc ccattgctgg   2040

ccttgcatct gaataggcct accctcacca tttattcact aatacatttt atttgtgttc   2100

tctaatttaa aattaccttt tcatcttgct tgattttcct tcagctaaat tagaaatttg   2160

tagtttttcc cctaaaaaat tcaatggcat tctttcttat aaattacatt ctctgatttt   2220

cttgtcagcc tgcttcaagg aaatccatgt gttcaaaatg cttgctcgca gtttgctcca   2280

taccaaatgg ttgcttaacc caaatatctg agcagcaaat tgagctgatc cttctggaga   2340

aagtacggtt gaacagccaa gaccactggg tagtcgaaga gaagaccaca catcctgaac   2400

tccccagtct ggtgtgaggg gaggacagct gataactgga tatgcagtgt tcccagacat   2460

cactggtccc aaaccattac ttctgcctgc cactgccaca aatacagtag gaatgccatc   2520

cccttcatac tcagctttaa tcctcagagt ttcatctggt cctttatgcg cagatgttac   2580

tcgaagttca catggaatgc caaaatttcc acaggccttc ttgatttttt cacagtgacc   2640

aagatcagaa gtagagccca tcaacactac aaccctgcac tgactttctg atttcaaaag   2700

caactctact ctctctgcaa cccactcaaa gtttttcttt accatttgga gcccttcagg   2760

agttacttct ttgaggtccc gataagactg tttgtctttc tgttggcttc gatctcctga   2820

tggccagagt ctccaggaat cattgtcaat aacatcagca agaacaattt ctttggtggt   2880

tacatcaaca ccaaattcaa tcttcatatc aaccagtgta caattctggg gcaaccagga   2940

tttctccagt atttcaaata tagcctgtgt agcatctcgt gccgaattca aaaagctt     2998
```

<210> SEQ ID NO 5
<211> LENGTH: 4152
<212> TYPE: DNA
<213> ORGANISM: Homo sapiens

<400> SEQUENCE: 5

```
aagcttttttg tgaaaaccct aggatatgtc ccctccctca ccacacccaa ccccccgccc     60

ctgccccagg acatgacgat gcctcacaca cacacacaca cacacataca cacaaggccg    120

tgagctgcac gcaggaacat gggctgcact cacgacaaca ttgaaaaaat atacattata    180

tatgtacacc cggggccccc acgtcccctc ccgtccccgc agcctggcca caccaggtca    240

cggaggaggg gccggggctg caggacctca ggactgcaag ggcaggaagg gaaacaggac    300

aagaaaggaa ggaagttgga aaggagggag aaatggggtc cccagactga aatggaaatg    360

aggtggggcg atcataagag aagcagggac gatggtccag ctgagggagc cctgcagagg    420

gggaaaagct tcccatggac aggagagaga agggaagggg agaggagagg gtttccttca    480

atcccacccc cagccccagc cccagcccca gccattgcaa tcgtcaccct ctccccaaca    540
```

-continued

```
cagtgagtgc taagggggca gctgccattg ggggtagaaa ggcagctgaa gtccagccca    600
ctttccaacc cagccagccc cagtgcaagg ggcacaccag gagcatgaca gcccagaagt    660
gagggatggg gggccggggg aggggcaggg cggactccag agggcccgct ggggttttga    720
aatgaaagga ggactggttc tgaagcctct ctccctcttg gtctctgtgt tcccagaaag    780
tccttctccc atgtctggag tgtctgtttc accagggcag aattcccccct ctgcgtgggg    840
agaggtgtag gccttagtag cggtgtgggg gggtctcgat gatgcgtctc tcgtcgctgc    900
tgggggaatc ggccacctcc gagtcactgc tgtcctcatc ctcctgctgg cccccaacag    960
cccccgtcac acaggactgc cgattctggt aggactccat ggggttcaca atgatggtga   1020
gagctgagtc atcccagaag aggtctgggt ccttggggtc actggaggcc cctggaggcc   1080
cgccggcccc tgagacgcgg cggtgaaggg aatggatgcg caccaggccc aggacgacca   1140
tgagcaccag gaagcccacg cacaccacaa tgatgagggt tgcggcgctg ggtatcatgg   1200
agtttctgtg ggagctggct aggctgtgtc cagccatctc aggcgggggc tggtgaccac   1260
ggtgcaggaa ctgctgggag ctgagcacgt ggctggggtg ggcaacccgg ttcatgctgt   1320
gcaggacatt gacctccacg atgaattcat tgctggagta acggccattc atttccgagc   1380
aggaaagccg gaacttcctg gtgtagaggg cagctccgtg tcgcagccga taacgagcct   1440
gcctcaggat ctcttcatac acagtgatgc tctccacccc agcaatagtg aggtaggcag   1500
atgtgttggt gagctccagc cccgctgct gcagagaggt tgtgtccagg agcaggcttt    1560
cccgctcggg atccaggtca tcccccacca gagaaatttc acagccatcc aggttgtgca   1620
caatctcatc cgacatgcgt gtgtctgtca ctgtgccctg ccaactctca tcctttttgg   1680
cctccacctg gtgagaaatg gagcaggtga tttgaagatc agggaacaaa gggacgccgt   1740
tggttccctc aaagtccaca gctgggcggg caaaatgagc agtgccactc agcaggatct   1800
ggggggcgtc aggctgaagg acgaccacgt agccctccac ttcagggatg gagacgcagg   1860
actcttcgct gaagcacttg acagcagtgg tgaggcgcag gggcctgacg ccgggcgtgg   1920
caaagcgcag agtgttcatg taagccacat gctgcagggc atggttgaag gtctccacat   1980
catccccctc cagggtgagc agggactgtg aggggttcac gtggaccttc atgcctttgc   2040
ccaggctctc gaaatcccta tagtccagcc cctcccgaca tgcatagagg cactcgatga   2100
cctcgcggct ctccaggcga cctgagcgca cgctgaaacc agccaggtag ccatggaagt   2160
agtggtggat cgacaaaggg tctccttggg tggtgtctgt actgttgtct cccttttcct   2220
tctctttgtt cttctcctca gtccagcagg ccccaatcat gagagcaggc tcccttcggg   2280
gtgggtggat gaggccattg tcatggatga gggcagggtc gaaggagatg ccgtcggtat   2340
agagtgtgac tgtggggaac tcgaggttca gagcgtagtg gtgccactca tcatcacaga   2400
cctgctccag cttccagagg aacttgactg ggcgggcact ctcaagcagg ggccagtaga   2460
ggaaggcaat cctacagccg tggacagtca gcgagtagtg agagaagccg tcctcattct   2520
ggacagtgtt acatacgatg gtttcctctt ccttcttgcc cttgttggga gttacgccat   2580
gcttcatcca gaaggacagg gtgaagtggt cactgaggct gtcctggggc ccagagccca   2640
gcccactggg gccacccagg ggcacctgca cagcctgggt gccattgaac cagtagatca   2700
ggctgctgtc ctggctgtag tgcaccgaga gtcctgctgt ccagttggca ttggggccag   2760
gcatgggcaa cagatccact tccccagtgg cagcaccaca gagtttccgc agcgcccgct   2820
ctgagtagtt gtcacggtca cagcccttgg ccacatggct ggtctgcagc tctatggtgg   2880
```

-continued

```
cctgaatgtt ccagagtggt tcatcacagg tctccaggcg gataccaggg aacaaagcca   2940

agctcccagc acctggtgca tattcgatcc ttttgttcca gccttgccag ctgggtttac   3000

aggtgggctt cacctgaatc tccacctcag catcatctgc tgcccgcttc ttcccacagt   3060

cataagctgt cactgtaaac ttatagagcc tctcaccact gtactgcagc ttctctgtgt   3120

tctcaatgtt cccgtcattg tcaatgagga aaggggtgtt gggtgtgaga atctcatagt   3180

agcagatctg gctgtactgg ggggagcagt caccgtcaat ggcttccacc cgcaggatgc   3240

gatcgtacag cttcccctct gtcacagccg cacgatacag ccgttccaca aacactgggg   3300

caaactcgtt cacatcgttg acccgcacat gcacagtggc cttgtgggac ttcttggtgt   3360

tggccccgtc ggggccctcg ccacagtcat aggcctggat ggtgaaggtg tgttccttct   3420

gggcctcgca gtccacaggc tccttggccc ggatcagccc ctctcctgtc gccttgtcaa   3480

ggatcacagc ctcaaagggc accccagacc catggagccg gaagccgcag atctcacctg   3540

catagcgcag cggggcatcc ttgtccaagg caaagagtgg tggattcagt aggaccgtgt   3600

tgtcattctc catgacgatg ccctggtact ctgcctcaat ccatggcttg tgcttgttgg   3660

ctttgttaca ggagcaggac gcgagcagag aggccagcag aaggggcagc agcaggaggg   3720

tcatggtgcg gcgtggggca gggcagggcc aggcgtttgc ctcccctggg agcctccagc   3780

ctgcggattc caccttgcgg gagggataca ggggggggaaa accaaaataa aacgtcaaat   3840

aaattgtgta ggaggagtcc agcttaggac cgggccagag ccaggccagg ctcggggagg   3900

gggcctctgc aggttcagag gatcactgct gccaccaccg ccaccctggg agccagttat   3960

tttgccatgg ccttgattgc aacagctgcc tcctctgtca tggcagacag caccgtgatc   4020

aggatctctt ctccacagtc gtacttctgc tcaatctcct tgccaaggtc tccctcaggg   4080

agacgaaggt cctctcgtac ctccccgctg tcctggagca gtgataggta cccatcctgg   4140

atctttggat cc                                                        4152
```

```
<210> SEQ ID NO 6
<211> LENGTH: 3117
<212> TYPE: DNA
<213> ORGANISM: Homo sapiens

<400> SEQUENCE: 6
```

```
ggatccaaag attcggcacg agtggccaca tcatgaacct ccaggcccag cccaaggctc     60

agaacaagcg gaagcgttgc ctctttgggg gccaggaacc agctcccaag gagcagcccc    120

ctcccctgca gcccccccag cagtccatca gagtgaagga ggagcagtac ctcgggcacg    180

agggtccagg aggggcagtc tccacctctc agcctgtgga actgcccccct cctagcagcc    240

tggccctgct gaactctgtg gtgtatgggc ctgagcggac ctcagcagcc atgctgtccc    300

agcaggtggc ctcagtaaag tggcccaact ctgtgatggc tccagggcgg ggcccggagc    360

gtggaggagg tgggggtgtc agtgacagca gctggcagca gcagccaggc cagcctccac    420

cccattcaac atggaactgc cacagtctgt ccctctacag tgcaaccaag gggagcccgc    480

atcctggagt gggagtcccg acttactata accaccctga ggcactgaag cgggagaaag    540

cgggggggccc acagctggac cgctatgtgc gaccaatgat gccacagaag gtgcagctgg    600

aggtagggcg gccccaggca cccctgaatt ctttccacgc agccaagaaa cccccaaacc    660

agtcactgcc cctgcaaccc ttccagctgg cattcggcca ccaggtgaac cggcaggtct    720

tccggcaggg cccaccgccc ccaaacccgg tggctgcctt ccctccacag aagcagcagc    780

agcagcagca accacagcag cagcagcagc agcagcaggc agccctaccc cagatgccgc    840
```

-continued

```
tctttgagaa cttctattcc atgccacagc aaccctcgca gcaaccccag gactttggcc    900
tgcagccagc tgggccactg ggacagtccc acctggctca ccacagcatg gcaccctacc    960
ccttcccccc caacccagat atgaacccag aactgcgcaa ggcccttctg caggactcag   1020
ccccgcagcc agcgctacct caggtccaga tccccttccc ccgccgctcc cgccgcctct   1080
ctaaggaggg tatcctgcct cccagcgccc tggatggggc tggcacccag cctgggcagg   1140
aggccactgg caacctgttc ctacatcact ggcccctgca gcagccgcca cctggctccc   1200
tggggcagcc ccatcctgaa gctctgggat tcccgctgga gctgagggag tcgcagctac   1260
tgcctgatgg ggagagacta gcacccaatg gccgggagcg agaggctcct gccatgggca   1320
gcgaggaggg catgagggca gtgagcacag ggactgtgg gcaggtgcta cggggcggag   1380
tgatccagag cacgcgacgg aggcgccggg catcccagga ggccaatttg ctgaccctgg   1440
cccagaaggc tgtggagctg gcctcactgc agaatgcaaa ggatggcagt ggttctgaag   1500
agaagcggaa aagtgtattg gcctcaacta ccaagtgtgg ggtggagttt tctgagcctt   1560
ccttagccac caagcgagca cgagaagaca gtgggatggt acccctcatc atcccagtgt   1620
ctgtgcctgt gcgaactgtg gacccaactg aggcagccca ggctggaggt cttgatgagg   1680
acgggaaggg tcttgaacag aaccctgctg agcacaagcc atcagtcatc gtcacccgca   1740
ggcggtccac ccgaatcccc gggacagatg ctcaagctca ggcggaggac atgaatgtca   1800
agttggaggg ggagccttcc gtgcggaaac caaagcagcg gcccaggccc gagcccctca   1860
tcatccccac caaggcgggc actttcatcg cccctcccgt ctactccaac atcaccccat   1920
accagagcca cctgcgctct cccgtgcgcc tagctgacca cccctctgag cggagctttg   1980
agctacctcc ctacacgccg ccccccatcc tcagccctgt gcgggaaggc tctggcctct   2040
acttcaatgc catcatatca accagcacca tccctgcccc tcctcccatc acgcctaaga   2100
gtgcccatcg cacgctgctc cggactaaca gtgctgaagt aaccccgcct gtcctctctg   2160
tgatggggga ggccacccca gtgagcatcg agccacggat caacgtgggc tcccggttcc   2220
aggcagaaat ccccttgatg agggaccgtg ccctggcagc tgcagatccc cacaaggctg   2280
acttggtgtg gcagccatgg gaggacctag agagcagccg ggagaagcag aggcaagtgg   2340
aagacctgct gacagccgcc tgctccagca ttttccctgg tgctggcacc aaccaggagc   2400
tggccctgca ctgtctgcac gaatccagag gagacatcct ggaaacgctg aataagctgc   2460
tgctgaagaa gcccctgcgg ccccacaacc atccgctggc aacttatcac tacacaggct   2520
ctgaccagtg gaagatggcc gagaggaagc tgttcaacaa aggcattgcc atctacaaga   2580
aggatttctt cctggtgcag aagctgatcc agaccaagac cgtggcccag tgcgtggagt   2640
tctactacac ctacaagaag caggtgaaaa tcggccgcaa tgggactcta acctttgggg   2700
atgtggatac gagcgatgag aagtcggccc aggaagaggt tgaagtggat attaagactt   2760
cccaaaagtt cccaagggtg cctcttccca gaagagagtc cccaagtgaa gagaggctgg   2820
agcccaagag ggaggtgaag gagcccagga aggaggggga ggaggaggtg ccagagatcc   2880
aagagaagga ggagcaggaa gaggggcgag agcgcagcag gcgggcagcg gcagtcaaag   2940
ccacgcagac actacaggcc aatgagtcgg ccagtgacat cctcatcctc cggagccacg   3000
agtccaacgc ccctgggtct gccggtggcc aggcctcgga gaagccaagg gaagggacag   3060
ggaagtcacg aagggcacta cctttttcag aaaaaaaaaa aaaaaaacaa aaagctt      3117
```

<210> SEQ ID NO 7

-continued

<211> LENGTH: 3306
<212> TYPE: DNA
<213> ORGANISM: Homo sapiens

<400> SEQUENCE: 7

```
gaattcggca cgaggtcagt ttcctgtgga acacagaggc tgcctgtccc attcagacaa     60
cgacggatac agaccaggct tgctctataa gggatcccaa cagtggattt gtgtttaatc    120
ttaatccgct aaacagttcg caaggatata acgtctctgg cattgggaag atttttatgt    180
ttaatgtctg cggcacaatg cctgtctgtg ggaccatcct gggaaaacct gcttctggct    240
gtgaggcaga aacccaaact gaagagctca agaattggaa gccagcaagg ccagtcggaa    300
ttgagaaaag cctccagctg tccacagagg gcttcatcac tctgacctac aaagggcctc    360
tctctgccaa aggtaccgct gatgctttta tcgtccgctt tgtttgcaat gatgatgttt    420
actcagggcc cctcaaattc ctgcatcaag atatcgactc tgggcaaggg atccgaaaca    480
cttactttga gtttgaaacc gcgttggcct gtgttccttc tccagtggac tgccaagtca    540
ccgacctggc tggaaatgag tacgacctga ctggcctaag cacagtcagg aaaccttgga    600
cggctgttga cacctctgtc gatgggagaa agaggacttt ctatttgagc gtttgcaatc    660
ctctccctta cattcctgga tgccagggca gcgcagtggg gtcttgctta gtgtcagaag    720
gcaatagctg gaatctgggt gtggtgcaga tgagtcccca agccgcggcg aatggatctt    780
tgagcatcat gtatgtcaac ggtgacaagt gtgggaacca gcgcttctcc accaggatca    840
cgtttgagtg tgctcagata tcgggctcac cagcatttca gcttcaggat ggttgtgagt    900
acgtgtttat ctggagaact gtggaagcct gtcccgttgt cagagtggaa ggggacaact    960
gtgaggtgaa agacccaagg catggcaact tgtatgacct gaagcccctg ggcctcaacg   1020
acaccatcgt gagcgctggc gaatacactt attacttccg ggtctgtggg aagctttcct   1080
cagacgtctg ccccacaagt gacaagtcca aggtggtctc ctcatgtcag gaaaagcggg   1140
aaccgcaggg atttcacaaa gtggcaggtc tcctgactca gaagctaact tatgaaaatg   1200
gcttgttaaa aatgaacttc acgggggggg acacttgcca taaggtttat cagcgctcca   1260
cagccatctt cttctactgt gaccgcggca cccagcggcc agtatttcta aaggagactt   1320
cagattgttc ctacttgttt gagtggcgaa cgcagtatgc ctgcccacct ttcgatctga   1380
ctgaatgttc attcaaagat ggggctggca actccttcga cctctcgtcc ctgtcaaggt   1440
acagtgacaa ctgggaagcc atcactggga cgggggaccc ggagcactac ctcatcaatg   1500
tctgcaagtc tctggccccg caggctggca ctgagccgtg ccctccagaa gcagccgcgt   1560
gtctgctggg tggctccaag cccgtgaacc tcggcagggt aagggacgga cctcagtgga   1620
gagatggcat aattgtcctg aaatacgttg atggcgactt atgtccagat gggattcgga   1680
aaaagtcaac caccatccga ttcacctgca gcgagagcca agtgaactcc aggcccatgt   1740
tcatcagcgc cgtggaggac tgtgagtaca cctttgcctg gcccacagcc acagcctgtc   1800
ccatgaagag caacgagcat gatgactgcc aggtcaccaa cccaagcaca ggacacctgt   1860
ttgatctgag ctccttaagt ggcagggcgg gattcacagc tgcttacagc gagaaggggt   1920
tggtttacat gagcatctgt ggggagaatg aaaactgccc tcctggcgtg gggggcctgct   1980
ttggacagac caggattagc gtgggcaagg ccaacaagag gctgagatac gtggaccagg   2040
tcctgcagct ggtgtacaag gatgggtccc cttgtccctc caaatccggc ctgagctata   2100
agagtgtgat cagtttcgtg tgcaggcctg aggccgggcc aaccaatagg cccatgctca   2160
tctccctgga caagcagaca tgcactctct tcttctcctg gcacacgccg ctggcctgcg   2220
```

-continued

```
agcaagcgac cgaatgttcc gtgaggaatg gaagctctat tgttgacttg tctcccctta   2280
ttcatcgcac tggtggttat gaggcttatg atgagagtga ggatgatgcc tccgatacca   2340
accctgattt ctacatcaat atttgtcagc cactaaatcc catgcacgga gtgccctgtc   2400
ctgccggagc cgctgtgtgc aaagttccta ttgatggtcc ccccatagat atcggccggg   2460
tagcaggacc accaatactc aatccaatag caaatgagat ttacttgaat tttgaaagca   2520
gtactccttg ccaggaattc agttgtaaat aaaattgaac ctgctcaaca gctgagggag   2580
actagaaatg atgggtccat atcctggtgc attgtcatac aattcaaaca atggtgcagc   2640
taccagcttg taatttttag ggactgcaaa caaggctttt tcttgaagct gaaccagaaa   2700
caacttctta tgttccttag gctttgtaat atgtgcagga atatatggat actgaggagg   2760
ttcaaaattt ggtctccacc agttaccaat gcaatcgtca atgacccagt cttgcaaaac   2820
tccatcctga cgacccagta tctctgtcat taagcgtttt agtccttcaa cttcatcttc   2880
tcctgggtta agttcaccac caggtagttt gaagaaagtt gttcccagct gcagcagtaa   2940
cacatggggt agccggtgct catgtacaat cagaacccct tctacagtcc tcctcattcc   3000
aattttatca aattcttccc tcatgcgctg aaatctggct gcaacagagc tgtccttctc   3060
gtagaggggc tcttttgtac caaaagtata attggtaaga gggtacaggt tgatggtgcg   3120
ctccagggtg aggggcttcg tctgctggat gtacttgttg ccgaactgag tgaccccccg   3180
gggccagccg gtctgcgagc gattgggcgg taccacagac atgctggcga gctccggcgc   3240
tgacggcgag cagaaagtgg caggcagggt agactttccc cgtgcgggaa gcctcgtgcc   3300
gaattc                                                              3306
```

<210> SEQ ID NO 8
<211> LENGTH: 4218
<212> TYPE: DNA
<213> ORGANISM: Homo sapiens

<400> SEQUENCE: 8

```
gaattcggca cgagaatgga tcaacctcaa caacacgtta aagctagacg aaagaagtaa     60
tacacagtgt atgagtctca catgaaatac ccggatgtaa atccaaagaa acaggaagca    120
gattggtggt tgccagggac aagggcggtg ggaggagaaa atggagagta acgggacttt    180
acttttggag tgatgagaat gttttggagc tagatagaag tggtggttgt acaccattgt    240
ggatgtacta ccacttaatt gttcacttaa aaagttaatt tatgtgaatt gcatcttaat    300
taaaaacaag gataacattc caactcctgg acattatcct tcctttccat ttgatgtcag    360
gcccgtgtta gaattctcat ccggtttggt cactgcactt aagatgtgga gaaattagga    420
cgcacagtta agaggaagga taacactgat taaggtagtg cttttctagg tttcccctaa    480
acaatttaac agatggatag tggcaccact tacgagatgg aaaaaccagc ggaaggaaga    540
tttgggggag aagttaagtt tgtcttgggc ctgtgttttg caacctgagt gtaaaagaca    600
tatgttaagt cttcagtggc gaaacactaa aactagaaat ggatcagaat tttatctttg    660
gatgtgactt ctcaaggatg gtcttgtcac ttcagtgcct ggtcaaatga caagatgggc    720
aatcttttcc tgaaggtcca agcacctgaa cgtggcaggg tgacccgatt ccgatttgct    780
tagaacaatc ctagttcatg cctattgtcc ctcatgtaat taatatcact ctcaaaatgt    840
ctcattttgt gcaataaatt ctgcaacgtg atggcgcgac tctcgcggcc cgagcggccg    900
gaccttgtct tcgaggaaga ggacctcccc tatgaggagg aaatcatgcg gaaccaattc    960
```

-continued

```
tctgtcaaat gctggcttca ctacatcgag ttcaaacagg gcgccccgaa gcccaggctc   1020
aatcagctat acgagcgggc actcaagctg ctgccctgca gctacaaact ctggtaccga   1080
tacctgaagg cgcgtcgggc acaggtgaag catcgctgtg tgaccgaccc tgcctatgaa   1140
gatgtcaaca actgtcatga gagggccttt gtgttcatgc acaagatgcc tcgtctgtgg   1200
ctagattact gccagttcct catggaccag ggggcgcgtca cacacacccg ccgcaccttc   1260
gaccgtgccc tccgggcact gcccatcacg cagcactctc gaatttggcc cctgtatctg   1320
cgcttcctgc gctcacaccc actgcctgag acagctgtgc gaggctatcg gcgcttcctc   1380
aagctgagtc ctgagagtgc agaggagtac attgagtacc tcaagtcaag tgaccggctg   1440
gatgaggccg cccagcgcct ggccaccgtg gtgaacgacg agcgtttcgt gtctaaggcc   1500
ggcaagtcca actaccagct gtggcacgag ctgtgcgacc tcatctccca gaatccggac   1560
aaggtacagt ccctcaatgt ggacgccatc atccgcgggg gcctcacccg cttcaccgac   1620
cagctgggca agctctggtg ttctctcgcc gactactaca tccgcagcgg ccatttcgag   1680
aaggctcggg acgtgtacga ggaggccatc cggacagtga tgaccgtgcg ggacttcaca   1740
caggtgtttg acagctacgc ccagttcgag gagagcatga tcgctgcaaa gatggagacc   1800
gcctcggagc tggggcgcga ggaggaggat gatgtggacc tggagctgcg cctggcccgc   1860
ttcgagcagc tcatcagccg gcggcccctg ctcctcaaca gcgtcttgct gcgccaaaac   1920
ccacaccacg tgcacgagtg gcacaagcgt gtcgccctgc accagggccg cccccgggag   1980
atcatcaaca cctacacaga ggctgtgcag acggtggacc ccttcaaggc cacaggcaag   2040
ccccacactc tgtgggtggc gtttgccaag ttttatgagg acaacggaca gctggacgat   2100
gcccgtgtca tcctggagaa ggccaccaag gtgaacttca agcaggtgga tgacctggca   2160
agcgtgtggt gtcagtgcgg agagctggag ctccgacacg agaactacga tgaggccttg   2220
cggctgctgc gaaaggccac ggcgctgcct gcccgccggg ccgagtactt tgatggttca   2280
gagcccgtgc agaaccgcgt gtacaagtca ctgaaggtct ggtccatgct cgccgacctg   2340
gaggagagcc tcggcacctt ccagtccacc aaggccgtgt acgaccgcat cctggacctg   2400
cgtatcgcaa cacccccagat cgtcatcaac tatgccatgt tcctggagga gcacaagtac   2460
ttcgaggaga gcttcaaggc gtacgagcgc ggcatctcgc tgttcaagtg gcccaacgtg   2520
tccgacatct ggagcaccta cctgaccaaa ttcattgccc gctatggggg ccgcaagctg   2580
gagcgggcac gggacctgtt tgaacaggct ctggacggct gccccccaaa atatgccaag   2640
accttgtacc tgctgtacgc acagctggag gaggagtggg gcctggcccg gcatgccatg   2700
gccgtgtacg agcgtgccac cagggccgtg gagcccgccc agcagtatga catgttcaac   2760
atctacatca agcgggcggc cgagatctat ggggtcaccc acacccgcgg catctaccag   2820
aaggccattg aggtgctgtc ggacgagcac gcgcgtgaga tgtgcctgcg gtttgcagac   2880
atggagtgca agctcgggga gattgaccgc gcccgggcca tctacagctt ctgctcccag   2940
atctgtgacc cccggacgac cggcgcgttc tggcagacgt ggaaggactt tgaggtccgg   3000
catggcaatg aggacaccat caaggaaatg ctgcgtatcc ggcgcagcgt gcaggccacg   3060
tacaacacgc aggtcaactt catggcctcg cagatgctca aggtctcggg cagtgccacg   3120
ggcaccgtgt ctgacctggc ccctgggcag agtggcatgg acgacatgaa gctgctggaa   3180
cagcgggcag agcagctggc ggctgaggcg gagcgtgacc agcccttgcg cgcccagagc   3240
aagatcctgt tcgtgaggag tgacgcctcc cgggaggagc tggcagagct ggcacagcag   3300
gtcaaccccg aggagatcca gctgggcgag gacgaggacg aggacgagat ggacctggag   3360
```

-continued

```
cccaacgagg ttcggctgga gcagcagagc gtgccagccg cagtgtttgg gagcctgaag   3420
gaagactgac ccgtcccctc gtgccgaatt cggcacgagc aagaccagcc cccagatcat   3480
ttgcctcaaa ggttttccct cgaagtcaca aatgtttcaa ggaatctcaa attttacaaa   3540
gtttgaagtg tgggcattgg tggcctgtgg ctgtgtcctc tctctgtagc tgttttctcc   3600
ctacatccct gaaaggaagt tgagcctgct cctccatccg cagacctccc tttccagcgc   3660
ccagggcatg gggtgctgtg agggcagcat gctaggtgtg accgtgctcc tggcctccag   3720
gcccgtgtcc ctctgtcctc tagcccacta aggccctggc ccatttgtgc taaacaggca   3780
gtcggaccta gaaagagcag acaatctctc tgggtcacca gtctggctag gagctggtct   3840
cctgactggg atccaggcct tctcccctgc ccatgtgaat tcccaggggc agagcctgaa   3900
atgttgaaca cagcactggc caaagagatg tcaccgtggg aaccgaggct ctcttctcct   3960
cctgcctgct ttcgtgggtt cagagtagct gaggcttgtc tgagaggagt tggagtgctg   4020
gttttcaccc tggttggtgt gctttgcttt gagggcactt agaaagccca gcccagccct   4080
tgctcctgcc ctgcacacag cggagcgact tttctaggta tgctcttgat ttctgcagaa   4140
gcagcaggtg gcatggagcc aagaggaagt gtgactgaaa ctgtccactc atagcccggc   4200
tgccgtattg agagggct                                                 4218
```

<210> SEQ ID NO 9
<211> LENGTH: 1187
<212> TYPE: DNA
<213> ORGANISM: Homo sapiens

<400> SEQUENCE: 9

```
gagctcgcgc gcctgcaggt cgacactagt ggatccaaag aattcggcac gagggaaact     60
caacggtgta cgagtggagg acagggacag agccctctgt ggtggaacga ccccacctcg    120
aggagcttcc tgagcaggtg gcagaagatg cgattgactg gggcgacttt ggggtagagg    180
cagtgtctga ggggactgac tctggcatct ctgccgaggc tgctggaatc gactggggca    240
tcttcccgga atcagattca aaggatcctg gaggtgatgg gatagactgg ggagacgatg    300
ctgttgcttt gcagatcaca gtgctggaag caggaaccca ggctccagaa ggtgttgcca    360
ggggcccaga tgccctgaca ctgcttgaat acactgagac ccggaatcag ttccttgatg    420
agctcatgga gcttgagatc ttcttagccc agagagcagt ggagttgagt gaggaggcag    480
atgtcctgtc tgtgagccag ttccagctgg ctccagccat cctgcagggc cagaccaaag    540
agaagatggt taccatggtg tcagtgctgg aggatctgat tggcaagctt accagtcttc    600
agctgcaaca cctgtttatg atcctggcct caccaaggta tgtggaccga gtgactgaat    660
tcctccagca aaagctgaag cagtcccagc tgctggcttt gaagaaagag ctgatggtgc    720
agaagcagca ggaggcactt gaggagcagg cggctctgga gcctaagctg gacctgctac    780
tggagaagac caaggagctg cagaagctga ttgaagctga catctccaag aggtacagcg    840
ggcgccctgt gaacctgatg ggaacctctc tgtgacaccc tccgtgttct tgcctgccca    900
tcttctccgc ttttgggatg aagatgatag ccagggctgt tgttttgggg cccttcaagg    960
caaaagacca ggctgactgg aagatggaaa gccacaggaa ggaagcggca cctgatggtg   1020
atcttggcac tctccatgtt ctctacaaga agctgtggtg attggccctg tggtctatca   1080
ggcgaaaacc acagattctc cttctagtta gtatagcgca aaaagcttct cgagagtact   1140
tctagagcgg ccgcgggccc atcgattttc cacccgggtg ggtacc                  1187
```

```
<210> SEQ ID NO 10
<211> LENGTH: 3306
<212> TYPE: DNA
<213> ORGANISM: Homo sapiens
<220> FEATURE:
<221> NAME/KEY: misc_feature
<222> LOCATION: (1593)..(1593)
<223> OTHER INFORMATION: N may be any nucleotide

<400> SEQUENCE: 10

ccctcactaa agggaacaaa agctggagct cgcgcgcctg caggtcgaca ctagtggatc     60

gaaagttcgt tacgccaagc tcgaaattaa ctctgggctg acccataaac atttgtctga    120

tctaggatat agttgcgttt cttgcgggca gcaatctgga tgaggcggtt gaggcactgg    180

gtggcctgct ggatcaggac atcccagcgg ccagcatagt tccgctgccg gcgtaggccc    240

atcacccgca tcttatccat gatggcattg gtacccagga tgttgtactt cttggaaggg    300

ttggaggctg catgtttgat ggcccatgtg gtcttgccag cagcaggcag gcccaccatc    360

atcagaatct cacattctgc cttgctcttt ggtccaacgg tgccccggat acgctcacta    420

aggggaaggt gctggatgaa ggtaaacccc gggaggacag aacagtaggg ctctgctctc    480

tgtccgaagt tgaactccac tgcgcaattc ttcaccagga catgaggata gagggcctga    540

ccccccaagg cttccttctg gattcggaaa gcaatgccca tccactttcc attcttggta    600

aaagacagtt ccacgtcatt tccacattca aaatccgcaa agcagccaat caccggagag    660

ctctgcggtg ctaggagagc ggctgggccc gcagactggg gggaaagctc cgcagccgca    720

gtgggcccca ggatcaggcc ccgcgtggcc tggagaagcc cagtctgggc tggagcggga    780

gctggacagt gtggccttgc gttcgccccc gggagcgctg cgagtgtcgc ggcctcgggt    840

ggatttgctg agcaccaata cctcacggtt gccaacctgg ggttttagct cccttggttt    900

taatccccta ggggcgggtg ggggcacggg aggaaggatg ggccagctgg gtgcaatcct    960

gctgtaagcc agccattcct tgatttctta gaattaacta aacggtcgcg ccggaggccg   1020

cgggggccgg agcggagcag ccgcggctga ggttcccgag tcggccgctc ggggctgcgc   1080

tccgccgccg ggaccccggc ctctggccgc gccggctccg gcctccgggg gggccggggc   1140

cgccgggaca tggtgccagt cgcacccctt ccccgccgcc gctgagctcg ccggccgcgc   1200

ccgggctggg acgtccgagc gggaagatgt tttccgccct gaagaagctg gtggggtcgg   1260

accaggcccc gggccgggac aagaacatcc ccgccgggct gcagtccatg aaccaggcgt   1320

tgcagaggcg cttcgccaag gggggtgcagt acaacatgaa gatagtgatc cggggagaca   1380

ggaacacggg caagacagcg ctgtggcacc gcctgcaggg ccggccgttc gtggaggagt   1440

acatccccac acaggagatc caggtcacca gcatccactg gagctacaag accacggatg   1500

acatcgtgaa ggttgaagtc tgggatgtag tagacaaagg aaaatgcaaa aagcgaggcg   1560

acggcttaaa gatggagaac gacccccagg agncggagtc tgaaatggcc ctggatgctg   1620

agttcctgga cgtgtacaag aactgcaacg gggtggtcat gatgttcgac attaccaagc   1680

agtggacctt caattacatt ctccgggagc ttccaaaagt gcccacccac gtgccagtgt   1740

gcgtgctggg gaactaccgg gacatgggcg agcaccgagt catcctgccg gacgacgtgc   1800

gtgacttcat cgacaacctg gacagacctc caggttcctc ctacttccgc tatgctgagt   1860

cttccatgaa gaacagcttc ggcctaaagt accttcataa gttcttcaat atcccatttt   1920

tgcagcttca gagggagacg ctgttgcggc agctggagac gaaccagctg gacatggacg   1980

ccacgctgga ggagctgtcg gtgcagcagg agacggagga ccagaactac ggcatcttcc   2040
```

-continued tggagatgat ggaggctcgc agccgtggcc atgcgtcccc actggcggcc aacgggcaga 2100
gcccatcccc gggctcccag tcaccagtcc tgcctgcacc cgctgtgtcc acggggagct 2160
ccagccccgg cacaccccag cccgccccac agctgcccct caatgctgcc ccaccatcct 2220
ctgtgccccc tgtaccaccc tcagaggccc tgcccccacc tgcgtgcccc tcagccccccg 2280 ccccacggcg cagcatcatc tctaggctgt ttgggacgtc acctgccacc gaggcagccc 2340
ctccacctcc agagccagtc ccggccgcac agggcccagc aacggtccag agtgtggagg 2400
actttgttcc tgacgaccgc ctggaccgca gcttcctgga agacacaacc cccgccaggg 2460
acgagaagaa ggtgggggcc aaggctgccc agcaggacag tgacagtgat ggggaggccc 2520
tgggcggcaa cccgatggtg gcagggttcc aggacgatgt ggacctcgaa gaccagccac 2580
gtgggagtcc cccgctgcct gcaggccccg tccccagtca agacatcact ctttcgagtg 2640
aggaggaagc agaagtggca gctcccacaa aaggccctgc cccagctccc cagcagtgct 2700
cagagccaga gaccaagtgg tcctccatac cagcttcgaa gccacggagg gggacagctc 2760
ccacgaggac cgcagcaccc ccctggccag gcggtgtctc tgttcgcaca ggtccggaga 2820
agcgcagcag caccaggccc cctgctgaga tggagccggg gaagggtgag caggcctcct 2880
cgtcggagag tgaccccgag ggacccattg ctgcacaaat gctgtccttc gtcatggatg 2940
accccgactt tgagagcgag ggatcagaca cacagcgcag ggcggatgac tttcccgtgc 3000
gagatgaccc ctccgatgtg actgacgagg atgagggccc tgccgagccg cccccacccc 3060
ccaagctccc tctccccgcc ttcagactga agaatgactc ggacctcttc gggctggggc 3120
tggaggaggc cggacccaag gagagcagtg aggaaggtaa ggagggcaaa accccctcta 3180
aggagaagaa aaaaaaaaca aaaagcttct cgagagtact tctagagcgg ccgcgggccc 3240
atcgattttc cacccgggtg gggtaccagg taagtgtacc caattcgccc tatagtgagt 3300
cgtatt 3306

<210> SEQ ID NO 11
<211> LENGTH: 1597
<212> TYPE: DNA
<213> ORGANISM: Homo sapiens

<400> SEQUENCE: 11
aagatcaacc ctcccccacg ggctcctgcc tgcctgccag gttttcctgt ctcctggagg 60
acaaggatga gggctttcca cttgagtctc cctggtggag cccagctcct gacatacctg 120
gtaaaagttc tcaagagaag aacatggagg aggaatgtgg ataacaaccc tggctgcctg 180
tgtgttccaa gctaggaaga tgtaatgtcc ccacaaacgg ggtaaatggc ttgcctgcgt 240
cacagctgtc tcaagcccag gccctgggcg ccagcccaag cccaaggact aggtccagag 300
ccacacagcg ccaggccaca tccgcctcac ctgggaccct ttgtggggta cagtctccgg 360
ccccacccag acctgctgaa ggagagaccc catggcaagg actcagccac ctgcagtttc 420
ataagccccc agtgggttcc taggcatgaa gaccaccggt tagaggctga actggcagga 480
acctgtctcc agccccttct caccccagcc gggccctgcc tcagaggcag cacccaggac 540
gtggccatga cccgtggact ccactcaatc cctcttctcc aggagccatg caaagtgtca 600
gccagccagg cccctggaag gcagtcatca cctcttaagg cattgcgggt gtcggtcctg 660
caactgccag gtgcagcaca cgacccgtgt ccggtgttcg atagcaggga gccatgacct 720
ggcaacgatt ccacgctcaa aggggcaccc ggggggccct gggtcggggc ggatcagctt 780

```
tccctgggca catctgcctc attccagatc tccagggctc atgtctgtga cagggaggga    840

aggctctgcc ctggccttcc gtcagctctg ccagtgcagg ctgggcagcc tgggctttag    900

agctggcttc tgcccacact ttctccgtga aaggaaaaca actatgagtc tgccaaacgc    960

atctcagatg cgttttaaaa aaattctggt ccccgctctc tgtcccatca tccgcctcgg   1020

ggacttcctc tctccgtggt tctcacccca tactctgtca ctgccacatt ttcacctggg   1080

cctggccttt gtctccacct gaaactcctg aaaatcttga aatggatttc taggtcactg   1140

gggactccgg cagcacattc ggcttcagaa taaagggcgc ccgcggtccc ccagcacctc   1200

cccaagccac accccctagct tccctcccta tccctgcagc ctgagggtcc cttcagccac   1260

ccttaagtcc ccacctgggc tcctgccccg cccctggcta gcagcgcctt ctccaccggg   1320

gccccctctg ctcacagagc cccctcacct ccctggggat gaggggccag gccatgaccc   1380

tgaaagccta gccctggcct tgacctccca ggagcgccct ccccgccctc tcccggcccc   1440

ggccccgtcc tctgctgctg gcctctgggt cgtgccccgc agactgagct gcgcttgggg   1500

gtcctggcgg cctgggccgt cccgcaccga acccaggcgg tcggagcccg gcggggaggc   1560

gcgaggtcct tctgggggct cctccgacgc ctgaggg                            1597
```

<210> SEQ ID NO 12
<211> LENGTH: 3322
<212> TYPE: DNA
<213> ORGANISM: Homo sapiens

<400> SEQUENCE: 12

```
cttgtgagtc tataactcgg agccgttggg tcggttcctg ctattccggc gcctccactc     60

cgtcccccgc gggtctgctc tgtgtgccat ggacggcatt gtcccagata tagccgttgg    120

tacaaagcgg ggatctgacg agcttttctc tacttgtgtc actaacggac cgtttatcat    180

gagcagcaac tcggcttctg cagcaaacgg aaatgacagc aagaagttca aaggtgacag    240

ccgaagtgca ggcgtcccct ctagagtgat ccacatccgg aagctcccca tcgacgtcac    300

ggagggggaa gtcatctccc tggggctgcc ctttgggaag gtcaccaacc tcctgatgct    360

gaaggggaaa aaccaggcct tcatcgagat gaacacggag gaggctgcca acaccatggt    420

gaactactac acctcggtga cccctgtgct gcgcggccag cccatctaca tccagttctc    480

caaccacaag gagctgaaga ccgacagctc tcccaaccag gcgcgggccc aggcggccct    540

gcaggcggtg aactcggtcc agtcggggaa cctggccttg gctgcctcgg cggcggccgt    600

ggacgcaggg atggcgatgg ccgggcagag ccccgtgctc aggatcatcg tggagaacct    660

cttctaccct gtgaccctgg atgtgctgca ccagattttc tccaagttcg gcacagtgtt    720

gaagatcatc accttcacca agaacaacca gttccaggcc ctgctgcagt atgcggaccc    780

cgtgagcgcc cagcacgcca agctgtcgct ggacgggcag aacatctaca acgcctgctg    840

cacgctgcgc atcgactttt ccaagctcac cagcctcaac gtcaagtaca acaatgacaa    900

gagccgtgac tacacacgcc cagacctgcc ttccggggac agccagccct cgctggacca    960

gaccatggcc gcggccttcg gtgcacctgg tataatctca gcctctccgt atgcaggagc   1020

tggtttccct cccacctttg ccattcctca agctgcaggc ctttccgttc cgaacgtcca   1080

cggcgccctg gccccccctgg ccatcccctc ggcggcggcg gcagctgcgg cggcaggtcg   1140

gatcgccatc ccgggcctgg cgggggcagg aaattctgta ttgctggtca gcaacctcaa   1200

cccagagaga gtcacacccc aaagcctctt tattcttttc ggcgtctacg gtgacgtgca   1260

gcgcgtgaag atcctgttca ataagaagga gaacgcccta gtgcagatgg cggacggcaa   1320
```

-continued

```
ccaggcccag ctggccatga gccacctgaa cgggcacaag ctgcacggga agcccatccg   1380

catcacgctc tcgaagcacc agaacgtgca gctgccccgc gagggccagg aggaccaggg   1440

cctgaccaag gactacggca actcacccct gcaccgcttc aagaagccgg gctccaagaa   1500

cttccagaac atattcccgc cctcggccac gctgcacctc tccaacatcc cgccctcagt   1560

ctccgaggag gatctcaagg tcctgttttc cagcaatggg ggcgtcgtca aaggattcaa   1620

gttcttccag aaggaccgca agatggcact gatccagatg ggctccgtgg aggaggcggt   1680

ccaggccctc attgacctgc acaaccacga cctcggggag aaccaccacc tgcgggtctc   1740

cttctccaag tccaccatct aggggcacag gcccccacgg ccgggccccc tggcgacaac   1800

ttccatcatt ccagagaaaa gccactttaa aaacagctga agtgacctta gcagaccaga   1860

gattttattt ttttaaagag aaatcagttt acctgttttt aaaaaaatta aatctagttc   1920

accttgctca ccctgcggtg acagggacag ctcaggctct tggtgactgt ggcagcggga   1980

gttcccggcc ctccacaccc ggggccagac cctcggggcc atgccttggt ggggcctgtg   2040

tcgggcgtgg ggcctgcagg tgggcgcccc gaccacgact tggcttcctt gtgccttaaa   2100

aaacctgcct tcctgcagcc acacacccac ccggggtgtc ctggggaccc aaggggtggg   2160

ggggtcacac cagagagagg caggggggcct ggccggctcc tgcaggatca tgcagctggg   2220

gcgcggcggc cgcggctgcg acaccccaac cccagccctc taatcaagtc acgtgattct   2280

cccttcaccc cgcccccagg gccttccctt ctgcccccag gcgggctccc cgctgctcca   2340

gctgcggagc tggtcgacat aatctctgta ttatatactt tgcagttgca gacgtctgtg   2400

cctagcaata tttccagttg accaaatatt ctaatctttt ttcatttata tgcaaaagaa   2460

atagttttaa gtaacttttt atagcaagat gatacaatgg tatgagtgta atctaaactt   2520

ccttgtggta ttaccttgta tgctgttact tttattttat tccttgtaat taagtcacag   2580

gcaggaccca gtttccagag agcaggcggg gccgcccagt gggtcaggca cagggagccc   2640

cggtcctatc ttagagcccc tgagcttcag ggaaggggcg ggcgtgtcgc cgcctctggc   2700

atcgcctccg gttgccttac accacgcctt cacctgcagt cgcctagaaa acttgctctc   2760

aaacttcagg gtttttttctt ccttcaaatt ttggaccaaa gtctcatttc tgtgttttgc   2820

ctgcctctga tgctgggacc cggaaggcgg gcgctcctcc tgtcttctct gtgctctttc   2880

taccgccccc gcgtcctgtc ccgggggctc tcctaggatc ccctttccgt aaaagcgtgt   2940

aacaagggtg taaatattta taattttttta tacctgttgt gagacccgag ggcggcggc   3000

gcggtttttt atggtgacac aaatgtatat tttgctaaca gcaattccag gctcagtatt   3060

gtgaccgcgg agccacaggg gaccccacgc acattccgtt gccttacccg atggcttgtg   3120

acgcggagag aaccgattaa aaccgtttga gaaactcctc ccttgtctag ccctgtgttc   3180

gctgtggacg ctgtagaggc aggttggcca gtctgtacct ggacttcgaa taaatcttct   3240

gtatcctcgc tccgttccgc cttaaaaaaa aaaaaaaaaa aaaaaaaaaa aaaaaaaaaa   3300

aaaaaaaaaa aaaaaaaaaa aa                                            3322
```

<210> SEQ ID NO 13
<211> LENGTH: 1654
<212> TYPE: DNA
<213> ORGANISM: Homo sapiens

<400> SEQUENCE: 13

```
tggagcccga ggtccccgcg cggcccgggc ctggcgccct gaggggaaga gcggcccggc     60
```

-continued

```
ccgagccatg acggacggga tcctagggaa ggcagccaca atggagatcc ctatccacgg    120

gaacggcgaa gccaggcagc ttcctgaaga tgatgggctg gagcaggacc tccagcaggt    180

gatggtgtca ggacccaacc tcaatgaaac cagcattgtg tctggtggct atgggggctc    240

tggtgatgga ctcatcccca cagggtctgg ccgccatcca tctcacagca ccactccttc    300

tggccctgga gatgaggtgg ctcggggcat tgctggagaa aagtttgaca tcgtcaagaa    360

atggggcatc aacacctata agtgcacaaa gcaactgtta tcagaacgat ttggtcgagg    420

ctcacggact gtggacctgg agctagagct gcagattgag ttgctgcgtg agacgaagcg    480

caagtatgag agtgtcctgc agctgggccg ggcactgaca gcccacctct acagcctgct    540

gcagacccag catgcactgg gtgatgcctt tgctgacctc agccagaagt ccccagagct    600

tcaggaggaa tttggctaca atgcagagac acagaaacta ctatgcaaga atggggaaac    660

gctgctagga gccgtgaact tctttgtctc tagcatcaac acattggtca ccaagaccat    720

ggaagacacg ctcatgactg tgaaacagta tgaggctgcc aggctggaat atgatgccta    780

ccgaacagac ttagaggagc tgagtctagg cccccgggat gcagggacac gtggtcgact    840

tgagagtgcc caggccactt tccaggccca tcgggacaag tatgagaagc tgcgggggaga    900

tgtggccatc aagctcaagt tcctggaaga aaacaagatc aaggtgatgc acaagcagct    960

gctgctcttc cacaatgctg tgtccgccta ctttgctggg aaccagaaac agctggagca   1020

gaccctgcag cagttcaaca tcaagctgcg gcctccagga gctgagaaac cctcctggct   1080

agaggagcag tgagctgctc ccagcccaac ttggctatca agaaagacat tgggaagggc   1140

agccccaggg tgtgggagat tggacatggt acatcctttg tcacttgccc tctggcttgg   1200

gctccttttt ctggctgggg cctgacacca gttttgccca cattgctatg gtgggaagag   1260

tgcctggagg cccagaagtt gctgccctgt ctatcttcct ggccacaggg cttcattccc   1320

agatcttttc cttccacttc acagccaacg gctatgacaa aaccactccc tggccaatgg   1380

catcactctt caggctgggg tgtgctccct gaccaatgac agagcctgaa aatgccctgt   1440

cagccaatgg cagctcttct cggactcccc tgggccaatg atgttgcgtc taataccctt   1500

tgtctctcct ctatgcgtgc ccattgcaga gaaggggact gggaccaaag ggtggggat    1560

aatggggagc cccattgctg gccttgcatc tgaataggcc taccctcacc cacccaccca   1620

gtttaattgt gcttagagcc caagaagatt ggga                               1654
```

```
<210> SEQ ID NO 14
<211> LENGTH: 3322
<212> TYPE: DNA
<213> ORGANISM: Homo sapiens

<400> SEQUENCE: 14

gaaagctgta tttgctgcac gtggaaatct ccgttatttt ccagcaccca acagtagcgt     60

aatgggagta acggacttaa cctcatttct ctttcagagc atttagcctt catatgccct    120

tccctgcatg cttcccccag gccgtcaaga cttgagttct gcctcgcttc ccggcgcggt    180

cgcagccctc agcccactta ggataatggc gacagctgag gtactgaaca ttggtaaaaa    240

attatatgag ggtaaaacaa aagaagtcta cgaattgtta gacagtccag gaaaagtcct    300

cctgcagtcc aaggaccaga ttacagcagg aaatgcagct agaaaaaacc acctggaagg    360

aaaagctgca atctcaaata aaatcaccag ttgtattttt cagttattac aggaagcagg    420

tattaaaact gccttcacca gaaaatgtgg ggagacagct ttcattgcac cgcagtgtga    480

aatgattcca attgaatggg tttgcagaag aatagcaact ggttcttttc tcaaaagaaa    540
```

-continued

```
tcctggtgtc aaggaaggat ataagtttta cccacctaaa gtggagttgt ttttcaagga    600
tgatgccaat aatgacccac agtggtctga ggaacagctg attgctgcaa aattttgctt    660
tgctggactt cttataggcc agactgaagt ggatatcatg agtcatgcta cacaggctat    720
atttgaaata ctggagaaat cctggttgcc ccagaattgt acactggttg atatgaagat    780
tgaatttggt gttgatgtaa ccaccaaaga aattgttctt gctgatgtta ttgacaatga    840
ttcctggaga ctctggccat caggagatcg aagccaacag aaagacaaac agtcttatcg    900
ggacctcaaa gaagtaactc ctgaagggct ccaaatggta aagaaaaact ttgagtgggt    960
tgcagagaga gtagagttgc ttttgaaatc agaaagtcag tgcagggttg tagtgttgat   1020
gggctctact tctgatcttg gtcactgtga aaaaatcaag aaggcctgtg gaaattttgg   1080
cattccatgt gaacttcgag taacatctgc gcataaagga ccagatgaaa ctctgaggat   1140
taaagctgag tatgaagggg atggcattcc tactgtattt gtggcagtgg caggcagaag   1200
taatggtttg ggaccagtga tgtctgggaa cactgcatat ccagttatca gctgtcctcc   1260
cctcacacca gactggggag ttcaggatgt gtggtcttct cttcgactac ccagtggtct   1320
tggctgttca accgtacttt ctccagaagg atcagctcaa tttgctgctc agatatttgg   1380
gttaagcaac catttggtat ggagcaaact gcgagcaagc attttgaaca catggatttc   1440
cttgaagcag gctgacaaga aaatcagaga atgtaattta taagaaagaa tgccattgaa   1500
tttttaggg gaaaaactac aaatttctaa tttagctgaa ggaaaatcaa gcaagatgaa    1560
aaggtaattt taaattagag aacacaaata aaatgtatta gtgaataaat gcttctctag   1620
atccatatta ataaacatga gcatctaacc cctcctttct taggctagac accaagatat   1680
ttcagccagc ctttatcatt cctcttactt tatccttttt ccttaagtat tggtggtcac   1740
tactattgag tttcttcctt aacactgatt aaatgatctt aactccctca gctaaaactg   1800
gcattactga ctcccagcta tatttctcca gacttgcatt tttttttttt tttttgagac   1860
agggtctcac tgtcgcccag gctggagtgc agtggcgtga tctcagttca ctgctgcttt   1920
ccctcctggg ctcaagcagt tctcccacct cagcctctcg actaacaggg actataatct   1980
tgcagcacca tgccgagcta attttatttt ttgtagagat gagctctcac tatgtcaccc   2040
aggttcgtct caaactcctg aaccctagta attctcctat ctcagcctcc caaagtgcta   2100
gggttacaga catgagccac tgtgcctgtc tagacttgta ctttcaactg tccatttctc   2160
cctgtctgtc ccatgggcac tcatgaaaaa acagaatgct cccaacttta ttcatcttcc   2220
aagcctgtag ctcttggtat actcactgtt gcaagtcaga agcttgattt catcattgat   2280
gtttttctca cgtttcacat ctcactcatc accaagtcat gttggtgtta atttctgatt   2340
aacccttgaa tttaccgtct tctcatcctc tgtacaaaag cctcaagtga gggtcaaatt   2400
caacattatc ctgatctaga cagcccccat tctcaatcca ccctttttcca agttgattgc  2460
ccaaggactt ctaacaataa actctctttt gcaccacaga cttctttgaa aatatacatg   2520
ctgttgaccc tctctgtaga aaaccgcaca cataaaactt accaacagat ttcattggtt   2580
cttgggttct cccgaagcct atccatggtt tatagattaa gaattgatga ggtagctggg   2640
cacagtggct cacacctacg atcacagcac ttcgggaggc tgaagcaagc agatcacttg   2700
aggtcaggag tttgagacca gcctggccaa catggtgaaa ccctgtctct actaaaaata   2760
caaaaagtag ccagccgtga tgacaggcac ctgtaatccc agctactcgg gaggctgagg   2820
catgagaatt gcttgaaccc gggaggcgga ggttgcagtg agcctggatc atgccactgc   2880
```

-continued

```
actccaacct gggcagcaga gcaagactct gtctcaaaag gggaaaaaaa aaattgctga   2940

tgtgacccat gaagggaact cattttcctc gtaattttgg actgccacac attggtacct   3000

ttagttctct gaaggcccac gtttttatca ttaagaccta tttgttagct agtagagctt   3060

tatgttcgct gtccatgaaa ccttctgtaa ccacagtgac tacaagtagt tctttctcta   3120

ttgaattatt aggtccagaa tagaagatgt cattgtacac tttatttccc tcacactgtg   3180

ttatgctctg atgtgctatg cttagctatc tgtcagagat tagtaaatta taaaactcat   3240

gtgtactact taagtttata tcttatgcta gtttataaga acaattaaaa ggacttagaa   3300

gattaaaaaa aaaaaaaaaa aa                                             3322
```

<210> SEQ ID NO 15
<211> LENGTH: 4300
<212> TYPE: DNA
<213> ORGANISM: Homo sapiens

<400> SEQUENCE: 15

```
gcattgattc ctctgctcca ttcctgcccc tctctgcccc ctccctctgt cctatatatc     60

ttcacttctc tcctttctcc ccatcctgtg ttctgggaga gtggcctcaa gttggggctt    120

ggctgggaga agtgcagagt gaagggatca ggactgaaat gagttgggag gaggataagc    180

aatcaggatc tcaggaaact tctagatctt tttctagttt caattctgcc cttaatctat    240

cccttccctt tcccagggcc ttctcacagc ccaccactgc tccctgaagt tccctgtctc    300

cattctctag cacgtgaaat cgctaaagaa cattctccac ttcctgacca tggttcccat    360

ggagatagtg atcccctcct cttcaccccc agggcaggtt gtttccatgg gaactgtcta    420

ccctgctata ggagaaggct atgacctccc gcagaccctc tgactccttt agtagctgat    480

ttcttgtcct caaccacccg cctcctgtaa ggtgctccta taggggggtgg aaaaggtgat   540

ggtgctgggg tgtgagttgt ctgggtcaac aagggttgtt gtgggagtag aggccctgct    600

cacaggtgct tcctctcctc tccctggggt ggggccagcc aacaagcaca agccatggat    660

tgaggcagag taccagggca tcgtcatgga gaatgacaac acggtcctac tgaatccacc    720

actctttgcc ttggacaagg atgccccgct gcgctatgca ggtgagatct gcggcttccg    780

gctccatggg tctggggtgc cctttgaggc tgtgatcctt gacaaggcga caggagaggg    840

gctgatccgg gccaaggagc ctgtggactg cgaggcccag aaggaacaca ccttcaccat    900

ccaggcctat gactgtggcg agggccccga cggggccaac accaagaagt cccacaaggc    960

cactgtgcat gtgcgggtca acgatgtgaa cgagtttgcc ccagtgtttg tggaacggct   1020

gtatcgtgcg gctgtgacag aggggaagct gtacgatcgc atcctgcggg tggaagccat   1080

tgacggtgac tgctccccc agtacagcca gatctgctac tatgagattc tcacacccaa    1140

cacccctttc ctcattgaca atgacgggaa cattgagaac acagagaagc tgcagtacag   1200

tggtgagagg ctctataagt ttacagtgac agcttatgac tgtgggaaga agcgggcagc   1260

agatgatgct gaggtggaga ttcaggtgaa gcccacctgt aaacccagct ggcaaggctg   1320

gaacaaaagg atcgaatatg caccaggtgc tgggagcttg gctttgttcc ctggtatccg   1380

cctggagacc tgtgatgaac cactctggaa cattcaggcc accatagagc tgcagaccag   1440

ccatgtggcc aagggctgtg accgtgacaa ctactcagag cgggcgctgc ggaaactctg   1500

tggtgctgcc actggggagg tggatctgtt gcccatgcct ggccccaatg ccaactggac   1560

agcaggactc tcggtgcact acagccagga cagcagcctg atctactggt tcaatggcac   1620

ccaggctgtg caggtgcccc tgggtggccc cagtgggctg ggctctgggc cccaggacag   1680
```

-continued

```
cctcagtgac cacttcaccc tgtccttctg gatgaagcat ggcgtaactc ccaacaaggg   1740
caagaaggaa gaggaaacca tcgtatgtaa cactgtccag aatgaggacg gcttctctca   1800
ctactcgctg actgtccacg gctgtaggat tgccttcctc tactggcccc tgcttgagag   1860
tgcccgccca gtcaagttcc tctggaagct ggagcaggtc tgtgatgatg agtggcacca   1920
ctacgctctg aacctcgagt tccccacagt cacactctat accgacggca tctccttcga   1980
ccctgccctc atccatgaca atggcctcat ccacccaccc cgaagggagc ctgctctcat   2040
gattggggcc tgctggactg aggagaagaa caaagagaag gaaaagggag acaacagtac   2100
agacaccacc caaggagacc ctttgtcgat ccaccactac ttccatggct acctggctgg   2160
tttcagcgtg cgctcaggtc gcctggagag ccgcgaggtc atcgagtgcc tctatgcatg   2220
tcgggagggg ctggactata gggatttcga gagcctgggc aaaggcatga aggtccacgt   2280
gaacccctca cagtccctgc tcaccctgga gggggatgat gtggagacct tcaaccatgc   2340
cctgcagcat gtggcttaca tgaacactct gcgctttgcc acgcccggcg tcaggcccct   2400
gcgcctcacc actgctgtca agtgcttcag cgaagagtcc tgcgtctcca tccctgaagt   2460
ggagggctac gtggtcgtcc ttcagcctga cgccccccag atcctgctga gtggcactgc   2520
tcattttgcc cgcccagctg tggactttga gggaaccaac ggcgtccctt tgttccctga   2580
tcttcaaatc acctgctcca tttctcacca ggtggaggcc aaaaaggatg agagttggca   2640
gggcacagtg acagacacac gcatgtcgga tgagattgtg cacaacctgg atggctgtga   2700
aatttctctg gtgggggatg acctggatcc cgagcgggaa agcctgctcc tggacacaac   2760
ctctctgcag cagcgggggc tggagctcac caacacatct gcctacctca ctattgctgg   2820
ggtggagagc atcactgtgt atgaagagat cctgaggcag gctcgttatc ggctgcgaca   2880
cggagctgcc ctctacacca ggaagttccg gctttcctgc tcggaaatga atggccgtta   2940
ctccagcaat gaattcatcg tggaggtcaa tgtcctgcac agcatgaacc gggttgccca   3000
ccccagccac gtgctcagct cccagcagtt cctgcaccgt ggtcaccagc cccgcctga    3060
gatggctgga cacagcctag ccagctccca cagaaactcc atgataccca gcgccgcaac   3120
cctcatcatt gtggtgtgcg tgggcttcct ggtgctcatg gtcgtcctgg gcctggtgcg   3180
catccattcc cttcaccgcc gcgtctcagg ggccggcggg cctccagggg cctccagtga   3240
ccccaaggac ccagacctct tctgggatga ctcagctctc accatcattg tgaaccccat   3300
ggagtcctac cagaatcggc agtcctgtgt gacgggggct gttgggggcc agcaggagga   3360
tgaggacagc agtgactcgg aggtggccga ttcccccagc agcgacgaga gacgcatcat   3420
cgagaccccc ccacaccgct actaaggcct acacctctcc ccacgcagag gggggaattct  3480
gccctggtga aacagacact ccagacatgg gagaaggact ttctgggaac acagagacca   3540
agagggagag aggcttcaga accagtcctc ctttcatttc aaaaccccag cgggccctct   3600
ggagtccgcc ctgcccctcc cccggccccc catccctcac ttctgggctg tcatgctcct   3660
ggtgtgcccc ttgcactggg gctggctggg ttggaaagtg ggctggactt cagctgcctt   3720
tctaccccca atggcagctg cccccttagc actcactgtg ttggggagag ggtgacgatt   3780
gcaatggctg gggctggggc tggggctggg ggtgggattg aaggaaaccc tctcctctcc   3840
ccttcccttc tctctcctgt ccatgggaag cttttccccc tctgcagggc tccctcagct   3900
ggaccatcgt ccctgcttct cttatgatcg ccccacctca tttccatttc agtctgggga   3960
ccccatttct ccctcctttc caacttcctt cctttcttgt cctgtttccc ttcctgccct   4020
```

-continued

```
tgcagtcctg aggtcctgca gccccggccc ctcctccgtg acctggtgtg gccaggctgc   4080

ggggacggga ggggacgtgg gggccccggg tgtacatata taatgtatat tttttcaatg   4140

ttgtcgtgag tgcagcccat gttcctgcgt gcagctcacg gccttgtgtg tatgtgtgtg   4200

tgtgtgtgtg tgaggcatcg tcatgtcctg gggcaggggc ggggggttgg gtgtggtgag   4260

ggaggggaca tatcctaggg ttttcaaata aaacaatcag                         4300
```

<210> SEQ ID NO 16
<211> LENGTH: 1299
<212> TYPE: DNA
<213> ORGANISM: Homo sapiens

<400> SEQUENCE: 16

```
ggcacgaggg cggcggcggc ggtagaggcg gcggcggcgg cggcagcggg ctcggaggca     60

gcggttgggc tcgcggcgag cggacggggt cgagtcagtg cgttcgcgcg agttggaatc    120

gaagcctctt aaaatggcag atgacttgga cttcgagaca ggagatgcag gggcctcagc    180

caccttccca atgcagtgct cagcattacg taagaatggc tttgtggtgc tcaaaggccg    240

gccatgtaag atcgtcgaga tgtctacttc gaagactggc aagcacggcc acgccaaggt    300

ccatctggtt ggtattgaca tctttactgg gaagaaatat gaagatatct gcccgtcaac    360

tcataaatatg gatgtcccca acatcaaaag gaatgacttc cagctgattg gcatccagga    420

tgggtaccta tcactgctcc aggacagcgg ggaggtacga gaggaccttc gtctccctga    480

gggagacctt ggcaaggaga ttgagcagaa gtacgactgt ggagaagaga tcctgatcac    540

ggtgctgtct gccatgacag aggaggcagc tgttgcaatc aaggccatgg caaaataact    600

ggctcccagg atggcggtgg tggcagcagt gatcctctga acctgcagag gccccctccc    660

cgagcctggc ctggctctgg cccggtccta agctggactc ctcctacaca atttatttga    720

cgttttattt tggttttccc cacccccctca atctgtcggg gagcccctgc ccttcaccta    780

gctcccttgg ccaggagcga gcgaagctgt ggccttggtg aagctgccct cctcttctcc    840

cctcacacta cagccctggt gggggagaag ggggtgggtg ctgcttgtgg tttagtcttt    900

tttttttttt tttttttttt tttaaattca atctggaatc agaaagcggt ggattctggc    960

aaatggtcct tgtgccctcc ccactcatcc ctggtctggt cccctgttgc ccatagccct   1020

ttaccctgag caccacccca acagactggg gaccagcccc ctcgcctgcc tgtgtctctc   1080

cccaaacccc tttagatggg gagggaagag gaggagaggg gaggggacct gccccctcct   1140

caggcatctg ggagggccct gcccccatgg gctttaccct tccctgcggg ctctctcccc   1200

gacacatttg ttaaaatcaa acctgaataa aactacaagt ttaatatgaa aaaaaaaaaa   1260

aaaaaaaaaa aaaaaaaaaa aaaaaaaaaa aaaaaaaaa                          1299
```

<210> SEQ ID NO 17
<211> LENGTH: 3489
<212> TYPE: DNA
<213> ORGANISM: Homo sapiens

<400> SEQUENCE: 17

```
cgcgggctgg cggaagcccc gcgagcgccg cggggaggcg acggcgcctg tttgttttta     60

aaatcgggag tgcgtgcagg cggctggagt cccggaggcg accgaaggcg gcgacccgcg    120

gcggaagggg gacagccgag cccggagccc ggagcccggg caagagctgg gtgccagaac    180

cctgtggagc atcatgaact gggaagagta gctgagcccc agagcctctc tggaagagaa    240

aggaagagcc agcagttctt tctcccagtg tcccacctca ctgtccagcg tcttcctctg    300
```

-continued

```
cccctgctct gccctccctg gctcctggac tagagcccgg cttccagcag gacgtttccc    360
caggggatgg gcgactgttg aaggggatct caccgccagg gctcagttgg ccacatcatg    420
aacctccagg cccagcccaa ggctcagaac aagcggaagc gttgcctctt cgggggccag    480
gaaccagctc ccaaggagca gccccctccc ctgcagcccc cccagcagtc catcagagtg    540
aaggaggagc agtacctcgg gcacgagggt ccaggagggg cagtctccac ctctcagcct    600
gtggaactgc cccctcctag cagcctggcc ctgctgaact ctgtggtgta tgggcctgag    660
cggacctcag cagccatgct gtcccagcag gtggcctcag taaagtggcc caactctgtg    720
atggctccag ggcggggccc ggagcgtgga ggaggtgggg gtgtcagtga cagcagctgg    780
cagcagcagc caggccagcc tccaccccat tcaacatgga actgccacag tctgtccctc    840
tacagtgcaa ccaaggggag cccgcatcct ggagtgggag tcccgactta ctataaccac    900
cctgaggcac tgaagcggga gaaagcgggg ggcccacagc tggaccgcta tgtgcgacca    960
atgatgccac agaaggtgca gctggaggta gggcggcccc aggcacccct gaattctttc   1020
cacgcagcca agaaaccccc aaaccagtca ctgcccctgc aacccttcca gctggcattc   1080
ggccaccagg tgaaccggca ggtcttccgg cagggcccac cgcccccaaa cccggtggct   1140
gccttccctc cacagaagca gcagcagcag cagcaaccac agcagcagca gcagcagcag   1200
caggcagccc taccccagat gccgctcttt gagaacttct attccatgcc gcagcaaccc   1260
tcgcagcaac cccaggactt tggcctgcag ccagctgggc cactgggaca gtcccacctg   1320
gctcaccaca gcatggcacc ctaccccttc ccccccaacc cagatatgaa cccagaactg   1380
cgcaaggccc ttctgcagga ctcagccccg cagccagcgc tacctcaggt ccagatcccc   1440
ttcccccgcc gctcccgccg cctctctaag gagggtatcc tgcctcccag cgccctggat   1500
ggggctggca cccagcctgg gcaggaggcc actggcaacc tgttcctaca tcactggccc   1560
ctgcagcagc cgccacctgg ctccctgggg cagccccatc ctgaagctct gggattcccg   1620
ctggagctga gggagtcgca gctactgcct gatggggaga gactagcacc caatggccgg   1680
gagcgagagg ctcctgccat gggcagcgag gagggcatga gggcagtgag cacaggggac   1740
tgtgggcagg tgctacgggg cggagtgatc cagagcacgc gacggaggcg ccgggcatcc   1800
caggaggcca atttgctgac cctggcccag aaggctgtgg agctggcctc actgcagaat   1860
gcaaaggatg gcagtggttc tgaagagaag cggaaaagtg tattggcctc aactaccaag   1920
tgtggggtgg agttttctga gccttcctta gccaccaagc gagcacgaga agacagtggg   1980
atggtacccc tcatcatccc agtgtctgtg cctgtgcgaa ctgtggaccc aactgaggca   2040
gcccaggctg gaggtcttga tgaggacggg aagggtcctg aacagaaccc tgctgagcac   2100
aagccatcag tcatcgtcac ccgcaggcgg tccacccgaa tccccgggac agatgctcaa   2160
gctcaggcag aggacatgaa tgtcaagttg gagggggagc cttccgtgcg gaaaccaaag   2220
cagcggccca ggcccgagcc cctcatcatc cccaccaagg cgggcacttt catcgcccct   2280
cccgtctact ccaacatcac cccataccag agccacctgc gctctcccgt gcgcctagct   2340
gaccacccct ctgagcggag ctttgagcta cctccctaca cgccgccccc catcctcagc   2400
cctgtgcggg aaggctctgg cctctacttc aatgccatca tatcaaccag caccatccct   2460
gcccctcctc ccatcacgcc taagagtgcc catcgcacgc tgctccggac taacagtgct   2520
gaagtaaccc cgcctgtcct ctctgtgatg ggggaggcca ccccagtgag catcgagcca   2580
cggatcaacg tgggctcccg gttccaggca gaaatcccct tgatgaggga ccgtgccctg   2640
```

-continued

```
gcagctgcag atccccacaa ggctgacttg gtgtggcagc catgggagga cctagagagc   2700

agccgggaga agcagaggca agtggaagac ctgctgacag ccgcctgctc cagcattttc   2760

cctggtgctg gcaccaacca ggagctggcc ctgcactgtc tgcacgaatc cagaggagac   2820

atcctggaaa cgctgaataa gctgctgctg aagaagcccc tgcggcccca caaccatccg   2880

ctggcaactt atcactacac aggctctgac cagtggaaga tggccgagag gaagctgttc   2940

aacaaaggca ttgccatcta caagaaggat ttcttcctgg tgcagaagct gatccagacc   3000

aagaccgtgg cccagtgcgt ggagttctac tacacctaca agaagcaggt gaaaatcggc   3060

cgcaatggga ctctaacctt tggggatgtg gatacgagcg atgagaagtc ggcccaggaa   3120

gaggttgaag tggatattaa gacttcccaa aagttcccaa gggtgcctct tcccagaaga   3180

gagtccccaa gtgaagagag gctggagccc aagagggagg tgaaggagcc caggaaggag   3240

ggggaggagg aggtgccaga gatccaagag aaggaggagc aggaagaggg gcgagagcgc   3300

agcaggcggg cagcggcagt caaagccacg cagacactac aggccaatga gtcggccagt   3360

gacatcctca tcctccggag ccacgagtcc aacgcccctg ggtctgccgg tggccaggcc   3420

tcggagaagc caagggaagg gacagggaag tcacgaaggg cactaccttt ttcaaaaaaa   3480

aaaaaaaaa                                                           3489
```

<210> SEQ ID NO 18
<211> LENGTH: 9090
<212> TYPE: DNA
<213> ORGANISM: Homo sapiens

<400> SEQUENCE: 18

```
cgagcccagt cgagccgcgc tcacctcggg ctcccgctcc gtctccacct ccgcctttgc     60

cctggcggcg cgaccccgtc ccggcgcggc ccccagcagt cgcgcgccgt tagcctcgcg    120

cccgccgcgc agtccgggcc cggcgcgatg gggggccgccg ccggccggag cccccacctg    180

gggcccgcgc ccgcccgccg cccgcagcgc tctctgctcc tgctgcagct gctgctgctc    240

gtcgctgccc cggggtccac gcaggcccag gccgccccgt tccccgagct gtgcagttat    300

acatgggaag ctgttgatac caaaaataat gtactttata aaatcaacat ctgtggaagt    360

gtggatattg tccagtgcgg gccatcaagt gctgtttgta tgcacgactt gaagacacgc    420

acttatcatt cagtgggtga ctctgttttg agaagtgcaa ccagatctct cctggaattc    480

aacacaacag tgagctgtga ccagcaaggc acaaatcaca gagtccagag cagcattgcc    540

ttcctgtgtg ggaaaaccct gggaactcct gaatttgtaa ctgcaacaga atgtgtgcac    600

tactttgagt ggaggaccac tgcagcctgc aagaaaagaca tatttaaagc aaataaggag    660

gtgccatgct atgtgtttga tgaagagttg aggaagcatg atctcaatcc tctgatcaag    720

cttagtggtg cctacttggt ggatgactcc gatccggaca cttctctatt catcaatgtt    780

tgtagagaca tagacacact acgagaccca ggttcacagc tgcgggcctg tccccccggc    840

actgccgcct gcctggtaag aggacaccag gcgtttgatg ttggccagcc ccgggacgga    900

ctgaagctgg tgcgcaagga caggcttgtc ctgagttacg tgagggaaga ggcaggaaag    960

ctagactttt gtgatggtca cagccctgcg gtgactatta catttgtttg cccgtcggag   1020

cggagagagg gcaccattcc caaactcaca gctaaatcca actgccgcta tgaaattgag   1080

tggattactg agtatgcctg ccacagagat tacctggaaa gtaaaacttg ttctctgagc   1140

ggcgagcagc aggatgtctc catagacctc acaccacttg cccagagcgg aggttcatcc   1200

tatatttcag atggaaaaga atatttgttt tatttgaatg tctgtggaga aactgaaata   1260
```

-continued

```
cagttctgta ataaaaaaca agctgcagtt tgccaagtga aaaagagcga tacctctcaa   1320
gtcaaagcag caggaagata ccacaatcag accctccgat attcggatgg agacctcacc   1380
ttgatatatt ttggaggtga tgaatgcagc tcagggtttc agcggatgag cgtcataaac   1440
tttgagtgca ataaaaccgc aggtaacgat gggaaaggaa ctcctgtatt cacaggggag   1500
gttgactgca cctacttctt cacatgggac acggaatacg cctgtgttaa ggagaaggaa   1560
gacctcctct gcggtgccac cgacgggaag aagcgctatg acctgtccgc gctggtccgc   1620
catgcagaac cagagcagaa ttgggaagct gtggatggca gtcagacgga aacagagaag   1680
aagcattttt tcattaatat ttgtcacaga gtgctgcagg aaggcaaggc acgagggtgt   1740
cccgaggacg cggcagtgtg tgcagtggat aaaaatggaa gtaaaaatct gggaaaattt   1800
atttcctctc ccatgaaaga gaaaggaaac attcaactct cttattcaga tggtgatgat   1860
tgtggtcatg gcaagaaaat taaaactaat atcacacttg tatgcaagcc aggtgatctg   1920
gaaagtgcac cagtgttgag aacttctggg gaaggcggtt gcttttatga gtttgagtgg   1980
cgcacagctg cggcctgtgt gctgtctaag acagaagggg agaactgcac ggtctttgac   2040
tcccaggcag ggtttttcttt tgacttatca cctctcacaa agaaaaatgg tgcctataaa   2100
gttgagacaa agaagtatga cttttatata aatgtgtgtg gcccggtgtc tgtgagcccc   2160
tgtcagccag actcaggagc ctgccaggtg gcaaaaagtg atgagaagac ttggaacttg   2220
ggtctgagta atgcgaagct ttcatattat gatgggatga tccaactgaa ctacagaggc   2280
ggcacaccct ataacaatga aagacacaca ccgagagcta cgctcatcac ctttctctgt   2340
gatcgagacg cgggagtggg cttccctgaa tatcaggaag aggataactc cacctacaac   2400
ttccggtggt acaccagcta tgcctgcccg gaggagcccc tggaatgcgt agtgaccgac   2460
ccctccacgc tggagcagta cgacctctcc agtctggcaa aatctgaagg tggccttgga   2520
ggaaactggt atgccatgga caactcaggg gaacatgtca cgtggaggaa atactacatt   2580
aacgtgtgtc ggcctctgaa tccagtgccg ggctgcaacc gatatgcatc ggcttgccag   2640
atgaagtatg aaaaagatca gggctccttc actgaagtgg tttccatcag taacttggga   2700
atggcaaaga ccggcccggt ggttgaggac agcggcagcc tccttctgga atacgtgaat   2760
gggtcggcct gcaccaccag cgatggcaga cagaccacat ataccacgag gatccatctc   2820
gtctgctcca ggggcaggct gaacagccac cccatctttt ctctcaactg ggagtgtgtg   2880
gtcagtttcc tgtggaacac agaggctgcc tgtcccattc agacaacgac ggatacagac   2940
caggcttgct ctataaggga tcccaacagt ggatttgtgt ttaatcttaa tccgctaaac   3000
agttcgcaag gatataacgt ctctggcatt gggaagattt ttatgtttaa tgtctgcggc   3060
acaatgcctg tctgtgggac catcctggga aaacctgctt ctggctgtga ggcagaaacc   3120
caaactgaag agctcaagaa ttggaagcca gcaaggccag tcggaattga gaaaagcctc   3180
cagctgtcca cagagggctt catcactctg acctacaaag ggcctctctc tgccaaaggt   3240
accgctgatg cttttatcgt ccgctttgtt tgcaatgatg atgtttactc agggcccctc   3300
aaattcctgc atcaagatat cgactctggg caagggatcc gaaacactta ctttgagttt   3360
gaaaccgcgt tggcctgtgt tccttctcca gtggactgcc aagtcaccga cctggctgga   3420
aatgagtacg acctgactgg cctaagcaca gtcaggaaac cttggacggc tgttgacacc   3480
tctgtcgatg ggagaaagag gactttctat ttgagcgttt gcaatcctct cccttacatt   3540
cctggatgcc agggcagcgc agtggggtct tgcttagtgt cagaaggcaa tagctggaat   3600
```

-continued

```
ctgggtgtgg tgcagatgag tccccaagcc gcggcgaatg gatctttgag catcatgtat   3660
gtcaacggtg acaagtgtgg gaaccagcgc ttctccacca ggatcacgtt tgagtgtgct   3720
cagatatcgg gctcaccagc atttcagctt caggatggtt gtgagtacgt gtttatctgg   3780
agaactgtgg aagcctgtcc cgttgtcaga gtggaagggg acaactgtga ggtgaaagac   3840
ccaaggcatg gcaacttgta tgacctgaag cccctgggcc tcaacgacac catcgtgagc   3900
gctggcgaat acacttatta cttccgggtc tgtgggaagc tttcctcaga cgtctgcccc   3960
acaagtgaca agtccaaggt ggtctcctca tgtcaggaaa agcgggaacc gcagggattt   4020
cacaaagtgg caggtctcct gactcagaag ctaacttatg aaaatggctt gttaaaaatg   4080
aacttcacgg ggggggacac ttgccataag gtttatcagc gctccacagc catcttcttc   4140
tactgtgacc gcggcaccca gcggccagta tttctaaagg agacttcaga ttgttcctac   4200
ttgtttgagt ggcgaacgca gtatgcctgc ccacctttcg atctgactga atgttcattc   4260
aaagatgggg ctggcaactc cttcgacctc tcgtccctgt caaggtacag tgacaactgg   4320
gaagccatca ctgggacggg ggacccggag cactacctca tcaatgtctg caagtctctg   4380
gccccgcagg ctggcactga gccgtgccct ccagaagcag ccgcgtgtct gctgggtggc   4440
tccaagcccg tgaacctcgg cagggtaagg gacggacctc agtggagaga tggcataatt   4500
gtcctgaaat acgttgatgg cgacttatgt ccagatggga ttcggaaaaa gtcaaccacc   4560
atccgattca cctgcagcga gagccaagtg aactccaggc ccatgttcat cagcgccgtg   4620
gaggactgtg agtacacctt tgcctggccc acagccacag cctgtcccat gaagagcaac   4680
gagcatgatg actgccaggt caccaaccca agcacaggac acctgtttga tctgagctcc   4740
ttaagtggca gggcgggatt cacagctgct tacagcgaga aggggttggt ttacatgagc   4800
atctgtgggg agaatgaaaa ctgccctcct ggcgtggggg cctgctttgg acagaccagg   4860
attagcgtgg gcaaggccaa caagaggctg agatacgtgg accaggtcct gcagctggtg   4920
tacaaggatg ggtccccttg tccctccaaa tccggcctga gctataagag tgtgatcagt   4980
ttcgtgtgca ggcctgaggc cgggccaacc aataggccca tgctcatctc cctggacaag   5040
cagacatgca ctctcttctt ctcctggcac acgccgctgg cctgcgagca agcgaccgaa   5100
tgttccgtga ggaatggaag ctctattgtt gacttgtctc cccttattca tcgcactggt   5160
ggttatgagg cttatgatga gagtgaggat gatgcctccg ataccaaccc tgatttctac   5220
atcaatattt gtcagccact aaatcccatg cacgcagtgc cctgtcctgc cggagccgct   5280
gtgtgcaaag ttcctattga tggtcccccc atagatatcg gccgggtagc aggaccacca   5340
atactcaatc caatagcaaa tgagatttac ttgaattttg aaagcagtac tccttgctta   5400
gcggacaagc atttcaacta cacctcgctc atcgcgtttc actgtaagag aggtgtgagc   5460
atgggaacgc ctaagctgtt aaggaccagc gagtgcgact ttgtgttcga atgggagact   5520
cctgtcgtct gtcctgatga agtgaggatg gatggctgta ccctgacaga tgagcagctc   5580
ctctacagct tcaacttgtc cagcctttcc acgagcacct ttaaggtgac tcgcgactcg   5640
cgcacctaca gcgttggggt gtgcaccttt gcagtcgggc cagaacaagg aggctgtaag   5700
gacggaggag tctgtctgct ctcaggcacc aagggggcat cctttggacg gctgcaatca   5760
atgaaactgg attacaggca ccaggatgaa gcggtcgttt taagttacgt gaatggtgat   5820
cgttgccctc cagaaaccga tgacggcgtc ccctgtgtct tccccttcat attcaatggg   5880
aagagctacg aggagtgcat catagagagc agggcgaagc tgtggtgtag cacaactgcg   5940
gactacgaca gagaccacga gtggggcttc tgcagacact caaacagcta ccggacatcc   6000
```

-continued

```
agcatcatat ttaagtgtga tgaagatgag gacattggga ggccacaagt cttcagtgaa   6060
gtgcgtgggt gtgatgtgac atttgagtgg aaaacaaaag ttgtctgccc tccaaagaag   6120
ttggagtgca aattcgtcca gaaacacaaa acctacgacc tgcggctgct ctcctctctc   6180
accgggtcct ggtccctggt ccacaacgga gtctcgtact atataaatct gtgccagaaa   6240
atatataaag ggcccctggg ctgctctgaa agggccagca tttgcagaag gaccacaact   6300
ggtgacgtcc aggtcctggg actcgttcac acgcagaagc tgggtgtcat aggtgacaaa   6360
gttgttgtca cgtactccaa aggttatccg tgtggtggaa ataagaccgc atcctccgtg   6420
atagaattga cctgtacaaa gacggtgggc agacctgcat tcaagaggtt tgatatcgac   6480
agctgcactt actacttcag ctgggactcc cgggctgcct gcgccgtgaa gcctcaggag   6540
gtgcagatgg tgaatgggac catcaccaac cctataaatg gcaagagctt cagcctcgga   6600
gatatttatt ttaagctgtt cagagcctct ggggacatga ggaccaatgg ggacaactac   6660
ctgtatgaga tccaactttc ctccatcaca agctccagaa acccggcgtg ctctggagcc   6720
aacatatgcc aggtgaagcc caacgatcag cacttcagtc ggaaagttgg aacctctgac   6780
aagaccaagt actaccttca agacggcgat ctcgatgtcg tgtttgcctc ttcctctaag   6840
tgcggaaagg ataagaccaa gtctgtttct tccaccatct tcttccactg tgaccctctg   6900
gtggaggacg ggatccccga gttcagtcac gagactgccg actgccagta cctcttctct   6960
tggtacacct cagccgtgtg tcctctgggg gtgggctttg acagcgagaa tcccggggac   7020
gacgggcaga tgcacaaggg gctgtcagaa cggagccagg cagtcggcgc ggtgctcagc   7080
ctgctgctgg tggcgctcac ctgctgcctg ctggccctgt tgctctacaa gaaggagagg   7140
agggaaacag tgataagtaa gctgaccact tgctgtagga gaagttccaa cgtgtcctac   7200
aaatactcaa aggtgaataa ggaagaagag acagatgaga atgaaacaga gtggctgatg   7260
gaagagatcc agctgcctcc tccacggcag ggaaaggaag ggcaggagaa cggccatatt   7320
accaccaagt cagtgaaagc cctcagctcc ctgcatgggg atgaccagga cagtgaggat   7380
gaggttctga ccatcccaga ggtgaaagtt cactcgggca ggggagctgg ggcagagagc   7440
tcccacccag tgagaaacgc acagagcaat gcccttcagg agcgtgagga cgatagggtg   7500
gggctggtca ggggtgagaa ggcgaggaaa gggaagtcca gctctgcaca gcagaagaca   7560
gtgagctcca ccaagctggt gtccttccat gacgacagcg acgaggacct cttacacatc   7620
tgactccgca gtgcctgcag gggagcacgg agccgcggga cagccaagca cctccaacca   7680
aataagactt ccactcgatg atgcttctat aattttgcct ttaacagaaa ctttcaaaag   7740
ggaagagttt ttgtgatggg ggagagggtg aaggaggtca ggccccactc cttcctgatt   7800
gtttacagtc attggaataa ggcatggctc agatcggcca cagggcggta ccttgtgccc   7860
agggttttgc cccaagtcct catttaaaag cataaggccg gacgcatctc aaaacagagg   7920
gctgcattcg aagaaaccct tgctgcttta gtcccgatag ggtatttgac cccgatatat   7980
tttagcattt taattctctc cccctattta ttgactttga caattactca ggtttgagaa   8040
aaaggaaaaa aaaacagcca ccgtttcttc ctgccagcag ggtgtgatg taccagtttg   8100
tccatcttga gatggtgagg ctgtcagtgt atggggcagc ttccggcggg atgttgaact   8160
ggtcattaat gtgtcccctg agttggagct cattctgtct cttttctctt ttgctttctg   8220
tttcttaagg gcacacacac gtgcgtgcga gcacacacac acatacgtgc acagggtccc   8280
cgagtgccta ggttttggag agtttgcctg ttctatgcct ttagtcagga atggctgcac   8340
```

-continued

```
ctttttgcat gatatcttca agcctgggcg tacagagcac atttgtcagt atttttgccg   8400

gctggtgaat tcaaacaacc tgcccaaaga ttgatttgtg tgtttgtgtg tgtgtgtgtg   8460

tgtgtgtgtg tgtgtgagtg gagttgaggt gtcagagaaa atgaattttt tccagatttg   8520

gggtataggt ctcatctctt caggttctca tgataccacc tttactgtgc ttattttttt   8580

aagaaaaaag tgttgatcaa ccattcgacc tataagaagc cttaatttgc acagtgtgtg   8640

acttacagaa actgcatgaa aaatcatggg ccagagcctc ggccctagca ttgcacttgg   8700

cctcatgctg gagggaggct gggcgggtac agcgcggagg aggagggagg ccaggcgggc   8760

atggcgtgga ggaggaggga ggccgggcgg tcacagcatg gaggaggagg gaggcgctgc   8820

tggtgttctt attctggcgg cagcgccttt cctgccatgt ttagtgaatg acttttctcg   8880

cattgtagaa ttgtatatag actctggtgt tctattgctg agaagcaaac cgccctgcag   8940

catccctcag cctgtaccgg tttggctggc ttgtttgatt tcaacatgag tgtatttttt   9000

aaaattgatt tttctcttca ttttttttc aatcaacttt actgtaatat aaagtattca    9060

acaatttcaa taaaagataa attattaaaa                                    9090
```

<210> SEQ ID NO 19
<211> LENGTH: 764
<212> TYPE: DNA
<213> ORGANISM: Homo sapiens

<400> SEQUENCE: 19

```
atgtctgtgg taccgcccaa tcgctcgcag accggctggc cccgggggt cactcagttc      60

ggcaacaagt acatccagca gacgaagccc ctcaccctgg agcgcaccat caacctgtac    120

cctcttacca attatacttt tggtacaaaa gagcccctct acgagaagga cagctctgtt    180

gcagccagat ttcagcgcat gagggaagaa tttgataaaa ttggaatgag gaggactgta    240

gaaggggttc tgattgtaca tgagcaccgg ctaccccatg tgttactgct gcagctggga    300

acaactttct tcaaactacc tggtggtgaa cttaacccag gagaagatga agttgaagga    360

ctaaaacgct taatgacaga gatactgggt cgtcaggatg gagttttgca agactgggtc    420

attgacgatt gcattggtaa ctggtggaga ccaaattttg aacctcctca gtatccatat    480

attcctgcac atattacaaa gcctaaggaa cataagaagt tgtttctggt tcagcttcaa    540

gaaaaagcct tgtttgcagt ccctaaaaat tacaagctgg tagctgcacc attgtttgaa    600

ttgtatgaca atgcaccagg atatggaccc atcatttcta gtctccctca gctgttgagc    660

aggttcaatt ttatttacaa ctgaattcct gcgcagtgga gaagtaaaag aagccgcttg    720

tctctgtgag cacagctata tacagtgtag aataaatgtg gtag                     764
```

<210> SEQ ID NO 20
<211> LENGTH: 2937
<212> TYPE: DNA
<213> ORGANISM: Homo sapiens

<400> SEQUENCE: 20

```
tgttggccaa gtgaaatgat ctatcattgt gtttgggagg ttttattttc ttatgttttt     60

aaaattggta aatgctttat agatgtattt ttatccaagt gccactccaa tttgtgtatg    120

taataaaatt atttatatta aaagtgggaa ataattgtca acattttttt tgagtataga    180

tttattaggg gtggcaaaga agagtgctag ttagcagttt tccatgtaaa gttgtccttg    240

actgatttgt ccacatgtca gttgtaactc ccccactccc tgcaaaagga attatttcta    300

acccagatgt atcacttgaa actttttaga agcaaaataa tcagggaagt tcctagaaag    360
```

-continued

```
gtgtttggct ttttggtttt tgagggttgg ggtaaagaag acttccccca caactgtcag    420
cacaaaacag ggtattgatt tttaactctg atgtttctat tggagttgaa tactaaataa    480
ataactataa tgagggaaat acatttctaa taaaattccc tacattctag aaacatccct    540
gttttaattt ttttatctaa atctttttgt gctttatgtg taaagaaaaa aatgtactga    600
gttacaatgc attttattaa cactatgtac ataatagctg ctttgtgttc agaatggtag    660
cagttgcttt gtatattaaa gtgatccttg tgaatttgtg aaatattgtc ataaagtgct    720
ttttcttact gtaatctttg tggtatcaac tgtcataatg ctctttttac acaaacattt    780
atgtgcagtc acataaacat gcttttaaaa actctgtaag tctctttttt ggggatggga    840
tctctatatt ttgttgggtt ttttttgcta gtagtgtgaa gccatgtttt attggactta    900
aagttacaat atattacaag cttgtgttgg aaggcagcaa aactaattca gacaacaaca    960
tgtcttcagt tactggatcc ctaattttca ggacaaaacc tgtttttcaa taagattgaa   1020
cagtgcctat ttgtggattt ggagatgtta ctgtcaagat gactaatgga gacatacgac   1080
cagctgtgtc tgatgtcata aaacacgtgt tcactgaaag gacaataaga atatatacct   1140
tctcaggtcc ccttgcaatt ctaaaactct gtgatcatat aaattggaag gaaaggggag   1200
gggatatggt taatctttgc ttaagctgta agaataaaaa agttatctcc tatactatta   1260
acttctgaaa taagttctga gacgagacat ctgaaaataa gcagctgcat tatttgtatg   1320
tttcttcact gccaagatgt gttcaagcct gctatacctg ccattgtatt ggaaggctta   1380
atgaatttca tttattttct gcaacaacga ttacagaatt tattgcacaa aatgagacat   1440
tttgagagtg atattaatta catgagggac aataggcatg aactaggatt gttctaagca   1500
aatcggaatc gggtcaccct gccacgttca ggtgcttgga ccttcaggaa aagattgccc   1560
atcttgtcat ttgaccaggc actgaagtga caagaccatc cttgagaagt cacatccaaa   1620
gataaaattc tgatccattt ctagttttag tgtttcgcca ctgaagactt aacgtatgtc   1680
ttttacactc aggttgcaaa acacaggccc aagacaaact taacttctcc cccaaatctt   1740
ccttccgctg gtttttccat ctcgtaagtg gtgccactat ccatctgtta aattgtttag   1800
gggaaaccta gaaaagcact accttaatca gtgttatcct tcctcttaac tgtgcgtcct   1860
aatttctcca catcttaagt gcagtgacca aaccggatga gaattctaac acgggcctga   1920
catcaaatgg aaaggaagga taatgtccag gagttggaat gttatccttg tttttaatta   1980
agatgcaatt cacataaatt aactttttaa gtgaacaatt aagtggtagt acatccacaa   2040
tggtgtacaa ccaccacttc tatctagctc caaaacattc tcatcactcc aaaagtaaag   2100
tcccgttact ctccattttc tcctcccacc gcccttgtcc ctggcaacca ccaatctgct   2160
tcctgtttct ttggatttac atccgggtat ttcatgtgag actcatacac tgtgtattac   2220
ttctttcgtc tagctttaac gtgttgttga ggttgatcca ttgtaacatg ttatcactac   2280
ttcattcctt tttatagcta agtatacttt ttatagtaag tatgccattg tagatatata   2340
ccacaagttt atcgattcat ccagttgagt tgtttctact gtttggctaa tgttcatagt   2400
gctgttatga atgttcgtgt acaagtattt gagtccgtgt tttcaattat ttggggtata   2460
tgcctgggag tggagttgct gggtcatgtt gaaaccgcac atttaacttt ttgaggaact   2520
gtcaaacttt ccctcagcag ctgtaccgtt ttaccttcca ccattgatgt atgagggttc   2580
caatttctcc acaccttcac caacacttat tttgccattt taaaaattat agccatcctc   2640
atgggtgtgg tctctcattg tggttttgat ttgcatttcc ctgattacta atgatgtgga   2700
```

-continued gcatcttttg ttgtctttgg ccatctgcgt atcttctttg aagaaatgtc tgttgaggtc 2760
ctttgttcat tgaaattttg ttgttgggtt ctgagttcct tatatattct gggtactagg 2820
cccttataat attttcgcct ataagttttt gctttataat gtcctcattg ttttcaaact 2880
tactttatgt aatatgtaca cttctaaaaa aaagaaacat ggaaaagggc aaactgt 2937

<210> SEQ ID NO 21
<211> LENGTH: 4555
<212> TYPE: DNA
<213> ORGANISM: Homo sapiens

<400> SEQUENCE: 21
aaatcatgcg gaaccaattc tctgtcaaat gctggcttcg ctacatcgag ttcaaacagg 60
gcgccccgaa gcccaggctc aatcagctat acgagcgggc actcaagctg ctgccctgca 120
ggtgggaatg gctccagctg ccctgcccac cagcccccac cccacctggt ccagttataa 180
caaaactgcc aagtgggtcc cgggtcccgg gtgattgctt cgtgtttcat cactgacctg 240
tacatccctt gatgggtcag cacaccttct ctgatgtccc agtctgtccc tgtcattgct 300
gagacatgtc accccctccca caccccttct tcccacattt gccaactggg gcagggcaaa 360
tggttctggg ggtgtccata aagctgaccg atcagcatct gtcccctcct attccccagc 420
tacaaactct ggtaccgata cctgaaggcg cgtcgggcac aggtgaagca tcgctgtgtg 480
accgaccctg cctatgaaga tgtcaacaac tgtcatgaga gggcctttgt gttcatgcac 540
aaggtttggg gctcggcgag gggatgaatc gggaagtgga gctcagtcca tggtggtggg 600
tggggcgggg acaggggctg ggctcagcat gttagggatg gggcttgga ttcctgttgc 660 ttctttgcat gggaagttgg gctggactca gtcctggagc tgggggtttc tgggtcccgc 720
cgcatttatg tggtggcccc aggtgtggct cagccacagg acatcgagtg tctgtggcca 780
ggccatggag tccgtggctt agccccagcc gcctctcccc acacccccag atgcctcgtc 840
tgtggctaga ttactgccag ttcctcatgg accaggggcg cgtcacacac acccgccgca 900
ccttcgaccg tgccctccgg gcactgccca tcacgcagca ctctcgaatt tggcccctgt 960
atctgcgctt cctgcgctca cacccactgc ctgagacagc tgtgcgaggc tatcggcgct 1020
tcctcaagct gagtcctgag agtgcagagg agtacattga gtacctcaag tcaagtgacc 1080
ggctggatga ggccgcccag cgcctggcca ccgtggtgaa cgacgagcgt ttcgtgtcta 1140
aggccggcaa gtccaactac caggtgggcc tgccgggagc cggcaactgg gtgggagggc 1200 cacccccctcc atgactgagc ctgagactct cccccactgc cccatgccct gcagctgtgg 1260
cacgagctgt gcgacctcat ctcccagaat ccggacaagg tacagtccct caatgtggac 1320
gccatcatcc gcgggggcct cacccgcttc accgaccagc tgggcaagct ctggtgttct 1380
ctcgccgact actacatccg cagcggccat ttcgagaagg ctcgggacgt gtacgaggag 1440
gccatccgga cagtgatgac cgtgcgggac ttcacacagg tgtttgacag ctacgcccag 1500
ttcgaggaga gcatgatcgc tgcaaagatg gagaccgcct cggagctggg gcgcgaggag 1560
gaggatgatg tggacctgga gctgcgcctg gcccgcttcg agcagctcat cagccggcgg 1620
cccctgctcc tcaacagcgt cttgctgcgc caaaacccac accacgtgca cgagtggcac 1680
aagcgtgtcg ccctgcacca gggccgcccc cgggagatca tcaacaccta cacagaggct 1740
gtgcagacgg tggacccctt caaggccaca ggcaagcccc acactctgtg ggtggcgttt 1800
gccaagtttt atgaggacaa cggacagctg gacgatgccc gtgtcatcct ggagaaggcc 1860
accaaggtga acttcaagca ggtggatgac ctggcaagcg tgtggtgtca gtgcggagag 1920

-continued

```
ctggagctcc gacacgagaa ctacgatgag gccttgcggc tgctgcgaaa ggccacggcg   1980
ctgcctgccc gccgggccga gtactttgat ggttcagagc ccgtgcagaa ccgcgtgtac   2040
aagtcactga aggtctggtc catgctcgcc gacctggagg agagcctcgg caccttccag   2100
tccaccaagg ccgtgtacga ccgcatcctg gacctgcgta tcgcaacacc ccagatcgtc   2160
atcaactatg ccatgttcct ggaggagcac aagtacttcg aggagagctt caaggtgagg   2220
ggctagggtg gacccagagg cccctgatgg cagtgtcccc tccccagggg tcctcagcaa   2280
cttacgaatc tgctggggct tgtgtgacac agtatacaga ctgggtgact taaacaacaa   2340
agatttagct tctccccgtc ctggaggctg gaagtccagg atcgaggcat gggcagggct   2400
ggttcctcct gaggcctctc tccttagctt acagacagcc gccttctccc tatgtctttg   2460
tgtggccttc tctttgtgtg tgtcactttt gaaatttcct cttcttataa aggacatcag   2520
tcataatgga ttaggtggcc cctaacgacc tcagtttaac ttagtgatct catcttcaaa   2580
cgaatctact ttctgaggta ctggggggta agatttgagc atatgaatgt tttgaggggg   2640
gcacagttca ttccatagca ggcacagagt cctacttcca cgtgcaccca tgactcatgg   2700
ggagggtgtt ggtgccagtg tgtgcgggct ctccctgccc cgctgctcag gagacgggtt   2760
gtggggtcca gggggtgggt tgcgtgtccg tgggaaggcc atgtcccgcg gccggagcag   2820
tcatgtttga gtgtgtgttt ctatggatcg tgtgggcatt atacagatac acaaatgggg   2880
aggtcgtaca tgcatacgcg tgctactgcc tgcccctctg tcagggggtg cggccttctc   2940
cctggggaca ggcagccagc gtcagcggag ctggggagcc acccaccttc acccatcatg   3000
tcacctccta tggggccaga ctgtgcttag caggtcccat tgcacccctg ttcttggggt   3060
tctcacagag ggagacagtg cagaggacag acccccacaa ctgccattag ggacagggag   3120
gcgtggacag ggaagggccc caagggagtt cctggcaggc tccctacaga cgccacccaa   3180
ggacatcccg ggtgcctggt ggtctctatc tgcagactct cacatgtgac tctccctctg   3240
gtaacaggcg tacgagcgcg gcatctcgct gttcaagtgg cccaacgtgt ccgacatctg   3300
gagcacctac ctgaccaaat tcattgcccg ctatgggggc cgcaagctgg agcgggcacg   3360
ggacctgttt gaacaggctc tggacggctg cccccccaaaa tatgccaaga gtgaggcggg   3420
cagagggcat gggggggggtg gcgggcgggc tgggtttctg actggccccg gctgaccgtg   3480
ctcccctctc cccgcctacc ccgcccagcc ttgtacctgc tgtacgcaca gctggaggag   3540
gagtggggcc tggcccggca tgccatggcc gtgtacgagc gtgccaccag ggccgtggag   3600
cccgcccagc agtatgacat gttcaacatc tacatcaagc gggcggccga gatctatggg   3660
gtcacccaca cccgcggcat ctaccagaag gccattgagg tgctgtcgga cgagcacgcg   3720
cgtgagatgt gcctgcggtt tgcagacatg gagtgcaagc tcggggagat tgaccgcgcc   3780
cgggccatct acagcttctg ctcccagatc tgtgaccccc gggtagggct gtggggaggg   3840
acgggtatca gggttggggg ctgcggcgga gtcagccagc tcacgggcac acacacccac   3900
ccctgccctg ccccccacgc agacgaccgg cgcgttctgg cagacgtgga aggactttga   3960
ggtccggcat ggcaatgagg acaccatcaa ggaaatgctg cgtatccggc gcagcgtgca   4020
ggccacgtac aacacgcagg tcaacttcat ggcctcgcag atgctcaagg tctcgggcag   4080
tgccacgggc accgtgtctg acctggcccc tgggcagagt ggcatggacg acatgaagct   4140
gctggaacag cgggcagagc agctggcggc tgaggcggag cgtgaccagc ccttgcgcgc   4200
ccagagcaag atcctgttcg tgaggagtga cgcctcccgg gaggagctgg cagagctggc   4260
```

-continued

```
acagcaggtc aaccccgagg agatccagct gggcgaggac gaggacgagg acgagatgga   4320

cctggagccc aacggtgagg gcccggctgg ggcggggacg gtggcattac caggtgggc   4380

ctcgggggac aggccaacgc caggagggtg actggctccc gccttcccca cagaggttcg   4440

gctggagcag cagagcgtgc cagccgcagt gtttgggagc ctgaaggaag actgacccgt   4500

ccctccccca tccccctcc ccaccccctc cccaatacag ctacgtttgt acatc         4555
```

<210> SEQ ID NO 22
<211> LENGTH: 2538
<212> TYPE: DNA
<213> ORGANISM: Homo sapiens

<400> SEQUENCE: 22

```
ctgaagcgga agtggaggaa agatggagga ccatcagcac gtgcccatcg acatccagac     60

cagcaagctg ctcgattggc tggtggacag aaggcactgc agcctgaaat ggcagagtct    120

ggtgctgacg atccgcgaga agatcaatgc tgccatccag gacatgccag agagcgaaga    180

gatcgcccag ctgctgtctg ggtcctacat tcactacttt cactgcctaa gaatcctgga    240

ccttctcaaa ggcacagagg cctccacgaa gaatattttt ggccgatact cttcacagcg    300

gatgaaggat tggcaggaga ttatagctct gtatgagaag gacaacacct acttaggtaa    360

agtggcccgg cctgggagcc ctggtatcca tggggaagcc cactctcaga gttctgagat    420

accaggctta taggaggcac agtctgtgag tgggaagaga ctggagtgta gatgttgccc    480

atttgtaggt ggtaaaatca attgtttttg atggaattga ttttccctga gtggagtgct    540

gggggaagga ggaggtccag gccggtagtg gccattcgcc gtgcctcagc gagcaggtgt    600

gtgtgggtcc tccaccactc acctcttggt tagcgggagt gtgctgcccc caccccccacc    660

cccgcacccc cattctacac aaggcagaag aggcacgggt tttcctggga gcgaatatca    720

agtgcctgag agcaactaca ggactaactg tgtttgggtt gggtgtagta taaataataa    780

taatggctaa tatttcctga gcatctacta aatgcaagga attgtgcttg gtgtgtcatg    840

tggattctct cttgcatctt catgataaat gttattgtcg ctgttttacc gatgagggtt    900

ggattagagg ggttaaacaa cttgtcttag gctccacagc tgggaacaag tggggctggg    960

aagctgactt cgtgctcttc accaccacaa aggatgtgtg tgcatcctgg ggcatgcctg   1020

cctcatgtgg gggtgtcctg ggctgaattt cctgggcact tctcagtgga actctctagc   1080

ctcctggttc ggaatgtcaa ctatgagatc ccctcactga agaagcagat tgccaagtgc   1140

cagcagctgc agcaagaata cagccgcaag gaggaggagt gccaggcagg ggctgccgag   1200

atgcgggagc agttctacca ctcctgcaag cagtatggca tcacgggcga aaatgtccga   1260

ggagaactgc tggccctggt gaaggacctg ccgagtcagc tggctgagat tggggcagcg   1320

gctcagcagt ccctgggggga agccattgac gtgtaccagg cgtctgtggg gtttgtgtgt   1380

gagagcccca cagagcaggt gttgccaatg ctgcggttcg tgcagaagcg ggaaaactca   1440

acggtgtacg agtggaggac agggacagag ccctctgtgg tggaacgacc ccacctcgag   1500

gagcttcctg agcaggtggc agaagatgcg attgactggg gcgactttgg ggtagaggca   1560

gtgtctgagg ggactgactc tggcatctct gccgaggctg ctggaatcga ctggggcatc   1620

ttcccggaat cagattcaaa ggatcctgga ggtgatggga tagactgggg agacgatgct   1680

gttgctttgc agatcacagt gctggaagca ggaacccagg ctccagaagg tgttgccagg   1740

ggcccagatg ccctgacact gcttgaatac actgagaccc ggaatcagtt ccttgatgag   1800

ctcatggagc ttgagatctt cttagcccag agagcagtgg agttgagtga ggaggcagat   1860
```

-continued

```
gtcctgtctg tgagccagtt ccagctggct ccagccatcc tgcagggcca gaccaaagag   1920

aagatggtta ccatggtgtc agtgctggag gatctgattg gcaagcttac cagtcttcag   1980

ctgcaacacc tgtttatgat cctggcctca ccaaggtatg tggaccgagt gactgaattc   2040

ctccagcaaa agctgaagca gtcccagctg ctggctttga agaaagagct gatggtgcag   2100

aagcagcagg aggcacttga ggagcaggcg gctctggagc ctaagctgga cctgctactg   2160

gagaagacca aggagctgca gaagctgatt gaagctgaca tctccaagag gtacagcggg   2220

cgccctgtga acctgatggg aacctctctg tgacaccctc cgtgttcttg cctgcccatc   2280

ttctccgctt ttgggatgaa gatgatagcc agggctgttg ttttggggcc tttcaaggca   2340

aaagaccagg ctgactggaa gatggaaagc cacaggaagg aagcggcacc tgatggtgat   2400

cttggcactc tccatgttct ctacaagaag ctgtggtgat tggccctgtg gtctaccagg   2460

cgaaaaccac agattctcct tctagttagt atagcggact taataaaaga ggaaaaaaca   2520

aaaaaaaaaa aaaaaaa                                                  2538
```

```
<210> SEQ ID NO 23
<211> LENGTH: 3872
<212> TYPE: DNA
<213> ORGANISM: Homo sapiens

<400> SEQUENCE: 23

cggacgaggc acgagtgagg ggggaggcgg tggcggcggc cattttgagc cgctgccgcc     60

attggagtgg gccccccccc tttccccctt cgcctcctga caggaaaggt ttaaggggga    120

cagagccctg ggaggccggg ccgggctcgg gggccacccc gggggcccgg gccatggatg    180

tgcgccgtct gaaggtgaac gaacttcgcg aggagctgca gcgccgcggc ctggacactc    240

gaggcctcaa ggccgagctt gctgagcggc tgcaggcggc gttggaggcc gaggagcctg    300

acgacgagcg ggagctcgac gccgacgacg aaccggggcg acccgggcac atcaacgagg    360

aggtcgagac cgaggggggc tccgagctgg aggggaccgc gcagccaccg ccgcccgggc    420

tgcagccgca cgcggagccc ggcggctact cggggccgga cggacattat gccatggaca    480

atattaccag gcagaaccaa ttctacgata cccaagtcat caaacaagaa aacgagtcag    540

gctacgagag gagaccactg gaaatggagc agcagcaggc ctatcgtcca gaaatgaaga    600

cagagatgaa gcaaggagca cccaccagct tcctcccgcc tgaagcttct caactcaagc    660

cagacaggca gcaattccag agtcgaaaga ggccttatga agaaaaccgg ggacgggggt    720

actttgagca ccgagaggat aggaggggcc gctctcctca gcctcctgct gaagaggatg    780

aagatgactt tgatgatacc cttgttgcta ttgacaccta taactgcgac ctccacttca    840

aggtggcccg agatcggagt agtggctatc cgctcacaat tgagggcttt gcatacctgt    900

ggtcaggagc ccgtgccagc tatggggtca gaaggggccg tgtatgcttc gagatgaaga    960

tcaatgagga aatctccgtg aagcaccttc cgtctacaga gcctgacccc cacgtggtcc   1020

gtatcggctg gtccctggac tcctgcagca cccagctagg cgaagagcct ttctcctatg   1080

gctatggagg cactgggaag aagtccacca atagccggtt tgaaaactac ggagacaagt   1140

ttgcagagaa cgatgtgatt ggctgctttg cggattttga atgtggaaat gacgtggaac   1200

tgtcttttac caagaatgga aagtggatgg gcattgcttt ccgaatccag aaggaagcct   1260

tgggggggtca ggccctctat cctcatgtcc tggtgaagaa ttgcgcagtg gagttcaact   1320

tcggacagag agcagagccc tactgttctg tcctcccggg gtttaccttc atccagcacc   1380
```

-continued

```
ttccccttag tgagcgtatc cggggcaccg ttggaccaaa gagcaaggca gaatgtgaga   1440
ttctgatgat ggtgggcctg cctgctgctg gcaagaccac atgggccatc aaacatgcag   1500
cctccaaccc ttccaagaag tacaacatcc tgggtaccaa tgccatcatg gataagatgc   1560
gggtgatggg cctacgccgg cagcggaact atgctggccg ctgggatgtc ctgatccagc   1620
aggccaccca gtgcctcaac cgcctcatcc agattgctgc ccgcaagaaa cgcaactata   1680
tcctagatca gacaaatgtt tatgggtcag cccagagacg aaaaatgaga ccatttgaag   1740
gcttccagcg caaagctatt gtaatttgtc ccactgacga ggacctaaaa gaccgaacaa   1800
taaagcgaac cgacgaggaa gggaaggatg tcccagatca tgcggtctta gaaatgaaag   1860
ccaacttcac gttgccagat gttggggact tcctggatga ggttctgttc attgagctgc   1920
agcgggagga agcggacaag ctagtgaggc agtacaacga ggaaggccgc aaggctgggc   1980
cacccccctga aaagcgcttt gacaaccgag gtggtggtgg cttccggggc cgcgggggtg   2040
gtggtggctt ccagcgctat gaaaaccgag gacccccctgg aggcaaccgt ggcggcttcc   2100
agaaccgagg gggaggcagc ggtggaggag gcaactaccg aggaggtttc aaccgcagcg   2160
gaggtggtgg ctatagccag aaccgctggg gtaacaacaa ccgggataac aacaactcca   2220
acaacagagg cagctacaac cgggctcccc agcaacagcc gccaccacag cagcctccgc   2280
caccacagcc accaccccag cagccaccgc caccacccag ctacagccct gctcggaacc   2340
ccccagggggc cagcacctac aataagaaca gcaacatccc tggctcaagc gccaatacca   2400
gcaccccccac cgtcagcagc tacagccctc cacagccgag ttacagccag ccaccctaca   2460
accagggagg ttacagccag ggctacacag ccccaccgcc tccacctcca ccaccacctg   2520
cctacaacta tgggagctac ggcggttaca acccggcccc ctatacccca ccgccacccc   2580
ccactgcaca gacctaccct cagcccagct ataaccagta tcagcagtat gcccagcagt   2640
ggaaccagta ctatcagaac cagggccagt ggccgccata ctacgggaac tacgactacg   2700
ggagctactc cgggaacaca cagggtggca caagtacaca gtagccagtg tgacccagag   2760
gctcccggag gcccctgccg gcttcctcca ccagcgcctg cctcggcccc tcctctgccc   2820
ccgccagatc ccgtggtgct ggggatgggg tcatcccagg gctgcctccc tccagcccac   2880
tgcctcccct ctgaggggct tccttcccct ccatagggcc aggcattttt ttctggattc   2940
aaacaggcaa caatgacctt ttattttctg tttgtcccca cctccccagc cttccacctc   3000
ctgttcttcc taccttcttc ctttttgact aaataatccc cacctccctt gatcatacag   3060
tgaggctaca gtgactgagg ggagaatccc ctcctgttca ctctcccaac cctgctccag   3120
cccctcagct tcccagaccc tcatgcagtt ggttgtaaat tctcccagga gctgttttac   3180
tgtctacttt tcaggattaa aaaaaaaatc aaaacttaaa aaaaaaaaag tttaaaaagc   3240
aaaatgggga gggggaggaa gcagtgactt ttttttggta attatgcgct tttttttaat   3300
ttttagaatt tgtcttttta ctgtgggtgg gctgttgata tttcatcaag ataagcattt   3360
ctttcctgag ttcaggtgac tgaggaagag ccacaaaaca aaacacaaca aaaccaaacc   3420
acagaatcat ctttaaccca actttttata cgatgcccca gttccccata actttgcaca   3480
caagcttctg tgttcagttg aattgtaact gctttttgta tttggagaga gtgactattg   3540
aacttgaaac cttttattcc gggcgtcttg gtagtttctg gtgggattca gtgggtgaga   3600
gggaagaagg ggaggttggg gggctccttc ccttcagaac ttgaagtttc tcccactgcc   3660
tcctctccag tggtctccca ggtgccagac ccaaaagctt ttcctacagt gatacccttt   3720
atttttactt ccccttgact catatgtttt aacatgattt taacaaactg cacttattaa   3780
```

-continued

```
gaaatgtgtt tgccctgttt tgtttggttt cgttttgttt tctttgaata aatgacatgg   3840

cacctcctag caggaaggaa gcagggttga aa                                 3872
```

<210> SEQ ID NO 24
<211> LENGTH: 4207
<212> TYPE: DNA
<213> ORGANISM: Homo sapiens

<400> SEQUENCE: 24

```
gcagggcagg agctgagtac acacacactc ggagggcggg cacctcctct ccaccccccac    60

cccaatcttt ctggatccag ggggcatgtg aggaggggct ctgctaggac ctgtgccctg   120

ggctccagtc accccagcat ccggtgggca ggtttcccac cacccaaccc gagggcttgg   180

catctgtgag cccacatcct gcagcagggg ccccctctgg ctctccggcc agctagggga   240

cacccgggcc ctcctctgca taccccccta ccacgtcgcc tccgaacttg gatggccagg   300

atggggtccc gcggctctct gctcctcgtg gaagcaggga tctcgctact gggctagcgt   360

gggatacaag aggccctggg gagaatgcct ggaggagcca gcggctgcgg gtgcgcaaag   420

ggcccgctct agctcagccg ccgccgctcc gcagtatgac cagtggacca tctccaaggc   480

ctgcgggaaa aacttgcctt tgcgactggc gcactgccgc agcaccatgg aggtggtgcg   540

ggagaagctg cgcaagtacg tcttcgaccg cgtgaacatg cacaacctac tgatccacct   600

ggtgcggcgg cgcgggcaga agctggagag catgcagctg gagctggaca gcctgcggag   660

ccagcccgac gccagcaagg aggagctgcg gctgctgcag atcatccgcc agctggagaa   720

caacatcgag aagacaatga tcaagatcat caccagccag aacatccacc tgctgtattt   780

ggacctgctg gattatctga agacagtgct ggcaggatac cccattgagc tggacaagct   840

gcagaacctc gtggtcaact actgctcaga gctgtcggat atgaagatca tgtcccaaga   900

tgccatgatg atcacggatg aggtcaagag gaacatgagg caaagggagg cgtccttcat   960

cgaggagcgc cgggcaaggg agaaccggct caaccagcag aagaagctga tcgacaagat  1020

ccacacgaag gagaccagcg agaagtaccg ccggggccag atggacttgg acttcccctc  1080

gaacctgatg agcacggaga ccctgaaatg acatcactag ccgcttcctg gcccagagga  1140

acacggagga gaacctggag ctgcagatgg aggactgtga ggagcggcgg gtgcagctga  1200

aggccctggt gaagcagctg gagctggagg aggccgtgct caagttccgc cagaagccta  1260

gctccatcag gtgccccggg cttccggggc tgcgggccac ccaccccagt ctcacaaagg  1320

ccccgggctg cagccaggct gggagctggg agtataccca ctgccaacaa gcctgtgtgt  1380

cccacagagg ggccagggga ctccacttgc acacacctga gcttctgagt ccctgattct  1440

ggcacagcac ccaactcagg actgggctcc tgggtggccc accatggctc tcgggcctgt  1500

gcccctcact gctgtgtccc tattgccttc tgcagcttca agtccgttga gaagaaaatg  1560

acagacatgc taaaagagga agaagagagg ctccagctgg cgcacagcaa catgaccaag  1620

ggccaggagc tgctgctgac catccagatg ggcatcgaca acctctatgt ccggctgatg  1680

ggcattacct tgcctgcgac ccagagagaa gtggtgctct ccaacaccct cgatttgaac  1740

agcaagctgg cgtactgcga ggggaagctc acgtacctgg ctgacagagt gcagatggtg  1800

tccaggaccg aggagggcga cacaaaggtg agggacaccc tggagtcctc gactctgatg  1860

gagaagtaca acaccaggat cagctttgag aaccgggagg aggatatgat cggactgctg  1920

cggacgctgg ggcgaccggg gtctcggaga ggagcacggg acacgcagga tcgggggagg  1980
```

-continued

```
ttctgcgtaa ggaggcagcc cgggcccgga actgcgcgcc agaaccgcgt gcgcatgcgc   2040
cgaccgcgcg cgccgcgccc ccgcggccct cgcggcgccc cgtagccgcg cacccctccc   2100
gtcccgccga gccggcgcca agatggcggc gctgactcct ggagagcggt cgcgccggag   2160
gccgcggggg ccggagcgga gcagccgcgg ctgaggttcc cgagtcgccg ctcggggctg   2220
cgctccgccg ccgggacccc ggcctctggc cgcgccggct ccggcctccg ggggggccgg   2280
ggccgccggg acatggtgcc agtcgcaccc cttccccgcc gccgctgagc tcgccggccg   2340
cgcccgggct gggacgtccg agcgggaaga tgttttccgc cctgaagaag ctggtggggt   2400
cggaccaggc ccccggccgg gacaagaaca tccccgccgg gctgcagtcc atgaaccagg   2460
cgttgcagag gcgcttcgcc aagggggtgc agtacaacag tgagtgcggc gggccggggg   2520
ggcgcgggag cgccgcgcgg gtctccgaac ccaggccccg ggcgccgcgc ggtggtgggt   2580
gtcggtctca cctgcttgcc ggttgtgggg tgcgctgggc ccgccgggtg ctccgggagc   2640
gggggcgcgg gccaggggac gcgaggagag gccaggccag ggccgggtcc tcgcggcccc   2700
cgagccgcgg gtcgtttccc agccgcactc gcctgccgcg tgtcgctccc gccgcgctgt   2760
gcagtggagc gggtcggcgg cggcggggtt ggcccggctg cccggcccgg gggtgattac   2820
ataatgccaa gcagggcccg ccggcccggg gcgccgcgcc cccgacgctc cacggtgccc   2880
agccccgggc accactcacc tgcaggaggt gcggggaacc cagccggcct tggcgctttc   2940
agcgggattt ttctttgttg acttcctact gagtttgaag acagaatatt agctacgcca   3000
cacattctcg cctttttttt aaaagaagcg tttgtaagag acgtatctag aaaagctcca   3060
gaaggcacgg gctgacttgc gactgtagga gacatcccat ttctcgtagg aaggaggagt   3120
catttacgga ctcctgagtg cctgggacgc tccattcctt tgttataaat tgtgtaaatt   3180
gtcctcgacc tcttatgagt ttttccatct tgcgggctct ttcccagtag tttttgaaag   3240
cttttatgtg gttccctgtt ttgacattgc ttccctctta gccatttccg tatgtttcta   3300
tgaggtttta ggacgctacg cctatccagt tttttggtca ctttaagggg agccttagag   3360
cctccgtgat atttccatgg taatgtagaa ttttaagaac taatgatcag aaagactctt   3420
gtgcaggttt aaaagcaagt tcatgaattc gcgtgccgtg tgcacggaga gaggccgtag   3480
ttcctggggc tggagctagt ccaggaggac agtgaagatg tcgccttcct tagtccccccg  3540
gcctgtgagc aagaggaagc tgcagaccac tcgggccacc ctcacccaga cacctttagc   3600
agtaagcaag ataaaacaac ttcttaaaga taagtctgag catctaggta tgaaagttgg   3660
tgtccgggcc gggcacggtg gctcatgcct gtaatcccag cactttggga ggccaaggcg   3720
ggcagatcac gaggtcagga attcgagacc agcctggcca acatagtgaa acaccgtctc   3780
tactaaaaat acgaaaaaaa aatttaaaag aaagttgatg tccgaaccaa gggccgtatt   3840
ggcttttctt atactctaga acatacgacg acaaagaaga ttttgatgaa gttcaaatta   3900
gagtcagcgt gctcatcaga aagaaagcgc agccaacacg tttaggaaca gaaacggatt   3960
atgttgaaga caaacaatcc attgcgtttg tgttcagtaa cccaagcatc aaaggaactt   4020
gtggctgggg agaaggcttg actatttgaa atctcaggac tcctctgtcc aggagctccc   4080
agactcccgt ggagtggaag cctgggggct cgctgaagaa gtcacgtgac tggaacgtgc   4140
ttaatgcttg gctgtctggt aaggaaaata aagtggtgca ttttgaataa aaataaaagc   4200
tgatttt                                                              4207
```

<210> SEQ ID NO 25
<211> LENGTH: 4109

-continued

<212> TYPE: DNA
<213> ORGANISM: Homo sapiens

<400> SEQUENCE: 25

```
gttcccgcag gggtgctggg cccctgcggc tcccaccaca ttgcgctgga ctcttgtggc      60

ccgtgctgac ctggtgttcc agatgctgtc tctgcagagc tctgcgtggt ctctggtgtt     120

agagaggtgg ccacccaccg ccctatcatt gtcctcatcc ccactgtgag gagaagctat     180

cagatctgcc tgtggccccc aggtggctca ggaagggccg tcctgacccc catcctggcc     240

cctttcggag ctgcagagat ttcctgtgcc tccagctctg gcttcctggg tctgtccttg     300

gcgtggagcg ggcacaggct tcccgtagac acggttgccc agagtggggt tcataactgg     360

gcactgtaaa gggtgtggtc tccacggctt aggatgggcc ccccttcct ggtggcctgc      420

tgtgcccggg gctggtgtgg aggcctgtgg gggtgcagag gccgcccggc cctgggcttc     480

ctctggggtt acatgtgtac ccttgcaccc acctgttagc acccaccggg agagtctcac     540

tcagcctaaa ccagggcccc tcaggaggaa aaggtcccca gcttcatgat ggggcccagt     600

gtgccttcca tccccgccct gactcagtgc ccactgtgcg aggtgtgagc actgtccaca     660

gcagccaggg cggccggtgg ggagtgcatt ggaggggggtt gaggtctctt gggcacctgg     720

tgagttctca agggtgagag gaagccgagg ccatcaggct tagctgacgc tgcatggggc     780

aggctgccaa gagggaggct gaatggagca gcctcaggtg agccgacaat cctcacctcc     840

gcctggtcag ccaggacccg gctcccctcc agtcccgcct gctttcccca aagcagatcc     900

agccagtctc aatggctcgc ccggggggtg ctggttaggc tgtgagcatc cttcctgggt     960

gcaggccccc gacagccagc agtgctgtgc tgtgtgtgtg ttggggactc tgctgagccc    1020

tttgtggcca gactggggag gctcctccgg gctggctctg tcccctgtac cttgtgaggg    1080

aggggctgac cccctgactg ggttacatcg tggtgagcag ttcagaaaca agctgtggaa    1140

tgaagtggac gtggcgtttt aaacacatga gccccatctg ttcttagggg ttttgtttgt    1200

tgtcccagtc cgtgactcca agactgggac ccccagagtt cccaggatgg tctggagcct    1260

ttatcctcag gtcagcattg tggagttaaa gggaggggac cacggcccct cattctcagg    1320

agagccatgg tgaccttgat ggcggaggct caggggggacc tggaccgtgg acaccacaca    1380

gctgccctcc tccctcccga ggccatttca gggctggaat ccctgccccc ctctcctttc    1440

ctcccgggct ggttgttgcc ttgagagtcc gtgcgctcat ctccccactt ttaccccagg    1500

gggaggcccc tcaccttccc accatatccc ttgtacttcc tcccaccctg gacttggggg    1560

agctgggggg agggggccct tccttcagca gcaaaccctc ctggtgtagg gctgtaggcc    1620

atcccaccgc agcctgtcca ggagctgctg agcctgtcag ccccaactag cacctcctgt    1680

ccaggcccgg cccagccctg cctccagagc ctacagaggg gcctcgccca ggtcctgctg    1740

ctccagagct tgtgggtgcc cacgctgcag gctgtttggg gtggtggagt agagcacccg    1800

ctggagctgg gggctgagtg gccatggggg gaccatgctc ctcctatggc ccaaggccca    1860

ggggttccac ctcgtaattt ttgtttgttt ttaaataagg aaaatgcaaa aagcgaggcg    1920

acggcttaaa gatggagaac gacccccagg aggcggagtc tgaaatggcc ctggatgctg    1980

agttcctgga cgtgtacaag aactgcaacg ggtggtcat gatgttcgac attaccaagc     2040

agtggacctt caattacatt ctccgggagc ttccaaaagt gcccacccac gtgccagtgt    2100

gcgtgctggg gaactaccgg gacatgggcg agcaccgagt catcctgccg gacgacgtgc    2160

gtgacttcat cgacaacctg gacaggtggg tgcggtggcc ctgctcccga gggaccctgc    2220
```

-continued

```
ccggtgctcc ggtgtgcggg ggagggtgct gaggcagagg cccagggagg ggttaacgtt   2280

agcatggggc ccggcggatg tgggtctcgc cgctgagtgg ggctcactga agcctgggtc   2340

tccccgatgg cagggccggg aactgtgtgc tggggaactg tgtgccaggg tgaagtgctg   2400

gcactgtggg gtcacctgca gaagggcact cggcttagct gcttagcagg gctcagcagg   2460

gtcctgtggc ctcaggagcc tgcaggagga gggagggcag tgcggaccca cagctgtggg   2520

cccaggggtg atccttggca ccagggcaag ggtctttctc ttgcatcttt tttcctttct   2580

gaaagcagac ctccaggttc ctcctacttc cgctatgctg agtcttccat gaagaacagc   2640

ttcggcctaa agtaccttca taagttcttc aatatcccat ttttgcagct tcagagggag   2700

acgctgttgc ggcagctgga gacgaaccag ctggacatgg acgccacgct ggaggagctg   2760

tcggtgcagc aggagacgga ggaccagaac tacggcatgt atgtggcggg acccgcccgt   2820

gcgggcggtg tgggggctgc gggcgtggcc gtggtgcagg gccatgggct gcaccaagga   2880

gacagcagag gggagtgtcc cctgtttggg gtaaattagt cacctttggg cacgggtgga   2940

ggaggactca ggtttgcact gcccccagca gccccccccac agtcacccct ggcgtggact   3000

cctcatacag gtcatgctgt gcctgccact ctgagtaccg ctgaccgtgg ccaggtgctg   3060

gtgctcatgg agtgctgctg ggctgcctg cccatcaggg gcttggcctc ccagattgat   3120

gccagcatgg ggtgtgcttt ctggggagct gcttgacttt gggaagctcc ctgtgttgaa   3180

gaggcataca ggccaggaca tggaggtctc tggtcctcga cagcagaggg aggctcagag   3240

catcctcctg agtgggcctg ggcagtgcat agccccgggg ttgcggccag tgggacagct   3300

ggcccgttct ctgcctcagg ctcctgtaca gctaggggct tggtgcctcc cctgggaccc   3360

aggcagggac cacggaatca gtggccctcc tgaggccccc caggaggtct ctgtttccag   3420

aaggagagcc ctgtgggtca ccttggatct ggctgttggc tcagacacag caagagaccg   3480

agagggaagg cagtttgatg cctggagagg gacccgtggc ttccagctgc caggccagcc   3540

ccagaatgga gcccccgca tgggcgcttc tctgttgaac caatcctggc atttcctggg   3600

cctgagagtt gggtcaagct gaatgctgcg atggccgcac gtgctccacc aagccccagc   3660

cccctcctct tcccagaaac ccccgctcac gggaaggtcc agttgcttgc catctggcca   3720

cctctgcatg gagcccccaa cagctgtgcc tcagaacaga tccgaagtga ctttcagggg   3780

agctggacac atgtacgctg gtgcctgctg tccccaccct ttggcactgc tgctctttct   3840

ttttctgaga tggagtctcg ctctgtcgcc caggctggag cgcagtggtg tgatctcggc   3900

tcaccgcaag ctccgcctcc cgggttcacg ccattctcct gcctcagcct cccagctact   3960

ggggaggctg aggcagggga attgcttgaa cccgggaggc agaggttatc gtgagctgac   4020

attgcgccac tgcactccag cgcggaagac agagtgagca aaaaaaaaaa aaaaaaaaga   4080

aaaagtgacc aaaaaaaaaa aaaaaaaaa                                     4109
```

<210> SEQ ID NO 26
<211> LENGTH: 1892
<212> TYPE: DNA
<213> ORGANISM: Musca domestica

<400> SEQUENCE: 26

```
gtttgtttcg gaactgaggc tcaagcacag ccgctcagga ttggtgctag gctgggccgg     60

ggtctttggc cggaagcgga agtggagaaa ggatgcagga ccatcagcac gtgcccatcg    120

acatccagac cagcaagctg ctcgactggc tggtggacag aagacactgt aacctaaaat    180

ggcagagcct ggtgctgacc atccgggaaa aaatcaacac tgccatccag gacatgccag    240
```

-continued

```
agagccagga gattgcccag ctgctctctg gatcctacat tcattacttc cactgcctaa    300

gaatagtgga ccttcttaaa ggcaccgagg cgtccaccaa aaatattttt ggccggtact    360

cttcacaacg gatgaaagat tggcaggaga tcgtaagcct gtatgagaag gacaacacct    420

atttagtgga actctgtagc ctcctggttc ggaatgtcag ctatgagatc cctcgctga     480

agaagcagat tgccaagtgc cagcaactgc agcaagaata cagccgcaag gaggaggagg    540

gccaggctgg ggccgctgag atgcgagagc aattctacca ctcctgcaaa cagtatggca    600

tcacgggaga caatgtccga agagaacttc tggccctggt gaaggacctg ccaagtcagc    660

tggctgagat aggggcaggg gctcagtccc tgggggaggc cattgacctg taccaggcct    720

gtgtggagtt tgtgtgtgac agccccacag agcaagtgct gcccatgctg cggtatgtgc    780

agaagaaggg aaactcgacg gtgtatgagt ggaggacggg gacagagccc tctgtggtgg    840

agcgaccaca gctggaggag cctcctgagc aggtgcaaga ggatgagatc gactggggtg    900

actttggggt ggaagctgtt tccgactctg gcatcgttgc tgagactcct ggaatagact    960

ggggtatctc cctggagtca gaggccaagg atgctggggc tgacaagata gactggggtg   1020

acgatgctgc tgctgcttca gagatcaccg tgctggagac aggaactgag gctccggagg   1080

gtgtagctcg gggctcagac gctctgactc ttctggaata ccctgaaact cggaatcagt   1140

tcattgatga gctcatggag cttgagatct tcttgtctca gagagcagta gagatgagcg   1200

aggaggccga catcctgtcc gtgagccagt tccagctggc tcctgccatc ctccagggcc   1260

agaccaaaga gaagatgctc agcctggtgt ccacgctgca gcagctgatc ggccggctca   1320

ccagtctgcg gatgcagcac ctgtttatga ttctggcctc gccaaggtat gtggaccgag   1380

tgacagagtt cctccagcag aagctgaagc agtcgcagct gttggctttg aagaaggagc   1440

tgatggtgga gaagcagcag gaggcgcttc aggagcaggc agctctggag cccaagctgg   1500

acctgctgct ggagaagacc agagagctgc agaaactgat tgaagccgac atctccaaga   1560

gatacagtgg ccgtcctgtg aacctgatgg ggacctctct gtgacgcgct ccctctgtgt   1620

cctccaccct ccttcccagc taccaggagg aggtgggaca gcccaggctg atgctactgg   1680

gcctcaccag caagaagtca ggcggacttg gagacagagc catgaggaag ggtcacacca   1740

tgatctctgc aagcagttgt cttgagtggc tctggcctgt cagccttaag gcacacttgc   1800

tgcttctagt tgtcaagtga ggcttaataa aaggaagtga ctctccttcg tggctggcag   1860

tcacttgcac caccaaaaaa aaaaaaaaaa aa                                 1892


<210> SEQ ID NO 27
<211> LENGTH: 1865
<212> TYPE: DNA
<213> ORGANISM: Musca domestica

<400> SEQUENCE: 27

cggcacgagc tgaattgagg ctcaggcacg ccggctcagg attggtgctg ggccgggccg     60

gggtctttgg ccggaagtgg aaaaaggatg caggaccatc agcacgtgcc catcgacatc    120

cagaccagca agctgctcga ttggctggtg gacagaagac actgcaactt aaaatggcaa    180

agcctggtgc tgaccatccg ggaaaagatc aacaccgcca tccaggacat gccagagagc    240

caagagattg cccagctgct ctctggttcc tacatccact acttccactg cctaagaata    300

gtggaccttc ttaaaggtac cgaggcttcc accaaaaata tttttggccg ctactcttca    360

cagcggatga aggattggca ggagatcata agcctgtatg agaaggacaa cacctattta    420
```

-continued

```
gtggaactct ctagcctcct ggttcggaat gtcaactatg agatcccctc tctgaagaag    480
cagattgcca agtgccagca actgcagcaa gactacagcc gcaaggagga ggagggccag    540
gctggggctg ctgagatgcg agagcagttc taccactcct gcaaacagta cggcatcacg    600
ggagacaatg tccgacgaga gcttctggcc ctggtgaagg acctgccaag tcagctggct    660
gagataggag cgggagctca gtccctgggg gaagccatcg acctgtacca ggcctgtgtg    720
gagtttgtat gtgacagccc cacagagcag gtgctgccca tgctgcggta cgttcagccg    780
aagggaaact ccacggtgta tgagtggagg acagggacag agccctctgt ggtagagcgg    840
ccacaactgg aggaccctcc cgagcaggtg caagaagacg agatcgactg ggcgactttt    900
ggcctggagg ctgtttctga ctctggaaac atcatctctg ctgagacccc tgggatagac    960
tggggtatct ccctggagtc agagtccaag gatgctgggg ctgacaagat agactggggt   1020
gacaatgctg ttgcttcgga gatcaccgtg ctggagacag gaacggaggc tccagagggt   1080
gttgctaggg gctcagacgc tctgactctc cttgaatacc ctgagactcg gaatcagttc   1140
atcgatgagc tcatggagct tgagatcttc ttgtctcaga gagcagtaga gatgagtgag   1200
gaggctgaca tcctgtccgt gagccagttc cagctggctc ctgccatcct tcagggccag   1260
accaaggaga agatgctcag cctggtgtcc acactgcagc atctgattgg ccagctcacc   1320
agtctggacc tgcagcacct gtttatgatt ctggcctcac cgaggtatgt ggaccgggtg   1380
acagagctcc tccagcagaa gctgaagcag tcccagctgt tggctctgaa gaaggacctg   1440
atggtggaga agcagcagga ggcgcttcag gagcaggcag cgctggagcc caagctggac   1500
ctgctgctgg agaagaccag agagctgcag aagctgattg aagctgacat ctccaagaga   1560
tacaacggcc gtcctgtgaa cctgatgggg acctctgtgt gacgtgctgg ccctgtgtcc   1620
gccaccagcg gcctggtggg ggtggacagc ccaggctggt attgctggac ctcaccagca   1680
agaagccagc agaggtggag cagagccaca aggaagcacc tgagtggtgg caccagcatt   1740
cattgtgacc tatgcaagaa gtctgagtgg ctctgtggat ctaagcctaa ggcacagttg   1800
cttcttctgg ttatcaagga aggcttaata aaaaaaggaa gtgactcctc aaaaaaaaaa   1860
aaaaa                                                               1865
```

<210> SEQ ID NO 28
<211> LENGTH: 1841
<212> TYPE: DNA
<213> ORGANISM: Homo sapiens

<400> SEQUENCE: 28

```
ggcacgaggg aaagatggag gaccatcagc acgtgcccat cgacatccag accagcaagc     60
tgctcgattg gctggtggac agaaggcact gcagcctgaa atggcagagt ctggtgctga    120
cgatccgcga gaagatcaat gctgccatcc aggacatgcc agagagcgaa gagatcgccc    180
agctgctgtc tgggtcctac attcactact ttcactgcct aagaatcctg gaccttctca    240
aaggcacaga ggcctccacg aagaatattt ttggccgata ctcttcacag cggatgaagg    300
attggcagga gattatagct ctgtatgaga aggacaacac ctacttagtg gaactctcta    360
gcctcctggt tcggaatgtc aactatgaga tcccctcact gaagaagcag attgccaagt    420
gccagcagct gcagcaagaa tacagccgca aggaggagga gtgccaggca ggggctgccg    480
agatgcggga gcagttctac cactcctgca agcagtatgg catcacgggc gaaaatgtcc    540
gaggagaact gctggccctg gtgaaggacc tgccgagtca gctggctgag attggggcag    600
cggctcagca gtccctgggg gaagccattg acgtgtacca ggcgtctgtg ggtttgtgt     660
```

-continued

```
gtgagagccc cacagagcag gtgttgccaa tgctgcggtt cgtgcagaag cggggaaact    720
caacggtgta cgagtggagg acagggacag agccctctgt ggtggaacga ccccacctcg    780
aggagcttcc tgagcaggtg gcagaagatg cgattgactg gggcgacttt ggggtagagg    840
cagtgtctga ggggactgac tctggcatct ctgccgaggc tgctggaatc gactggggca    900
tcttcccgga atcagattca aaggatcctg gaggtgatgg gatagactgg ggagacgatg    960
ctgttgcttt gcagatcaca gtgctggaag caggaaccca ggctccagaa ggtgttgcca   1020
ggggcccaga tgccctgaca ctgcttgaat acactgagac ccggaatcag ttccttgatg   1080
agctcatgga gcttgagatc ttcttagccc agagagcagt ggagttgagt gaggaggcag   1140
atgtcctgtc tgtgagccag ttccagctgg ctccagccat cctgcagggc cagaccaaag   1200
agaagatggt taccatggtg tcagtgctgg aggatctgat tggcaagctt accagtcttc   1260
agctgcaaca cctgtttatg atcctggcct caccaaggta tgtggaccga gtgactgaat   1320
tcctccagca aaagctgaag cagtcccagc tgctggcttt gaagaaagag ctgatggtgc   1380
agaagcagca ggaggcactt gaggagcagg cggctctgga gcctaagctg gacctgctac   1440
tggagaagac caaggagctg cagaagctga ttgaagctga catctccaag aggtacagcg   1500
ggcgccctgt gaacctgatg ggaacctctc tgtgacaccc tccgtgttct tgcctgccca   1560
tcttctccgc ttttgggatg aagatgatag ccagggctgt tgttttgggg cccttcaagg   1620
caaaagacca ggctgactgg aagatggaaa gccacaggaa ggaagcggca cctgatggtg   1680
atcttggcac tctccatgtt ctctacaaga agctgtggtg attggccctg tggtctacca   1740
ggcgaaaacc acagattctc cttctagtta gtatagcgga cttaataaaa gaggaaaaac   1800
caaaaaaaaa aaaaaaaaaa aaaaaaaaaa aaaaaaaaaa a                       1841
```

<210> SEQ ID NO 29
<211> LENGTH: 1892
<212> TYPE: DNA
<213> ORGANISM: Homo sapiens

<400> SEQUENCE: 29

```
gtttgtttcg gaactgaggc tcaagcacag ccgctcagga ttggtgctag gctgggccgg     60
ggtctttggc cggaagcgga agtggagaaa ggatgcagga ccatcagcac gtgcccatcg    120
acatccagac cagcaagctg ctcgactggc tggtggacag aagacactgt aacctaaaat    180
ggcagagcct ggtgctgacc atccgggaaa aaatcaacac tgccatccag gacatgccag    240
agagccagga gattgcccag ctgctctctg gatcctacat tcattacttc cactgcctaa    300
gaatagtgga ccttcttaaa ggcaccgagg cgtccaccaa aaatattttt ggccggtact    360
cttcacaacg gatgaaagat tggcaggaga tcgtaagcct gtatgagaag gacaacacct    420
atttagtgga actctgtagc ctcctggttc ggaatgtcag ctatgagatc ccctcgctga    480
agaagcagat tgccaagtgc cagcaactgc agcaagaata cagccgcaag gaggaggagg    540
gccaggctgg ggccgctgag atgcgagagc aattctacca ctcctgcaaa cagtatggca    600
tcacgggaga caatgtccga agagaacttc tggccctggt gaaggacctg ccaagtcagc    660
tggctgagat aggggcaggg gctcagtccc tgggggaggc cattgacctg taccaggcct    720
gtgtggagtt tgtgtgtgac agccccacag agcaagtgct gcccatgctg cggtatgtgc    780
agaagaaggg aaactcgacg gtgtatgagt ggaggacggg gacagagccc tctgtggtgg    840
agcgaccaca gctggaggag cctcctgagc aggtgcaaga ggatgagatc gactggggtg    900
```

-continued

```
actttggggt ggaagctgtt tccgactctg gcatcgttgc tgagactcct ggaatagact    960

ggggtatctc cctggagtca gaggccaagg atgctggggc tgacaagata gactggggtg   1020

acgatgctgc tgctgcttca gagatcaccg tgctggagac aggaactgag gctccggagg   1080

gtgtagctcg gggctcagac gctctgactc ttctggaata ccctgaaact cggaatcagt   1140

tcattgatga gctcatggag cttgagatct tcttgtctca gagagcagta gagatgagcg   1200

aggaggccga catcctgtcc gtgagccagt tccagctggc tcctgccatc ctccagggcc   1260

agaccaaaga gaagatgctc agcctggtgt ccacgctgca gcagctgatc ggccggctca   1320

ccagtctgcg gatgcagcac ctgtttatga ttctggcctc gccaaggtat gtggaccgag   1380

tgacagagtt cctccagcag aagctgaagc agtcgcagct gttggctttg aagaaggagc   1440

tgatggtgga gaagcagcag gaggcgcttc aggagcaggc agctctggag cccaagctgg   1500

acctgctgct ggagaagacc agagagctgc agaaactgat tgaagccgac atctccaaga   1560

gatacagtgg ccgtcctgtg aacctgatgg ggacctctct gtgacgcgct ccctctgtgt   1620

cctccaccct ccttcccagc taccaggagg aggtgggaca gcccaggctg atgctactgg   1680

gcctcaccag caagaagtca ggcggacttg gagacagagc catgaggaag ggtcacacca   1740

tgatctctgc aagcagttgt cttgagtggc tctggcctgt cagccttaag gcacacttgc   1800

tgcttctagt tgtcaagtga ggcttaataa aaggaagtga ctctccttcg tggctggcag   1860

tcacttgcac caccaaaaaa aaaaaaaaaa aa                                 1892


<210> SEQ ID NO 30
<211> LENGTH: 482
<212> TYPE: PRT
<213> ORGANISM: Homo sapiens

<400> SEQUENCE: 30

Ala Thr Pro Phe Gln Lys Phe Arg Met Asn Gly Asp Met Pro His Val
1               5                   10                  15

Pro Ile Thr Thr Leu Ala Gly Ile Ala Ser Leu Thr Asp Leu Leu Asn
            20                  25                  30

Gln Leu Pro Leu Pro Ser Pro Leu Pro Ala Thr Thr Thr Lys Ser Leu
        35                  40                  45

Leu Phe Asn Ala Arg Ile Ala Glu Glu Val Asn Cys Leu Leu Ala Cys
    50                  55                  60

Arg Asp Asp Asn Leu Val Ser Gln Leu Val His Ser Leu Asn Gln Val
65                  70                  75                  80

Ser Thr Asp His Ile Glu Leu Lys Asp Asn Leu Gly Ser Asp Asp Pro
                85                  90                  95

Glu Gly Asp Ile Pro Val Leu Leu Gln Ala Val Leu Ala Arg Ser Pro
            100                 105                 110

Asn Val Phe Arg Glu Lys Ser Met Gln Asn Arg Tyr Val Gln Ser Gly
        115                 120                 125

Met Met Met Ser Gln Tyr Lys Leu Ser Gln Asn Ser Met His Ser Ser
    130                 135                 140

Pro Ala Ser Ser Asn Tyr Gln Gln Thr Thr Ile Ser His Ser Pro Ser
145                 150                 155                 160

Ser Arg Phe Val Pro Pro Gln Thr Ser Ser Gly Asn Arg Phe Met Pro
                165                 170                 175

Gln Gln Asn Ser Pro Val Pro Ser Pro Tyr Ala Pro Gln Ser Pro Ala
            180                 185                 190

Gly Tyr Met Pro Tyr Ser His Pro Ser Ser Tyr Thr Thr His Pro Gln
```

```
        195                 200                 205

Met Gln Gln Ala Ser Val Ser Ser Pro Ile Val Ala Gly Gly Leu Arg
    210                 215                 220

Asn Ile His Asp Asn Lys Val Ser Gly Pro Leu Ser Gly Asn Ser Ala
225                 230                 235                 240

Asn His His Ala Asp Asn Pro Arg His Gly Ser Ser Glu Asp Tyr Leu
                245                 250                 255

His Met Val His Arg Leu Ser Ser Asp Asp Gly Asp Ser Ser Thr Met
            260                 265                 270

Arg Asn Ala Ala Ser Phe Pro Leu Arg Ser Pro Gln Pro Val Cys Ser
        275                 280                 285

Pro Ala Gly Ser Glu Gly Thr Pro Lys Gly Ser Arg Pro Pro Leu Ile
    290                 295                 300

Leu Gln Ser Gln Ser Leu Pro Cys Ser Ser Pro Arg Asp Val Pro Pro
305                 310                 315                 320

Asp Ile Leu Leu Asp Ser Pro Glu Arg Lys Gln Lys Lys Gln Lys Lys
                325                 330                 335

Met Lys Leu Gly Lys Asp Glu Lys Glu Gln Ser Glu Lys Ala Ala Met
            340                 345                 350

Tyr Asp Ile Ile Ser Ser Pro Ser Lys Asp Ser Thr Lys Leu Thr Leu
        355                 360                 365

Arg Leu Ser Arg Val Arg Ser Ser Asp Met Asp Gln Gln Glu Asp Met
    370                 375                 380

Ile Ser Gly Val Glu Asn Ser Asn Val Ser Glu Asn Asp Ile Pro Phe
385                 390                 395                 400

Asn Val Gln Tyr Pro Gly Gln Thr Ser Lys Thr Pro Ile Thr Pro Gln
                405                 410                 415

Asp Ile Asn Arg Pro Leu Asn Ala Ala Gln Cys Leu Ser Gln Gln Glu
            420                 425                 430

Gln Thr Ala Phe Leu Pro Ala Asn Gln Val Pro Val Leu Gln Gln Asn
        435                 440                 445

Thr Ser Val Ala Ala Lys Gln Pro Gln Thr Asn Ser His Lys Thr Leu
    450                 455                 460

Val Gln Pro Gly Thr Gly Ile Glu Val Ser Ala Glu Leu Pro Lys Asp
465                 470                 475                 480

Lys Thr


<210> SEQ ID NO 31
<211> LENGTH: 163
<212> TYPE: PRT
<213> ORGANISM: Homo sapiens

<400> SEQUENCE: 31

Met Ala Cys Leu Arg His Ser Cys Leu Lys Pro Arg Pro Trp Ala Pro
1               5                   10                  15

Ala Gln Ala Gln Gly Leu Gly Pro Glu Pro His Ser Ala Arg Pro His
            20                  25                  30

Pro Pro His Leu Gly Pro Phe Val Gly Tyr Ser Leu Arg Pro His Pro
        35                  40                  45

Asp Leu Leu Lys Glu Arg Pro His Gly Lys Asp Ser Ala Thr Cys Ser
    50                  55                  60

Phe Ile Ser Pro Gln Trp Val Pro Arg His Glu Asp His Arg Leu Glu
65                  70                  75                  80

Ala Glu Leu Ala Gly Thr Cys Leu Gln Pro Leu Leu Thr Pro Ala Gly
```

-continued

```
                85                  90                  95

Pro Cys Leu Arg Gly Ser Thr Gln Asp Val Ala Met Thr Arg Gly Leu
            100                 105                 110

His Ser Ile Pro Leu Leu Gln Glu Pro Cys Lys Val Ser Ala Ser Gln
        115                 120                 125

Ala Pro Gly Arg Gln Ser Ser Pro Leu Lys Ala Leu Trp Val Ser Val
    130                 135                 140

Leu Gln Leu Pro Gly Ala Ala His Asp Pro Cys Pro Val Phe Asp Ser
145                 150                 155                 160

Arg Glu Pro


<210> SEQ ID NO 32
<211> LENGTH: 482
<212> TYPE: PRT
<213> ORGANISM: Homo sapiens

<400> SEQUENCE: 32

Ala Thr Pro Phe Gln Lys Phe Arg Met Asn Gly Asp Met Pro His Val
1               5                   10                  15

Pro Ile Thr Thr Leu Ala Gly Ile Ala Ser Leu Thr Asp Leu Leu Asn
            20                  25                  30

Gln Leu Pro Leu Pro Ser Pro Leu Pro Ala Thr Thr Thr Lys Ser Leu
        35                  40                  45

Leu Phe Asn Ala Arg Ile Ala Glu Glu Val Asn Cys Leu Leu Ala Cys
    50                  55                  60

Arg Asp Asp Asn Leu Val Ser Gln Leu Val His Ser Leu Asn Gln Val
65                  70                  75                  80

Ser Thr Asp His Ile Glu Leu Lys Asp Asn Leu Gly Ser Asp Asp Pro
                85                  90                  95

Glu Gly Asp Ile Pro Val Leu Leu Gln Ala Val Leu Ala Arg Ser Pro
            100                 105                 110

Asn Val Phe Arg Glu Lys Ser Met Gln Asn Arg Tyr Val Gln Ser Gly
        115                 120                 125

Met Met Met Ser Gln Tyr Lys Leu Ser Gln Asn Ser Met His Ser Ser
    130                 135                 140

Pro Ala Ser Ser Asn Tyr Gln Gln Thr Thr Ile Ser His Ser Pro Ser
145                 150                 155                 160

Ser Arg Phe Val Pro Pro Gln Thr Ser Ser Gly Asn Arg Phe Met Pro
                165                 170                 175

Gln Gln Asn Ser Pro Val Pro Ser Pro Tyr Ala Pro Gln Ser Pro Ala
            180                 185                 190

Gly Tyr Met Pro Tyr Ser His Pro Ser Ser Tyr Thr Thr His Pro Gln
        195                 200                 205

Met Gln Gln Ala Ser Val Ser Ser Pro Ile Val Ala Gly Gly Leu Arg
    210                 215                 220

Asn Ile His Asp Asn Lys Val Ser Gly Pro Leu Ser Gly Asn Ser Ala
225                 230                 235                 240

Asn His His Ala Asp Asn Pro Arg His Gly Ser Ser Glu Asp Tyr Leu
                245                 250                 255

His Met Val His Arg Leu Ser Ser Asp Asp Gly Asp Ser Ser Thr Met
            260                 265                 270

Arg Asn Ala Ala Ser Phe Pro Leu Arg Ser Pro Gln Pro Val Cys Ser
        275                 280                 285

Pro Ala Gly Ser Glu Gly Thr Pro Lys Gly Ser Arg Pro Pro Leu Ile
```

-continued

```
    290                 295                 300

Leu Gln Ser Gln Ser Leu Pro Cys Ser Ser Pro Arg Asp Val Pro Pro
305                 310                 315                 320

Asp Ile Leu Leu Asp Ser Pro Glu Arg Lys Gln Lys Lys Gln Lys Lys
                325                 330                 335

Met Lys Leu Gly Lys Asp Glu Lys Glu Gln Ser Glu Lys Ala Ala Met
            340                 345                 350

Tyr Asp Ile Ile Ser Ser Pro Ser Lys Asp Ser Thr Lys Leu Thr Leu
        355                 360                 365

Arg Leu Ser Arg Val Arg Ser Ser Asp Met Asp Gln Gln Glu Asp Met
    370                 375                 380

Ile Ser Gly Val Glu Asn Ser Asn Val Ser Glu Asn Asp Ile Pro Phe
385                 390                 395                 400

Asn Val Gln Tyr Pro Gly Gln Thr Ser Lys Thr Pro Ile Thr Pro Gln
                405                 410                 415

Asp Ile Asn Arg Pro Leu Asn Ala Ala Gln Cys Leu Ser Gln Gln Glu
            420                 425                 430

Gln Thr Ala Phe Leu Pro Ala Asn Gln Val Pro Val Leu Gln Gln Asn
        435                 440                 445

Thr Ser Val Ala Ala Lys Gln Pro Gln Thr Asn Ser His Lys Thr Leu
    450                 455                 460

Val Gln Pro Gly Thr Gly Ile Glu Val Ser Ala Glu Leu Pro Lys Asp
465                 470                 475                 480

Lys Thr


<210> SEQ ID NO 33
<211> LENGTH: 368
<212> TYPE: PRT
<213> ORGANISM: Homo sapiens

<400> SEQUENCE: 33

Gly Gln Gln Arg His His Pro Val His Ala Gly Ser Ala Ala Gly Cys
1               5                   10                  15

Arg Gly Gly Leu Ser Val Pro Gly Pro Ala Ala Gly His Ser His Thr
            20                  25                  30

Cys Ala Ser Ser His Ala Ala Thr Gln Ser Ala Ala Leu Ala Pro Gly
        35                  40                  45

Phe Arg Arg Leu His Ser Val Pro Arg Gly Ser Ala Leu Cys Ala Met
    50                  55                  60

Asp Gly Ile Val Pro Asp Ile Ala Val Gly Thr Lys Arg Gly Ser Asp
65                  70                  75                  80

Glu Leu Phe Ser Thr Cys Val Thr Asn Gly Pro Phe Ile Met Ser Ser
                85                  90                  95

Asn Ser Ala Ser Ala Ala Asn Gly Asn Asp Ser Lys Lys Phe Lys Gly
            100                 105                 110

Asp Ser Arg Ser Ala Gly Val Pro Ser Arg Val Ile His Ile Arg Lys
        115                 120                 125

Leu Pro Ile Asp Val Thr Glu Gly Glu Val Ile Ser Leu Gly Leu Pro
    130                 135                 140

Phe Gly Lys Val Thr Asn Leu Leu Met Leu Lys Gly Lys Asn Gln Ala
145                 150                 155                 160

Phe Ile Glu Met Asn Thr Glu Glu Ala Ala Asn Thr Met Val Asn Tyr
                165                 170                 175

Tyr Thr Ser Val Thr Pro Val Leu Arg Gly Gln Pro Ile Tyr Ile Gln
```

-continued

```
            180                 185                 190

Phe Ser Asn His Lys Glu Leu Lys Thr Asp Ser Ser Pro Asn Gln Ala
        195                 200                 205

Arg Ala Gln Ala Ala Leu Gln Ala Val Asn Ser Val Gln Ser Gly Asn
    210                 215                 220

Leu Ala Leu Ala Ala Ser Ala Ala Ala Val Asp Ala Gly Met Ala Met
225                 230                 235                 240

Ala Gly Gln Ser Pro Val Leu Arg Ile Ile Val Glu Asn Leu Phe Tyr
                245                 250                 255

Pro Val Thr Leu Asp Val Leu His Gln Ile Phe Ser Lys Phe Gly Thr
            260                 265                 270

Val Leu Lys Ile Ile Thr Phe Thr Lys Asn Asn Gln Phe Gln Ala Leu
        275                 280                 285

Leu Gln Tyr Ala Asp Pro Val Ser Ala Gln His Ala Lys Leu Ser Leu
    290                 295                 300

Asp Gly Gln Asn Ile Tyr Asn Ala Cys Cys Thr Leu Arg Ile Asp Phe
305                 310                 315                 320

Ser Lys Leu Thr Ser Leu Asn Val Lys Tyr Asn Asn Asp Lys Ser Arg
                325                 330                 335

Asp Tyr Leu Val Pro Asn Ser Leu Asp Pro Ala Pro Ala Trp Ser Glu
            340                 345                 350

Cys Gly Ser Leu Ala Pro Ala Phe Pro Gly Glu Gly Lys Gln Lys Ala
        355                 360                 365


<210> SEQ ID NO 34
<211> LENGTH: 363
<212> TYPE: PRT
<213> ORGANISM: Homo sapiens

<400> SEQUENCE: 34

Pro Gly Glu Thr Pro Gly Glu Ala Ala Gly Glu Ala Arg Ala Leu Leu
1               5                   10                  15

Pro Gly Pro Lys Arg Thr Gly Cys Pro Ser Gly Gly Thr Ala Thr Ser
            20                  25                  30

Thr His Gly Ala Gly Ala Arg Thr Ala Ala Pro Pro Ala Pro Ala Ala
        35                  40                  45

Trp Thr Pro Pro Glu Ala Ala Pro Pro Gly Pro Thr Arg Gly Pro Ile
    50                  55                  60

Arg Arg Pro Gly Leu Pro Ser Arg Ser Trp Arg Pro Pro Ala Trp Arg
65                  70                  75                  80

Ser Arg Pro Gln Thr Pro Ser Gln Pro Ser Pro Ala His Ser Gly Pro
                85                  90                  95

Ala Ser Phe Leu Asn Ser Ala Arg Asp Ala Thr Gln Ala Ile Phe Glu
            100                 105                 110

Ile Leu Glu Lys Ser Trp Leu Pro Gln Asn Cys Thr Leu Val Asp Met
        115                 120                 125

Lys Ile Glu Phe Gly Val Asp Val Thr Thr Lys Glu Ile Val Leu Ala
    130                 135                 140

Asp Val Ile Asp Asn Asp Ser Trp Arg Leu Trp Pro Ser Gly Asp Arg
145                 150                 155                 160

Ser Gln Gln Lys Asp Lys Gln Ser Tyr Arg Asp Leu Lys Glu Val Thr
                165                 170                 175

Pro Glu Gly Leu Gln Met Val Lys Lys Asn Phe Glu Trp Val Ala Glu
            180                 185                 190
```

-continued

```
Arg Val Glu Leu Leu Leu Lys Ser Glu Ser Gln Cys Arg Val Val Val
        195                 200                 205

Leu Met Gly Ser Thr Ser Asp Leu Gly His Cys Glu Lys Ile Lys Lys
    210                 215                 220

Ala Cys Gly Asn Phe Gly Ile Pro Cys Glu Leu Arg Val Thr Ser Ala
225                 230                 235                 240

His Lys Gly Pro Asp Glu Thr Leu Arg Ile Lys Ala Glu Tyr Glu Gly
                245                 250                 255

Asp Gly Ile Pro Thr Val Phe Val Ala Val Ala Gly Arg Ser Asn Gly
            260                 265                 270

Leu Gly Pro Val Met Ser Gly Asn Thr Ala Tyr Pro Val Ile Ser Cys
        275                 280                 285

Pro Pro Leu Thr Pro Asp Trp Gly Val Gln Asp Val Trp Ser Ser Leu
    290                 295                 300

Arg Leu Pro Ser Gly Leu Gly Cys Ser Thr Val Leu Ser Pro Glu Gly
305                 310                 315                 320

Ser Ala Gln Phe Ala Ala Gln Ile Phe Gly Leu Ser Asn His Leu Val
                325                 330                 335

Trp Ser Lys Leu Arg Ala Ser Ile Leu Asn Thr Trp Ile Ser Leu Lys
            340                 345                 350

Gln Ala Asp Lys Lys Ile Arg Glu Cys Asn Leu
        355                 360


<210> SEQ ID NO 35
<211> LENGTH: 254
<212> TYPE: PRT
<213> ORGANISM: Homo sapiens

<400> SEQUENCE: 35

Arg Lys Ala Arg Gln Ile Pro Ala Leu Tyr Gln Arg Leu Tyr Leu Gly
1               5                   10                  15

Gln Cys Arg Pro Trp His Thr Glu Gln Thr Arg Gly Gly Arg Ser Gly
            20                  25                  30

Gly Ala Gly Ile Leu Glu Leu Glu Leu Gln Ile Glu Leu Leu Arg Glu
        35                  40                  45

Thr Lys Arg Lys Tyr Glu Ser Val Leu Gln Leu Gly Arg Ala Leu Thr
    50                  55                  60

Ala His Leu Tyr Ser Leu Leu Gln Thr Gln His Ala Leu Gly Asp Ala
65                  70                  75                  80

Phe Ala Asp Leu Ser Gln Lys Ser Pro Glu Leu Gln Glu Glu Phe Gly
                85                  90                  95

Tyr Asn Ala Glu Thr Gln Lys Leu Leu Cys Lys Asn Gly Glu Thr Leu
            100                 105                 110

Leu Gly Ala Val Asn Phe Phe Val Ser Ser Ile Asn Thr Leu Val Thr
        115                 120                 125

Lys Thr Met Glu Asp Thr Leu Met Thr Val Lys Gln Tyr Glu Ala Ala
    130                 135                 140

Arg Leu Glu Tyr Asp Ala Tyr Arg Thr Asp Leu Glu Glu Leu Ser Leu
145                 150                 155                 160

Gly Pro Arg Asp Ala Gly Thr Arg Gly Arg Leu Glu Ser Ala Gln Ala
                165                 170                 175

Thr Phe Gln Ala His Arg Asp Lys Tyr Glu Lys Leu Arg Gly Asp Val
            180                 185                 190

Ala Ile Lys Leu Lys Phe Leu Glu Glu Asn Lys Ile Lys Val Met His
        195                 200                 205
```

-continued

```
Lys Gln Leu Leu Leu Phe His Asn Ala Val Ser Ala Tyr Phe Ala Gly
    210                 215                 220

Asn Gln Lys Gln Leu Glu Gln Thr Leu Gln Gln Phe Asn Ile Lys Leu
225                 230                 235                 240

Arg Pro Pro Gly Ala Glu Lys Pro Ser Trp Leu Glu Glu Gln
                245                 250


<210> SEQ ID NO 36
<211> LENGTH: 1022
<212> TYPE: PRT
<213> ORGANISM: Homo sapiens

<400> SEQUENCE: 36

Ser Ser Glu Pro Ala Glu Ala Pro Ser Pro Ser Leu Ala Trp Leu Trp
1               5                   10                  15

Pro Gly Pro Lys Leu Asp Ser Ser Tyr Thr Ile Tyr Leu Thr Phe Tyr
            20                  25                  30

Phe Gly Phe Pro Pro Leu Tyr Pro Ser Arg Lys Val Glu Ser Ala Gly
        35                  40                  45

Trp Arg Leu Pro Gly Glu Ala Asn Ala Trp Pro Cys Pro Ala Pro Arg
    50                  55                  60

Arg Thr Met Thr Leu Leu Leu Leu Pro Leu Leu Leu Ala Ser Leu Leu
65                  70                  75                  80

Ala Ser Cys Ser Cys Asn Lys Ala Asn Lys His Lys Pro Trp Ile Glu
                85                  90                  95

Ala Glu Tyr Gln Gly Ile Val Met Glu Asn Asp Asn Thr Val Leu Leu
            100                 105                 110

Asn Pro Pro Leu Phe Ala Leu Asp Lys Asp Ala Pro Leu Arg Tyr Ala
        115                 120                 125

Gly Glu Ile Cys Gly Phe Arg Leu His Gly Ser Gly Val Pro Phe Glu
    130                 135                 140

Ala Val Ile Leu Asp Lys Ala Thr Gly Glu Gly Leu Ile Arg Ala Lys
145                 150                 155                 160

Glu Pro Val Asp Cys Glu Ala Gln Lys Glu His Thr Phe Thr Ile Gln
                165                 170                 175

Ala Tyr Asp Cys Gly Glu Gly Pro Asp Gly Ala Asn Thr Lys Lys Ser
            180                 185                 190

His Lys Ala Thr Val His Val Arg Val Asn Asp Val Asn Glu Phe Ala
        195                 200                 205

Pro Val Phe Val Glu Arg Leu Tyr Arg Ala Ala Val Thr Glu Gly Lys
    210                 215                 220

Leu Tyr Asp Arg Ile Leu Arg Val Glu Ala Ile Asp Gly Asp Cys Ser
225                 230                 235                 240

Pro Gln Tyr Ser Gln Ile Cys Tyr Tyr Glu Ile Leu Thr Pro Asn Thr
                245                 250                 255

Pro Phe Leu Ile Asp Asn Asp Gly Asn Ile Glu Asn Thr Glu Lys Leu
            260                 265                 270

Gln Tyr Ser Gly Glu Arg Leu Tyr Lys Phe Thr Val Thr Ala Tyr Asp
        275                 280                 285

Cys Gly Lys Lys Arg Ala Ala Asp Asp Ala Glu Val Glu Ile Gln Val
    290                 295                 300

Lys Pro Thr Cys Lys Pro Ser Trp Gln Gly Trp Asn Lys Arg Ile Glu
305                 310                 315                 320

Tyr Ala Pro Gly Ala Gly Ser Leu Ala Leu Phe Pro Gly Ile Arg Leu
```

-continued

```
                325                 330                 335

Glu Thr Cys Asp Glu Pro Leu Trp Asn Ile Gln Ala Thr Ile Glu Leu
            340                 345                 350

Gln Thr Ser His Val Ala Lys Gly Cys Asp Arg Asp Asn Tyr Ser Glu
        355                 360                 365

Arg Ala Leu Arg Lys Leu Cys Gly Ala Ala Thr Gly Glu Val Asp Leu
    370                 375                 380

Leu Pro Met Pro Gly Pro Asn Ala Asn Trp Thr Ala Gly Leu Ser Val
385                 390                 395                 400

His Tyr Ser Gln Asp Ser Ser Leu Ile Tyr Trp Phe Asn Gly Thr Gln
                405                 410                 415

Ala Val Gln Val Pro Leu Gly Gly Pro Ser Gly Leu Gly Ser Gly Pro
            420                 425                 430

Gln Asp Ser Leu Ser Asp His Phe Thr Leu Ser Phe Trp Met Lys His
        435                 440                 445

Gly Val Thr Pro Asn Lys Gly Lys Lys Glu Glu Glu Thr Ile Val Cys
    450                 455                 460

Asn Thr Val Gln Asn Glu Asp Gly Phe Ser His Tyr Ser Leu Thr Val
465                 470                 475                 480

His Gly Cys Arg Ile Ala Phe Leu Tyr Trp Pro Leu Leu Glu Ser Ala
                485                 490                 495

Arg Pro Val Lys Phe Leu Trp Lys Leu Glu Gln Val Cys Asp Asp Glu
            500                 505                 510

Trp His His Tyr Ala Leu Asn Leu Glu Phe Pro Thr Val Thr Leu Tyr
        515                 520                 525

Thr Asp Gly Ile Ser Phe Asp Pro Ala Leu Ile His Asp Asn Gly Leu
    530                 535                 540

Ile His Pro Pro Arg Arg Glu Pro Ala Leu Met Ile Gly Ala Cys Trp
545                 550                 555                 560

Thr Glu Glu Lys Asn Lys Glu Lys Glu Lys Gly Asp Asn Ser Thr Asp
                565                 570                 575

Thr Thr Gln Gly Asp Pro Leu Ser Ile His His Tyr Phe His Gly Tyr
            580                 585                 590

Leu Ala Gly Phe Ser Val Arg Ser Gly Arg Leu Glu Ser Arg Glu Val
        595                 600                 605

Ile Glu Cys Leu Tyr Ala Cys Arg Glu Gly Leu Asp Tyr Arg Asp Phe
    610                 615                 620

Glu Ser Leu Gly Lys Gly Met Lys Val His Val Asn Pro Ser Gln Ser
625                 630                 635                 640

Leu Leu Thr Leu Glu Gly Asp Asp Val Glu Thr Phe Asn His Ala Leu
                645                 650                 655

Gln His Val Ala Tyr Met Asn Thr Leu Arg Phe Ala Thr Pro Gly Val
            660                 665                 670

Arg Pro Leu Arg Leu Thr Thr Ala Val Lys Cys Phe Ser Glu Glu Ser
        675                 680                 685

Cys Val Ser Ile Pro Glu Val Glu Gly Tyr Val Val Val Leu Gln Pro
    690                 695                 700

Asp Ala Pro Gln Ile Leu Leu Ser Gly Thr Ala His Phe Ala Arg Pro
705                 710                 715                 720

Ala Val Asp Phe Glu Gly Thr Asn Gly Val Pro Leu Phe Pro Asp Leu
                725                 730                 735

Gln Ile Thr Cys Ser Ile Ser His Gln Val Glu Ala Lys Lys Asp Glu
            740                 745                 750
```

```
Ser Trp Gln Gly Thr Val Thr Asp Thr Arg Met Ser Asp Glu Ile Val
        755                 760                 765

His Asn Leu Asp Gly Cys Glu Ile Ser Leu Val Gly Asp Asp Leu Asp
    770                 775                 780

Pro Glu Arg Glu Ser Leu Leu Leu Asp Thr Thr Ser Leu Gln Gln Arg
785                 790                 795                 800

Gly Leu Glu Leu Thr Asn Thr Ser Ala Tyr Leu Thr Ile Ala Gly Val
                805                 810                 815

Glu Ser Ile Thr Val Tyr Glu Glu Ile Leu Arg Gln Ala Arg Tyr Arg
            820                 825                 830

Leu Arg His Gly Ala Ala Leu Tyr Thr Arg Lys Phe Arg Leu Ser Cys
        835                 840                 845

Ser Glu Met Asn Gly Arg Tyr Ser Ser Asn Glu Phe Ile Val Glu Val
    850                 855                 860

Asn Val Leu His Ser Met Asn Arg Val Ala His Pro Ser His Val Leu
865                 870                 875                 880

Ser Ser Gln Gln Phe Leu His Arg Gly His Gln Pro Pro Pro Glu Met
                885                 890                 895

Ala Gly His Ser Leu Ala Ser Ser His Arg Asn Ser Met Ile Pro Ser
            900                 905                 910

Ala Ala Thr Leu Ile Ile Val Val Cys Val Gly Phe Leu Val Leu Met
        915                 920                 925

Val Val Leu Gly Leu Val Arg Ile His Ser Leu His Arg Arg Val Ser
    930                 935                 940

Gly Ala Gly Gly Pro Pro Gly Ala Ser Ser Asp Pro Lys Asp Pro Asp
945                 950                 955                 960

Leu Phe Trp Asp Asp Ser Ala Leu Thr Ile Ile Val Asn Pro Met Glu
                965                 970                 975

Ser Tyr Gln Asn Arg Gln Ser Cys Val Thr Gly Ala Val Gly Gly Gln
            980                 985                 990

Gln Glu Asp Glu Asp Ser Ser Asp  Ser Glu Val Ala Asp  Ser Pro Ser
        995                 1000                 1005

Ser Asp  Glu Arg Arg Ile Ile  Glu Thr Pro Pro His  Arg Tyr
    1010                 1015                 1020


<210> SEQ ID NO 37
<211> LENGTH: 1038
<212> TYPE: PRT
<213> ORGANISM: Homo sapiens

<400> SEQUENCE: 37

Ile Gln Arg Phe Gly Thr Ser Gly His Ile Met Asn Leu Gln Ala Gln
1               5                   10                  15

Pro Lys Ala Gln Asn Lys Arg Lys Arg Cys Leu Phe Gly Gly Gln Glu
            20                  25                  30

Pro Ala Pro Lys Glu Gln Pro Pro Pro Leu Gln Pro Pro Gln Gln Ser
        35                  40                  45

Ile Arg Val Lys Glu Glu Gln Tyr Leu Gly His Glu Gly Pro Gly Gly
    50                  55                  60

Ala Val Ser Thr Ser Gln Pro Val Glu Leu Pro Pro Pro Ser Ser Leu
65                  70                  75                  80

Ala Leu Leu Asn Ser Val Val Tyr Gly Pro Glu Arg Thr Ser Ala Ala
                85                  90                  95

Met Leu Ser Gln Gln Val Ala Ser Val Lys Trp Pro Asn Ser Val Met
```

-continued

```
            100                 105                 110

Ala Pro Gly Arg Gly Pro Glu Arg Gly Gly Gly Gly Gly Val Ser Asp
        115                 120                 125

Ser Ser Trp Gln Gln Gln Pro Gly Gln Pro Pro Pro His Ser Thr Trp
    130                 135                 140

Asn Cys His Ser Leu Ser Leu Tyr Ser Ala Thr Lys Gly Ser Pro His
145                 150                 155                 160

Pro Gly Val Gly Val Pro Thr Tyr Tyr Asn His Pro Glu Ala Leu Lys
                165                 170                 175

Arg Glu Lys Ala Gly Gly Pro Gln Leu Asp Arg Tyr Val Arg Pro Met
            180                 185                 190

Met Pro Gln Lys Val Gln Leu Glu Val Gly Arg Pro Gln Ala Pro Leu
        195                 200                 205

Asn Ser Phe His Ala Ala Lys Lys Pro Pro Asn Gln Ser Leu Pro Leu
    210                 215                 220

Gln Pro Phe Gln Leu Ala Phe Gly His Gln Val Asn Arg Gln Val Phe
225                 230                 235                 240

Arg Gln Gly Pro Pro Pro Pro Asn Pro Val Ala Ala Phe Pro Pro Gln
                245                 250                 255

Lys Gln Gln Gln Gln Gln Gln Pro Gln Gln Gln Gln Gln Gln Gln Gln
            260                 265                 270

Ala Ala Leu Pro Gln Met Pro Leu Phe Glu Asn Phe Tyr Ser Met Pro
        275                 280                 285

Gln Gln Pro Ser Gln Gln Pro Gln Asp Phe Gly Leu Gln Pro Ala Gly
    290                 295                 300

Pro Leu Gly Gln Ser His Leu Ala His His Ser Met Ala Pro Tyr Pro
305                 310                 315                 320

Phe Pro Pro Asn Pro Asp Met Asn Pro Glu Leu Arg Lys Ala Leu Leu
                325                 330                 335

Gln Asp Ser Ala Pro Gln Pro Ala Leu Pro Gln Val Gln Ile Pro Phe
            340                 345                 350

Pro Arg Arg Ser Arg Arg Leu Ser Lys Glu Gly Ile Leu Pro Pro Ser
        355                 360                 365

Ala Leu Asp Gly Ala Gly Thr Gln Pro Gly Gln Glu Ala Thr Gly Asn
    370                 375                 380

Leu Phe Leu His His Trp Pro Leu Gln Gln Pro Pro Pro Gly Ser Leu
385                 390                 395                 400

Gly Gln Pro His Pro Glu Ala Leu Gly Phe Pro Leu Glu Leu Arg Glu
                405                 410                 415

Ser Gln Leu Leu Pro Asp Gly Glu Arg Leu Ala Pro Asn Gly Arg Glu
            420                 425                 430

Arg Glu Ala Pro Ala Met Gly Ser Glu Glu Gly Met Arg Ala Val Ser
        435                 440                 445

Thr Gly Asp Cys Gly Gln Val Leu Arg Gly Gly Val Ile Gln Ser Thr
    450                 455                 460

Arg Arg Arg Arg Arg Ala Ser Gln Glu Ala Asn Leu Leu Thr Leu Ala
465                 470                 475                 480

Gln Lys Ala Val Glu Leu Ala Ser Leu Gln Asn Ala Lys Asp Gly Ser
                485                 490                 495

Gly Ser Glu Glu Lys Arg Lys Ser Val Leu Ala Ser Thr Thr Lys Cys
            500                 505                 510

Gly Val Glu Phe Ser Glu Pro Ser Leu Ala Thr Lys Arg Ala Arg Glu
        515                 520                 525
```

-continued

```
Asp Ser Gly Met Val Pro Leu Ile Ile Pro Val Ser Val Pro Val Arg
    530                 535                 540

Thr Val Asp Pro Thr Glu Ala Ala Gln Ala Gly Gly Leu Asp Glu Asp
545                 550                 555                 560

Gly Lys Gly Leu Glu Gln Asn Pro Ala Glu His Lys Pro Ser Val Ile
                565                 570                 575

Val Thr Arg Arg Arg Ser Thr Arg Ile Pro Gly Thr Asp Ala Gln Ala
            580                 585                 590

Gln Ala Glu Asp Met Asn Val Lys Leu Glu Gly Glu Pro Ser Val Arg
        595                 600                 605

Lys Pro Lys Gln Arg Pro Arg Pro Glu Pro Leu Ile Ile Pro Thr Lys
    610                 615                 620

Ala Gly Thr Phe Ile Ala Pro Pro Val Tyr Ser Asn Ile Thr Pro Tyr
625                 630                 635                 640

Gln Ser His Leu Arg Ser Pro Val Arg Leu Ala Asp His Pro Ser Glu
                645                 650                 655

Arg Ser Phe Glu Leu Pro Pro Tyr Thr Pro Pro Pro Ile Leu Ser Pro
            660                 665                 670

Val Arg Glu Gly Ser Gly Leu Tyr Phe Asn Ala Ile Ile Ser Thr Ser
        675                 680                 685

Thr Ile Pro Ala Pro Pro Pro Ile Thr Pro Lys Ser Ala His Arg Thr
    690                 695                 700

Leu Leu Arg Thr Asn Ser Ala Glu Val Thr Pro Pro Val Leu Ser Val
705                 710                 715                 720

Met Gly Glu Ala Thr Pro Val Ser Ile Glu Pro Arg Ile Asn Val Gly
                725                 730                 735

Ser Arg Phe Gln Ala Glu Ile Pro Leu Met Arg Asp Arg Ala Leu Ala
            740                 745                 750

Ala Ala Asp Pro His Lys Ala Asp Leu Val Trp Gln Pro Trp Glu Asp
        755                 760                 765

Leu Glu Ser Ser Arg Glu Lys Gln Arg Gln Val Glu Asp Leu Leu Thr
    770                 775                 780

Ala Ala Cys Ser Ser Ile Phe Pro Gly Ala Gly Thr Asn Gln Glu Leu
785                 790                 795                 800

Ala Leu His Cys Leu His Glu Ser Arg Gly Asp Ile Leu Glu Thr Leu
                805                 810                 815

Asn Lys Leu Leu Leu Lys Lys Pro Leu Arg Pro His Asn His Pro Leu
            820                 825                 830

Ala Thr Tyr His Tyr Thr Gly Ser Asp Gln Trp Lys Met Ala Glu Arg
        835                 840                 845

Lys Leu Phe Asn Lys Gly Ile Ala Ile Tyr Lys Lys Asp Phe Phe Leu
    850                 855                 860

Val Gln Lys Leu Ile Gln Thr Lys Thr Val Ala Gln Cys Val Glu Phe
865                 870                 875                 880

Tyr Tyr Thr Tyr Lys Lys Gln Val Lys Ile Gly Arg Asn Gly Thr Leu
                885                 890                 895

Thr Phe Gly Asp Val Asp Thr Ser Asp Glu Lys Ser Ala Gln Glu Glu
            900                 905                 910

Val Glu Val Asp Ile Lys Thr Ser Gln Lys Phe Pro Arg Val Pro Leu
        915                 920                 925

Pro Arg Arg Glu Ser Pro Ser Glu Glu Arg Leu Glu Pro Lys Arg Glu
    930                 935                 940
```

-continued

```
Val Lys Glu Pro Arg Lys Glu Gly Glu Glu Glu Val Pro Glu Ile Gln
945                 950                 955                 960

Glu Lys Glu Glu Gln Glu Glu Gly Arg Glu Arg Ser Arg Arg Ala Ala
                965                 970                 975

Ala Val Lys Ala Thr Gln Thr Leu Gln Ala Asn Glu Ser Ala Ser Asp
            980                 985                 990

Ile Leu Ile Leu Arg Ser His Glu  Ser Asn Ala Pro Gly  Ser Ala Gly
        995                 1000                 1005

Gly Gln  Ala Ser Glu Lys Pro  Arg Glu Gly Thr Gly  Lys Ser Arg
    1010                 1015                 1020

Arg Ala  Leu Pro Phe Ser Glu  Lys Lys Lys Lys Lys  Gln Lys Ala
    1025                 1030                 1035


<210> SEQ ID NO 38
<211> LENGTH: 849
<212> TYPE: PRT
<213> ORGANISM: Homo sapiens

<400> SEQUENCE: 38

Ile Arg His Glu Val Ser Phe Leu Trp Asn Thr Glu Ala Ala Cys Pro
1               5                   10                  15

Ile Gln Thr Thr Thr Asp Thr Asp Gln Ala Cys Ser Ile Arg Asp Pro
            20                  25                  30

Asn Ser Gly Phe Val Phe Asn Leu Asn Pro Leu Asn Ser Ser Gln Gly
        35                  40                  45

Tyr Asn Val Ser Gly Ile Gly Lys Ile Phe Met Phe Asn Val Cys Gly
    50                  55                  60

Thr Met Pro Val Cys Gly Thr Ile Leu Gly Lys Pro Ala Ser Gly Cys
65                  70                  75                  80

Glu Ala Glu Thr Gln Thr Glu Glu Leu Lys Asn Trp Lys Pro Ala Arg
                85                  90                  95

Pro Val Gly Ile Glu Lys Ser Leu Gln Leu Ser Thr Glu Gly Phe Ile
            100                 105                 110

Thr Leu Thr Tyr Lys Gly Pro Leu Ser Ala Lys Gly Thr Ala Asp Ala
        115                 120                 125

Phe Ile Val Arg Phe Val Cys Asn Asp Asp Val Tyr Ser Gly Pro Leu
    130                 135                 140

Lys Phe Leu His Gln Asp Ile Asp Ser Gly Gln Gly Ile Arg Asn Thr
145                 150                 155                 160

Tyr Phe Glu Phe Glu Thr Ala Leu Ala Cys Val Pro Ser Pro Val Asp
                165                 170                 175

Cys Gln Val Thr Asp Leu Ala Gly Asn Glu Tyr Asp Leu Thr Gly Leu
            180                 185                 190

Ser Thr Val Arg Lys Pro Trp Thr Ala Val Asp Thr Ser Val Asp Gly
        195                 200                 205

Arg Lys Arg Thr Phe Tyr Leu Ser Val Cys Asn Pro Leu Pro Tyr Ile
    210                 215                 220

Pro Gly Cys Gln Gly Ser Ala Val Gly Ser Cys Leu Val Ser Glu Gly
225                 230                 235                 240

Asn Ser Trp Asn Leu Gly Val Val Gln Met Ser Pro Gln Ala Ala Ala
                245                 250                 255

Asn Gly Ser Leu Ser Ile Met Tyr Val Asn Gly Asp Lys Cys Gly Asn
            260                 265                 270

Gln Arg Phe Ser Thr Arg Ile Thr Phe Glu Cys Ala Gln Ile Ser Gly
        275                 280                 285
```

-continued

```
Ser Pro Ala Phe Gln Leu Gln Asp Gly Cys Glu Tyr Val Phe Ile Trp
    290                 295                 300

Arg Thr Val Glu Ala Cys Pro Val Val Arg Val Glu Gly Asp Asn Cys
305                 310                 315                 320

Glu Val Lys Asp Pro Arg His Gly Asn Leu Tyr Asp Leu Lys Pro Leu
                325                 330                 335

Gly Leu Asn Asp Thr Ile Val Ser Ala Gly Glu Tyr Thr Tyr Tyr Phe
            340                 345                 350

Arg Val Cys Gly Lys Leu Ser Ser Asp Val Cys Pro Thr Ser Asp Lys
        355                 360                 365

Ser Lys Val Val Ser Ser Cys Gln Glu Lys Arg Glu Pro Gln Gly Phe
    370                 375                 380

His Lys Val Ala Gly Leu Leu Thr Gln Lys Leu Thr Tyr Glu Asn Gly
385                 390                 395                 400

Leu Leu Lys Met Asn Phe Thr Gly Gly Asp Thr Cys His Lys Val Tyr
                405                 410                 415

Gln Arg Ser Thr Ala Ile Phe Phe Tyr Cys Asp Arg Gly Thr Gln Arg
            420                 425                 430

Pro Val Phe Leu Lys Glu Thr Ser Asp Cys Ser Tyr Leu Phe Glu Trp
        435                 440                 445

Arg Thr Gln Tyr Ala Cys Pro Pro Phe Asp Leu Thr Glu Cys Ser Phe
    450                 455                 460

Lys Asp Gly Ala Gly Asn Ser Phe Asp Leu Ser Ser Leu Ser Arg Tyr
465                 470                 475                 480

Ser Asp Asn Trp Glu Ala Ile Thr Gly Thr Gly Asp Pro Glu His Tyr
                485                 490                 495

Leu Ile Asn Val Cys Lys Ser Leu Ala Pro Gln Ala Gly Thr Glu Pro
            500                 505                 510

Cys Pro Pro Glu Ala Ala Ala Cys Leu Leu Gly Gly Ser Lys Pro Val
        515                 520                 525

Asn Leu Gly Arg Val Arg Asp Gly Pro Gln Trp Arg Asp Gly Ile Ile
    530                 535                 540

Val Leu Lys Tyr Val Asp Gly Asp Leu Cys Pro Asp Gly Ile Arg Lys
545                 550                 555                 560

Lys Ser Thr Thr Ile Arg Phe Thr Cys Ser Glu Ser Gln Val Asn Ser
                565                 570                 575

Arg Pro Met Phe Ile Ser Ala Val Glu Asp Cys Glu Tyr Thr Phe Ala
            580                 585                 590

Trp Pro Thr Ala Thr Ala Cys Pro Met Lys Ser Asn Glu His Asp Asp
        595                 600                 605

Cys Gln Val Thr Asn Pro Ser Thr Gly His Leu Phe Asp Leu Ser Ser
    610                 615                 620

Leu Ser Gly Arg Ala Gly Phe Thr Ala Ala Tyr Ser Glu Lys Gly Leu
625                 630                 635                 640

Val Tyr Met Ser Ile Cys Gly Glu Asn Glu Asn Cys Pro Pro Gly Val
                645                 650                 655

Gly Ala Cys Phe Gly Gln Thr Arg Ile Ser Val Gly Lys Ala Asn Lys
            660                 665                 670

Arg Leu Arg Tyr Val Asp Gln Val Leu Gln Leu Val Tyr Lys Asp Gly
        675                 680                 685

Ser Pro Cys Pro Ser Lys Ser Gly Leu Ser Tyr Lys Ser Val Ile Ser
    690                 695                 700
```

```
Phe Val Cys Arg Pro Glu Ala Gly Pro Thr Asn Arg Pro Met Leu Ile
705                 710                 715                 720

Ser Leu Asp Lys Gln Thr Cys Thr Leu Phe Phe Ser Trp His Thr Pro
                725                 730                 735

Leu Ala Cys Glu Gln Ala Thr Glu Cys Ser Val Arg Asn Gly Ser Ser
            740                 745                 750

Ile Val Asp Leu Ser Pro Leu Ile His Arg Thr Gly Gly Tyr Glu Ala
        755                 760                 765

Tyr Asp Glu Ser Glu Asp Asp Ala Ser Asp Thr Asn Pro Asp Phe Tyr
    770                 775                 780

Ile Asn Ile Cys Gln Pro Leu Asn Pro Met His Gly Val Pro Cys Pro
785                 790                 795                 800

Ala Gly Ala Ala Val Cys Lys Val Pro Ile Asp Gly Pro Pro Ile Asp
                805                 810                 815

Ile Gly Arg Val Ala Gly Pro Pro Ile Leu Asn Pro Ile Ala Asn Glu
            820                 825                 830

Ile Tyr Leu Asn Phe Glu Ser Ser Thr Pro Cys Gln Glu Phe Ser Cys
        835                 840                 845

Lys


<210> SEQ ID NO 39
<211> LENGTH: 255
<212> TYPE: PRT
<213> ORGANISM: Homo sapiens

<400> SEQUENCE: 39

Glu Phe Gly Thr Arg Leu Pro Ala Arg Gly Lys Ser Thr Leu Pro Ala
1               5                   10                  15

Thr Phe Cys Ser Pro Ser Ala Pro Glu Leu Ala Ser Met Ser Val Val
            20                  25                  30

Pro Pro Asn Arg Ser Gln Thr Gly Trp Pro Arg Gly Val Thr Gln Phe
        35                  40                  45

Gly Asn Lys Tyr Ile Gln Gln Thr Lys Pro Leu Thr Leu Glu Arg Thr
    50                  55                  60

Ile Asn Leu Tyr Pro Leu Thr Asn Tyr Thr Phe Gly Thr Lys Glu Pro
65                  70                  75                  80

Leu Tyr Glu Lys Asp Ser Ser Val Ala Ala Arg Phe Gln Arg Met Arg
                85                  90                  95

Glu Glu Phe Asp Lys Ile Gly Met Arg Arg Thr Val Glu Gly Val Leu
            100                 105                 110

Ile Val His Glu His Arg Leu Pro His Val Leu Leu Leu Gln Leu Gly
        115                 120                 125

Thr Thr Phe Phe Lys Leu Pro Gly Gly Glu Leu Asn Pro Gly Glu Asp
    130                 135                 140

Glu Val Glu Gly Leu Lys Arg Leu Met Thr Glu Ile Leu Gly Arg Gln
145                 150                 155                 160

Asp Gly Val Leu Gln Asp Trp Val Ile Asp Asp Cys Ile Gly Asn Trp
                165                 170                 175

Trp Arg Pro Asn Phe Glu Pro Pro Gln Tyr Pro Tyr Ile Pro Ala His
            180                 185                 190

Ile Thr Lys Pro Lys Glu His Lys Lys Leu Phe Leu Val Gln Leu Gln
        195                 200                 205

Glu Lys Ala Leu Phe Ala Val Pro Lys Asn Tyr Lys Leu Val Ala Ala
    210                 215                 220
```

-continued

```
Pro Leu Phe Glu Leu Tyr Asp Asn Ala Pro Gly Tyr Gly Pro Ile Ile
225                 230                 235                 240

Ser Ser Leu Pro Gln Leu Leu Ser Arg Phe Asn Phe Ile Tyr Asn
                245                 250                 255


<210> SEQ ID NO 40
<211> LENGTH: 888
<212> TYPE: PRT
<213> ORGANISM: Homo sapiens

<400> SEQUENCE: 40

Glu Phe Gly Thr Arg Met Asp Gln Pro Gln Gln His Val Lys Ala Arg
1               5                   10                  15

Arg Lys Lys Leu Ile Ser Leu Ser Lys Cys Leu Ile Leu Cys Asn Lys
            20                  25                  30

Phe Cys Asn Val Met Ala Arg Leu Ser Arg Pro Glu Arg Pro Asp Leu
        35                  40                  45

Val Phe Glu Glu Glu Asp Leu Pro Tyr Glu Glu Glu Ile Met Arg Asn
    50                  55                  60

Gln Phe Ser Val Lys Cys Trp Leu His Tyr Ile Glu Phe Lys Gln Gly
65                  70                  75                  80

Ala Pro Lys Pro Arg Leu Asn Gln Leu Tyr Glu Arg Ala Leu Lys Leu
                85                  90                  95

Leu Pro Cys Ser Tyr Lys Leu Trp Tyr Arg Tyr Leu Lys Ala Arg Arg
            100                 105                 110

Ala Gln Val Lys His Arg Cys Val Thr Asp Pro Ala Tyr Glu Asp Val
        115                 120                 125

Asn Asn Cys His Glu Arg Ala Phe Val Phe Met His Lys Met Pro Arg
    130                 135                 140

Leu Trp Leu Asp Tyr Cys Gln Phe Leu Met Asp Gln Gly Arg Val Thr
145                 150                 155                 160

His Thr Arg Arg Thr Phe Asp Arg Ala Leu Arg Ala Leu Pro Ile Thr
                165                 170                 175

Gln His Ser Arg Ile Trp Pro Leu Tyr Leu Arg Phe Leu Arg Ser His
            180                 185                 190

Pro Leu Pro Glu Thr Ala Val Arg Gly Tyr Arg Arg Phe Leu Lys Leu
        195                 200                 205

Ser Pro Glu Ser Ala Glu Glu Tyr Ile Glu Tyr Leu Lys Ser Ser Asp
    210                 215                 220

Arg Leu Asp Glu Ala Ala Gln Arg Leu Ala Thr Val Val Asn Asp Glu
225                 230                 235                 240

Arg Phe Val Ser Lys Ala Gly Lys Ser Asn Tyr Gln Leu Trp His Glu
                245                 250                 255

Leu Cys Asp Leu Ile Ser Gln Asn Pro Asp Lys Val Gln Ser Leu Asn
            260                 265                 270

Val Asp Ala Ile Ile Arg Gly Gly Leu Thr Arg Phe Thr Asp Gln Leu
        275                 280                 285

Gly Lys Leu Trp Cys Ser Leu Ala Asp Tyr Tyr Ile Arg Ser Gly His
    290                 295                 300

Phe Glu Lys Ala Arg Asp Val Tyr Glu Glu Ala Ile Arg Thr Val Met
305                 310                 315                 320

Thr Val Arg Asp Phe Thr Gln Val Phe Asp Ser Tyr Ala Gln Phe Glu
                325                 330                 335

Glu Ser Met Ile Ala Ala Lys Met Glu Thr Ala Ser Glu Leu Gly Arg
            340                 345                 350
```

-continued

```
Glu Glu Glu Asp Asp Val Asp Leu Glu Leu Arg Leu Ala Arg Phe Glu
        355                 360                 365

Gln Leu Ile Ser Arg Arg Pro Leu Leu Leu Asn Ser Val Leu Leu Arg
    370                 375                 380

Gln Asn Pro His His Val His Glu Trp His Lys Arg Val Ala Leu His
385                 390                 395                 400

Gln Gly Arg Pro Arg Glu Ile Ile Asn Thr Tyr Thr Glu Ala Val Gln
                405                 410                 415

Thr Val Asp Pro Phe Lys Ala Thr Gly Lys Pro His Thr Leu Trp Val
            420                 425                 430

Ala Phe Ala Lys Phe Tyr Glu Asp Asn Gly Gln Leu Asp Asp Ala Arg
        435                 440                 445

Val Ile Leu Glu Lys Ala Thr Lys Val Asn Phe Lys Gln Val Asp Asp
    450                 455                 460

Leu Ala Ser Val Trp Cys Gln Cys Gly Glu Leu Glu Leu Arg His Glu
465                 470                 475                 480

Asn Tyr Asp Glu Ala Leu Arg Leu Leu Arg Lys Ala Thr Ala Leu Pro
                485                 490                 495

Ala Arg Arg Ala Glu Tyr Phe Asp Gly Ser Glu Pro Val Gln Asn Arg
            500                 505                 510

Val Tyr Lys Ser Leu Lys Val Trp Ser Met Leu Ala Asp Leu Glu Glu
        515                 520                 525

Ser Leu Gly Thr Phe Gln Ser Thr Lys Ala Val Tyr Asp Arg Ile Leu
    530                 535                 540

Asp Leu Arg Ile Ala Thr Pro Gln Ile Val Ile Asn Tyr Ala Met Phe
545                 550                 555                 560

Leu Glu Glu His Lys Tyr Phe Glu Glu Ser Phe Lys Ala Tyr Glu Arg
                565                 570                 575

Gly Ile Ser Leu Phe Lys Trp Pro Asn Val Ser Asp Ile Trp Ser Thr
            580                 585                 590

Tyr Leu Thr Lys Phe Ile Ala Arg Tyr Gly Gly Arg Lys Leu Glu Arg
        595                 600                 605

Ala Arg Asp Leu Phe Glu Gln Ala Leu Asp Gly Cys Pro Pro Lys Tyr
    610                 615                 620

Ala Lys Thr Leu Tyr Leu Leu Tyr Ala Gln Leu Glu Glu Glu Trp Gly
625                 630                 635                 640

Leu Ala Arg His Ala Met Ala Val Tyr Glu Arg Ala Thr Arg Ala Val
                645                 650                 655

Glu Pro Ala Gln Gln Tyr Asp Met Phe Asn Ile Tyr Ile Lys Arg Ala
            660                 665                 670

Ala Glu Ile Tyr Gly Val Thr His Thr Arg Gly Ile Tyr Gln Lys Ala
        675                 680                 685

Ile Glu Val Leu Ser Asp Glu His Ala Arg Glu Met Cys Leu Arg Phe
    690                 695                 700

Ala Asp Met Glu Cys Lys Leu Gly Glu Ile Asp Arg Ala Arg Ala Ile
705                 710                 715                 720

Tyr Ser Phe Cys Ser Gln Ile Cys Asp Pro Arg Thr Thr Gly Ala Phe
                725                 730                 735

Trp Gln Thr Trp Lys Asp Phe Glu Val Arg His Gly Asn Glu Asp Thr
            740                 745                 750

Ile Lys Glu Met Leu Arg Ile Arg Arg Ser Val Gln Ala Thr Tyr Asn
        755                 760                 765
```

```
Thr Gln Val Asn Phe Met Ala Ser Gln Met Leu Lys Val Ser Gly Ser
    770                 775                 780

Ala Thr Gly Thr Val Ser Asp Leu Ala Pro Gly Gln Ser Gly Met Asp
785                 790                 795                 800

Asp Met Lys Leu Leu Glu Gln Arg Ala Glu Gln Leu Ala Ala Glu Ala
                805                 810                 815

Glu Arg Asp Gln Pro Leu Arg Ala Gln Ser Lys Ile Leu Phe Val Arg
            820                 825                 830

Ser Asp Ala Ser Arg Glu Glu Leu Ala Glu Leu Ala Gln Gln Val Asn
        835                 840                 845

Pro Glu Glu Ile Gln Leu Gly Glu Asp Glu Asp Glu Asp Glu Met Asp
    850                 855                 860

Leu Glu Pro Asn Glu Val Arg Leu Glu Gln Gln Ser Val Pro Ala Ala
865                 870                 875                 880

Val Phe Gly Ser Leu Lys Glu Asp
                885


<210> SEQ ID NO 41
<211> LENGTH: 281
<212> TYPE: PRT
<213> ORGANISM: Homo sapiens

<400> SEQUENCE: 41

Trp Ile Gln Arg Ile Arg His Glu Gly Asn Ser Thr Val Tyr Glu Trp
1               5                   10                  15

Arg Thr Gly Thr Glu Pro Ser Val Val Glu Arg Pro His Leu Glu Glu
            20                  25                  30

Leu Pro Glu Gln Val Ala Glu Asp Ala Ile Asp Trp Gly Asp Phe Gly
        35                  40                  45

Val Glu Ala Val Ser Glu Gly Thr Asp Ser Gly Ile Ser Ala Glu Ala
    50                  55                  60

Ala Gly Ile Asp Trp Gly Ile Phe Pro Glu Ser Asp Ser Lys Asp Pro
65                  70                  75                  80

Gly Gly Asp Gly Ile Asp Trp Gly Asp Asp Ala Val Ala Leu Gln Ile
                85                  90                  95

Thr Val Leu Glu Ala Gly Thr Gln Ala Pro Glu Gly Val Ala Arg Gly
            100                 105                 110

Pro Asp Ala Leu Thr Leu Leu Glu Tyr Thr Glu Thr Arg Asn Gln Phe
        115                 120                 125

Leu Asp Glu Leu Met Glu Leu Glu Ile Phe Leu Ala Gln Arg Ala Val
    130                 135                 140

Glu Leu Ser Glu Glu Ala Asp Val Leu Ser Val Ser Gln Phe Gln Leu
145                 150                 155                 160

Ala Pro Ala Ile Leu Gln Gly Gln Thr Lys Glu Lys Met Val Thr Met
                165                 170                 175

Val Ser Val Leu Glu Asp Leu Ile Gly Lys Leu Thr Ser Leu Gln Leu
            180                 185                 190

Gln His Leu Phe Met Ile Leu Ala Ser Pro Arg Tyr Val Asp Arg Val
        195                 200                 205

Thr Glu Phe Leu Gln Gln Lys Leu Lys Gln Ser Gln Leu Leu Ala Leu
    210                 215                 220

Lys Lys Glu Leu Met Val Gln Lys Gln Gln Glu Ala Leu Glu Glu Gln
225                 230                 235                 240

Ala Ala Leu Glu Pro Lys Leu Asp Leu Leu Leu Glu Lys Thr Lys Glu
                245                 250                 255
```

```
Leu Gln Lys Leu Ile Glu Ala Asp Ile Ser Lys Arg Tyr Ser Gly Arg
            260                 265                 270

Pro Val Asn Leu Met Gly Thr Ser Leu
        275                 280


<210> SEQ ID NO 42
<211> LENGTH: 768
<212> TYPE: PRT
<213> ORGANISM: Homo sapiens
<220> FEATURE:
<221> NAME/KEY: MISC_FEATURE
<222> LOCATION: (198)..(198)
<223> OTHER INFORMATION: X may be any amino acid

<400> SEQUENCE: 42

Thr Val Ala Pro Glu Ala Ala Gly Ala Gly Ala Glu Gln Pro Arg Leu
1               5                   10                  15

Arg Phe Pro Ser Arg Pro Leu Gly Ala Ala Leu Arg Arg Arg Asp Pro
            20                  25                  30

Gly Leu Trp Pro Arg Arg Leu Arg Pro Pro Gly Gly Pro Gly Pro Pro
        35                  40                  45

Gly His Gly Ala Ser Arg Thr Pro Ser Pro Pro Pro Leu Ser Ser Pro
    50                  55                  60

Ala Ala Pro Gly Leu Gly Arg Pro Ser Gly Lys Met Phe Ser Ala Leu
65                  70                  75                  80

Lys Lys Leu Val Gly Ser Asp Gln Ala Pro Gly Arg Asp Lys Asn Ile
                85                  90                  95

Pro Ala Gly Leu Gln Ser Met Asn Gln Ala Leu Gln Arg Arg Phe Ala
            100                 105                 110

Lys Gly Val Gln Tyr Asn Met Lys Ile Val Ile Arg Gly Asp Arg Asn
        115                 120                 125

Thr Gly Lys Thr Ala Leu Trp His Arg Leu Gln Gly Arg Pro Phe Val
    130                 135                 140

Glu Glu Tyr Ile Pro Thr Gln Glu Ile Gln Val Thr Ser Ile His Trp
145                 150                 155                 160

Ser Tyr Lys Thr Thr Asp Asp Ile Val Lys Val Glu Val Trp Asp Val
                165                 170                 175

Val Asp Lys Gly Lys Cys Lys Lys Arg Gly Asp Gly Leu Lys Met Glu
            180                 185                 190

Asn Asp Pro Gln Glu Xaa Glu Ser Glu Met Ala Leu Asp Ala Glu Phe
        195                 200                 205

Leu Asp Val Tyr Lys Asn Cys Asn Gly Val Val Met Met Phe Asp Ile
    210                 215                 220

Thr Lys Gln Trp Thr Phe Asn Tyr Ile Leu Arg Glu Leu Pro Lys Val
225                 230                 235                 240

Pro Thr His Val Pro Val Cys Val Leu Gly Asn Tyr Arg Asp Met Gly
                245                 250                 255

Glu His Arg Val Ile Leu Pro Asp Asp Val Arg Asp Phe Ile Asp Asn
            260                 265                 270

Leu Asp Arg Pro Pro Gly Ser Ser Tyr Phe Arg Tyr Ala Glu Ser Ser
        275                 280                 285

Met Lys Asn Ser Phe Gly Leu Lys Tyr Leu His Lys Phe Phe Asn Ile
    290                 295                 300

Pro Phe Leu Gln Leu Gln Arg Glu Thr Leu Leu Arg Gln Leu Glu Thr
305                 310                 315                 320
```

-continued

```
Asn Gln Leu Asp Met Asp Ala Thr Leu Glu Glu Leu Ser Val Gln Gln
                325                 330                 335

Glu Thr Glu Asp Gln Asn Tyr Gly Ile Phe Leu Glu Met Met Glu Ala
            340                 345                 350

Arg Ser Arg Gly His Ala Ser Pro Leu Ala Ala Asn Gly Gln Ser Pro
        355                 360                 365

Ser Pro Gly Ser Gln Ser Pro Val Leu Pro Ala Pro Ala Val Ser Thr
    370                 375                 380

Gly Ser Ser Ser Pro Gly Thr Pro Gln Pro Ala Pro Gln Leu Pro Leu
385                 390                 395                 400

Asn Ala Ala Pro Pro Ser Ser Val Pro Pro Val Pro Pro Ser Glu Ala
                405                 410                 415

Leu Pro Pro Pro Ala Cys Pro Ser Ala Pro Ala Pro Arg Arg Ser Ile
            420                 425                 430

Ile Ser Arg Leu Phe Gly Thr Ser Pro Ala Thr Glu Ala Ala Pro Pro
        435                 440                 445

Pro Pro Glu Pro Val Pro Ala Ala Gln Gly Pro Ala Thr Val Gln Ser
    450                 455                 460

Val Glu Asp Phe Val Pro Asp Asp Arg Leu Asp Arg Ser Phe Leu Glu
465                 470                 475                 480

Asp Thr Thr Pro Ala Arg Asp Glu Lys Lys Val Gly Ala Lys Ala Ala
                485                 490                 495

Gln Gln Asp Ser Asp Ser Asp Gly Glu Ala Leu Gly Gly Asn Pro Met
            500                 505                 510

Val Ala Gly Phe Gln Asp Asp Val Asp Leu Glu Asp Gln Pro Arg Gly
        515                 520                 525

Ser Pro Pro Leu Pro Ala Gly Pro Val Pro Ser Gln Asp Ile Thr Leu
    530                 535                 540

Ser Ser Glu Glu Glu Ala Glu Val Ala Ala Pro Thr Lys Gly Pro Ala
545                 550                 555                 560

Pro Ala Pro Gln Gln Cys Ser Glu Pro Glu Thr Lys Trp Ser Ser Ile
                565                 570                 575

Pro Ala Ser Lys Pro Arg Arg Gly Thr Ala Pro Thr Arg Thr Ala Ala
            580                 585                 590

Pro Pro Trp Pro Gly Gly Val Ser Val Arg Thr Gly Pro Glu Lys Arg
        595                 600                 605

Ser Ser Thr Arg Pro Pro Ala Glu Met Glu Pro Gly Lys Gly Glu Gln
    610                 615                 620

Ala Ser Ser Ser Glu Ser Asp Pro Glu Gly Pro Ile Ala Ala Gln Met
625                 630                 635                 640

Leu Ser Phe Val Met Asp Asp Pro Asp Phe Glu Ser Glu Gly Ser Asp
                645                 650                 655

Thr Gln Arg Arg Ala Asp Asp Phe Pro Val Arg Asp Asp Pro Ser Asp
            660                 665                 670

Val Thr Asp Glu Asp Glu Gly Pro Ala Glu Pro Pro Pro Pro Pro Lys
        675                 680                 685

Leu Pro Leu Pro Ala Phe Arg Leu Lys Asn Asp Ser Asp Leu Phe Gly
    690                 695                 700

Leu Gly Leu Glu Glu Ala Gly Pro Lys Glu Ser Ser Glu Glu Gly Lys
705                 710                 715                 720

Glu Gly Lys Thr Pro Ser Lys Glu Lys Lys Lys Lys Thr Lys Ser Phe
                725                 730                 735

Ser Arg Val Leu Leu Glu Arg Pro Arg Ala His Arg Phe Ser Thr Arg
```

-continued

```
            740                 745                 750

Val Gly Tyr Gln Val Ser Val Pro Asn Ser Pro Tyr Ser Glu Ser Tyr
        755                 760                 765


<210> SEQ ID NO 43
<211> LENGTH: 163
<212> TYPE: PRT
<213> ORGANISM: Homo sapiens

<400> SEQUENCE: 43

Met Ala Cys Leu Arg His Ser Cys Leu Lys Pro Arg Pro Trp Ala Pro
1               5                   10                  15

Ala Gln Ala Gln Gly Leu Gly Pro Glu Pro His Ser Ala Arg Pro His
            20                  25                  30

Pro Pro His Leu Gly Pro Phe Val Gly Tyr Ser Leu Arg Pro His Pro
        35                  40                  45

Asp Leu Leu Lys Glu Arg Pro His Gly Lys Asp Ser Ala Thr Cys Ser
    50                  55                  60

Phe Ile Ser Pro Gln Trp Val Pro Arg His Glu Asp His Arg Leu Glu
65                  70                  75                  80

Ala Glu Leu Ala Gly Thr Cys Leu Gln Pro Leu Leu Thr Pro Ala Gly
                85                  90                  95

Pro Cys Leu Arg Gly Ser Thr Gln Asp Val Ala Met Thr Arg Gly Leu
            100                 105                 110

His Ser Ile Pro Leu Leu Gln Glu Pro Cys Lys Val Ser Ala Ser Gln
        115                 120                 125

Ala Pro Gly Arg Gln Ser Ser Pro Leu Lys Ala Leu Arg Val Ser Val
    130                 135                 140

Leu Gln Leu Pro Gly Ala Ala His Asp Pro Cys Pro Val Phe Asp Ser
145                 150                 155                 160

Arg Glu Pro


<210> SEQ ID NO 44
<211> LENGTH: 557
<212> TYPE: PRT
<213> ORGANISM: Homo sapiens

<400> SEQUENCE: 44

Met Asp Gly Ile Val Pro Asp Ile Ala Val Gly Thr Lys Arg Gly Ser
1               5                   10                  15

Asp Glu Leu Phe Ser Thr Cys Val Thr Asn Gly Pro Phe Ile Met Ser
            20                  25                  30

Ser Asn Ser Ala Ser Ala Ala Asn Gly Asn Asp Ser Lys Lys Phe Lys
        35                  40                  45

Gly Asp Ser Arg Ser Ala Gly Val Pro Ser Arg Val Ile His Ile Arg
    50                  55                  60

Lys Leu Pro Ile Asp Val Thr Glu Gly Glu Val Ile Ser Leu Gly Leu
65                  70                  75                  80

Pro Phe Gly Lys Val Thr Asn Leu Leu Met Leu Lys Gly Lys Asn Gln
                85                  90                  95

Ala Phe Ile Glu Met Asn Thr Glu Glu Ala Ala Asn Thr Met Val Asn
            100                 105                 110

Tyr Tyr Thr Ser Val Thr Pro Val Leu Arg Gly Gln Pro Ile Tyr Ile
        115                 120                 125

Gln Phe Ser Asn His Lys Glu Leu Lys Thr Asp Ser Ser Pro Asn Gln
    130                 135                 140
```

-continued

```
Ala Arg Ala Gln Ala Ala Leu Gln Ala Val Asn Ser Val Gln Ser Gly
145                 150                 155                 160

Asn Leu Ala Leu Ala Ala Ser Ala Ala Ala Val Asp Ala Gly Met Ala
                165                 170                 175

Met Ala Gly Gln Ser Pro Val Leu Arg Ile Ile Val Glu Asn Leu Phe
            180                 185                 190

Tyr Pro Val Thr Leu Asp Val Leu His Gln Ile Phe Ser Lys Phe Gly
        195                 200                 205

Thr Val Leu Lys Ile Ile Thr Phe Thr Lys Asn Asn Gln Phe Gln Ala
    210                 215                 220

Leu Leu Gln Tyr Ala Asp Pro Val Ser Ala Gln His Ala Lys Leu Ser
225                 230                 235                 240

Leu Asp Gly Gln Asn Ile Tyr Asn Ala Cys Cys Thr Leu Arg Ile Asp
                245                 250                 255

Phe Ser Lys Leu Thr Ser Leu Asn Val Lys Tyr Asn Asn Asp Lys Ser
            260                 265                 270

Arg Asp Tyr Thr Arg Pro Asp Leu Pro Ser Gly Asp Ser Gln Pro Ser
        275                 280                 285

Leu Asp Gln Thr Met Ala Ala Ala Phe Gly Ala Pro Gly Ile Ile Ser
    290                 295                 300

Ala Ser Pro Tyr Ala Gly Ala Gly Phe Pro Pro Thr Phe Ala Ile Pro
305                 310                 315                 320

Gln Ala Ala Gly Leu Ser Val Pro Asn Val His Gly Ala Leu Ala Pro
                325                 330                 335

Leu Ala Ile Pro Ser Ala Ala Ala Ala Ala Ala Ala Ala Gly Arg Ile
            340                 345                 350

Ala Ile Pro Gly Leu Ala Gly Ala Gly Asn Ser Val Leu Leu Val Ser
        355                 360                 365

Asn Leu Asn Pro Glu Arg Val Thr Pro Gln Ser Leu Phe Ile Leu Phe
    370                 375                 380

Gly Val Tyr Gly Asp Val Gln Arg Val Lys Ile Leu Phe Asn Lys Lys
385                 390                 395                 400

Glu Asn Ala Leu Val Gln Met Ala Asp Gly Asn Gln Ala Gln Leu Ala
                405                 410                 415

Met Ser His Leu Asn Gly His Lys Leu His Gly Lys Pro Ile Arg Ile
            420                 425                 430

Thr Leu Ser Lys His Gln Asn Val Gln Leu Pro Arg Glu Gly Gln Glu
        435                 440                 445

Asp Gln Gly Leu Thr Lys Asp Tyr Gly Asn Ser Pro Leu His Arg Phe
    450                 455                 460

Lys Lys Pro Gly Ser Lys Asn Phe Gln Asn Ile Phe Pro Pro Ser Ala
465                 470                 475                 480

Thr Leu His Leu Ser Asn Ile Pro Pro Ser Val Ser Glu Glu Asp Leu
                485                 490                 495

Lys Val Leu Phe Ser Ser Asn Gly Gly Val Val Lys Gly Phe Lys Phe
            500                 505                 510

Phe Gln Lys Asp Arg Lys Met Ala Leu Ile Gln Met Gly Ser Val Glu
        515                 520                 525

Glu Ala Val Gln Ala Leu Ile Asp Leu His Asn His Asp Leu Gly Glu
    530                 535                 540

Asn His His Leu Arg Val Ser Phe Ser Lys Ser Thr Ile
545                 550                 555
```

<210> SEQ ID NO 45
<211> LENGTH: 341
<212> TYPE: PRT
<213> ORGANISM: Homo sapiens

<400> SEQUENCE: 45

```
Met Thr Asp Gly Ile Leu Gly Lys Ala Ala Thr Met Glu Ile Pro Ile
1               5                   10                  15

His Gly Asn Gly Glu Ala Arg Gln Leu Pro Glu Asp Asp Gly Leu Glu
            20                  25                  30

Gln Asp Leu Gln Gln Val Met Val Ser Gly Pro Asn Leu Asn Glu Thr
        35                  40                  45

Ser Ile Val Ser Gly Gly Tyr Gly Gly Ser Gly Asp Gly Leu Ile Pro
    50                  55                  60

Thr Gly Ser Gly Arg His Pro Ser His Ser Thr Thr Pro Ser Gly Pro
65                  70                  75                  80

Gly Asp Glu Val Ala Arg Gly Ile Ala Gly Glu Lys Phe Asp Ile Val
                85                  90                  95

Lys Lys Trp Gly Ile Asn Thr Tyr Lys Cys Thr Lys Gln Leu Leu Ser
            100                 105                 110

Glu Arg Phe Gly Arg Gly Ser Arg Thr Val Asp Leu Glu Leu Glu Leu
        115                 120                 125

Gln Ile Glu Leu Leu Arg Glu Thr Lys Arg Lys Tyr Glu Ser Val Leu
    130                 135                 140

Gln Leu Gly Arg Ala Leu Thr Ala His Leu Tyr Ser Leu Leu Gln Thr
145                 150                 155                 160

Gln His Ala Leu Gly Asp Ala Phe Ala Asp Leu Ser Gln Lys Ser Pro
                165                 170                 175

Glu Leu Gln Glu Glu Phe Gly Tyr Asn Ala Glu Thr Gln Lys Leu Leu
            180                 185                 190

Cys Lys Asn Gly Glu Thr Leu Leu Gly Ala Val Asn Phe Phe Val Ser
        195                 200                 205

Ser Ile Asn Thr Leu Val Thr Lys Thr Met Glu Asp Thr Leu Met Thr
    210                 215                 220

Val Lys Gln Tyr Glu Ala Ala Arg Leu Glu Tyr Asp Ala Tyr Arg Thr
225                 230                 235                 240

Asp Leu Glu Glu Leu Ser Leu Gly Pro Arg Asp Ala Gly Thr Arg Gly
                245                 250                 255

Arg Leu Glu Ser Ala Gln Ala Thr Phe Gln Ala His Arg Asp Lys Tyr
            260                 265                 270

Glu Lys Leu Arg Gly Asp Val Ala Ile Lys Leu Lys Phe Leu Glu Glu
        275                 280                 285

Asn Lys Ile Lys Val Met His Lys Gln Leu Leu Leu Phe His Asn Ala
    290                 295                 300

Val Ser Ala Tyr Phe Ala Gly Asn Gln Lys Gln Leu Glu Gln Thr Leu
305                 310                 315                 320

Gln Gln Phe Asn Ile Lys Leu Arg Pro Pro Gly Ala Glu Lys Pro Ser
                325                 330                 335

Trp Leu Glu Glu Gln
            340
```

<210> SEQ ID NO 46
<211> LENGTH: 425
<212> TYPE: PRT
<213> ORGANISM: Homo sapiens

<400> SEQUENCE: 46

```
Met Ala Thr Ala Glu Val Leu Asn Ile Gly Lys Lys Leu Tyr Glu Gly
1               5                   10                  15

Lys Thr Lys Glu Val Tyr Glu Leu Leu Asp Ser Pro Gly Lys Val Leu
            20                  25                  30

Leu Gln Ser Lys Asp Gln Ile Thr Ala Gly Asn Ala Ala Arg Lys Asn
        35                  40                  45

His Leu Glu Gly Lys Ala Ala Ile Ser Asn Lys Ile Thr Ser Cys Ile
    50                  55                  60

Phe Gln Leu Leu Gln Glu Ala Gly Ile Lys Thr Ala Phe Thr Arg Lys
65                  70                  75                  80

Cys Gly Glu Thr Ala Phe Ile Ala Pro Gln Cys Glu Met Ile Pro Ile
                85                  90                  95

Glu Trp Val Cys Arg Arg Ile Ala Thr Gly Ser Phe Leu Lys Arg Asn
            100                 105                 110

Pro Gly Val Lys Glu Gly Tyr Lys Phe Tyr Pro Pro Lys Val Glu Leu
        115                 120                 125

Phe Phe Lys Asp Asp Ala Asn Asn Asp Pro Gln Trp Ser Glu Glu Gln
    130                 135                 140

Leu Ile Ala Ala Lys Phe Cys Phe Ala Gly Leu Leu Ile Gly Gln Thr
145                 150                 155                 160

Glu Val Asp Ile Met Ser His Ala Thr Gln Ala Ile Phe Glu Ile Leu
                165                 170                 175

Glu Lys Ser Trp Leu Pro Gln Asn Cys Thr Leu Val Asp Met Lys Ile
            180                 185                 190

Glu Phe Gly Val Asp Val Thr Thr Lys Glu Ile Val Leu Ala Asp Val
        195                 200                 205

Ile Asp Asn Asp Ser Trp Arg Leu Trp Pro Ser Gly Asp Arg Ser Gln
    210                 215                 220

Gln Lys Asp Lys Gln Ser Tyr Arg Asp Leu Lys Glu Val Thr Pro Glu
225                 230                 235                 240

Gly Leu Gln Met Val Lys Lys Asn Phe Glu Trp Val Ala Glu Arg Val
                245                 250                 255

Glu Leu Leu Leu Lys Ser Glu Ser Gln Cys Arg Val Val Val Leu Met
            260                 265                 270

Gly Ser Thr Ser Asp Leu Gly His Cys Glu Lys Ile Lys Lys Ala Cys
        275                 280                 285

Gly Asn Phe Gly Ile Pro Cys Glu Leu Arg Val Thr Ser Ala His Lys
    290                 295                 300

Gly Pro Asp Glu Thr Leu Arg Ile Lys Ala Glu Tyr Glu Gly Asp Gly
305                 310                 315                 320

Ile Pro Thr Val Phe Val Ala Val Ala Gly Arg Ser Asn Gly Leu Gly
                325                 330                 335

Pro Val Met Ser Gly Asn Thr Ala Tyr Pro Val Ile Ser Cys Pro Pro
            340                 345                 350

Leu Thr Pro Asp Trp Gly Val Gln Asp Val Trp Ser Ser Leu Arg Leu
        355                 360                 365

Pro Ser Gly Leu Gly Cys Ser Thr Val Leu Ser Pro Glu Gly Ser Ala
    370                 375                 380

Gln Phe Ala Ala Gln Ile Phe Gly Leu Ser Asn His Leu Val Trp Ser
385                 390                 395                 400

Lys Leu Arg Ala Ser Ile Leu Asn Thr Trp Ile Ser Leu Lys Gln Ala
```

```
                405                 410                 415

Asp Lys Lys Ile Arg Glu Cys Asn Leu
            420                 425


<210> SEQ ID NO 47
<211> LENGTH: 968
<212> TYPE: PRT
<213> ORGANISM: Homo sapiens

<400> SEQUENCE: 47

Met Val Leu Gly Cys Glu Leu Ser Gly Ser Thr Arg Val Val Val Gly
1               5                   10                  15

Val Glu Ala Leu Leu Thr Gly Ala Ser Ser Pro Leu Pro Gly Val Gly
            20                  25                  30

Pro Ala Asn Lys His Lys Pro Trp Ile Glu Ala Glu Tyr Gln Gly Ile
        35                  40                  45

Val Met Glu Asn Asp Asn Thr Val Leu Leu Asn Pro Pro Leu Phe Ala
    50                  55                  60

Leu Asp Lys Asp Ala Pro Leu Arg Tyr Ala Gly Glu Ile Cys Gly Phe
65                  70                  75                  80

Arg Leu His Gly Ser Gly Val Pro Phe Glu Ala Val Ile Leu Asp Lys
                85                  90                  95

Ala Thr Gly Glu Gly Leu Ile Arg Ala Lys Glu Pro Val Asp Cys Glu
            100                 105                 110

Ala Gln Lys Glu His Thr Phe Thr Ile Gln Ala Tyr Asp Cys Gly Glu
        115                 120                 125

Gly Pro Asp Gly Ala Asn Thr Lys Lys Ser His Lys Ala Thr Val His
    130                 135                 140

Val Arg Val Asn Asp Val Asn Glu Phe Ala Pro Val Phe Val Glu Arg
145                 150                 155                 160

Leu Tyr Arg Ala Ala Val Thr Glu Gly Lys Leu Tyr Asp Arg Ile Leu
                165                 170                 175

Arg Val Glu Ala Ile Asp Gly Asp Cys Ser Pro Gln Tyr Ser Gln Ile
            180                 185                 190

Cys Tyr Tyr Glu Ile Leu Thr Pro Asn Thr Pro Phe Leu Ile Asp Asn
        195                 200                 205

Asp Gly Asn Ile Glu Asn Thr Glu Lys Leu Gln Tyr Ser Gly Glu Arg
    210                 215                 220

Leu Tyr Lys Phe Thr Val Thr Ala Tyr Asp Cys Gly Lys Lys Arg Ala
225                 230                 235                 240

Ala Asp Asp Ala Glu Val Glu Ile Gln Val Lys Pro Thr Cys Lys Pro
                245                 250                 255

Ser Trp Gln Gly Trp Asn Lys Arg Ile Glu Tyr Ala Pro Gly Ala Gly
            260                 265                 270

Ser Leu Ala Leu Phe Pro Gly Ile Arg Leu Glu Thr Cys Asp Glu Pro
        275                 280                 285

Leu Trp Asn Ile Gln Ala Thr Ile Glu Leu Gln Thr Ser His Val Ala
    290                 295                 300

Lys Gly Cys Asp Arg Asp Asn Tyr Ser Glu Arg Ala Leu Arg Lys Leu
305                 310                 315                 320

Cys Gly Ala Ala Thr Gly Glu Val Asp Leu Leu Pro Met Pro Gly Pro
                325                 330                 335

Asn Ala Asn Trp Thr Ala Gly Leu Ser Val His Tyr Ser Gln Asp Ser
            340                 345                 350
```

-continued

```
Ser Leu Ile Tyr Trp Phe Asn Gly Thr Gln Ala Val Gln Val Pro Leu
        355                 360                 365

Gly Gly Pro Ser Gly Leu Gly Ser Gly Pro Gln Asp Ser Leu Ser Asp
    370                 375                 380

His Phe Thr Leu Ser Phe Trp Met Lys His Gly Val Thr Pro Asn Lys
385                 390                 395                 400

Gly Lys Lys Glu Glu Glu Thr Ile Val Cys Asn Thr Val Gln Asn Glu
                405                 410                 415

Asp Gly Phe Ser His Tyr Ser Leu Thr Val His Gly Cys Arg Ile Ala
                420                 425                 430

Phe Leu Tyr Trp Pro Leu Leu Glu Ser Ala Arg Pro Val Lys Phe Leu
        435                 440                 445

Trp Lys Leu Glu Gln Val Cys Asp Asp Glu Trp His His Tyr Ala Leu
    450                 455                 460

Asn Leu Glu Phe Pro Thr Val Thr Leu Tyr Thr Asp Gly Ile Ser Phe
465                 470                 475                 480

Asp Pro Ala Leu Ile His Asp Asn Gly Leu Ile His Pro Pro Arg Arg
                485                 490                 495

Glu Pro Ala Leu Met Ile Gly Ala Cys Trp Thr Glu Glu Lys Asn Lys
                500                 505                 510

Glu Lys Glu Lys Gly Asp Asn Ser Thr Asp Thr Thr Gln Gly Asp Pro
        515                 520                 525

Leu Ser Ile His His Tyr Phe His Gly Tyr Leu Ala Gly Phe Ser Val
    530                 535                 540

Arg Ser Gly Arg Leu Glu Ser Arg Glu Val Ile Glu Cys Leu Tyr Ala
545                 550                 555                 560

Cys Arg Glu Gly Leu Asp Tyr Arg Asp Phe Glu Ser Leu Gly Lys Gly
                565                 570                 575

Met Lys Val His Val Asn Pro Ser Gln Ser Leu Leu Thr Leu Glu Gly
                580                 585                 590

Asp Asp Val Glu Thr Phe Asn His Ala Leu Gln His Val Ala Tyr Met
        595                 600                 605

Asn Thr Leu Arg Phe Ala Thr Pro Gly Val Arg Pro Leu Arg Leu Thr
    610                 615                 620

Thr Ala Val Lys Cys Phe Ser Glu Glu Ser Cys Val Ser Ile Pro Glu
625                 630                 635                 640

Val Glu Gly Tyr Val Val Val Leu Gln Pro Asp Ala Pro Gln Ile Leu
                645                 650                 655

Leu Ser Gly Thr Ala His Phe Ala Arg Pro Ala Val Asp Phe Glu Gly
                660                 665                 670

Thr Asn Gly Val Pro Leu Phe Pro Asp Leu Gln Ile Thr Cys Ser Ile
        675                 680                 685

Ser His Gln Val Glu Ala Lys Lys Asp Glu Ser Trp Gln Gly Thr Val
    690                 695                 700

Thr Asp Thr Arg Met Ser Asp Glu Ile Val His Asn Leu Asp Gly Cys
705                 710                 715                 720

Glu Ile Ser Leu Val Gly Asp Asp Leu Asp Pro Glu Arg Glu Ser Leu
                725                 730                 735

Leu Leu Asp Thr Thr Ser Leu Gln Gln Arg Gly Leu Glu Leu Thr Asn
                740                 745                 750

Thr Ser Ala Tyr Leu Thr Ile Ala Gly Val Glu Ser Ile Thr Val Tyr
        755                 760                 765

Glu Glu Ile Leu Arg Gln Ala Arg Tyr Arg Leu Arg His Gly Ala Ala
```

```
    770                 775                 780

Leu Tyr Thr Arg Lys Phe Arg Leu Ser Cys Ser Glu Met Asn Gly Arg
785                 790                 795                 800

Tyr Ser Ser Asn Glu Phe Ile Val Glu Val Asn Val Leu His Ser Met
                805                 810                 815

Asn Arg Val Ala His Pro Ser His Val Leu Ser Ser Gln Gln Phe Leu
            820                 825                 830

His Arg Gly His Gln Pro Pro Pro Glu Met Ala Gly His Ser Leu Ala
        835                 840                 845

Ser Ser His Arg Asn Ser Met Ile Pro Ser Ala Ala Thr Leu Ile Ile
    850                 855                 860

Val Val Cys Val Gly Phe Leu Val Leu Met Val Val Leu Gly Leu Val
865                 870                 875                 880

Arg Ile His Ser Leu His Arg Arg Val Ser Gly Ala Gly Gly Pro Pro
                885                 890                 895

Gly Ala Ser Ser Asp Pro Lys Asp Pro Asp Leu Phe Trp Asp Asp Ser
            900                 905                 910

Ala Leu Thr Ile Ile Val Asn Pro Met Glu Ser Tyr Gln Asn Arg Gln
        915                 920                 925

Ser Cys Val Thr Gly Ala Val Gly Gly Gln Gln Glu Asp Glu Asp Ser
    930                 935                 940

Ser Asp Ser Glu Val Ala Asp Ser Pro Ser Ser Asp Glu Arg Arg Ile
945                 950                 955                 960

Ile Glu Thr Pro Pro His Arg Tyr
                965


<210> SEQ ID NO 48
<211> LENGTH: 154
<212> TYPE: PRT
<213> ORGANISM: Homo sapiens

<400> SEQUENCE: 48

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150


<210> SEQ ID NO 49
<211> LENGTH: 1024
```

-continued

<212> TYPE: PRT
<213> ORGANISM: Homo sapiens

<400> SEQUENCE: 49

```
Met Asn Leu Gln Ala Gln Pro Lys Ala Gln Asn Lys Arg Lys Arg Cys
1               5                   10                  15

Leu Phe Gly Gly Gln Glu Pro Ala Pro Lys Glu Gln Pro Pro Pro Leu
            20                  25                  30

Gln Pro Pro Gln Gln Ser Ile Arg Val Lys Glu Glu Gln Tyr Leu Gly
        35                  40                  45

His Glu Gly Pro Gly Gly Ala Val Ser Thr Ser Gln Pro Val Glu Leu
    50                  55                  60

Pro Pro Pro Ser Ser Leu Ala Leu Leu Asn Ser Val Val Tyr Gly Pro
65                  70                  75                  80

Glu Arg Thr Ser Ala Ala Met Leu Ser Gln Gln Val Ala Ser Val Lys
                85                  90                  95

Trp Pro Asn Ser Val Met Ala Pro Gly Arg Gly Pro Glu Arg Gly Gly
            100                 105                 110

Gly Gly Gly Val Ser Asp Ser Ser Trp Gln Gln Gln Pro Gly Gln Pro
        115                 120                 125

Pro Pro His Ser Thr Trp Asn Cys His Ser Leu Ser Leu Tyr Ser Ala
    130                 135                 140

Thr Lys Gly Ser Pro His Pro Gly Val Gly Val Pro Thr Tyr Tyr Asn
145                 150                 155                 160

His Pro Glu Ala Leu Lys Arg Glu Lys Ala Gly Gly Pro Gln Leu Asp
                165                 170                 175

Arg Tyr Val Arg Pro Met Met Pro Gln Lys Val Gln Leu Glu Val Gly
            180                 185                 190

Arg Pro Gln Ala Pro Leu Asn Ser Phe His Ala Ala Lys Lys Pro Pro
        195                 200                 205

Asn Gln Ser Leu Pro Leu Gln Pro Phe Gln Leu Ala Phe Gly His Gln
    210                 215                 220

Val Asn Arg Gln Val Phe Arg Gln Gly Pro Pro Pro Pro Asn Pro Val
225                 230                 235                 240

Ala Ala Phe Pro Pro Gln Lys Gln Gln Gln Gln Gln Gln Pro Gln Gln
                245                 250                 255

Gln Gln Gln Gln Gln Gln Ala Ala Leu Pro Gln Met Pro Leu Phe Glu
            260                 265                 270

Asn Phe Tyr Ser Met Pro Gln Gln Pro Ser Gln Gln Pro Gln Asp Phe
        275                 280                 285

Gly Leu Gln Pro Ala Gly Pro Leu Gly Gln Ser His Leu Ala His His
    290                 295                 300

Ser Met Ala Pro Tyr Pro Phe Pro Pro Asn Pro Asp Met Asn Pro Glu
305                 310                 315                 320

Leu Arg Lys Ala Leu Leu Gln Asp Ser Ala Pro Gln Pro Ala Leu Pro
                325                 330                 335

Gln Val Gln Ile Pro Phe Pro Arg Arg Ser Arg Arg Leu Ser Lys Glu
            340                 345                 350

Gly Ile Leu Pro Pro Ser Ala Leu Asp Gly Ala Gly Thr Gln Pro Gly
        355                 360                 365

Gln Glu Ala Thr Gly Asn Leu Phe Leu His His Trp Pro Leu Gln Gln
    370                 375                 380

Pro Pro Pro Gly Ser Leu Gly Gln Pro His Pro Glu Ala Leu Gly Phe
385                 390                 395                 400
```

-continued

```
Pro Leu Glu Leu Arg Glu Ser Gln Leu Leu Pro Asp Gly Glu Arg Leu
                405                 410                 415

Ala Pro Asn Gly Arg Glu Arg Glu Ala Pro Ala Met Gly Ser Glu Glu
            420                 425                 430

Gly Met Arg Ala Val Ser Thr Gly Asp Cys Gly Gln Val Leu Arg Gly
        435                 440                 445

Gly Val Ile Gln Ser Thr Arg Arg Arg Arg Arg Ala Ser Gln Glu Ala
    450                 455                 460

Asn Leu Leu Thr Leu Ala Gln Lys Ala Val Glu Leu Ala Ser Leu Gln
465                 470                 475                 480

Asn Ala Lys Asp Gly Ser Gly Ser Glu Glu Lys Arg Lys Ser Val Leu
                485                 490                 495

Ala Ser Thr Thr Lys Cys Gly Val Glu Phe Ser Glu Pro Ser Leu Ala
            500                 505                 510

Thr Lys Arg Ala Arg Glu Asp Ser Gly Met Val Pro Leu Ile Ile Pro
        515                 520                 525

Val Ser Val Pro Val Arg Thr Val Asp Pro Thr Glu Ala Ala Gln Ala
    530                 535                 540

Gly Gly Leu Asp Glu Asp Gly Lys Gly Pro Glu Gln Asn Pro Ala Glu
545                 550                 555                 560

His Lys Pro Ser Val Ile Val Thr Arg Arg Arg Ser Thr Arg Ile Pro
                565                 570                 575

Gly Thr Asp Ala Gln Ala Gln Ala Glu Asp Met Asn Val Lys Leu Glu
            580                 585                 590

Gly Glu Pro Ser Val Arg Lys Pro Lys Gln Arg Pro Arg Pro Glu Pro
        595                 600                 605

Leu Ile Ile Pro Thr Lys Ala Gly Thr Phe Ile Ala Pro Pro Val Tyr
    610                 615                 620

Ser Asn Ile Thr Pro Tyr Gln Ser His Leu Arg Ser Pro Val Arg Leu
625                 630                 635                 640

Ala Asp His Pro Ser Glu Arg Ser Phe Glu Leu Pro Pro Tyr Thr Pro
                645                 650                 655

Pro Pro Ile Leu Ser Pro Val Arg Glu Gly Ser Gly Leu Tyr Phe Asn
            660                 665                 670

Ala Ile Ile Ser Thr Ser Thr Ile Pro Ala Pro Pro Pro Ile Thr Pro
        675                 680                 685

Lys Ser Ala His Arg Thr Leu Leu Arg Thr Asn Ser Ala Glu Val Thr
    690                 695                 700

Pro Pro Val Leu Ser Val Met Gly Glu Ala Thr Pro Val Ser Ile Glu
705                 710                 715                 720

Pro Arg Ile Asn Val Gly Ser Arg Phe Gln Ala Glu Ile Pro Leu Met
                725                 730                 735

Arg Asp Arg Ala Leu Ala Ala Ala Asp Pro His Lys Ala Asp Leu Val
            740                 745                 750

Trp Gln Pro Trp Glu Asp Leu Glu Ser Ser Arg Glu Lys Gln Arg Gln
        755                 760                 765

Val Glu Asp Leu Leu Thr Ala Ala Cys Ser Ser Ile Phe Pro Gly Ala
    770                 775                 780

Gly Thr Asn Gln Glu Leu Ala Leu His Cys Leu His Glu Ser Arg Gly
785                 790                 795                 800

Asp Ile Leu Glu Thr Leu Asn Lys Leu Leu Leu Lys Lys Pro Leu Arg
                805                 810                 815
```

-continued

```
Pro His Asn His Pro Leu Ala Thr Tyr His Tyr Thr Gly Ser Asp Gln
            820                 825                 830

Trp Lys Met Ala Glu Arg Lys Leu Phe Asn Lys Gly Ile Ala Ile Tyr
        835                 840                 845

Lys Lys Asp Phe Phe Leu Val Gln Lys Leu Ile Gln Thr Lys Thr Val
    850                 855                 860

Ala Gln Cys Val Glu Phe Tyr Tyr Thr Tyr Lys Lys Gln Val Lys Ile
865                 870                 875                 880

Gly Arg Asn Gly Thr Leu Thr Phe Gly Asp Val Asp Thr Ser Asp Glu
                885                 890                 895

Lys Ser Ala Gln Glu Glu Val Glu Val Asp Ile Lys Thr Ser Gln Lys
            900                 905                 910

Phe Pro Arg Val Pro Leu Pro Arg Arg Glu Ser Pro Ser Glu Glu Arg
        915                 920                 925

Leu Glu Pro Lys Arg Glu Val Lys Glu Pro Arg Lys Glu Gly Glu Glu
    930                 935                 940

Glu Val Pro Glu Ile Gln Glu Lys Glu Glu Gln Glu Glu Gly Arg Glu
945                 950                 955                 960

Arg Ser Arg Arg Ala Ala Ala Val Lys Ala Thr Gln Thr Leu Gln Ala
                965                 970                 975

Asn Glu Ser Ala Ser Asp Ile Leu Ile Leu Arg Ser His Glu Ser Asn
            980                 985                 990

Ala Pro Gly Ser Ala Gly Gly Gln  Ala Ser Glu Lys Pro  Arg Glu Gly
        995                 1000                 1005

Thr Gly  Lys Ser Arg Arg Ala  Leu Pro Phe Ser Lys  Lys Lys Lys
    1010                 1015                 1020

Lys


<210> SEQ ID NO 50
<211> LENGTH: 2491
<212> TYPE: PRT
<213> ORGANISM: Homo sapiens

<400> SEQUENCE: 50

Met Gly Ala Ala Ala Gly Arg Ser Pro His Leu Gly Pro Ala Pro Ala
1               5                   10                  15

Arg Arg Pro Gln Arg Ser Leu Leu Leu Leu Gln Leu Leu Leu Leu Val
            20                  25                  30

Ala Ala Pro Gly Ser Thr Gln Ala Gln Ala Ala Pro Phe Pro Glu Leu
        35                  40                  45

Cys Ser Tyr Thr Trp Glu Ala Val Asp Thr Lys Asn Asn Val Leu Tyr
    50                  55                  60

Lys Ile Asn Ile Cys Gly Ser Val Asp Ile Val Gln Cys Gly Pro Ser
65                  70                  75                  80

Ser Ala Val Cys Met His Asp Leu Lys Thr Arg Thr Tyr His Ser Val
                85                  90                  95

Gly Asp Ser Val Leu Arg Ser Ala Thr Arg Ser Leu Leu Glu Phe Asn
            100                 105                 110

Thr Thr Val Ser Cys Asp Gln Gln Gly Thr Asn His Arg Val Gln Ser
        115                 120                 125

Ser Ile Ala Phe Leu Cys Gly Lys Thr Leu Gly Thr Pro Glu Phe Val
    130                 135                 140

Thr Ala Thr Glu Cys Val His Tyr Phe Glu Trp Arg Thr Thr Ala Ala
145                 150                 155                 160
```

-continued

```
Cys Lys Lys Asp Ile Phe Lys Ala Asn Lys Glu Val Pro Cys Tyr Val
                165                 170                 175

Phe Asp Glu Glu Leu Arg Lys His Asp Leu Asn Pro Leu Ile Lys Leu
            180                 185                 190

Ser Gly Ala Tyr Leu Val Asp Asp Ser Asp Pro Asp Thr Ser Leu Phe
        195                 200                 205

Ile Asn Val Cys Arg Asp Ile Asp Thr Leu Arg Asp Pro Gly Ser Gln
    210                 215                 220

Leu Arg Ala Cys Pro Pro Gly Thr Ala Ala Cys Leu Val Arg Gly His
225                 230                 235                 240

Gln Ala Phe Asp Val Gly Gln Pro Arg Asp Gly Leu Lys Leu Val Arg
                245                 250                 255

Lys Asp Arg Leu Val Leu Ser Tyr Val Arg Glu Glu Ala Gly Lys Leu
            260                 265                 270

Asp Phe Cys Asp Gly His Ser Pro Ala Val Thr Ile Thr Phe Val Cys
        275                 280                 285

Pro Ser Glu Arg Arg Glu Gly Thr Ile Pro Lys Leu Thr Ala Lys Ser
    290                 295                 300

Asn Cys Arg Tyr Glu Ile Glu Trp Ile Thr Glu Tyr Ala Cys His Arg
305                 310                 315                 320

Asp Tyr Leu Glu Ser Lys Thr Cys Ser Leu Ser Gly Glu Gln Gln Asp
                325                 330                 335

Val Ser Ile Asp Leu Thr Pro Leu Ala Gln Ser Gly Gly Ser Ser Tyr
            340                 345                 350

Ile Ser Asp Gly Lys Glu Tyr Leu Phe Tyr Leu Asn Val Cys Gly Glu
        355                 360                 365

Thr Glu Ile Gln Phe Cys Asn Lys Lys Gln Ala Ala Val Cys Gln Val
    370                 375                 380

Lys Lys Ser Asp Thr Ser Gln Val Lys Ala Ala Gly Arg Tyr His Asn
385                 390                 395                 400

Gln Thr Leu Arg Tyr Ser Asp Gly Asp Leu Thr Leu Ile Tyr Phe Gly
                405                 410                 415

Gly Asp Glu Cys Ser Ser Gly Phe Gln Arg Met Ser Val Ile Asn Phe
            420                 425                 430

Glu Cys Asn Lys Thr Ala Gly Asn Asp Gly Lys Gly Thr Pro Val Phe
        435                 440                 445

Thr Gly Glu Val Asp Cys Thr Tyr Phe Phe Thr Trp Asp Thr Glu Tyr
    450                 455                 460

Ala Cys Val Lys Glu Lys Glu Asp Leu Leu Cys Gly Ala Thr Asp Gly
465                 470                 475                 480

Lys Lys Arg Tyr Asp Leu Ser Ala Leu Val Arg His Ala Glu Pro Glu
                485                 490                 495

Gln Asn Trp Glu Ala Val Asp Gly Ser Gln Thr Glu Thr Glu Lys Lys
            500                 505                 510

His Phe Phe Ile Asn Ile Cys His Arg Val Leu Gln Glu Gly Lys Ala
        515                 520                 525

Arg Gly Cys Pro Glu Asp Ala Ala Val Cys Ala Val Asp Lys Asn Gly
    530                 535                 540

Ser Lys Asn Leu Gly Lys Phe Ile Ser Ser Pro Met Lys Glu Lys Gly
545                 550                 555                 560

Asn Ile Gln Leu Ser Tyr Ser Asp Gly Asp Asp Cys Gly His Gly Lys
                565                 570                 575

Lys Ile Lys Thr Asn Ile Thr Leu Val Cys Lys Pro Gly Asp Leu Glu
```

```
            580                 585                 590

Ser Ala Pro Val Leu Arg Thr Ser Gly Glu Gly Gly Cys Phe Tyr Glu
        595                 600                 605

Phe Glu Trp Arg Thr Ala Ala Ala Cys Val Leu Ser Lys Thr Glu Gly
    610                 615                 620

Glu Asn Cys Thr Val Phe Asp Ser Gln Ala Gly Phe Ser Phe Asp Leu
625                 630                 635                 640

Ser Pro Leu Thr Lys Lys Asn Gly Ala Tyr Lys Val Glu Thr Lys Lys
                645                 650                 655

Tyr Asp Phe Tyr Ile Asn Val Cys Gly Pro Val Ser Val Ser Pro Cys
            660                 665                 670

Gln Pro Asp Ser Gly Ala Cys Gln Val Ala Lys Ser Asp Glu Lys Thr
        675                 680                 685

Trp Asn Leu Gly Leu Ser Asn Ala Lys Leu Ser Tyr Tyr Asp Gly Met
    690                 695                 700

Ile Gln Leu Asn Tyr Arg Gly Gly Thr Pro Tyr Asn Asn Glu Arg His
705                 710                 715                 720

Thr Pro Arg Ala Thr Leu Ile Thr Phe Leu Cys Asp Arg Asp Ala Gly
                725                 730                 735

Val Gly Phe Pro Glu Tyr Gln Glu Glu Asp Asn Ser Thr Tyr Asn Phe
            740                 745                 750

Arg Trp Tyr Thr Ser Tyr Ala Cys Pro Glu Glu Pro Leu Glu Cys Val
        755                 760                 765

Val Thr Asp Pro Ser Thr Leu Glu Gln Tyr Asp Leu Ser Ser Leu Ala
    770                 775                 780

Lys Ser Glu Gly Gly Leu Gly Gly Asn Trp Tyr Ala Met Asp Asn Ser
785                 790                 795                 800

Gly Glu His Val Thr Trp Arg Lys Tyr Tyr Ile Asn Val Cys Arg Pro
                805                 810                 815

Leu Asn Pro Val Pro Gly Cys Asn Arg Tyr Ala Ser Ala Cys Gln Met
            820                 825                 830

Lys Tyr Glu Lys Asp Gln Gly Ser Phe Thr Glu Val Val Ser Ile Ser
        835                 840                 845

Asn Leu Gly Met Ala Lys Thr Gly Pro Val Val Glu Asp Ser Gly Ser
    850                 855                 860

Leu Leu Leu Glu Tyr Val Asn Gly Ser Ala Cys Thr Thr Ser Asp Gly
865                 870                 875                 880

Arg Gln Thr Thr Tyr Thr Thr Arg Ile His Leu Val Cys Ser Arg Gly
                885                 890                 895

Arg Leu Asn Ser His Pro Ile Phe Ser Leu Asn Trp Glu Cys Val Val
            900                 905                 910

Ser Phe Leu Trp Asn Thr Glu Ala Ala Cys Pro Ile Gln Thr Thr Thr
        915                 920                 925

Asp Thr Asp Gln Ala Cys Ser Ile Arg Asp Pro Asn Ser Gly Phe Val
    930                 935                 940

Phe Asn Leu Asn Pro Leu Asn Ser Ser Gln Gly Tyr Asn Val Ser Gly
945                 950                 955                 960

Ile Gly Lys Ile Phe Met Phe Asn Val Cys Gly Thr Met Pro Val Cys
                965                 970                 975

Gly Thr Ile Leu Gly Lys Pro Ala Ser Gly Cys Glu Ala Glu Thr Gln
            980                 985                 990

Thr Glu Glu Leu Lys Asn Trp Lys  Pro Ala Arg Pro Val  Gly Ile Glu
        995                 1000                1005
```

-continued

```
Lys Ser  Leu Gln Leu Ser Thr  Glu Gly Phe Ile Thr  Leu Thr Tyr
    1010                 1015                 1020

Lys Gly  Pro Leu Ser Ala Lys  Gly Thr Ala Asp Ala  Phe Ile Val
    1025                 1030                 1035

Arg Phe  Val Cys Asn Asp Asp  Val Tyr Ser Gly Pro  Leu Lys Phe
    1040                 1045                 1050

Leu His  Gln Asp Ile Asp Ser  Gly Gln Gly Ile Arg  Asn Thr Tyr
    1055                 1060                 1065

Phe Glu  Phe Glu Thr Ala Leu  Ala Cys Val Pro Ser  Pro Val Asp
    1070                 1075                 1080

Cys Gln  Val Thr Asp Leu Ala  Gly Asn Glu Tyr Asp  Leu Thr Gly
    1085                 1090                 1095

Leu Ser  Thr Val Arg Lys Pro  Trp Thr Ala Val Asp  Thr Ser Val
    1100                 1105                 1110

Asp Gly  Arg Lys Arg Thr Phe  Tyr Leu Ser Val Cys  Asn Pro Leu
    1115                 1120                 1125

Pro Tyr  Ile Pro Gly Cys Gln  Gly Ser Ala Val Gly  Ser Cys Leu
    1130                 1135                 1140

Val Ser  Glu Gly Asn Ser Trp  Asn Leu Gly Val Val  Gln Met Ser
    1145                 1150                 1155

Pro Gln  Ala Ala Ala Asn Gly  Ser Leu Ser Ile Met  Tyr Val Asn
    1160                 1165                 1170

Gly Asp  Lys Cys Gly Asn Gln  Arg Phe Ser Thr Arg  Ile Thr Phe
    1175                 1180                 1185

Glu Cys  Ala Gln Ile Ser Gly  Ser Pro Ala Phe Gln  Leu Gln Asp
    1190                 1195                 1200

Gly Cys  Glu Tyr Val Phe Ile  Trp Arg Thr Val Glu  Ala Cys Pro
    1205                 1210                 1215

Val Val  Arg Val Glu Gly Asp  Asn Cys Glu Val Lys  Asp Pro Arg
    1220                 1225                 1230

His Gly  Asn Leu Tyr Asp Leu  Lys Pro Leu Gly Leu  Asn Asp Thr
    1235                 1240                 1245

Ile Val  Ser Ala Gly Glu Tyr  Thr Tyr Tyr Phe Arg  Val Cys Gly
    1250                 1255                 1260

Lys Leu  Ser Ser Asp Val Cys  Pro Thr Ser Asp Lys  Ser Lys Val
    1265                 1270                 1275

Val Ser  Ser Cys Gln Glu Lys  Arg Glu Pro Gln Gly  Phe His Lys
    1280                 1285                 1290

Val Ala  Gly Leu Leu Thr Gln  Lys Leu Thr Tyr Glu  Asn Gly Leu
    1295                 1300                 1305

Leu Lys  Met Asn Phe Thr Gly  Gly Asp Thr Cys His  Lys Val Tyr
    1310                 1315                 1320

Gln Arg  Ser Thr Ala Ile Phe  Phe Tyr Cys Asp Arg  Gly Thr Gln
    1325                 1330                 1335

Arg Pro  Val Phe Leu Lys Glu  Thr Ser Asp Cys Ser  Tyr Leu Phe
    1340                 1345                 1350

Glu Trp  Arg Thr Gln Tyr Ala  Cys Pro Pro Phe Asp  Leu Thr Glu
    1355                 1360                 1365

Cys Ser  Phe Lys Asp Gly Ala  Gly Asn Ser Phe Asp  Leu Ser Ser
    1370                 1375                 1380

Leu Ser  Arg Tyr Ser Asp Asn  Trp Glu Ala Ile Thr  Gly Thr Gly
    1385                 1390                 1395
```

-continued

```
Asp Pro  Glu His Tyr Leu Ile  Asn Val Cys Lys Ser  Leu Ala Pro
    1400                 1405                 1410

Gln Ala  Gly Thr Glu Pro Cys  Pro Pro Glu Ala Ala  Ala Cys Leu
    1415                 1420                 1425

Leu Gly  Gly Ser Lys Pro Val  Asn Leu Gly Arg Val  Arg Asp Gly
    1430                 1435                 1440

Pro Gln  Trp Arg Asp Gly Ile  Ile Val Leu Lys Tyr  Val Asp Gly
    1445                 1450                 1455

Asp Leu  Cys Pro Asp Gly Ile  Arg Lys Lys Ser Thr  Thr Ile Arg
    1460                 1465                 1470

Phe Thr  Cys Ser Glu Ser Gln  Val Asn Ser Arg Pro  Met Phe Ile
    1475                 1480                 1485

Ser Ala  Val Glu Asp Cys Glu  Tyr Thr Phe Ala Trp  Pro Thr Ala
    1490                 1495                 1500

Thr Ala  Cys Pro Met Lys Ser  Asn Glu His Asp Asp  Cys Gln Val
    1505                 1510                 1515

Thr Asn  Pro Ser Thr Gly His  Leu Phe Asp Leu Ser  Ser Leu Ser
    1520                 1525                 1530

Gly Arg  Ala Gly Phe Thr Ala  Ala Tyr Ser Glu Lys  Gly Leu Val
    1535                 1540                 1545

Tyr Met  Ser Ile Cys Gly Glu  Asn Glu Asn Cys Pro  Pro Gly Val
    1550                 1555                 1560

Gly Ala  Cys Phe Gly Gln Thr  Arg Ile Ser Val Gly  Lys Ala Asn
    1565                 1570                 1575

Lys Arg  Leu Arg Tyr Val Asp  Gln Val Leu Gln Leu  Val Tyr Lys
    1580                 1585                 1590

Asp Gly  Ser Pro Cys Pro Ser  Lys Ser Gly Leu Ser  Tyr Lys Ser
    1595                 1600                 1605

Val Ile  Ser Phe Val Cys Arg  Pro Glu Ala Gly Pro  Thr Asn Arg
    1610                 1615                 1620

Pro Met  Leu Ile Ser Leu Asp  Lys Gln Thr Cys Thr  Leu Phe Phe
    1625                 1630                 1635

Ser Trp  His Thr Pro Leu Ala  Cys Glu Gln Ala Thr  Glu Cys Ser
    1640                 1645                 1650

Val Arg  Asn Gly Ser Ser Ile  Val Asp Leu Ser Pro  Leu Ile His
    1655                 1660                 1665

Arg Thr  Gly Gly Tyr Glu Ala  Tyr Asp Glu Ser Glu  Asp Asp Ala
    1670                 1675                 1680

Ser Asp  Thr Asn Pro Asp Phe  Tyr Ile Asn Ile Cys  Gln Pro Leu
    1685                 1690                 1695

Asn Pro  Met His Ala Val Pro  Cys Pro Ala Gly Ala  Ala Val Cys
    1700                 1705                 1710

Lys Val  Pro Ile Asp Gly Pro  Pro Ile Asp Ile Gly  Arg Val Ala
    1715                 1720                 1725

Gly Pro  Pro Ile Leu Asn Pro  Ile Ala Asn Glu Ile  Tyr Leu Asn
    1730                 1735                 1740

Phe Glu  Ser Ser Thr Pro Cys  Leu Ala Asp Lys His  Phe Asn Tyr
    1745                 1750                 1755

Thr Ser  Leu Ile Ala Phe His  Cys Lys Arg Gly Val  Ser Met Gly
    1760                 1765                 1770

Thr Pro  Lys Leu Leu Arg Thr  Ser Glu Cys Asp Phe  Val Phe Glu
    1775                 1780                 1785

Trp Glu  Thr Pro Val Val Cys  Pro Asp Glu Val Arg  Met Asp Gly
```

-continued

```
    1790                1795                1800

Cys Thr  Leu Thr Asp Glu Gln  Leu Leu Tyr Ser Phe  Asn Leu Ser
    1805                1810                1815

Ser Leu  Ser Thr Ser Thr Phe  Lys Val Thr Arg Asp  Ser Arg Thr
    1820                1825                1830

Tyr Ser  Val Gly Val Cys Thr  Phe Ala Val Gly Pro  Glu Gln Gly
    1835                1840                1845

Gly Cys  Lys Asp Gly Gly Val  Cys Leu Leu Ser Gly  Thr Lys Gly
    1850                1855                1860

Ala Ser  Phe Gly Arg Leu Gln  Ser Met Lys Leu Asp  Tyr Arg His
    1865                1870                1875

Gln Asp  Glu Ala Val Val Leu  Ser Tyr Val Asn Gly  Asp Arg Cys
    1880                1885                1890

Pro Pro  Glu Thr Asp Asp Gly  Val Pro Cys Val Phe  Pro Phe Ile
    1895                1900                1905

Phe Asn  Gly Lys Ser Tyr Glu  Glu Cys Ile Ile Glu  Ser Arg Ala
    1910                1915                1920

Lys Leu  Trp Cys Ser Thr Thr  Ala Asp Tyr Asp Arg  Asp His Glu
    1925                1930                1935

Trp Gly  Phe Cys Arg His Ser  Asn Ser Tyr Arg Thr  Ser Ser Ile
    1940                1945                1950

Ile Phe  Lys Cys Asp Glu Asp  Glu Asp Ile Gly Arg  Pro Gln Val
    1955                1960                1965

Phe Ser  Glu Val Arg Gly Cys  Asp Val Thr Phe Glu  Trp Lys Thr
    1970                1975                1980

Lys Val  Val Cys Pro Pro Lys  Lys Leu Glu Cys Lys  Phe Val Gln
    1985                1990                1995

Lys His  Lys Thr Tyr Asp Leu  Arg Leu Leu Ser Ser  Leu Thr Gly
    2000                2005                2010

Ser Trp  Ser Leu Val His Asn  Gly Val Ser Tyr Tyr  Ile Asn Leu
    2015                2020                2025

Cys Gln  Lys Ile Tyr Lys Gly  Pro Leu Gly Cys Ser  Glu Arg Ala
    2030                2035                2040

Ser Ile  Cys Arg Arg Thr Thr  Thr Gly Asp Val Gln  Val Leu Gly
    2045                2050                2055

Leu Val  His Thr Gln Lys Leu  Gly Val Ile Gly Asp  Lys Val Val
    2060                2065                2070

Val Thr  Tyr Ser Lys Gly Tyr  Pro Cys Gly Gly Asn  Lys Thr Ala
    2075                2080                2085

Ser Ser  Val Ile Glu Leu Thr  Cys Thr Lys Thr Val  Gly Arg Pro
    2090                2095                2100

Ala Phe  Lys Arg Phe Asp Ile  Asp Ser Cys Thr Tyr  Tyr Phe Ser
    2105                2110                2115

Trp Asp  Ser Arg Ala Ala Cys  Ala Val Lys Pro Gln  Glu Val Gln
    2120                2125                2130

Met Val  Asn Gly Thr Ile Thr  Asn Pro Ile Asn Gly  Lys Ser Phe
    2135                2140                2145

Ser Leu  Gly Asp Ile Tyr Phe  Lys Leu Phe Arg Ala  Ser Gly Asp
    2150                2155                2160

Met Arg  Thr Asn Gly Asp Asn  Tyr Leu Tyr Glu Ile  Gln Leu Ser
    2165                2170                2175

Ser Ile  Thr Ser Ser Arg Asn  Pro Ala Cys Ser Gly  Ala Asn Ile
    2180                2185                2190
```

-continued

```
Cys Gln  Val Lys Pro Asn Asp  Gln His Phe Ser Arg  Lys Val Gly
    2195                 2200                 2205

Thr Ser  Asp Lys Thr Lys Tyr  Tyr Leu Gln Asp Gly  Asp Leu Asp
    2210                 2215                 2220

Val Val  Phe Ala Ser Ser Ser  Lys Cys Gly Lys Asp  Lys Thr Lys
    2225                 2230                 2235

Ser Val  Ser Ser Thr Ile Phe  Phe His Cys Asp Pro  Leu Val Glu
    2240                 2245                 2250

Asp Gly  Ile Pro Glu Phe Ser  His Glu Thr Ala Asp  Cys Gln Tyr
    2255                 2260                 2265

Leu Phe  Ser Trp Tyr Thr Ser  Ala Val Cys Pro Leu  Gly Val Gly
    2270                 2275                 2280

Phe Asp  Ser Glu Asn Pro Gly  Asp Asp Gly Gln Met  His Lys Gly
    2285                 2290                 2295

Leu Ser  Glu Arg Ser Gln Ala  Val Gly Ala Val Leu  Ser Leu Leu
    2300                 2305                 2310

Leu Val  Ala Leu Thr Cys Cys  Leu Leu Ala Leu Leu  Leu Tyr Lys
    2315                 2320                 2325

Lys Glu  Arg Arg Glu Thr Val  Ile Ser Lys Leu Thr  Thr Cys Cys
    2330                 2335                 2340

Arg Arg  Ser Ser Asn Val Ser  Tyr Lys Tyr Ser Lys  Val Asn Lys
    2345                 2350                 2355

Glu Glu  Glu Thr Asp Glu Asn  Glu Thr Glu Trp Leu  Met Glu Glu
    2360                 2365                 2370

Ile Gln  Leu Pro Pro Pro Arg  Gln Gly Lys Glu Gly  Gln Glu Asn
    2375                 2380                 2385

Gly His  Ile Thr Thr Lys Ser  Val Lys Ala Leu Ser  Ser Leu His
    2390                 2395                 2400

Gly Asp  Asp Gln Asp Ser Glu  Asp Glu Val Leu Thr  Ile Pro Glu
    2405                 2410                 2415

Val Lys  Val His Ser Gly Arg  Gly Ala Gly Ala Glu  Ser Ser His
    2420                 2425                 2430

Pro Val  Arg Asn Ala Gln Ser  Asn Ala Leu Gln Glu  Arg Glu Asp
    2435                 2440                 2445

Asp Arg  Val Gly Leu Val Arg  Gly Glu Lys Ala Arg  Lys Gly Lys
    2450                 2455                 2460

Ser Ser  Ser Ala Gln Gln Lys  Thr Val Ser Ser Thr  Lys Leu Val
    2465                 2470                 2475

Ser Phe  His Asp Asp Ser Asp  Glu Asp Leu Leu His  Ile
    2480                 2485                 2490
```

<210> SEQ ID NO 51
<211> LENGTH: 227
<212> TYPE: PRT
<213> ORGANISM: Homo sapiens

<400> SEQUENCE: 51

```
Met Ser Val Val Pro Pro Asn Arg Ser Gln Thr Gly Trp Pro Arg Gly
1               5                   10                  15

Val Thr Gln Phe Gly Asn Lys Tyr Ile Gln Gln Thr Lys Pro Leu Thr
            20                  25                  30

Leu Glu Arg Thr Ile Asn Leu Tyr Pro Leu Thr Asn Tyr Thr Phe Gly
        35                  40                  45

Thr Lys Glu Pro Leu Tyr Glu Lys Asp Ser Ser Val Ala Ala Arg Phe
```

-continued

```
    50                  55                  60

Gln Arg Met Arg Glu Glu Phe Asp Lys Ile Gly Met Arg Arg Thr Val
65                  70                  75                  80

Glu Gly Val Leu Ile Val His Glu His Arg Leu Pro His Val Leu Leu
                85                  90                  95

Leu Gln Leu Gly Thr Thr Phe Phe Lys Leu Pro Gly Gly Glu Leu Asn
            100                 105                 110

Pro Gly Glu Asp Glu Val Glu Gly Leu Lys Arg Leu Met Thr Glu Ile
        115                 120                 125

Leu Gly Arg Gln Asp Gly Val Leu Gln Asp Trp Val Ile Asp Asp Cys
    130                 135                 140

Ile Gly Asn Trp Trp Arg Pro Asn Phe Glu Pro Pro Gln Tyr Pro Tyr
145                 150                 155                 160

Ile Pro Ala His Ile Thr Lys Pro Lys Glu His Lys Lys Leu Phe Leu
                165                 170                 175

Val Gln Leu Gln Glu Lys Ala Leu Phe Ala Val Pro Lys Asn Tyr Lys
            180                 185                 190

Leu Val Ala Ala Pro Leu Phe Glu Leu Tyr Asp Asn Ala Pro Gly Tyr
        195                 200                 205

Gly Pro Ile Ile Ser Ser Leu Pro Gln Leu Leu Ser Arg Phe Asn Phe
    210                 215                 220

Ile Tyr Asn
225


<210> SEQ ID NO 52
<211> LENGTH: 333
<212> TYPE: PRT
<213> ORGANISM: Homo sapiens

<400> SEQUENCE: 52

Asp Ser Pro Pro Leu Pro His Ala Leu Gln Leu Trp His Glu Leu Cys
1               5                   10                  15

Asp Leu Ile Ser Gln Asn Pro Asp Lys Val Gln Ser Leu Asn Val Asp
            20                  25                  30

Ala Ile Ile Arg Gly Gly Leu Thr Arg Phe Thr Asp Gln Leu Gly Lys
        35                  40                  45

Leu Trp Cys Ser Leu Ala Asp Tyr Tyr Ile Arg Ser Gly His Phe Glu
    50                  55                  60

Lys Ala Arg Asp Val Tyr Glu Glu Ala Ile Arg Thr Val Met Thr Val
65                  70                  75                  80

Arg Asp Phe Thr Gln Val Phe Asp Ser Tyr Ala Gln Phe Glu Glu Ser
                85                  90                  95

Met Ile Ala Ala Lys Met Glu Thr Ala Ser Glu Leu Gly Arg Glu Glu
            100                 105                 110

Glu Asp Asp Val Asp Leu Glu Leu Arg Leu Ala Arg Phe Glu Gln Leu
        115                 120                 125

Ile Ser Arg Arg Pro Leu Leu Leu Asn Ser Val Leu Leu Arg Gln Asn
    130                 135                 140

Pro His His Val His Glu Trp His Lys Arg Val Ala Leu His Gln Gly
145                 150                 155                 160

Arg Pro Arg Glu Ile Ile Asn Thr Tyr Thr Glu Ala Val Gln Thr Val
                165                 170                 175

Asp Pro Phe Lys Ala Thr Gly Lys Pro His Thr Leu Trp Val Ala Phe
            180                 185                 190
```

-continued

```
Ala Lys Phe Tyr Glu Asp Asn Gly Gln Leu Asp Asp Ala Arg Val Ile
        195                 200                 205

Leu Glu Lys Ala Thr Lys Val Asn Phe Lys Gln Val Asp Asp Leu Ala
    210                 215                 220

Ser Val Trp Cys Gln Cys Gly Glu Leu Glu Leu Arg His Glu Asn Tyr
225                 230                 235                 240

Asp Glu Ala Leu Arg Leu Leu Arg Lys Ala Thr Ala Leu Pro Ala Arg
                245                 250                 255

Arg Ala Glu Tyr Phe Asp Gly Ser Glu Pro Val Gln Asn Arg Val Tyr
            260                 265                 270

Lys Ser Leu Lys Val Trp Ser Met Leu Ala Asp Leu Glu Glu Ser Leu
        275                 280                 285

Gly Thr Phe Gln Ser Thr Lys Ala Val Tyr Asp Arg Ile Leu Asp Leu
    290                 295                 300

Arg Ile Ala Thr Pro Gln Ile Val Ile Asn Tyr Ala Met Phe Leu Glu
305                 310                 315                 320

Glu His Lys Tyr Phe Glu Glu Ser Phe Lys Val Arg Gly
                325                 330


<210> SEQ ID NO 53
<211> LENGTH: 419
<212> TYPE: PRT
<213> ORGANISM: Homo sapiens

<400> SEQUENCE: 53

Met Cys Val His Pro Gly Ala Cys Leu Pro His Val Gly Val Ser Trp
1               5                   10                  15

Ala Glu Phe Pro Gly His Phe Ser Val Glu Leu Ser Ser Leu Leu Val
            20                  25                  30

Arg Asn Val Asn Tyr Glu Ile Pro Ser Leu Lys Lys Gln Ile Ala Lys
        35                  40                  45

Cys Gln Gln Leu Gln Gln Glu Tyr Ser Arg Lys Glu Glu Glu Cys Gln
    50                  55                  60

Ala Gly Ala Ala Glu Met Arg Glu Gln Phe Tyr His Ser Cys Lys Gln
65                  70                  75                  80

Tyr Gly Ile Thr Gly Glu Asn Val Arg Gly Glu Leu Leu Ala Leu Val
                85                  90                  95

Lys Asp Leu Pro Ser Gln Leu Ala Glu Ile Gly Ala Ala Ala Gln Gln
            100                 105                 110

Ser Leu Gly Glu Ala Ile Asp Val Tyr Gln Ala Ser Val Gly Phe Val
        115                 120                 125

Cys Glu Ser Pro Thr Glu Gln Val Leu Pro Met Leu Arg Phe Val Gln
    130                 135                 140

Lys Arg Gly Asn Ser Thr Val Tyr Glu Trp Arg Thr Gly Thr Glu Pro
145                 150                 155                 160

Ser Val Val Glu Arg Pro His Leu Glu Glu Leu Pro Glu Gln Val Ala
                165                 170                 175

Glu Asp Ala Ile Asp Trp Gly Asp Phe Gly Val Glu Ala Val Ser Glu
            180                 185                 190

Gly Thr Asp Ser Gly Ile Ser Ala Glu Ala Ala Gly Ile Asp Trp Gly
        195                 200                 205

Ile Phe Pro Glu Ser Asp Ser Lys Asp Pro Gly Gly Asp Gly Ile Asp
    210                 215                 220

Trp Gly Asp Asp Ala Val Ala Leu Gln Ile Thr Val Leu Glu Ala Gly
225                 230                 235                 240
```

-continued

```
Thr Gln Ala Pro Glu Gly Val Ala Arg Gly Pro Asp Ala Leu Thr Leu
                245                 250                 255

Leu Glu Tyr Thr Glu Thr Arg Asn Gln Phe Leu Asp Glu Leu Met Glu
            260                 265                 270

Leu Glu Ile Phe Leu Ala Gln Arg Ala Val Glu Leu Ser Glu Glu Ala
        275                 280                 285

Asp Val Leu Ser Val Ser Gln Phe Gln Leu Ala Pro Ala Ile Leu Gln
    290                 295                 300

Gly Gln Thr Lys Glu Lys Met Val Thr Met Val Ser Val Leu Glu Asp
305                 310                 315                 320

Leu Ile Gly Lys Leu Thr Ser Leu Gln Leu Gln His Leu Phe Met Ile
                325                 330                 335

Leu Ala Ser Pro Arg Tyr Val Asp Arg Val Thr Glu Phe Leu Gln Gln
            340                 345                 350

Lys Leu Lys Gln Ser Gln Leu Leu Ala Leu Lys Lys Glu Leu Met Val
        355                 360                 365

Gln Lys Gln Gln Glu Ala Leu Glu Glu Gln Ala Ala Leu Glu Pro Lys
    370                 375                 380

Leu Asp Leu Leu Leu Glu Lys Thr Lys Glu Leu Gln Lys Leu Ile Glu
385                 390                 395                 400

Ala Asp Ile Ser Lys Arg Tyr Ser Gly Arg Pro Val Asn Leu Met Gly
                405                 410                 415

Thr Ser Leu


<210> SEQ ID NO 54
<211> LENGTH: 856
<212> TYPE: PRT
<213> ORGANISM: Homo sapiens

<400> SEQUENCE: 54

Met Asp Val Arg Arg Leu Lys Val Asn Glu Leu Arg Glu Glu Leu Gln
1               5                   10                  15

Arg Arg Gly Leu Asp Thr Arg Gly Leu Lys Ala Glu Leu Ala Glu Arg
            20                  25                  30

Leu Gln Ala Ala Leu Glu Ala Glu Glu Pro Asp Asp Glu Arg Glu Leu
        35                  40                  45

Asp Ala Asp Asp Glu Pro Gly Arg Pro Gly His Ile Asn Glu Glu Val
    50                  55                  60

Glu Thr Glu Gly Gly Ser Glu Leu Glu Gly Thr Ala Gln Pro Pro Pro
65                  70                  75                  80

Pro Gly Leu Gln Pro His Ala Glu Pro Gly Gly Tyr Ser Gly Pro Asp
                85                  90                  95

Gly His Tyr Ala Met Asp Asn Ile Thr Arg Gln Asn Gln Phe Tyr Asp
            100                 105                 110

Thr Gln Val Ile Lys Gln Glu Asn Glu Ser Gly Tyr Glu Arg Arg Pro
        115                 120                 125

Leu Glu Met Glu Gln Gln Gln Ala Tyr Arg Pro Glu Met Lys Thr Glu
    130                 135                 140

Met Lys Gln Gly Ala Pro Thr Ser Phe Leu Pro Pro Glu Ala Ser Gln
145                 150                 155                 160

Leu Lys Pro Asp Arg Gln Gln Phe Gln Ser Arg Lys Arg Pro Tyr Glu
                165                 170                 175

Glu Asn Arg Gly Arg Gly Tyr Phe Glu His Arg Glu Asp Arg Arg Gly
            180                 185                 190
```

-continued

```
Arg Ser Pro Gln Pro Pro Ala Glu Glu Asp Glu Asp Asp Phe Asp Asp
        195                 200                 205

Thr Leu Val Ala Ile Asp Thr Tyr Asn Cys Asp Leu His Phe Lys Val
    210                 215                 220

Ala Arg Asp Arg Ser Ser Gly Tyr Pro Leu Thr Ile Glu Gly Phe Ala
225                 230                 235                 240

Tyr Leu Trp Ser Gly Ala Arg Ala Ser Tyr Gly Val Arg Arg Gly Arg
                245                 250                 255

Val Cys Phe Glu Met Lys Ile Asn Glu Glu Ile Ser Val Lys His Leu
            260                 265                 270

Pro Ser Thr Glu Pro Asp Pro His Val Val Arg Ile Gly Trp Ser Leu
        275                 280                 285

Asp Ser Cys Ser Thr Gln Leu Gly Glu Glu Pro Phe Ser Tyr Gly Tyr
    290                 295                 300

Gly Gly Thr Gly Lys Lys Ser Thr Asn Ser Arg Phe Glu Asn Tyr Gly
305                 310                 315                 320

Asp Lys Phe Ala Glu Asn Asp Val Ile Gly Cys Phe Ala Asp Phe Glu
                325                 330                 335

Cys Gly Asn Asp Val Glu Leu Ser Phe Thr Lys Asn Gly Lys Trp Met
            340                 345                 350

Gly Ile Ala Phe Arg Ile Gln Lys Glu Ala Leu Gly Gly Gln Ala Leu
        355                 360                 365

Tyr Pro His Val Leu Val Lys Asn Cys Ala Val Glu Phe Asn Phe Gly
    370                 375                 380

Gln Arg Ala Glu Pro Tyr Cys Ser Val Leu Pro Gly Phe Thr Phe Ile
385                 390                 395                 400

Gln His Leu Pro Leu Ser Glu Arg Ile Arg Gly Thr Val Gly Pro Lys
                405                 410                 415

Ser Lys Ala Glu Cys Glu Ile Leu Met Met Val Gly Leu Pro Ala Ala
            420                 425                 430

Gly Lys Thr Thr Trp Ala Ile Lys His Ala Ala Ser Asn Pro Ser Lys
        435                 440                 445

Lys Tyr Asn Ile Leu Gly Thr Asn Ala Ile Met Asp Lys Met Arg Val
    450                 455                 460

Met Gly Leu Arg Arg Gln Arg Asn Tyr Ala Gly Arg Trp Asp Val Leu
465                 470                 475                 480

Ile Gln Gln Ala Thr Gln Cys Leu Asn Arg Leu Ile Gln Ile Ala Ala
                485                 490                 495

Arg Lys Lys Arg Asn Tyr Ile Leu Asp Gln Thr Asn Val Tyr Gly Ser
            500                 505                 510

Ala Gln Arg Arg Lys Met Arg Pro Phe Glu Gly Phe Gln Arg Lys Ala
        515                 520                 525

Ile Val Ile Cys Pro Thr Asp Glu Asp Leu Lys Asp Arg Thr Ile Lys
    530                 535                 540

Arg Thr Asp Glu Glu Gly Lys Asp Val Pro Asp His Ala Val Leu Glu
545                 550                 555                 560

Met Lys Ala Asn Phe Thr Leu Pro Asp Val Gly Asp Phe Leu Asp Glu
                565                 570                 575

Val Leu Phe Ile Glu Leu Gln Arg Glu Glu Ala Asp Lys Leu Val Arg
            580                 585                 590

Gln Tyr Asn Glu Glu Gly Arg Lys Ala Gly Pro Pro Pro Glu Lys Arg
        595                 600                 605
```

-continued

```
Phe Asp Asn Arg Gly Gly Gly Gly Phe Arg Gly Arg Gly Gly Gly Gly
    610                 615                 620

Gly Phe Gln Arg Tyr Glu Asn Arg Gly Pro Pro Gly Gly Asn Arg Gly
625                 630                 635                 640

Gly Phe Gln Asn Arg Gly Gly Gly Ser Gly Gly Gly Gly Asn Tyr Arg
                645                 650                 655

Gly Gly Phe Asn Arg Ser Gly Gly Gly Gly Tyr Ser Gln Asn Arg Trp
            660                 665                 670

Gly Asn Asn Asn Arg Asp Asn Asn Asn Ser Asn Asn Arg Gly Ser Tyr
        675                 680                 685

Asn Arg Ala Pro Gln Gln Gln Pro Pro Pro Gln Gln Pro Pro Pro Pro
    690                 695                 700

Gln Pro Pro Pro Gln Gln Pro Pro Pro Pro Pro Ser Tyr Ser Pro Ala
705                 710                 715                 720

Arg Asn Pro Pro Gly Ala Ser Thr Tyr Asn Lys Asn Ser Asn Ile Pro
                725                 730                 735

Gly Ser Ser Ala Asn Thr Ser Thr Pro Thr Val Ser Ser Tyr Ser Pro
            740                 745                 750

Pro Gln Pro Ser Tyr Ser Gln Pro Pro Tyr Asn Gln Gly Gly Tyr Ser
        755                 760                 765

Gln Gly Tyr Thr Ala Pro Pro Pro Pro Pro Pro Pro Pro Pro Ala Tyr
    770                 775                 780

Asn Tyr Gly Ser Tyr Gly Gly Tyr Asn Pro Ala Pro Tyr Thr Pro Pro
785                 790                 795                 800

Pro Pro Pro Thr Ala Gln Thr Tyr Pro Gln Pro Ser Tyr Asn Gln Tyr
                805                 810                 815

Gln Gln Tyr Ala Gln Gln Trp Asn Gln Tyr Tyr Gln Asn Gln Gly Gln
            820                 825                 830

Trp Pro Pro Tyr Tyr Gly Asn Tyr Asp Tyr Gly Ser Tyr Ser Gly Asn
        835                 840                 845

Thr Gln Gly Gly Thr Ser Thr Gln
    850                 855
```

<210> SEQ ID NO 55
<211> LENGTH: 339
<212> TYPE: PRT
<213> ORGANISM: Homo sapiens

<400> SEQUENCE: 55

```
Gly Gly Ala Leu Leu Gly Pro Val Pro Trp Ala Pro Val Thr Pro Ala
1               5                   10                  15

Ser Gly Gly Gln Val Ser His His Pro Thr Arg Gly Leu Gly Ile Cys
            20                  25                  30

Glu Pro Thr Ser Cys Ser Arg Gly Pro Leu Trp Leu Ser Gly Gln Leu
        35                  40                  45

Gly Asp Thr Arg Ala Leu Leu Cys Ile Pro Pro Tyr His Val Ala Ser
    50                  55                  60

Glu Leu Gly Trp Pro Gly Trp Gly Pro Ala Ala Leu Cys Ser Ser Trp
65                  70                  75                  80

Lys Gln Gly Ser Arg Tyr Trp Ala Ser Val Gly Tyr Lys Arg Pro Trp
                85                  90                  95

Gly Glu Cys Leu Glu Glu Pro Ala Ala Ala Gly Ala Gln Arg Ala Arg
            100                 105                 110

Ser Ser Ser Ala Ala Ala Ala Pro Gln Tyr Asp Gln Trp Thr Ile Ser
        115                 120                 125
```

```
Lys Ala Cys Gly Lys Asn Leu Pro Leu Arg Leu Ala His Cys Arg Ser
    130                 135                 140

Thr Met Glu Val Val Arg Glu Lys Leu Arg Lys Tyr Val Phe Asp Arg
145                 150                 155                 160

Val Asn Met His Asn Leu Leu Ile His Leu Val Arg Arg Arg Gly Gln
                165                 170                 175

Lys Leu Glu Ser Met Gln Leu Glu Leu Asp Ser Leu Arg Ser Gln Pro
            180                 185                 190

Asp Ala Ser Lys Glu Glu Leu Arg Leu Leu Gln Ile Ile Arg Gln Leu
        195                 200                 205

Glu Asn Asn Ile Glu Lys Thr Met Ile Lys Ile Ile Thr Ser Gln Asn
    210                 215                 220

Ile His Leu Leu Tyr Leu Asp Leu Leu Asp Tyr Leu Lys Thr Val Leu
225                 230                 235                 240

Ala Gly Tyr Pro Ile Glu Leu Asp Lys Leu Gln Asn Leu Val Val Asn
                245                 250                 255

Tyr Cys Ser Glu Leu Ser Asp Met Lys Ile Met Ser Gln Asp Ala Met
            260                 265                 270

Met Ile Thr Asp Glu Val Lys Arg Asn Met Arg Gln Arg Glu Ala Ser
        275                 280                 285

Phe Ile Glu Glu Arg Arg Ala Arg Glu Asn Arg Leu Asn Gln Gln Lys
    290                 295                 300

Lys Leu Ile Asp Lys Ile His Thr Lys Glu Thr Ser Glu Lys Tyr Arg
305                 310                 315                 320

Arg Gly Gln Met Asp Leu Asp Phe Pro Ser Asn Leu Met Ser Thr Glu
                325                 330                 335

Thr Leu Lys
```

<210> SEQ ID NO 56
<211> LENGTH: 190
<212> TYPE: PRT
<213> ORGANISM: Homo sapiens

<400> SEQUENCE: 56

```
Met Ala Gly Pro Gly Thr Val Cys Trp Gly Thr Val Cys Gln Gly Glu
1               5                   10                  15

Val Leu Ala Leu Trp Gly His Leu Gln Lys Gly Thr Arg Leu Ser Cys
            20                  25                  30

Leu Ala Gly Leu Ser Arg Val Leu Trp Pro Gln Glu Pro Ala Gly Gly
        35                  40                  45

Gly Arg Ala Val Arg Thr His Ser Cys Gly Pro Arg Gly Asp Pro Trp
    50                  55                  60

His Gln Gly Lys Gly Leu Ser Leu Ala Ser Phe Phe Leu Ser Glu Ser
65                  70                  75                  80

Arg Pro Pro Gly Ser Ser Tyr Phe Arg Tyr Ala Glu Ser Ser Met Lys
                85                  90                  95

Asn Ser Phe Gly Leu Lys Tyr Leu His Lys Phe Phe Asn Ile Pro Phe
            100                 105                 110

Leu Gln Leu Gln Arg Glu Thr Leu Leu Arg Gln Leu Glu Thr Asn Gln
        115                 120                 125

Leu Asp Met Asp Ala Thr Leu Glu Glu Leu Ser Val Gln Gln Glu Thr
    130                 135                 140

Glu Asp Gln Asn Tyr Gly Met Tyr Val Ala Gly Pro Ala Arg Ala Gly
145                 150                 155                 160
```

-continued

```
Gly Val Gly Ala Ala Gly Val Ala Val Val Gln Gly His Gly Leu His
                165                 170                 175

Gln Gly Asp Ser Arg Gly Glu Cys Pro Leu Phe Gly Val Asn
            180                 185                 190


<210> SEQ ID NO 57
<211> LENGTH: 503
<212> TYPE: PRT
<213> ORGANISM: Musca domestica

<400> SEQUENCE: 57

Met Gln Asp His Gln His Val Pro Ile Asp Ile Gln Thr Ser Lys Leu
1               5                   10                  15

Leu Asp Trp Leu Val Asp Arg Arg His Cys Asn Leu Lys Trp Gln Ser
            20                  25                  30

Leu Val Leu Thr Ile Arg Glu Lys Ile Asn Thr Ala Ile Gln Asp Met
        35                  40                  45

Pro Glu Ser Gln Glu Ile Ala Gln Leu Leu Ser Gly Ser Tyr Ile His
    50                  55                  60

Tyr Phe His Cys Leu Arg Ile Val Asp Leu Leu Lys Gly Thr Glu Ala
65                  70                  75                  80

Ser Thr Lys Asn Ile Phe Gly Arg Tyr Ser Ser Gln Arg Met Lys Asp
                85                  90                  95

Trp Gln Glu Ile Val Ser Leu Tyr Glu Lys Asp Asn Thr Tyr Leu Val
            100                 105                 110

Glu Leu Cys Ser Leu Leu Val Arg Asn Val Ser Tyr Glu Ile Pro Ser
        115                 120                 125

Leu Lys Lys Gln Ile Ala Lys Cys Gln Gln Leu Gln Gln Glu Tyr Ser
    130                 135                 140

Arg Lys Glu Glu Glu Gly Gln Ala Gly Ala Ala Glu Met Arg Glu Gln
145                 150                 155                 160

Phe Tyr His Ser Cys Lys Gln Tyr Gly Ile Thr Gly Asp Asn Val Arg
                165                 170                 175

Arg Glu Leu Leu Ala Leu Val Lys Asp Leu Pro Ser Gln Leu Ala Glu
            180                 185                 190

Ile Gly Ala Gly Ala Gln Ser Leu Gly Glu Ala Ile Asp Leu Tyr Gln
        195                 200                 205

Ala Cys Val Glu Phe Val Cys Asp Ser Pro Thr Glu Gln Val Leu Pro
    210                 215                 220

Met Leu Arg Tyr Val Gln Lys Lys Gly Asn Ser Thr Val Tyr Glu Trp
225                 230                 235                 240

Arg Thr Gly Thr Glu Pro Ser Val Val Glu Arg Pro Gln Leu Glu Glu
                245                 250                 255

Pro Pro Glu Gln Val Gln Glu Asp Glu Ile Asp Trp Gly Asp Phe Gly
            260                 265                 270

Val Glu Ala Val Ser Asp Ser Gly Ile Val Ala Glu Thr Pro Gly Ile
        275                 280                 285

Asp Trp Gly Ile Ser Leu Glu Ser Glu Ala Lys Asp Ala Gly Ala Asp
    290                 295                 300

Lys Ile Asp Trp Gly Asp Asp Ala Ala Ala Ala Ser Glu Ile Thr Val
305                 310                 315                 320

Leu Glu Thr Gly Thr Glu Ala Pro Glu Gly Val Ala Arg Gly Ser Asp
                325                 330                 335

Ala Leu Thr Leu Leu Glu Tyr Pro Glu Thr Arg Asn Gln Phe Ile Asp
```

```
            340                 345                 350

Glu Leu Met Glu Leu Glu Ile Phe Leu Ser Gln Arg Ala Val Glu Met
        355                 360                 365

Ser Glu Glu Ala Asp Ile Leu Ser Val Ser Gln Phe Gln Leu Ala Pro
    370                 375                 380

Ala Ile Leu Gln Gly Gln Thr Lys Glu Lys Met Leu Ser Leu Val Ser
385                 390                 395                 400

Thr Leu Gln Gln Leu Ile Gly Arg Leu Thr Ser Leu Arg Met Gln His
                405                 410                 415

Leu Phe Met Ile Leu Ala Ser Pro Arg Tyr Val Asp Arg Val Thr Glu
            420                 425                 430

Phe Leu Gln Gln Lys Leu Lys Gln Ser Gln Leu Leu Ala Leu Lys Lys
        435                 440                 445

Glu Leu Met Val Glu Lys Gln Gln Glu Ala Leu Gln Glu Gln Ala Ala
    450                 455                 460

Leu Glu Pro Lys Leu Asp Leu Leu Leu Glu Lys Thr Arg Glu Leu Gln
465                 470                 475                 480

Lys Leu Ile Glu Ala Asp Ile Ser Lys Arg Tyr Ser Gly Arg Pro Val
                485                 490                 495

Asn Leu Met Gly Thr Ser Leu
            500


<210> SEQ ID NO 58
<211> LENGTH: 504
<212> TYPE: PRT
<213> ORGANISM: Musca domestica

<400> SEQUENCE: 58

Met Gln Asp His Gln His Val Pro Ile Asp Ile Gln Thr Ser Lys Leu
1               5                   10                  15

Leu Asp Trp Leu Val Asp Arg Arg His Cys Asn Leu Lys Trp Gln Ser
            20                  25                  30

Leu Val Leu Thr Ile Arg Glu Lys Ile Asn Thr Ala Ile Gln Asp Met
        35                  40                  45

Pro Glu Ser Gln Glu Ile Ala Gln Leu Leu Ser Gly Ser Tyr Ile His
    50                  55                  60

Tyr Phe His Cys Leu Arg Ile Val Asp Leu Leu Lys Gly Thr Glu Ala
65                  70                  75                  80

Ser Thr Lys Asn Ile Phe Gly Arg Tyr Ser Ser Gln Arg Met Lys Asp
                85                  90                  95

Trp Gln Glu Ile Ile Ser Leu Tyr Glu Lys Asp Asn Thr Tyr Leu Val
            100                 105                 110

Glu Leu Ser Ser Leu Leu Val Arg Asn Val Asn Tyr Glu Ile Pro Ser
        115                 120                 125

Leu Lys Lys Gln Ile Ala Lys Cys Gln Gln Leu Gln Gln Asp Tyr Ser
    130                 135                 140

Arg Lys Glu Glu Glu Gly Gln Ala Gly Ala Ala Glu Met Arg Glu Gln
145                 150                 155                 160

Phe Tyr His Ser Cys Lys Gln Tyr Gly Ile Thr Gly Asp Asn Val Arg
                165                 170                 175

Arg Glu Leu Leu Ala Leu Val Lys Asp Leu Pro Ser Gln Leu Ala Glu
            180                 185                 190

Ile Gly Ala Gly Ala Gln Ser Leu Gly Glu Ala Ile Asp Leu Tyr Gln
        195                 200                 205
```

-continued

```
Ala Cys Val Glu Phe Val Cys Asp Ser Pro Thr Glu Gln Val Leu Pro
    210                 215                 220

Met Leu Arg Tyr Val Gln Pro Lys Gly Asn Ser Thr Val Tyr Glu Trp
225                 230                 235                 240

Arg Thr Gly Thr Glu Pro Ser Val Val Glu Arg Pro Gln Leu Glu Asp
                245                 250                 255

Pro Pro Glu Gln Val Gln Glu Asp Glu Ile Asp Trp Gly Asp Phe Gly
            260                 265                 270

Leu Glu Ala Val Ser Asp Ser Gly Asn Ile Ile Ser Ala Glu Thr Pro
        275                 280                 285

Gly Ile Asp Trp Gly Ile Ser Leu Glu Ser Glu Ser Lys Asp Ala Gly
    290                 295                 300

Ala Asp Lys Ile Asp Trp Gly Asp Asn Ala Val Ala Ser Glu Ile Thr
305                 310                 315                 320

Val Leu Glu Thr Gly Thr Glu Ala Pro Glu Gly Val Ala Arg Gly Ser
                325                 330                 335

Asp Ala Leu Thr Leu Leu Glu Tyr Pro Glu Thr Arg Asn Gln Phe Ile
            340                 345                 350

Asp Glu Leu Met Glu Leu Glu Ile Phe Leu Ser Gln Arg Ala Val Glu
        355                 360                 365

Met Ser Glu Glu Ala Asp Ile Leu Ser Val Ser Gln Phe Gln Leu Ala
    370                 375                 380

Pro Ala Ile Leu Gln Gly Gln Thr Lys Glu Lys Met Leu Ser Leu Val
385                 390                 395                 400

Ser Thr Leu Gln His Leu Ile Gly Gln Leu Thr Ser Leu Asp Leu Gln
                405                 410                 415

His Leu Phe Met Ile Leu Ala Ser Pro Arg Tyr Val Asp Arg Val Thr
            420                 425                 430

Glu Leu Leu Gln Gln Lys Leu Lys Gln Ser Gln Leu Leu Ala Leu Lys
        435                 440                 445

Lys Asp Leu Met Val Glu Lys Gln Gln Glu Ala Leu Gln Glu Gln Ala
    450                 455                 460

Ala Leu Glu Pro Lys Leu Asp Leu Leu Leu Glu Lys Thr Arg Glu Leu
465                 470                 475                 480

Gln Lys Leu Ile Glu Ala Asp Ile Ser Lys Arg Tyr Asn Gly Arg Pro
                485                 490                 495

Val Asn Leu Met Gly Thr Ser Val
            500


<210> SEQ ID NO 59
<211> LENGTH: 510
<212> TYPE: PRT
<213> ORGANISM: Homo sapiens

<400> SEQUENCE: 59

His Glu Gly Lys Met Glu Asp His Gln His Val Pro Ile Asp Ile Gln
1               5                   10                  15

Thr Ser Lys Leu Leu Asp Trp Leu Val Asp Arg Arg His Cys Ser Leu
            20                  25                  30

Lys Trp Gln Ser Leu Val Leu Thr Ile Arg Glu Lys Ile Asn Ala Ala
        35                  40                  45

Ile Gln Asp Met Pro Glu Ser Glu Glu Ile Ala Gln Leu Leu Ser Gly
    50                  55                  60

Ser Tyr Ile His Tyr Phe His Cys Leu Arg Ile Leu Asp Leu Leu Lys
65                  70                  75                  80
```

-continued

```
Gly Thr Glu Ala Ser Thr Lys Asn Ile Phe Gly Arg Tyr Ser Ser Gln
                85                  90                  95

Arg Met Lys Asp Trp Gln Glu Ile Ile Ala Leu Tyr Glu Lys Asp Asn
            100                 105                 110

Thr Tyr Leu Val Glu Leu Ser Ser Leu Leu Val Arg Asn Val Asn Tyr
        115                 120                 125

Glu Ile Pro Ser Leu Lys Lys Gln Ile Ala Lys Cys Gln Gln Leu Gln
    130                 135                 140

Gln Glu Tyr Ser Arg Lys Glu Glu Glu Cys Gln Ala Gly Ala Ala Glu
145                 150                 155                 160

Met Arg Glu Gln Phe Tyr His Ser Cys Lys Gln Tyr Gly Ile Thr Gly
                165                 170                 175

Glu Asn Val Arg Gly Glu Leu Leu Ala Leu Val Lys Asp Leu Pro Ser
            180                 185                 190

Gln Leu Ala Glu Ile Gly Ala Ala Ala Gln Gln Ser Leu Gly Glu Ala
        195                 200                 205

Ile Asp Val Tyr Gln Ala Ser Val Gly Phe Val Cys Glu Ser Pro Thr
    210                 215                 220

Glu Gln Val Leu Pro Met Leu Arg Phe Val Gln Lys Arg Gly Asn Ser
225                 230                 235                 240

Thr Val Tyr Glu Trp Arg Thr Gly Thr Glu Pro Ser Val Val Glu Arg
                245                 250                 255

Pro His Leu Glu Glu Leu Pro Glu Gln Val Ala Glu Asp Ala Ile Asp
            260                 265                 270

Trp Gly Asp Phe Gly Val Glu Ala Val Ser Glu Gly Thr Asp Ser Gly
        275                 280                 285

Ile Ser Ala Glu Ala Ala Gly Ile Asp Trp Gly Ile Phe Pro Glu Ser
    290                 295                 300

Asp Ser Lys Asp Pro Gly Gly Asp Gly Ile Asp Trp Gly Asp Asp Ala
305                 310                 315                 320

Val Ala Leu Gln Ile Thr Val Leu Glu Ala Gly Thr Gln Ala Pro Glu
                325                 330                 335

Gly Val Ala Arg Gly Pro Asp Ala Leu Thr Leu Leu Glu Tyr Thr Glu
            340                 345                 350

Thr Arg Asn Gln Phe Leu Asp Glu Leu Met Glu Leu Glu Ile Phe Leu
        355                 360                 365

Ala Gln Arg Ala Val Glu Leu Ser Glu Glu Ala Asp Val Leu Ser Val
    370                 375                 380

Ser Gln Phe Gln Leu Ala Pro Ala Ile Leu Gln Gly Gln Thr Lys Glu
385                 390                 395                 400

Lys Met Val Thr Met Val Ser Val Leu Glu Asp Leu Ile Gly Lys Leu
                405                 410                 415

Thr Ser Leu Gln Leu Gln His Leu Phe Met Ile Leu Ala Ser Pro Arg
            420                 425                 430

Tyr Val Asp Arg Val Thr Glu Phe Leu Gln Gln Lys Leu Lys Gln Ser
        435                 440                 445

Gln Leu Leu Ala Leu Lys Lys Glu Leu Met Val Gln Lys Gln Gln Glu
    450                 455                 460

Ala Leu Glu Glu Gln Ala Ala Leu Glu Pro Lys Leu Asp Leu Leu Leu
465                 470                 475                 480

Glu Lys Thr Lys Glu Leu Gln Lys Leu Ile Glu Ala Asp Ile Ser Lys
                485                 490                 495
```

-continued

```
Arg Tyr Ser Gly Arg Pro Val Asn Leu Met Gly Thr Ser Leu
            500                 505                 510


<210> SEQ ID NO 60
<211> LENGTH: 517
<212> TYPE: PRT
<213> ORGANISM: Musca domestica

<400> SEQUENCE: 60

Ala Gly Pro Gly Ser Leu Ala Gly Ser Gly Ser Gly Glu Arg Met Gln
1               5                   10                  15

Asp His Gln His Val Pro Ile Asp Ile Gln Thr Ser Lys Leu Leu Asp
            20                  25                  30

Trp Leu Val Asp Arg Arg His Cys Asn Leu Lys Trp Gln Ser Leu Val
        35                  40                  45

Leu Thr Ile Arg Glu Lys Ile Asn Thr Ala Ile Gln Asp Met Pro Glu
    50                  55                  60

Ser Gln Glu Ile Ala Gln Leu Leu Ser Gly Ser Tyr Ile His Tyr Phe
65                  70                  75                  80

His Cys Leu Arg Ile Val Asp Leu Leu Lys Gly Thr Glu Ala Ser Thr
                85                  90                  95

Lys Asn Ile Phe Gly Arg Tyr Ser Ser Gln Arg Met Lys Asp Trp Gln
            100                 105                 110

Glu Ile Val Ser Leu Tyr Glu Lys Asp Asn Thr Tyr Leu Val Glu Leu
        115                 120                 125

Cys Ser Leu Leu Val Arg Asn Val Ser Tyr Glu Ile Pro Ser Leu Lys
    130                 135                 140

Lys Gln Ile Ala Lys Cys Gln Gln Leu Gln Gln Glu Tyr Ser Arg Lys
145                 150                 155                 160

Glu Glu Glu Gly Gln Ala Gly Ala Ala Glu Met Arg Glu Gln Phe Tyr
                165                 170                 175

His Ser Cys Lys Gln Tyr Gly Ile Thr Gly Asp Asn Val Arg Arg Glu
            180                 185                 190

Leu Leu Ala Leu Val Lys Asp Leu Pro Ser Gln Leu Ala Glu Ile Gly
        195                 200                 205

Ala Gly Ala Gln Ser Leu Gly Glu Ala Ile Asp Leu Tyr Gln Ala Cys
    210                 215                 220

Val Glu Phe Val Cys Asp Ser Pro Thr Glu Gln Val Leu Pro Met Leu
225                 230                 235                 240

Arg Tyr Val Gln Lys Lys Gly Asn Ser Thr Val Tyr Glu Trp Arg Thr
                245                 250                 255

Gly Thr Glu Pro Ser Val Val Glu Arg Pro Gln Leu Glu Glu Pro Pro
            260                 265                 270

Glu Gln Val Gln Glu Asp Glu Ile Asp Trp Gly Asp Phe Gly Val Glu
        275                 280                 285

Ala Val Ser Asp Ser Gly Ile Val Ala Glu Thr Pro Gly Ile Asp Trp
    290                 295                 300

Gly Ile Ser Leu Glu Ser Glu Ala Lys Asp Ala Gly Ala Asp Lys Ile
305                 310                 315                 320

Asp Trp Gly Asp Asp Ala Ala Ala Ala Ser Glu Ile Thr Val Leu Glu
                325                 330                 335

Thr Gly Thr Glu Ala Pro Glu Gly Val Ala Arg Gly Ser Asp Ala Leu
            340                 345                 350

Thr Leu Leu Glu Tyr Pro Glu Thr Arg Asn Gln Phe Ile Asp Glu Leu
        355                 360                 365
```

```
Met Glu Leu Glu Ile Phe Leu Ser Gln Arg Ala Val Glu Met Ser Glu
    370                 375                 380

Glu Ala Asp Ile Leu Ser Val Ser Gln Phe Gln Leu Ala Pro Ala Ile
385                 390                 395                 400

Leu Gln Gly Gln Thr Lys Glu Lys Met Leu Ser Leu Val Ser Thr Leu
                405                 410                 415

Gln Gln Leu Ile Gly Arg Leu Thr Ser Leu Arg Met Gln His Leu Phe
            420                 425                 430

Met Ile Leu Ala Ser Pro Arg Tyr Val Asp Arg Val Thr Glu Phe Leu
        435                 440                 445

Gln Gln Lys Leu Lys Gln Ser Gln Leu Leu Ala Leu Lys Lys Glu Leu
    450                 455                 460

Met Val Glu Lys Gln Gln Glu Ala Leu Gln Glu Gln Ala Ala Leu Glu
465                 470                 475                 480

Pro Lys Leu Asp Leu Leu Leu Glu Lys Thr Arg Glu Leu Gln Lys Leu
                485                 490                 495

Ile Glu Ala Asp Ile Ser Lys Arg Tyr Ser Gly Arg Pro Val Asn Leu
            500                 505                 510

Met Gly Thr Ser Leu
        515


<210> SEQ ID NO 61
<211> LENGTH: 2111
<212> TYPE: DNA
<213> ORGANISM: Homo sapiens
<220> FEATURE:
<221> NAME/KEY: CDS
<222> LOCATION: (187)..(1554)

<400> SEQUENCE: 61

gaattcgggg gggttcaaga tcactgggac caggccgtga tctctatgcc cgagtctcaa      60

ccctcaactg tcaccccaag gcacttggga cgtcctggac agaccgagtc ccgggaagcc     120

ccagcactgc cgctgccaca ctgccctgag cccaaatggg ggagtgagag gccatagctg     180

tctggc atg ggc ctc tcc acc gtg cct gac ctg ctg ctg ccg ctg gtg        228
       Met Gly Leu Ser Thr Val Pro Asp Leu Leu Leu Pro Leu Val
       1               5                   10

ctc ctg gag ctg ttg gtg gga ata tac ccc tca ggg gtt att gga ctg       276
Leu Leu Glu Leu Leu Val Gly Ile Tyr Pro Ser Gly Val Ile Gly Leu
15                  20                  25                  30

gtc cct cac cta ggg gac agg gag aag aga gat agt gtg tgt ccc caa       324
Val Pro His Leu Gly Asp Arg Glu Lys Arg Asp Ser Val Cys Pro Gln
                35                  40                  45

gga aaa tat atc cac cct caa aat aat tcg att tgc tgt acc aag tgc       372
Gly Lys Tyr Ile His Pro Gln Asn Asn Ser Ile Cys Cys Thr Lys Cys
            50                  55                  60

cac aaa gga acc tac ttg tac aat gac tgt cca ggc ccg ggg cag gat       420
His Lys Gly Thr Tyr Leu Tyr Asn Asp Cys Pro Gly Pro Gly Gln Asp
        65                  70                  75

acg gac tgc agg gag tgt gag agc ggc tcc ttc acc gct tca gaa aac       468
Thr Asp Cys Arg Glu Cys Glu Ser Gly Ser Phe Thr Ala Ser Glu Asn
    80                  85                  90

cac ctc aga cac tgc ctc agc tgc tcc aaa tgc cga aag gaa atg ggt       516
His Leu Arg His Cys Leu Ser Cys Ser Lys Cys Arg Lys Glu Met Gly
95                  100                 105                 110

cag gtg gag atc tct tct tgc aca gtg gac cgg gac acc gtg tgt ggc       564
Gln Val Glu Ile Ser Ser Cys Thr Val Asp Arg Asp Thr Val Cys Gly
                115                 120                 125
```

-continued

```
tgc agg aag aac cag tac cgg cat tat tgg agt gaa aac ctt ttc cag      612
Cys Arg Lys Asn Gln Tyr Arg His Tyr Trp Ser Glu Asn Leu Phe Gln
            130                 135                 140

tgc ttc aat tgc agc ctc tgc ctc aat ggg acc gtg cac ctc tcc tgc      660
Cys Phe Asn Cys Ser Leu Cys Leu Asn Gly Thr Val His Leu Ser Cys
        145                 150                 155

cag gag aaa cag aac acc gtg tgc acc tgc cat gca ggt ttc ttt cta      708
Gln Glu Lys Gln Asn Thr Val Cys Thr Cys His Ala Gly Phe Phe Leu
    160                 165                 170

aga gaa aac gag tgt gtc tcc tgt agt aac tgt aag aaa agc ctg gag      756
Arg Glu Asn Glu Cys Val Ser Cys Ser Asn Cys Lys Lys Ser Leu Glu
175                 180                 185                 190

tgc acg aag ttg tgc cta ccc cag att gag aat gtt aag ggc act gag      804
Cys Thr Lys Leu Cys Leu Pro Gln Ile Glu Asn Val Lys Gly Thr Glu
                195                 200                 205

gac tca ggc acc aca gtg ctg ttg ccc ctg gtc att ttc ttt ggt ctt      852
Asp Ser Gly Thr Thr Val Leu Leu Pro Leu Val Ile Phe Phe Gly Leu
            210                 215                 220

tgc ctt tta tcc ctc ctc ttc att ggt tta atg tat cgc tac caa cgg      900
Cys Leu Leu Ser Leu Leu Phe Ile Gly Leu Met Tyr Arg Tyr Gln Arg
        225                 230                 235

tgg aag tcc aag ctc tac tcc att gtt tgt ggg aaa tcg aca cct gaa      948
Trp Lys Ser Lys Leu Tyr Ser Ile Val Cys Gly Lys Ser Thr Pro Glu
    240                 245                 250

aaa gag ggg gag ctt gaa gga act act act aag ccc ctg gcc cca aac      996
Lys Glu Gly Glu Leu Glu Gly Thr Thr Thr Lys Pro Leu Ala Pro Asn
255                 260                 265                 270

cca agc ttc agt ccc act cca ggc ttc acc ccc acc ctg ggc ttc agt     1044
Pro Ser Phe Ser Pro Thr Pro Gly Phe Thr Pro Thr Leu Gly Phe Ser
                275                 280                 285

ccc gtg ccc agt tcc acc ttc acc tcc agc tcc acc tat acc ccc ggt     1092
Pro Val Pro Ser Ser Thr Phe Thr Ser Ser Ser Thr Tyr Thr Pro Gly
            290                 295                 300

gac tgt ccc aac ttt gcg gct ccc cgc aga gag gtg gca cca ccc tat     1140
Asp Cys Pro Asn Phe Ala Ala Pro Arg Arg Glu Val Ala Pro Pro Tyr
        305                 310                 315

cag ggg gct gac ccc atc ctt gcg aca gcc ctc gcc tcc gac ccc atc     1188
Gln Gly Ala Asp Pro Ile Leu Ala Thr Ala Leu Ala Ser Asp Pro Ile
    320                 325                 330

ccc aac ccc ctt cag aag tgg gag gac agc gcc cac aag cca cag agc     1236
Pro Asn Pro Leu Gln Lys Trp Glu Asp Ser Ala His Lys Pro Gln Ser
335                 340                 345                 350

cta gac act gat gac ccc gcg acg ctg tac gcc gtg gtg gag aac gtg     1284
Leu Asp Thr Asp Asp Pro Ala Thr Leu Tyr Ala Val Val Glu Asn Val
                355                 360                 365

ccc ccg ttg cgc tgg aag gaa ttc gtg cgg cgc cta ggg ctg agc gac     1332
Pro Pro Leu Arg Trp Lys Glu Phe Val Arg Arg Leu Gly Leu Ser Asp
            370                 375                 380

cac gag atc gat cgg ctg gag ctg cag aac ggg cgc tgc ctg cgc gag     1380
His Glu Ile Asp Arg Leu Glu Leu Gln Asn Gly Arg Cys Leu Arg Glu
        385                 390                 395

gcg caa tac agc atg ctg gcg acc tgg agg cgg cgc acg ccg cgg cgc     1428
Ala Gln Tyr Ser Met Leu Ala Thr Trp Arg Arg Arg Thr Pro Arg Arg
    400                 405                 410

gag gcc acg ctg gag ctg ctg gga cgc gtg ctc cgc gac atg gac ctg     1476
Glu Ala Thr Leu Glu Leu Leu Gly Arg Val Leu Arg Asp Met Asp Leu
415                 420                 425                 430

ctg ggc tgc ctg gag gac atc gag gag gcg ctt tgc ggc ccc gcc gcc     1524
Leu Gly Cys Leu Glu Asp Ile Glu Glu Ala Leu Cys Gly Pro Ala Ala
```

-continued

```
            435                 440                 445

ctc ccg ccc gcg ccc agt ctt ctc aga tga ggctgcgccc ctgcgggcag      1574
Leu Pro Pro Ala Pro Ser Leu Leu Arg
            450                 455

ctctaaggac cgtcctgcga gatcgccttc caaccccact tttttctgga aaggaggggt   1634

cctgcagggg caagcaggag ctagcagccg cctacttggt gctaacccct cgatgtacat   1694

agcttttctc agctgcctgc gcgccgccga cagtcagcgc tgtgcgcgcg gagagaggtg   1754

cgccgtgggc tcaagagcct gagtgggtgg tttgcgagga tgagggacgc tatgcctcat   1814

gcccgttttg ggtgtcctca ccagcaaggc tgctcggggg cccctggttc gtccctgagc   1874

ctttttcaca gtgcataagc agtttttttt gtttttgttt tgttttgttt tgtttttaaa   1934

tcaatcatgt tacactaata gaaacttggc actcctgtgc cctctgcctg gacaagcaca   1994

tagcaagctg aactgtccta aggcaggggc gagcacggaa caatggggcc ttcagctgga   2054

gctgtggact tttgtacata cactaaaatt ctgaagttaa aaaaaaaacc cgaattc      2111


<210> SEQ ID NO 62
<211> LENGTH: 455
<212> TYPE: PRT
<213> ORGANISM: Homo sapiens

<400> SEQUENCE: 62

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255
```

```
Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 63
<211> LENGTH: 3682
<212> TYPE: DNA
<213> ORGANISM: Homo sapiens
<220> FEATURE:
<221> NAME/KEY: CDS
<222> LOCATION: (90)..(1475)

<400> SEQUENCE: 63

gcgagcgcag cggagcctgg agagaaggcg ctgggctgcg agggcgcgag ggcgcgaggg      60

caggggcaa ccggaccccg cccgcaccc atg gcg ccc gtc gcc gtc tgg gcc      113
                                Met Ala Pro Val Ala Val Trp Ala
                                1               5

gcg ctg gcc gtc gga ctg gag ctc tgg gct gcg gcg cac gcc ttg ccc      161
Ala Leu Ala Val Gly Leu Glu Leu Trp Ala Ala Ala His Ala Leu Pro
    10                  15                  20

gcc cag gtg gca ttt aca ccc tac gcc ccg gag ccc ggg agc aca tgc      209
Ala Gln Val Ala Phe Thr Pro Tyr Ala Pro Glu Pro Gly Ser Thr Cys
25                  30                  35                  40

cgg ctc aga gaa tac tat gac cag aca gct cag atg tgc tgc agc aaa      257
Arg Leu Arg Glu Tyr Tyr Asp Gln Thr Ala Gln Met Cys Cys Ser Lys
                45                  50                  55

tgc tcg ccg ggc caa cat gca aaa gtc ttc tgt acc aag acc tcg gac      305
Cys Ser Pro Gly Gln His Ala Lys Val Phe Cys Thr Lys Thr Ser Asp
            60                  65                  70

acc gtg tgt gac tcc tgt gag gac agc aca tac acc cag ctc tgg aac      353
Thr Val Cys Asp Ser Cys Glu Asp Ser Thr Tyr Thr Gln Leu Trp Asn
        75                  80                  85

tgg gtt ccc gag tgc ttg agc tgt ggc tcc cgc tgt agc tct gac cag      401
Trp Val Pro Glu Cys Leu Ser Cys Gly Ser Arg Cys Ser Ser Asp Gln
```

-continued

```
    90                  95                  100

gtg gaa act caa gcc tgc act cgg gaa cag aac cgc atc tgc acc tgc      449
Val Glu Thr Gln Ala Cys Thr Arg Glu Gln Asn Arg Ile Cys Thr Cys
105                 110                 115                 120

agg ccc ggc tgg tac tgc gcg ctg agc aag cag gag ggg tgc cgg ctg      497
Arg Pro Gly Trp Tyr Cys Ala Leu Ser Lys Gln Glu Gly Cys Arg Leu
                125                 130                 135

tgc gcg ccg ctg cgc aag tgc cgc ccg ggc ttc ggc gtg gcc aga cca      545
Cys Ala Pro Leu Arg Lys Cys Arg Pro Gly Phe Gly Val Ala Arg Pro
            140                 145                 150

gga act gaa aca tca gac gtg gtg tgc aag ccc tgt gcc ccg ggg acg      593
Gly Thr Glu Thr Ser Asp Val Val Cys Lys Pro Cys Ala Pro Gly Thr
        155                 160                 165

ttc tcc aac acg act tca tcc acg gat att tgc agg ccc cac cag atc      641
Phe Ser Asn Thr Thr Ser Ser Thr Asp Ile Cys Arg Pro His Gln Ile
    170                 175                 180

tgt aac gtg gtg gcc atc cct ggg aat gca agc atg gat gca gtc tgc      689
Cys Asn Val Val Ala Ile Pro Gly Asn Ala Ser Met Asp Ala Val Cys
185                 190                 195                 200

acg tcc acg tcc ccc acc cgg agt atg gcc cca ggg gca gta cac tta      737
Thr Ser Thr Ser Pro Thr Arg Ser Met Ala Pro Gly Ala Val His Leu
                205                 210                 215

ccc cag cca gtg tcc aca cga tcc caa cac acg cag cca act cca gaa      785
Pro Gln Pro Val Ser Thr Arg Ser Gln His Thr Gln Pro Thr Pro Glu
            220                 225                 230

ccc agc act gct cca agc acc tcc ttc ctg ctc cca atg ggc ccc agc      833
Pro Ser Thr Ala Pro Ser Thr Ser Phe Leu Leu Pro Met Gly Pro Ser
        235                 240                 245

ccc cca gct gaa ggg agc act ggc gac ttc gct ctt cca gtt gga ctg      881
Pro Pro Ala Glu Gly Ser Thr Gly Asp Phe Ala Leu Pro Val Gly Leu
    250                 255                 260

att gtg ggt gtg aca gcc ttg ggt cta cta ata ata gga gtg gtg aac      929
Ile Val Gly Val Thr Ala Leu Gly Leu Leu Ile Ile Gly Val Val Asn
265                 270                 275                 280

tgt gtc atc atg acc cag gtg aaa aag aag ccc ttg tgc ctg cag aga      977
Cys Val Ile Met Thr Gln Val Lys Lys Lys Pro Leu Cys Leu Gln Arg
                285                 290                 295

gaa gcc aag gtg cct cac ttg cct gcc gat aag gcc cgg ggt aca cag     1025
Glu Ala Lys Val Pro His Leu Pro Ala Asp Lys Ala Arg Gly Thr Gln
            300                 305                 310

ggc ccc gag cag cag cac ctg ctg atc aca gcg ccg agc tcc agc agc     1073
Gly Pro Glu Gln Gln His Leu Leu Ile Thr Ala Pro Ser Ser Ser Ser
        315                 320                 325

agc tcc ctg gag agc tcg gcc agt gcg ttg gac aga agg gcg ccc act     1121
Ser Ser Leu Glu Ser Ser Ala Ser Ala Leu Asp Arg Arg Ala Pro Thr
    330                 335                 340

cgg aac cag cca cag gca cca ggc gtg gag gcc agt ggg gcc ggg gag     1169
Arg Asn Gln Pro Gln Ala Pro Gly Val Glu Ala Ser Gly Ala Gly Glu
345                 350                 355                 360

gcc cgg gcc agc acc ggg agc tca gat tct tcc cct ggt ggc cat ggg     1217
Ala Arg Ala Ser Thr Gly Ser Ser Asp Ser Ser Pro Gly Gly His Gly
                365                 370                 375

acc cag gtc aat gtc acc tgc atc gtg aac gtc tgt agc agc tct gac     1265
Thr Gln Val Asn Val Thr Cys Ile Val Asn Val Cys Ser Ser Ser Asp
            380                 385                 390

cac agc tca cag tgc tcc tcc caa gcc agc tcc aca atg gga gac aca     1313
His Ser Ser Gln Cys Ser Ser Gln Ala Ser Ser Thr Met Gly Asp Thr
        395                 400                 405

gat tcc agc ccc tcg gag tcc ccg aag gac gag cag gtc ccc ttc tcc     1361
```

-continued

```
Asp Ser Ser Pro Ser Glu Ser Pro Lys Asp Glu Gln Val Pro Phe Ser
    410                 415                 420

aag gag gaa tgt gcc ttt cgg tca cag ctg gag acg cca gag acc ctg     1409
Lys Glu Glu Cys Ala Phe Arg Ser Gln Leu Glu Thr Pro Glu Thr Leu
425                 430                 435                 440

ctg ggg agc acc gaa gag aag ccc ctg ccc ctt gga gtg cct gat gct     1457
Leu Gly Ser Thr Glu Glu Lys Pro Leu Pro Leu Gly Val Pro Asp Ala
                445                 450                 455

ggg atg aag ccc agt taa ccaggccggt gtgggctgtg tcgtagccaa            1505
Gly Met Lys Pro Ser
            460

ggtgggctga gccctggcag gatgaccctg cgaaggggcc ctggtccttc caggccccca   1565

ccactaggac tctgaggctc tttctgggcc aagttcctct agtgccctcc acagccgcag   1625

cctccctctg acctgcaggc caagagcaga ggcagcgagt tgtggaaagc ctctgctgcc   1685

atggcgtgtc cctctcggaa ggctggctgg gcatggacgt tcggggcatg ctggggcaag   1745

tccctgactc tctgtgacct gccccgccca gctgcacctg ccagcctggc ttctggagcc   1805

cttgggtttt ttgtttgttt gtttgtttgt ttgtttgttt ctccccctgg gctctgcccc   1865

agctctggct tccagaaaac cccagcatcc ttttctgcag aggggctttc tggagaggag   1925

ggatgctgcc tgagtcaccc atgaagacag gacagtgctt cagcctgagg ctgagactgc   1985

gggatggtcc tggggctctg tgcagggagg aggtggcagc cctgtaggga acggggtcct   2045

tcaagttagc tcaggaggct tggaaagcat cacctcaggc caggtgcagt ggctcacgcc   2105

tatgatccca gcactttggg aggctgaggc gggtggatca cctgaggtta ggagttcgag   2165

accagcctgg ccaacatggt aaaaccccat ctctactaaa aatacagaaa ttagccgggc   2225

gtggtggcgg gcacctatag tcccagctac tcagaagcct gaggctggga aatcgtttga   2285

acccgggaag cggaggttgc agggagccga gatcacgcca ctgcactcca gcctgggcga   2345

cagagcgaga gtctgtctca aaagaaaaaa aaaagcaccg cctccaaatg ccaacttgtc   2405

cttttgtacc atggtgtgaa agtcagatgc ccagagggcc caggcaggcc accatattca   2465

gtgctgtggc ctgggcaaga taacgcactt ctaactagaa atctgccaat tttttaaaaa   2525

agtaagtacc actcaggcca acaagccaac gacaaagcca aactctgcca gccacatcca   2585

accccccacc tgccatttgc accctccgcc ttcactccgg tgtgcctgca gccccgcgcc   2645

tccttccttg ctgtcctagg ccacaccatc tcctttcagg gaatttcagg aactagagat   2705

gactgagtcc tcgtagccat ctctctactc ctacctcagc ctagaccctc ctcctccccc   2765

agaggggtgg gttcctcttc cccactcccc accttcaatt cctgggcccc aaacgggctg   2825

ccctgccact ttggtacatg gccagtgtga tcccaagtgc cagtcttgtg tctgcgtctg   2885

tgttgcgtgt cgtgggtgtg tgtagccaag gtcggtaagt tgaatggcct gccttgaagc   2945

cactgaagct gggattcctc cccattagag tcagccttcc ccctcccagg gccagggccc   3005

tgcagagggg aaaccagtgt agccttgccc ggattctggg aggaagcagg ttgaggggct   3065

cctggaaagg ctcagtctca ggagcatggg gataaaggag aaggcatgaa attgtctagc   3125

agagcagggg cagggtgata aattgttgat aaattccact ggacttgagc ttggcagctg   3185

aactattgga gggtgggaga gcccagccat taccatggag acaagaaggg ttttccaccc   3245

tggaatcaag atgtcagact ggctggctgc agtgacgtgc acctgtactc aggaggctga   3305

ggggaggatc actggagccc aggagtttga ggctgcagcg agctatgatc gcgccactac   3365

actccagcct gagcaacaga gtgagaccct gtctcttaaa gaaaaaaaaa gtcagactgc   3425
```

-continued

```
tgggactggc caggtttctg cccacattgg acccacatga ggacatgatg gagcgcacct   3485

gccccctggt ggacagtcct gggagaacct caggcttcct tggcatcaca gggcagagcc   3545

gggaagcgat gaatttggag actctgtggg gccttggttc ccttgtgtgt gtgtgttgat   3605

cccaagacaa tgaaagtttg cactgtatgc tggacggcat tcctgcttat caataaacct   3665

gtttgtttta aaaaaaa                                                  3682


<210> SEQ ID NO 64
<211> LENGTH: 461
<212> TYPE: PRT
<213> ORGANISM: Homo sapiens

<400> SEQUENCE: 64

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
```

```
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460


<210> SEQ ID NO 65
<211> LENGTH: 4176
<212> TYPE: DNA
<213> ORGANISM: Homo sapiens
<220> FEATURE:
<221> NAME/KEY: CDS
<222> LOCATION: (438)..(1844)

<400> SEQUENCE: 65

ggcggtcccc tgttctcccc gctcaggtgc ggcgctgtgg caggaagcca ccccctcggt      60

cggccggtgc gcggggctgt tgcgccatcc gctccggctt tcgtaaccgc accctgggac     120

ggcccagaga cgctccagcg cgagttcctc aaatgttttc ctgcgttgcc aggaccgtcc     180

gccgctctga gtcatgtgcg agtgggaagt cgcactgaca ctgagccggg ccagagggag     240

aggagccgag cgcggcgcgg ggccgaggga ctcgcagtgt gtgtagagag ccgggctcct     300

gcggatgggg gctgccccg gggcctgagc ccgcctgccc gcccaccgcc ccgccccgcc     360

cctgccaccc ctgccgcccg gttcccatta gcctgtccgc ctctgcggga ccatggagtg     420

gtagccgagg aggaagc atg ctg gcc gtc ggc tgc gcg ctg ctg gct gcc        470
                   Met Leu Ala Val Gly Cys Ala Leu Leu Ala Ala
                   1               5                   10

ctg ctg gcc gcg ccg gga gcg gcg ctg gcc cca agg cgc tgc cct gcg       518
Leu Leu Ala Ala Pro Gly Ala Ala Leu Ala Pro Arg Arg Cys Pro Ala
            15                  20                  25

cag gag gtg gcg aga ggc gtg ctg acc agt ctg cca gga gac agc gtg       566
Gln Glu Val Ala Arg Gly Val Leu Thr Ser Leu Pro Gly Asp Ser Val
        30                  35                  40

act ctg acc tgc ccg ggg gta gag ccg gaa gac aat gcc act gtt cac       614
Thr Leu Thr Cys Pro Gly Val Glu Pro Glu Asp Asn Ala Thr Val His
    45                  50                  55

tgg gtg ctc agg aag ccg gct gca ggc tcc cac ccc agc aga tgg gct       662
Trp Val Leu Arg Lys Pro Ala Ala Gly Ser His Pro Ser Arg Trp Ala
60                  65                  70                  75

ggc atg gga agg agg ctg ctg ctg agg tcg gtg cag ctc cac gac tct       710
Gly Met Gly Arg Arg Leu Leu Leu Arg Ser Val Gln Leu His Asp Ser
                80                  85                  90

gga aac tat tca tgc tac cgg gcc ggc cgc cca gct ggg act gtg cac       758
Gly Asn Tyr Ser Cys Tyr Arg Ala Gly Arg Pro Ala Gly Thr Val His
            95                  100                 105
```

-continued

```
ttg ctg gtg gat gtt ccc ccc gag gag ccc cag ctc tcc tgc ttc cgg      806
Leu Leu Val Asp Val Pro Pro Glu Glu Pro Gln Leu Ser Cys Phe Arg
        110                 115                 120

aag agc ccc ctc agc aat gtt gtt tgt gag tgg ggt cct cgg agc acc      854
Lys Ser Pro Leu Ser Asn Val Val Cys Glu Trp Gly Pro Arg Ser Thr
    125                 130                 135

cca tcc ctg acg aca aag gct gtg ctc ttg gtg agg aag ttt cag aac      902
Pro Ser Leu Thr Thr Lys Ala Val Leu Leu Val Arg Lys Phe Gln Asn
140                 145                 150                 155

agt ccg gcc gaa gac ttc cag gag ccg tgc cag tat tcc cag gag tcc      950
Ser Pro Ala Glu Asp Phe Gln Glu Pro Cys Gln Tyr Ser Gln Glu Ser
                160                 165                 170

cag aag ttc tcc tgc cag tta gca gtc ccg gag gga gac agc tct ttc      998
Gln Lys Phe Ser Cys Gln Leu Ala Val Pro Glu Gly Asp Ser Ser Phe
            175                 180                 185

tac ata gtg tcc atg tgc gtc gcc agt agt gtc ggg agc aag ttc agc     1046
Tyr Ile Val Ser Met Cys Val Ala Ser Ser Val Gly Ser Lys Phe Ser
        190                 195                 200

aaa act caa acc ttt cag ggt tgt gga atc ttg cag cct gat ccg cct     1094
Lys Thr Gln Thr Phe Gln Gly Cys Gly Ile Leu Gln Pro Asp Pro Pro
    205                 210                 215

gcc aac atc aca gtc act gcc gtg gcc aga aac ccc cgc tgg ctc agt     1142
Ala Asn Ile Thr Val Thr Ala Val Ala Arg Asn Pro Arg Trp Leu Ser
220                 225                 230                 235

gtc acc tgg caa gac ccc cac tcc tgg aac tca tct ttc tac aga cta     1190
Val Thr Trp Gln Asp Pro His Ser Trp Asn Ser Ser Phe Tyr Arg Leu
                240                 245                 250

cgg ttt gag ctc aga tat cgg gct gaa cgg tca aag aca ttc aca aca     1238
Arg Phe Glu Leu Arg Tyr Arg Ala Glu Arg Ser Lys Thr Phe Thr Thr
            255                 260                 265

tgg atg gtc aag gac ctc cag cat cac tgt gtc atc cac gac gcc tgg     1286
Trp Met Val Lys Asp Leu Gln His His Cys Val Ile His Asp Ala Trp
        270                 275                 280

agc ggc ctg agg cac gtg gtg cag ctt cgt gcc cag gag gag ttc ggg     1334
Ser Gly Leu Arg His Val Val Gln Leu Arg Ala Gln Glu Glu Phe Gly
    285                 290                 295

caa ggc gag tgg agc gag tgg agc ccg gag gcc atg ggc acg cct tgg     1382
Gln Gly Glu Trp Ser Glu Trp Ser Pro Glu Ala Met Gly Thr Pro Trp
300                 305                 310                 315

aca gaa tcc agg agt cct cca gct gag aac gag gtg tcc acc ccc atg     1430
Thr Glu Ser Arg Ser Pro Pro Ala Glu Asn Glu Val Ser Thr Pro Met
                320                 325                 330

cag gca ctt act act aat aaa gac gat gat aat att ctc ttc aga gat     1478
Gln Ala Leu Thr Thr Asn Lys Asp Asp Asp Asn Ile Leu Phe Arg Asp
            335                 340                 345

tct gca aat gcg aca agc ctc cca gtg caa gat tct tct tca gta cca     1526
Ser Ala Asn Ala Thr Ser Leu Pro Val Gln Asp Ser Ser Ser Val Pro
        350                 355                 360

ctg ccc aca ttc ctg gtt gct gga ggg agc ctg gcc ttc gga acg ctc     1574
Leu Pro Thr Phe Leu Val Ala Gly Gly Ser Leu Ala Phe Gly Thr Leu
    365                 370                 375

ctc tgc att gcc att gtt ctg agg ttc aag aag acg tgg aag ctg cgg     1622
Leu Cys Ile Ala Ile Val Leu Arg Phe Lys Lys Thr Trp Lys Leu Arg
380                 385                 390                 395

gct ctg aag gaa ggc aag aca agc atg cat ccg ccg tac tct ttg ggg     1670
Ala Leu Lys Glu Gly Lys Thr Ser Met His Pro Pro Tyr Ser Leu Gly
                400                 405                 410

cag ctg gtc ccg gag agg cct cga ccc acc cca gtg ctt gtt cct ctc     1718
Gln Leu Val Pro Glu Arg Pro Arg Pro Thr Pro Val Leu Val Pro Leu
            415                 420                 425
```

-continued

```
atc tcc cca ccg gtg tcc ccc agc agc ctg ggg tct gac aat acc tcg     1766
Ile Ser Pro Pro Val Ser Pro Ser Ser Leu Gly Ser Asp Asn Thr Ser
        430                 435                 440

agc cac aac cga cca gat gcc agg gac cca cgg agc cct tat gac atc     1814
Ser His Asn Arg Pro Asp Ala Arg Asp Pro Arg Ser Pro Tyr Asp Ile
    445                 450                 455

agc aat aca gac tac ttc ttc ccc aga tag ctggctgggt ggcaccagca      1864
Ser Asn Thr Asp Tyr Phe Phe Pro Arg
460                 465

gcctggaccc tgtggatgat aaaacacaaa cgggctcagc aaaagatgct tctcactgcc   1924

atgccagctt atctcagggg tgtgcggcct ttggcttcac ggaagagcct tgcggaaggt   1984

tctacgccag gggaaaatca gcctgctcca gctgttcagc tggttgaggt ttcaaacctc   2044

cctttccaaa tgcccagctt aaaggggcta gagtgaactt gggccactgt gaagagaacc   2104

atatcaagac tctttggaca ctcacacgga cactcaaaag ctgggcaggt tggtgggggc   2164

ctcggtgtgg agaagcggct ggcagcccac ccctcaacac ctctgcacaa gctgcaccct   2224

caggcaggtg ggatggattt ccagccaaag cctcctccag ccgccatgct cctggcccac   2284

tgcatcgttt catcttccaa ctcaaactct taaaacccaa gtgccttagc aaattctgtt   2344

tttctaggcc tggggacggc ttttacttaa accgccaagg ctgggggaag aagctctctc   2404

ctccctttct tccctacagt tgaaaaacag ctgagggtga gtgggtgaat aatacagtat   2464

ctcagggcct ggtcgttttc aacagaatta taattagttc ctcattagca ttttgctaaa   2524

tgtgaatgat gatcctaggc atttgctgaa tacagaggca actgcattgg ctttgggttg   2584

caggacctca ggtgagaagc agaggaagga gaggagaggg gcacagggtc tctaccatcc   2644

cctgtagagt gggagctgag tgggggatca cagcctctga aaaccaatgt tctctcttct   2704

ccacctccca caaaggagag ctagcagcag ggagggcttc tgccatttct gagatcaaaa   2764

cggttttact gcagctttgt ttgttgtcag ctgaacctgg gtaactaggg aagataatat   2824

taaggaagac aatgtgaaaa gaaaaatgag cctggcaaga atgtgtttaa acttggtttt   2884

taaaaaactg ctgactgttt tctcttgaga gggtggaata tccaatattc gctgtgtcag   2944

catagaagta acttacttag gtgtggggga agcaccataa ctttgtttag cccaaaacca   3004

agtcaagtga aaaaggagga agagaaaaaa tattttcctg ccaggcatgg tggcccacgc   3064

acttcgggag gtcgaggcag gaggatcact tgagtccaga agtttgagat cagcctgggc   3124

aatgtgataa aaccccatct ctacaaaaag cataaaaatt agccaagtgt ggtagagtgt   3184

gcctgaagtc ccagatactt ggggggctga ggtgggagga tctcttgagc ctgggaggtc   3244

aaggctgcag tgagccgaga ttgcaccact gcactccagc ctgggtgaca gagcaagtga   3304

gaccctgtct caaaaaaaga aaaagaaaaa gaaaaaatat tttccctatt agagaagaga   3364

ttgtggtttc attctgtatt ttgtttttgt cttaaaaagt ggaaaaatag cctgcctctt   3424

ctctactcta gggaaaaacc agcgtgtgac tactccccca ggtggttatg gagagggtgt   3484

ccggtccctg tcccagtgcc gagaaggaag cctcccacga ctgcccggca gggtcctaga   3544

aattccccac cctgaaagcc ctgagctttc tgctatcaaa gaggttttaa aaaaatccca   3604

tttaaaaaaa atcccttacc tcggtgcctt cctcttttta tttagttcct tgagttgatt   3664

cagctctgca agaattgaag caggactaaa tgtctagttg taacaccatg attaaccact   3724

tcagctgact ttctgtccg agctttgaaa attcagtggt gttagtggtt acccagttag   3784

ctctcaagtt atcagggtat tccagagtgg ggatatgatt taaatcagcc gtgtaaccat   3844
```

-continued

```
ggacccaata tttaccagac cacaaaactt ttctaatact ctaccctctt agaaaaacca   3904

ccaccatcac cagacaggtg cgaaaggatg aaagtgacca tgttttgttt acggttttcc   3964

aggtttaagc tgttactgtc ttcagtaagc cgtgattttc attgctgggc ttgtctgtag   4024

attttagacc ctattgctgc ttgaggcaac tcatcttagg ttggcaaaaa ggcaggatgg   4084

ccgggcgcgg tggctcacgc ctgtaatcct agcactttgg gaggccaagg tgggaggatt   4144

gcttgagctc aggagtttga gaccaacctg gg                                 4176
```

<210> SEQ ID NO 66
<211> LENGTH: 468
<212> TYPE: PRT
<213> ORGANISM: Homo sapiens

<400> SEQUENCE: 66

```
Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320
```

-continued

```
Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Ser Val Pro Leu Pro Thr Phe Leu
        355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
    450                 455                 460

Phe Phe Pro Arg
465


<210> SEQ ID NO 67
<211> LENGTH: 1789
<212> TYPE: DNA
<213> ORGANISM: Homo sapiens
<220> FEATURE:
<221> NAME/KEY: CDS
<222> LOCATION: (65)..(1774)

<400> SEQUENCE: 67

atggtgactc cctcctgaga agctggaccc cttggtaaaa gacaaggcct tctccaagaa      60

gaat atg aaa gtg tta ctc aga ctt att tgt ttc ata gct cta ctg att      109
     Met Lys Val Leu Leu Arg Leu Ile Cys Phe Ile Ala Leu Leu Ile
     1               5                   10                  15

tct tct ctg gag gct gat aaa tgc aag gaa cgt gaa gaa aaa ata att      157
Ser Ser Leu Glu Ala Asp Lys Cys Lys Glu Arg Glu Glu Lys Ile Ile
                20                  25                  30

tta gtg tca tct gca aat gaa att gat gtt cgt ccc tgt cct ctt aac      205
Leu Val Ser Ser Ala Asn Glu Ile Asp Val Arg Pro Cys Pro Leu Asn
            35                  40                  45

cca aat gaa cac aaa ggc act ata act tgg tat aaa gat gac agc aag      253
Pro Asn Glu His Lys Gly Thr Ile Thr Trp Tyr Lys Asp Asp Ser Lys
        50                  55                  60

aca cct gta tct aca gaa caa gcc tcc agg att cat caa cac aaa gag      301
Thr Pro Val Ser Thr Glu Gln Ala Ser Arg Ile His Gln His Lys Glu
    65                  70                  75

aaa ctt tgg ttt gtt cct gct aag gtg gag gat tca gga cat tac tat      349
Lys Leu Trp Phe Val Pro Ala Lys Val Glu Asp Ser Gly His Tyr Tyr
80                  85                  90                  95

tgc gtg gta aga aat tca tct tac tgc ctc aga att aaa ata agt gca      397
Cys Val Val Arg Asn Ser Ser Tyr Cys Leu Arg Ile Lys Ile Ser Ala
                100                 105                 110

aaa ttt gtg gag aat gag cct aac tta tgt tat aat gca caa gcc ata      445
Lys Phe Val Glu Asn Glu Pro Asn Leu Cys Tyr Asn Ala Gln Ala Ile
            115                 120                 125

ttt aag cag aac cta ccc gtt gca gga gac gga gga ctt gtg tgc cct      493
Phe Lys Gln Asn Leu Pro Val Ala Gly Asp Gly Gly Leu Val Cys Pro
        130                 135                 140
```

-continued

```
tat atg gag ttt ttt aaa aat gaa aat aat gag tta cct aaa tta cag      541
Tyr Met Glu Phe Phe Lys Asn Glu Asn Asn Glu Leu Pro Lys Leu Gln
    145                 150                 155

tgg tat aag gat tgc aaa cct cta ctt ctt gac aat ata cac ttt agt      589
Trp Tyr Lys Asp Cys Lys Pro Leu Leu Leu Asp Asn Ile His Phe Ser
160                 165                 170                 175

gga gtc aaa gat agg ctc atc gtg atg aat gtg gct gaa aag cat aga      637
Gly Val Lys Asp Arg Leu Ile Val Met Asn Val Ala Glu Lys His Arg
                180                 185                 190

ggg aac tat act tgt cat gca tcc tac aca tac ttg ggc aag caa tat      685
Gly Asn Tyr Thr Cys His Ala Ser Tyr Thr Tyr Leu Gly Lys Gln Tyr
            195                 200                 205

cct att acc cgg gta ata gaa ttt att act cta gag gaa aac aaa ccc      733
Pro Ile Thr Arg Val Ile Glu Phe Ile Thr Leu Glu Glu Asn Lys Pro
        210                 215                 220

aca agg cct gtg att gtg agc cca gct aat gag aca atg gaa gta gac      781
Thr Arg Pro Val Ile Val Ser Pro Ala Asn Glu Thr Met Glu Val Asp
    225                 230                 235

ttg gga tcc cag ata caa ttg atc tgt aat gtc acc ggc cag ttg agt      829
Leu Gly Ser Gln Ile Gln Leu Ile Cys Asn Val Thr Gly Gln Leu Ser
240                 245                 250                 255

gac att gct tac tgg aag tgg aat ggg tca gta att gat gaa gat gac      877
Asp Ile Ala Tyr Trp Lys Trp Asn Gly Ser Val Ile Asp Glu Asp Asp
                260                 265                 270

cca gtg cta ggg gaa gac tat tac agt gtg gaa aat cct gca aac aaa      925
Pro Val Leu Gly Glu Asp Tyr Tyr Ser Val Glu Asn Pro Ala Asn Lys
            275                 280                 285

aga agg agt acc ctc atc aca gtg ctt aat ata tcg gaa att gaa agt      973
Arg Arg Ser Thr Leu Ile Thr Val Leu Asn Ile Ser Glu Ile Glu Ser
        290                 295                 300

aga ttt tat aaa cat cca ttt acc tgt ttt gcc aag aat aca cat ggt     1021
Arg Phe Tyr Lys His Pro Phe Thr Cys Phe Ala Lys Asn Thr His Gly
    305                 310                 315

ata gat gca gca tat atc cag tta ata tat cca gtc act aat ttc cag     1069
Ile Asp Ala Ala Tyr Ile Gln Leu Ile Tyr Pro Val Thr Asn Phe Gln
320                 325                 330                 335

aag cac atg att ggt ata tgt gtc acg ttg aca gtc ata att gtg tgt     1117
Lys His Met Ile Gly Ile Cys Val Thr Leu Thr Val Ile Ile Val Cys
                340                 345                 350

tct gtt ttc atc tat aaa atc ttc aag att gac att gtg ctt tgg tac     1165
Ser Val Phe Ile Tyr Lys Ile Phe Lys Ile Asp Ile Val Leu Trp Tyr
            355                 360                 365

agg gat tcc tgc tat gat ttt ctc cca ata aaa gct tca gat gga aag     1213
Arg Asp Ser Cys Tyr Asp Phe Leu Pro Ile Lys Ala Ser Asp Gly Lys
        370                 375                 380

acc tat gac gca tat ata ctg tat cca aag act gtt ggg gaa ggg tct     1261
Thr Tyr Asp Ala Tyr Ile Leu Tyr Pro Lys Thr Val Gly Glu Gly Ser
    385                 390                 395

acc tct gac tgt gat att ttt gtg ttt aaa gtc ttg cct gag gtc ttg     1309
Thr Ser Asp Cys Asp Ile Phe Val Phe Lys Val Leu Pro Glu Val Leu
400                 405                 410                 415

gaa aaa cag tgt gga tat aag ctg ttc att tat gga agg gat gac tac     1357
Glu Lys Gln Cys Gly Tyr Lys Leu Phe Ile Tyr Gly Arg Asp Asp Tyr
                420                 425                 430

gtt ggg gaa gac att gtt gag gtc att aat gaa aac gta aag aaa agc     1405
Val Gly Glu Asp Ile Val Glu Val Ile Asn Glu Asn Val Lys Lys Ser
            435                 440                 445

aga aga ctg att atc att tta gtc aga gaa aca tca agc ttc agc tgg     1453
Arg Arg Leu Ile Ile Ile Leu Val Arg Glu Thr Ser Ser Phe Ser Trp
```

-continued

```
        450                 455                 460

ctg ggt ggt tca tct gaa gag caa ata gcc atg tat aat gct ctt gtt      1501
Leu Gly Gly Ser Ser Glu Glu Gln Ile Ala Met Tyr Asn Ala Leu Val
    465                 470                 475

cag gat gga att aaa gtt gtc ctg ctt gag ctg gag aaa atc caa gac      1549
Gln Asp Gly Ile Lys Val Val Leu Leu Glu Leu Glu Lys Ile Gln Asp
480                 485                 490                 495

tat gag aaa atg cca gaa tcg att aaa ttc att aag cag aaa cat ggg      1597
Tyr Glu Lys Met Pro Glu Ser Ile Lys Phe Ile Lys Gln Lys His Gly
                500                 505                 510

gct atc cgc tgg tca ggg gac ttt aca cag gga cca cag tct gca aag      1645
Ala Ile Arg Trp Ser Gly Asp Phe Thr Gln Gly Pro Gln Ser Ala Lys
            515                 520                 525

aca agg ttc tgg aag aat gtc agg tac cac atg cca gtc cag cga cgg      1693
Thr Arg Phe Trp Lys Asn Val Arg Tyr His Met Pro Val Gln Arg Arg
        530                 535                 540

tca cct tca tct aaa cac cag tta ctg tca cca gcc act aag gag aaa      1741
Ser Pro Ser Ser Lys His Gln Leu Leu Ser Pro Ala Thr Lys Glu Lys
    545                 550                 555

ctg caa aga gag gct cac gtg cct ctc ggg tag catggagaac ttgcc         1789
Leu Gln Arg Glu Ala His Val Pro Leu Gly
560                 565


<210> SEQ ID NO 68
<211> LENGTH: 569
<212> TYPE: PRT
<213> ORGANISM: Homo sapiens

<400> SEQUENCE: 68

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Asn Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220
```

```
Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
    370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445

Arg Leu Ile Ile Ile Leu Val Arg Glu Thr Ser Ser Phe Ser Trp Leu
    450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
    530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565
```

<210> SEQ ID NO 69
<211> LENGTH: 1436
<212> TYPE: DNA
<213> ORGANISM: Homo sapiens
<220> FEATURE:
<221> NAME/KEY: CDS
<222> LOCATION: (182)..(1378)

<400> SEQUENCE: 69

```
gggatgggag atactgttgt ggtcacctct ggaaaataca ttctgctact cttaaaaact     60
```

```
agtgacgctc atacaaatca acagaaagag cttctgaagg aagactttaa agctgcttct    120

gccacgtgct gctgggtctc agtcctccac ttcccgtgtc ctctggaagt tgtcaggagc    180

a atg ttg cgc ttg tac gtg ttg gta atg gga gtt tct gcc ttc acc ctt    229
  Met Leu Arg Leu Tyr Val Leu Val Met Gly Val Ser Ala Phe Thr Leu
  1               5                   10                  15

cag cct gcg gca cac aca ggg gct gcc aga agc tgc cgg ttt cgt ggg      277
Gln Pro Ala Ala His Thr Gly Ala Ala Arg Ser Cys Arg Phe Arg Gly
            20                  25                  30

agg cat tac aag cgg gag ttc agg ctg gaa ggg gag cct gta gcc ctg      325
Arg His Tyr Lys Arg Glu Phe Arg Leu Glu Gly Glu Pro Val Ala Leu
        35                  40                  45

agg tgc ccc cag gtg ccc tac tgg ttg tgg gcc tct gtc agc ccc cgc      373
Arg Cys Pro Gln Val Pro Tyr Trp Leu Trp Ala Ser Val Ser Pro Arg
    50                  55                  60

atc aac ctg aca tgg cat aaa aat gac tct gct agg acg gtc cca gga      421
Ile Asn Leu Thr Trp His Lys Asn Asp Ser Ala Arg Thr Val Pro Gly
65                  70                  75                  80

gaa gaa gag aca cgg atg tgg gcc cag gac ggt gct ctg tgg ctt ctg      469
Glu Glu Glu Thr Arg Met Trp Ala Gln Asp Gly Ala Leu Trp Leu Leu
                85                  90                  95

cca gcc ttg cag gag gac tct ggc acc tac gtc tgc act act aga aat      517
Pro Ala Leu Gln Glu Asp Ser Gly Thr Tyr Val Cys Thr Thr Arg Asn
            100                 105                 110

gct tct tac tgt gac aaa atg tcc att gag ctc aga gtt ttt gag aat      565
Ala Ser Tyr Cys Asp Lys Met Ser Ile Glu Leu Arg Val Phe Glu Asn
        115                 120                 125

aca gat gct ttc ctg ccg ttc atc tca tac ccg caa att tta acc ttg      613
Thr Asp Ala Phe Leu Pro Phe Ile Ser Tyr Pro Gln Ile Leu Thr Leu
    130                 135                 140

tca acc tct ggg gta tta gta tgc cct gac ctg agt gaa ttc acc cgt      661
Ser Thr Ser Gly Val Leu Val Cys Pro Asp Leu Ser Glu Phe Thr Arg
145                 150                 155                 160

gac aaa act gac gtg aag att caa tgg tac aag gat tct ctt ctt ttg      709
Asp Lys Thr Asp Val Lys Ile Gln Trp Tyr Lys Asp Ser Leu Leu Leu
                165                 170                 175

gat aaa gac aat gag aaa ttt cta agt gtg agg ggg acc act cac tta      757
Asp Lys Asp Asn Glu Lys Phe Leu Ser Val Arg Gly Thr Thr His Leu
            180                 185                 190

ctc gta cac gat gtg gcc ctg gaa gat gct ggc tat tac cgc tgt gtc      805
Leu Val His Asp Val Ala Leu Glu Asp Ala Gly Tyr Tyr Arg Cys Val
        195                 200                 205

ctg aca ttt gcc cat gaa ggc cag caa tac aac atc act agg agt att      853
Leu Thr Phe Ala His Glu Gly Gln Gln Tyr Asn Ile Thr Arg Ser Ile
    210                 215                 220

gag cta cgc atc aag aaa aaa aaa gaa gag acc att cct gtg atc att      901
Glu Leu Arg Ile Lys Lys Lys Lys Glu Glu Thr Ile Pro Val Ile Ile
225                 230                 235                 240

tcc ccc ctc aag acc ata tca gct tct ctg ggg tca aga ctg aca atc      949
Ser Pro Leu Lys Thr Ile Ser Ala Ser Leu Gly Ser Arg Leu Thr Ile
                245                 250                 255

ccg tgt aag gtg ttt ctg gga acc ggc aca ccc tta acc acc atg ctg      997
Pro Cys Lys Val Phe Leu Gly Thr Gly Thr Pro Leu Thr Thr Met Leu
            260                 265                 270

tgg tgg acg gcc aat gac acc cac ata gag agc gcc tac ccg gga ggc     1045
Trp Trp Thr Ala Asn Asp Thr His Ile Glu Ser Ala Tyr Pro Gly Gly
        275                 280                 285

cgc gtg acc gag ggg cca cgc cag gaa tat tca gaa aat aat gag aac     1093
Arg Val Thr Glu Gly Pro Arg Gln Glu Tyr Ser Glu Asn Asn Glu Asn
```

-continued

```
    290                 295                 300

tac att gaa gtg cca ttg att ttt gat cct gtc aca aga gag gat ttg     1141
Tyr Ile Glu Val Pro Leu Ile Phe Asp Pro Val Thr Arg Glu Asp Leu
305                 310                 315                 320

cac atg gat ttt aaa tgt gtt gtc cat aat acc ctg agt ttt cag aca     1189
His Met Asp Phe Lys Cys Val Val His Asn Thr Leu Ser Phe Gln Thr
                325                 330                 335

cta cgc acc aca gtc aag gaa gcc tcc tcc acg ttc tcc tgg ggc att     1237
Leu Arg Thr Thr Val Lys Glu Ala Ser Ser Thr Phe Ser Trp Gly Ile
            340                 345                 350

gtg ctg gcc cca ctt tca ctg gcc ttc ttg gtt ttg ggg gga ata tgg     1285
Val Leu Ala Pro Leu Ser Leu Ala Phe Leu Val Leu Gly Gly Ile Trp
        355                 360                 365

atg cac aga cgg tgc aaa cac aga act gga aaa gca gat ggt ctg act     1333
Met His Arg Arg Cys Lys His Arg Thr Gly Lys Ala Asp Gly Leu Thr
    370                 375                 380

gtg cta tgg cct cat cat caa gac ttt caa tcc tat ccc aag tga         1378
Val Leu Trp Pro His His Gln Asp Phe Gln Ser Tyr Pro Lys
385                 390                 395

aataaatgga atgaaataat tcaaacacaa aaaaaaaaaa aaaaaaaaaa aaaaaaa     1436


<210> SEQ ID NO 70
<211> LENGTH: 398
<212> TYPE: PRT
<213> ORGANISM: Homo sapiens

<400> SEQUENCE: 70

Met Leu Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
```

```
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Trp Gly Ile
            340                 345                 350

Val Leu Ala Pro Leu Ser Leu Ala Phe Leu Val Leu Gly Gly Ile Trp
        355                 360                 365

Met His Arg Arg Cys Lys His Arg Thr Gly Lys Ala Asp Gly Leu Thr
    370                 375                 380

Val Leu Trp Pro His His Gln Asp Phe Gln Ser Tyr Pro Lys
385                 390                 395


<210> SEQ ID NO 71
<211> LENGTH: 9
<212> TYPE: PRT
<213> ORGANISM: Homo sapiens

<400> SEQUENCE: 71

Asn Val Lys Gly Thr Glu Asp Ser Gly
1               5


<210> SEQ ID NO 72
<211> LENGTH: 9
<212> TYPE: PRT
<213> ORGANISM: Homo sapiens

<400> SEQUENCE: 72

Lys Gly Thr Glu Asp Ser Gly Thr Thr
1               5


<210> SEQ ID NO 73
<211> LENGTH: 8
<212> TYPE: PRT
<213> ORGANISM: Homo sapiens

<400> SEQUENCE: 73

Cys Thr Ser Thr Ser Pro Thr Arg
1               5


<210> SEQ ID NO 74
<211> LENGTH: 7
<212> TYPE: PRT
<213> ORGANISM: Homo sapiens

<400> SEQUENCE: 74

Ala Asn Ala Thr Ser Leu Pro
1               5


<210> SEQ ID NO 75
<211> LENGTH: 10
```

<212> TYPE: PRT
<213> ORGANISM: Homo sapiens

<400> SEQUENCE: 75

Thr His Gly Ile Asp Ala Ala Tyr Ile Gln
1 5 10

<210> SEQ ID NO 76
<211> LENGTH: 10
<212> TYPE: PRT
<213> ORGANISM: Homo sapiens

<400> SEQUENCE: 76

Gln Thr Lys Arg Thr Thr Val Lys Glu Ala
1 5 10

<210> SEQ ID NO 77
<211> LENGTH: 10
<212> TYPE: PRT
<213> ORGANISM: Homo sapiens

<400> SEQUENCE: 77

Leu Ala Gln Ala Val Arg Ser Ser Ser Arg
1 5 10

<210> SEQ ID NO 78
<211> LENGTH: 7
<212> TYPE: PRT
<213> ORGANISM: Homo sapiens

<400> SEQUENCE: 78

Pro Gln Gly Leu Glu Ala Lys
1 5

<210> SEQ ID NO 79
<211> LENGTH: 8648
<212> TYPE: DNA
<213> ORGANISM: Homo sapiens

<400> SEQUENCE: 79
cagggaggga cgcccccgcc gacaggagaa ttggttcccg ggcccgcggc gatgcccccc 60
cggtagctcg ggcccgtggt cgggtgtttg tgagtgtttc tatgtgggag aaggaggagg 120
aggaggaaga agaagcaacg atttgtcttc tcggctggtc tccccccggc tctacatgtt 180
ccccgcactg aggagacgga agaggagccg tagccacccc ccctcccggc ccggattata 240
gtctctcgcc acagcggcct cggcctcccc ttggattcag acgccgattc gcccagtgtt 300
tgggaaatgg gaagtaatga cagctggcac ctgaactaag tacttttata ggcaacacca 360
ttccagaaat tcaggatgaa tggggatatg ccccatgtcc ccattactac tcttgcgggg 420
attgctagtc tcacagacct cctgaaccag ctgcctcttc catctccttt acctgctaca 480
actacaaaga gccttctctt taatgcacga atagcagaag aggtgaactg cctttttggct 540 tgtagggatg acaatttggt ttcacagctt gtccatagcc tcaaccaggt atcaacagat 600
cacatagagt tgaaagataa ccttggcagt gatgacccag aaggtgacat accagtcttg 660
ttgcaggccg tcctggcaag gagtcctaat gttttcaggg agaaaagcat gcagaacaga 720
tatgtacaaa gtggaatgat gatgtctcag tataaacttt ctcagaattc catgcacagt 780
agtcctgcat cttccaatta tcaacaaacc actatctcac atagcccctc cagccggttt 840
gtgccaccac agacaagctc tgggaacaga tttatgccac agcaaaatag cccagtgcct 900

-continued

```
agtccatacg ccccacaaag ccctgcagga tacatgccat attcccatcc ttcaagttac    960
acaacacatc cacagatgca acaagcatcg gtatcaagtc ccattgttgc aggtggtttg   1020
agaaacatac atgataataa agtttctggt ccgttgtctg gcaattcagc taatcatcat   1080
gctgataatc ctagacatgg ttcaagtgag gactacctac acatggtgca caggctaagt   1140
agtgacgatg gagattcttc aacaatgagg aatgctgcat cttttccctt gagatctcca   1200
cagccagtat gctcccctgc tggaagtgaa ggaactccta aaggctcaag accaccttta   1260
atcctacaat ctcagtctct accttgttca tcacctcgag atgttccacc agatatcttg   1320
ctagattctc cagaaagaaa acaaaagaag cagaagaaaa tgaaattagg caaggatgaa   1380
aaagagcaga gtgagaaagc ggcaatgtat gatataatta gttctccatc caaggactct   1440
actaaactta cattaagact ttctcgtgta aggtcttcag acatggacca gcaagaggat   1500
atgatttctg gtgtggaaaa tagcaatgtt tcagaaaatg atattccttt taatgtgcag   1560
tacccaggac agacttcaaa aacacccatt actccacaag atataaaccg cccactaaat   1620
gctgctcaat gtttgtcgca gcaagaacaa acagcattcc ttccagcaaa tcaagtgcct   1680
gttttacaac agaacacttc agttgctgca aaacaacccc agacttctgt ggtacagaat   1740
caacaacaga tatcacaaca gggacctata tatgatgaag tggaattgga tgcattggct   1800
gaaattgagc gaatagagag agaatcagct attgaaaggg agcgcttctc aaaagaagtt   1860
caagataaag ataagccttt gaaaaaaaga aaacaagatt cttacccaca ggaggctggg   1920
ggtgctacag gaggtaatag accagcttct caggagacgg gttctacggg aaatgggtca   1980
aggccagcat taatggttag cattgatctt catcaggcag gaagagtgga ctctcaggct   2040
tctataactc aggattcaga ctccataaaa aagcctgaag aaatcaaaca atgtaatgat   2100
gcacctgttt ctgttcttca ggaagatatt gttggaagtc ttaaatctac accagaaaac   2160
catcctgaga cacctaaaaa aaagtctgat cctgagcttt caaagagtga aatgaaacaa   2220
agtgaaagta gattagcaga atctaaacca aatgaaaacc gattggtgga gacaaaatca   2280
agtgaaaata agttagaaac taaagttgag acccaaacag aagaacttaa acagaatgag   2340
agcagaacaa ctgaatgcaa acaaaacgag agcaccatag ttgagcctaa acaaaatgaa   2400
aatagactgt ctgacacaaa accaaatgac aacaaacaaa ataatggcag atcagaaaca   2460
acaaaatcaa ggcctgaaac cccaaagcaa aagggtgaaa gccggcctga gactccaaaa   2520
caaaagagtg atgggcatcc tgaaacccca aaacagaagg gtgatggaag gcctgaaact   2580
ccaaagcaaa aggtgagag ccgccctgaa actccaaagc aaaaaaatga agggcgacct    2640
gaaacaccaa aacacaggca tgacaatagg agggattctg gaaagccatc tacagagaaa   2700
aaacctgaag tgtctaaaca taaacaagat actaaatctg actcacctcg gttaaaatca   2760
gaacgagctg aagccttaaa gcagagacct gatgggcgat ctgtttctga gtcactaaga   2820
cgtgaccatg ataataaaca aaaatcagat gacaggggtg aatcagagcg acatcgaggg   2880
gatcagtcta gggttcgaag accagaaaca ttgagatcct ctagtagaaa tgaacatggc   2940
attaaatctg atagttcaaa aactgataaa ctagaacgaa aacacaggca tgaatcaggg   3000
gactcaaggg aaagaccatc ttctggggaa caaaaatcaa gacctgacag tcctcgtgtt   3060
aaacaaggag attctaataa atcaagatct gataaacttg gttttaaatc accaactagt   3120
aaagatgaca aaaggacaga gggtaacaag agtaaagtag acactaataa agcacaccct   3180
gacaataagg cagaatttcc aagttatttg ttgggggggca ggtctggtgc gttgaaaaat  3240
tttgtcattc cgaaaatcaa gagggataaa gatggcaatg ttactcagga gacaaagaaa   3300
```

-continued

```
atggaaatga aaggagagcc gaaagacaaa gtagaaaaaa taggattagt tgaagatcta   3360
aataaaggag ctaagcctgt agttgtgcta caaaaactgt ctttggatga tgttcagaaa   3420
cttattaaag atagagagga caaatcaaga agttccctta aacctatcaa gaataaacca   3480
tcaaagtcaa ataaaggtag tatagatcaa tcagtgttaa aagaattacc ccctgaactc   3540
ctggcagaaa ttgagtccac catgccactt tgtgaacgtg tgaaaatgaa caaacgcaag   3600
cgtagcacag ttaatgaaaa gccaaaatat gctgaaatca gttcagatga agataatgat   3660
agtgatgaag cttttgaatc ctctaggaaa cgacataaaa aagatgatga taaagcttgg   3720
gaatatgaag agcgtgacag aagaagctct ggggatcata ggagaagtgg ccactctcat   3780
gaaggaagaa ggagttcagg tggtggtcgt tatcgaaacc gaagtccgtc agattctgac   3840
atggaagatt attctcctcc tcccagcctt agtgaggttg ctaggaaaat gaagaaaaaa   3900
gaaaaacaga agaaaaggaa agcatatgaa ccaaaactaa cacctgaaga aatgatggac   3960
tcttcaactt ttaagagatt cacagcctca atagagaata ttttggataa tttggaagat   4020
atggatttta ctgcgtttgg tgatgatgat gaaattcctc aggaactgct cttaggaaaa   4080
catcagctta atgaacttgg cagtgaatct gctaaaataa aagcaatggg tataatggat   4140
aagctttcaa ctgacaaaac tgtgaaagtc ttaaatatct tggagaagaa tattcaggat   4200
gggtcaaagc tttccacttt gttaaatcat aataacgata ctgaagaaga agaaaggtta   4260
tggagagacc ttattatgga gagagttaca aaatcagcgg atgcttgtct tacaactatc   4320
aacattatga catcccctaa catgccaaaa gctgtgtaca ttgaggatgt aattgaaaga   4380
gttatacagt acactaaatt tcatttgcag aatacacttt atcctcagta tgatcctgtt   4440
tacagattag atcctcatgg aggaggctta ttaagttcaa aagcaaaacg ggctaaatgt   4500
tctacccata agcagagagt aatagtaatg ctttataaca aagtttgtga cattgttagc   4560
agcttatcag aattgctaga gatacaactt cttacagaca caacaattct tcaggtttca   4620
tctatgggaa taacaccatt ttttgtggaa aatgtcagtg aactacagtt gtgtgccatt   4680
aagttagtca ctgcagtatt ctcaagatat gaaaaacata ggcagttaat tttggaagaa   4740
atttttactt cacttgcaag attaccaacc agcaagagga gtttaaggaa cttcaggtta   4800
aacagtagtg atatggatgg agaacctatg tatattcaga tggttacagc actggtttta   4860
caacttattc agtgtgtggt acacttacca tcatcagaga aggactctaa tgcagaagaa   4920
gattcaaata aaaaaattga ccaggatgtt gtcattacta actcttatga aacagctatg   4980
cgaacagccc aaaacttcct ctccatcttc cttaaaaaat gtggtagtaa gcaaggtgaa   5040
gaagattaca gaccactgtt tgaaaatttt gttcaagacc ttctttcaac agtcaataag   5100
cctgaatggc cagctgctga actactcctt agtttgttag ggagactgtt ggttcatcag   5160
ttcagtaaca agtcaacaga gatggcttta agagtggcat ctcttgatta ccttggaact   5220
gttgctgcac ggctaagaaa agatgctgtt acaagcaaaa tggatcaagg atctatagaa   5280
cgcattttaa aacaggtttc aggaggggaa gatgaaatcc aacaattaca aaaagcattg   5340
cttgattact tggatgaaaa cactgagact gatccttcac tagtgttttc tcgtaaattc   5400
tatatagccc agtggtttcg agacacaact ctggaaacag aaaaagcaat gaaatcacaa   5460
aaagatgaag aatcatctga aggaacacat catgcaaagg aaattgagac aactggccaa   5520
attatgcatc gagctgaaaa ccgaaaaaag tttcttagaa gcattatcaa aaccacacct   5580
tctcagttta gcacattaaa gatgaactct gatactgtgg actatgatga tgcttgcttg   5640
```

-continued

```
attgttcgat acttggcctc catgaggccg tttgcccaga gctttgatat ttatttgaca   5700
cagatcctac gagttcttgg tgaaaatgca attgctgttc gaacaaaagc catgaagtgt   5760
ttgtctgagg ttgttgctgt agaccccagt attctagcaa ggcttgatat gcaacgaggt   5820
gttcatggac gattgatgga taattcgact agtgtccgag aagcagcagt agaattacta   5880
ggtcgatttg tcctttgtcg acctcagctt gctgaacagt attatgatat gctgattgaa   5940
agaatattgg atactggtat cagtgtcagg aaaagagtaa taaagattct cagagacatt   6000
tgtattgaac aaccaacatt tccaaaaatc acagaaatgt gtgtaaaaat gattcgcaga   6060
gtcaatgatg aagagggcat taagaaatta gtaaatgaaa cattccagaa actctggttt   6120
actccaactc cacacaatga caaagaagca atgacaagga aaattttaaa cattaccgat   6180
gtggttgcag catgcagaga tactggatat gactggtttg agcaactgct tcaaaacttg   6240
ttgaagtccg aagaggattc ctcatataaa cctgtgaaga aagcttgtac tcaacttgtt   6300
gataacctag ttgagcacat tcttaaatat gaggaatctc tagctgactc tgacaataaa   6360
ggtgtgaatt ctggaagatt ggtagcttgc ataaccactt tgttcttatt cagcaaaata   6420
agaccccagc tcatggttaa acatgcaatg actatgcaac catacettac cactaaatgt   6480
agtacgcaaa atgatttcat ggttatctgc aatgttgcaa aaatcctaga gctagttgta   6540
ccactgatgg agcatccaag tgaaactttt cttgccacta ttgaggaaga tctaatgaag   6600
ctcatcatca aatatggcat gactgtagtg caacattgtg tgagctgtct tggagctgtt   6660
gtaaataaag tgacacaaaa ttttaaattt gtgtgggctt gtttcaatag atactatggt   6720
gccatttcaa aattaaaaag tcaacaccaa gaggacccaa ataacacttc acttctaaca   6780
aacaaaccag cacttcttag atccctttc accgttggag cactatgtcg gcattttgat   6840
tttgatctgg aagattttaa aggcaacagc aaggttaaca taaaagataa agtacttgaa   6900
ctattgatgt attttacaaa acactcagat gaagaagtac aaacaaaagc tatcattggt   6960
ctaggatttg cctttattca gcatccaagt ctaatgttcg agcaagaagt gaagaatcta   7020
tataataata ttttatctga taagaactcc tcagtcaatt taaaaataca agtgttaaaa   7080
aacctccaga cctacctaca agaagaagat acacgtatgc agcaggcaga tagagactgg   7140
aagaaagttg caaaacagga agacttaaaa gaaatgggtg atgtttcctc agggatgagt   7200
agttccatca tgcagcttta tctcaaacag gtgcttgagg catttttca cacccagtca    7260
agtgtacgcc actttgccct aaatgtcatt gcattgactc taaatcaagg tcttattcat   7320
ccagttcagt gtgtgccata tttaattgct atgggcacag acccagaacc tgctatgcgg   7380
aacaaggctg atcagcaact tgtggaaata gacaaaaaat atgctggatt cattcatatg   7440
aaagcagtgg ctggtatgaa gatgtcttac caggtacaac aggcaatcaa cacatgccta   7500
aaagatcctg taaggggttt cagacaagac gagtcctcta gcgctttgtg ttcacacctt   7560
tactccatga tccgtggaaa ccgccaacac agacgagcct ttcttatttc tttactcaac   7620
ctctttgatg acacagcaaa aacagacgtg actatgctct tgtatatagc agacaatcta   7680
gcctgttttc cataccagac acaggaagag ccgttgttta taatgcatca tatagacatt   7740
acactctcag tttctggtag taacctactg cagtcattca aggagtctat ggtaaaggac   7800
aaaaggaaag agagaaaatc atcacctagt aaggaaaatg agtcaagcga cagtgaagaa   7860
gaagtttcca ggcctcggaa gtcacggaaa cgtgtagatt cagattcaga ttcagattca   7920
gaagacgata taaattcagt gatgaaatgt ttgccagaaa attcagctcc tttaatcgaa   7980
tttgcaaatg tgtcccaggg tattttatta cttctcatgt taaaacaaca tttgaagaat   8040
```

-continued

```
ctttgtggat tttctgatag taaaattcag aagtactctc catctgaatc tgcaaaagta   8100

tatgataaag cgataaaccg aaaaacagga gttcattttc atccaaaaca aacactggac   8160

ttcctgcgga gtgacatggc taattccaaa atcacagaag aggtgaaaag gagtatagta   8220

aaacagtatc tagatttcaa acttctcatg gaacatctgg accctgatga agaagaagaa   8280

gaaggggagg tttcagctag cacaaatgct cggaacaaag caattacctc actgcttgga   8340

ggaggcagcc ctaaaaataa tacagcagca gagacagaag atgatgaaag tgatggggag   8400

gatagaggag gaggcacttc aggggtgagg cggaggagga gtcaacgtat ttcgcagcgt   8460

attacgtaaa atgattttta tgtgcttata tatgtcagtc tattaaatgt acaccaagta   8520

atgtaatact taaaagagaa aacattttgt agatagagat tctctactta cccgtttata   8580

catccttttg tagaaagttt aacataaaag acaataaaaa aacagaaatg agatttatcc   8640

agcaaaaa                                                              8648
```

<210> SEQ ID NO 80
<211> LENGTH: 2697
<212> TYPE: PRT
<213> ORGANISM: Homo sapiens

<400> SEQUENCE: 80

```
Met Asn Gly Asp Met Pro His Val Pro Ile Thr Thr Leu Ala Gly Ile
1               5                   10                  15

Ala Ser Leu Thr Asp Leu Leu Asn Gln Leu Pro Leu Pro Ser Pro Leu
            20                  25                  30

Pro Ala Thr Thr Thr Lys Ser Leu Leu Phe Asn Ala Arg Ile Ala Glu
        35                  40                  45

Glu Val Asn Cys Leu Leu Ala Cys Arg Asp Asp Asn Leu Val Ser Gln
    50                  55                  60

Leu Val His Ser Leu Asn Gln Val Ser Thr Asp His Ile Glu Leu Lys
65                  70                  75                  80

Asp Asn Leu Gly Ser Asp Asp Pro Glu Gly Asp Ile Pro Val Leu Leu
                85                  90                  95

Gln Ala Val Leu Ala Arg Ser Pro Asn Val Phe Arg Glu Lys Ser Met
            100                 105                 110

Gln Asn Arg Tyr Val Gln Ser Gly Met Met Met Ser Gln Tyr Lys Leu
        115                 120                 125

Ser Gln Asn Ser Met His Ser Ser Pro Ala Ser Ser Asn Tyr Gln Gln
    130                 135                 140

Thr Thr Ile Ser His Ser Pro Ser Ser Arg Phe Val Pro Pro Gln Thr
145                 150                 155                 160

Ser Ser Gly Asn Arg Phe Met Pro Gln Gln Asn Ser Pro Val Pro Ser
                165                 170                 175

Pro Tyr Ala Pro Gln Ser Pro Ala Gly Tyr Met Pro Tyr Ser His Pro
            180                 185                 190

Ser Ser Tyr Thr Thr His Pro Gln Met Gln Gln Ala Ser Val Ser Ser
        195                 200                 205

Pro Ile Val Ala Gly Gly Leu Arg Asn Ile His Asp Asn Lys Val Ser
    210                 215                 220

Gly Pro Leu Ser Gly Asn Ser Ala Asn His His Ala Asp Asn Pro Arg
225                 230                 235                 240

His Gly Ser Ser Glu Asp Tyr Leu His Met Val His Arg Leu Ser Ser
                245                 250                 255
```

-continued

```
Asp Asp Gly Asp Ser Ser Thr Met Arg Asn Ala Ala Ser Phe Pro Leu
            260                 265                 270

Arg Ser Pro Gln Pro Val Cys Ser Pro Ala Gly Ser Glu Gly Thr Pro
        275                 280                 285

Lys Gly Ser Arg Pro Pro Leu Ile Leu Gln Ser Gln Ser Leu Pro Cys
    290                 295                 300

Ser Ser Pro Arg Asp Val Pro Pro Asp Ile Leu Leu Asp Ser Pro Glu
305                 310                 315                 320

Arg Lys Gln Lys Lys Gln Lys Lys Met Lys Leu Gly Lys Asp Glu Lys
                325                 330                 335

Glu Gln Ser Glu Lys Ala Ala Met Tyr Asp Ile Ile Ser Ser Pro Ser
            340                 345                 350

Lys Asp Ser Thr Lys Leu Thr Leu Arg Leu Ser Arg Val Arg Ser Ser
        355                 360                 365

Asp Met Asp Gln Gln Glu Asp Met Ile Ser Gly Val Glu Asn Ser Asn
    370                 375                 380

Val Ser Glu Asn Asp Ile Pro Phe Asn Val Gln Tyr Pro Gly Gln Thr
385                 390                 395                 400

Ser Lys Thr Pro Ile Thr Pro Gln Asp Ile Asn Arg Pro Leu Asn Ala
                405                 410                 415

Ala Gln Cys Leu Ser Gln Gln Glu Gln Thr Ala Phe Leu Pro Ala Asn
            420                 425                 430

Gln Val Pro Val Leu Gln Gln Asn Thr Ser Val Ala Ala Lys Gln Pro
        435                 440                 445

Gln Thr Ser Val Val Gln Asn Gln Gln Gln Ile Ser Gln Gln Gly Pro
    450                 455                 460

Ile Tyr Asp Glu Val Glu Leu Asp Ala Leu Ala Glu Ile Glu Arg Ile
465                 470                 475                 480

Glu Arg Glu Ser Ala Ile Glu Arg Glu Arg Phe Ser Lys Glu Val Gln
                485                 490                 495

Asp Lys Asp Lys Pro Leu Lys Lys Arg Lys Gln Asp Ser Tyr Pro Gln
            500                 505                 510

Glu Ala Gly Gly Ala Thr Gly Gly Asn Arg Pro Ala Ser Gln Glu Thr
        515                 520                 525

Gly Ser Thr Gly Asn Gly Ser Arg Pro Ala Leu Met Val Ser Ile Asp
    530                 535                 540

Leu His Gln Ala Gly Arg Val Asp Ser Gln Ala Ser Ile Thr Gln Asp
545                 550                 555                 560

Ser Asp Ser Ile Lys Lys Pro Glu Glu Ile Lys Gln Cys Asn Asp Ala
                565                 570                 575

Pro Val Ser Val Leu Gln Glu Asp Ile Val Gly Ser Leu Lys Ser Thr
            580                 585                 590

Pro Glu Asn His Pro Glu Thr Pro Lys Lys Lys Ser Asp Pro Glu Leu
        595                 600                 605

Ser Lys Ser Glu Met Lys Gln Ser Glu Ser Arg Leu Ala Glu Ser Lys
    610                 615                 620

Pro Asn Glu Asn Arg Leu Val Glu Thr Lys Ser Ser Glu Asn Lys Leu
625                 630                 635                 640

Glu Thr Lys Val Glu Thr Gln Thr Glu Glu Leu Lys Gln Asn Glu Ser
                645                 650                 655

Arg Thr Thr Glu Cys Lys Gln Asn Glu Ser Thr Ile Val Glu Pro Lys
            660                 665                 670

Gln Asn Glu Asn Arg Leu Ser Asp Thr Lys Pro Asn Asp Asn Lys Gln
```

-continued

```
        675                 680                 685

Asn Asn Gly Arg Ser Glu Thr Thr Lys Ser Arg Pro Glu Thr Pro Lys
    690                 695                 700

Gln Lys Gly Glu Ser Arg Pro Glu Thr Pro Lys Gln Lys Ser Asp Gly
705                 710                 715                 720

His Pro Glu Thr Pro Lys Gln Lys Gly Asp Gly Arg Pro Glu Thr Pro
                725                 730                 735

Lys Gln Lys Gly Glu Ser Arg Pro Glu Thr Pro Lys Gln Lys Asn Glu
            740                 745                 750

Gly Arg Pro Glu Thr Pro Lys His Arg His Asp Asn Arg Arg Asp Ser
        755                 760                 765

Gly Lys Pro Ser Thr Glu Lys Lys Pro Glu Val Ser Lys His Lys Gln
    770                 775                 780

Asp Thr Lys Ser Asp Ser Pro Arg Leu Lys Ser Glu Arg Ala Glu Ala
785                 790                 795                 800

Leu Lys Gln Arg Pro Asp Gly Arg Ser Val Ser Glu Ser Leu Arg Arg
                805                 810                 815

Asp His Asp Asn Lys Gln Lys Ser Asp Asp Arg Gly Glu Ser Glu Arg
            820                 825                 830

His Arg Gly Asp Gln Ser Arg Val Arg Arg Pro Glu Thr Leu Arg Ser
        835                 840                 845

Ser Ser Arg Asn Glu His Gly Ile Lys Ser Asp Ser Ser Lys Thr Asp
    850                 855                 860

Lys Leu Glu Arg Lys His Arg His Glu Ser Gly Asp Ser Arg Glu Arg
865                 870                 875                 880

Pro Ser Ser Gly Glu Gln Lys Ser Arg Pro Asp Ser Pro Arg Val Lys
                885                 890                 895

Gln Gly Asp Ser Asn Lys Ser Arg Ser Asp Lys Leu Gly Phe Lys Ser
            900                 905                 910

Pro Thr Ser Lys Asp Asp Lys Arg Thr Glu Gly Asn Lys Ser Lys Val
        915                 920                 925

Asp Thr Asn Lys Ala His Pro Asp Asn Lys Ala Glu Phe Pro Ser Tyr
    930                 935                 940

Leu Leu Gly Gly Arg Ser Gly Ala Leu Lys Asn Phe Val Ile Pro Lys
945                 950                 955                 960

Ile Lys Arg Asp Lys Asp Gly Asn Val Thr Gln Glu Thr Lys Lys Met
                965                 970                 975

Glu Met Lys Gly Glu Pro Lys Asp Lys Val Glu Lys Ile Gly Leu Val
            980                 985                 990

Glu Asp Leu Asn Lys Gly Ala Lys  Pro Val Val Val Leu  Gln Lys Leu
        995                 1000                1005

Ser Leu  Asp Asp Val Gln Lys  Leu Ile Lys Asp Arg  Glu Asp Lys
    1010                1015                1020

Ser Arg  Ser Ser Leu Lys Pro  Ile Lys Asn Lys Pro  Ser Lys Ser
    1025                1030                1035

Asn Lys  Gly Ser Ile Asp Gln  Ser Val Leu Lys Glu  Leu Pro Pro
    1040                1045                1050

Glu Leu  Leu Ala Glu Ile Glu  Ser Thr Met Pro Leu  Cys Glu Arg
    1055                1060                1065

Val Lys  Met Asn Lys Arg Lys  Arg Ser Thr Val Asn  Glu Lys Pro
    1070                1075                1080

Lys Tyr  Ala Glu Ile Ser Ser  Asp Glu Asp Asn Asp  Ser Asp Glu
    1085                1090                1095
```

```
Ala Phe Glu Ser Ser Arg Lys Arg His Lys Lys Asp Asp Asp Lys
    1100                1105                1110

Ala Trp Glu Tyr Glu Glu Arg Asp Arg Arg Ser Ser Gly Asp His
    1115                1120                1125

Arg Arg Ser Gly His Ser His Glu Gly Arg Arg Ser Ser Gly Gly
    1130                1135                1140

Gly Arg Tyr Arg Asn Arg Ser Pro Ser Asp Ser Asp Met Glu Asp
    1145                1150                1155

Tyr Ser Pro Pro Pro Ser Leu Ser Glu Val Ala Arg Lys Met Lys
    1160                1165                1170

Lys Lys Glu Lys Gln Lys Lys Arg Lys Ala Tyr Glu Pro Lys Leu
    1175                1180                1185

Thr Pro Glu Glu Met Met Asp Ser Ser Thr Phe Lys Arg Phe Thr
    1190                1195                1200

Ala Ser Ile Glu Asn Ile Leu Asp Asn Leu Glu Asp Met Asp Phe
    1205                1210                1215

Thr Ala Phe Gly Asp Asp Asp Glu Ile Pro Gln Glu Leu Leu Leu
    1220                1225                1230

Gly Lys His Gln Leu Asn Glu Leu Gly Ser Glu Ser Ala Lys Ile
    1235                1240                1245

Lys Ala Met Gly Ile Met Asp Lys Leu Ser Thr Asp Lys Thr Val
    1250                1255                1260

Lys Val Leu Asn Ile Leu Glu Lys Asn Ile Gln Asp Gly Ser Lys
    1265                1270                1275

Leu Ser Thr Leu Leu Asn His Asn Asn Asp Thr Glu Glu Glu Glu
    1280                1285                1290

Arg Leu Trp Arg Asp Leu Ile Met Glu Arg Val Thr Lys Ser Ala
    1295                1300                1305

Asp Ala Cys Leu Thr Thr Ile Asn Ile Met Thr Ser Pro Asn Met
    1310                1315                1320

Pro Lys Ala Val Tyr Ile Glu Asp Val Ile Glu Arg Val Ile Gln
    1325                1330                1335

Tyr Thr Lys Phe His Leu Gln Asn Thr Leu Tyr Pro Gln Tyr Asp
    1340                1345                1350

Pro Val Tyr Arg Leu Asp Pro His Gly Gly Gly Leu Leu Ser Ser
    1355                1360                1365

Lys Ala Lys Arg Ala Lys Cys Ser Thr His Lys Gln Arg Val Ile
    1370                1375                1380

Val Met Leu Tyr Asn Lys Val Cys Asp Ile Val Ser Ser Leu Ser
    1385                1390                1395

Glu Leu Leu Glu Ile Gln Leu Leu Thr Asp Thr Thr Ile Leu Gln
    1400                1405                1410

Val Ser Ser Met Gly Ile Thr Pro Phe Phe Val Glu Asn Val Ser
    1415                1420                1425

Glu Leu Gln Leu Cys Ala Ile Lys Leu Val Thr Ala Val Phe Ser
    1430                1435                1440

Arg Tyr Glu Lys His Arg Gln Leu Ile Leu Glu Glu Ile Phe Thr
    1445                1450                1455

Ser Leu Ala Arg Leu Pro Thr Ser Lys Arg Ser Leu Arg Asn Phe
    1460                1465                1470

Arg Leu Asn Ser Ser Asp Met Asp Gly Glu Pro Met Tyr Ile Gln
    1475                1480                1485
```

-continued

```
Met Val  Thr Ala Leu Val Leu  Gln Leu Ile Gln Cys  Val Val His
    1490                 1495                 1500

Leu Pro  Ser Ser Glu Lys Asp  Ser Asn Ala Glu Glu  Asp Ser Asn
    1505                 1510                 1515

Lys Lys  Ile Asp Gln Asp Val  Val Ile Thr Asn Ser  Tyr Glu Thr
    1520                 1525                 1530

Ala Met  Arg Thr Ala Gln Asn  Phe Leu Ser Ile Phe  Leu Lys Lys
    1535                 1540                 1545

Cys Gly  Ser Lys Gln Gly Glu  Glu Asp Tyr Arg Pro  Leu Phe Glu
    1550                 1555                 1560

Asn Phe  Val Gln Asp Leu Leu  Ser Thr Val Asn Lys  Pro Glu Trp
    1565                 1570                 1575

Pro Ala  Ala Glu Leu Leu Leu  Ser Leu Leu Gly Arg  Leu Leu Val
    1580                 1585                 1590

His Gln  Phe Ser Asn Lys Ser  Thr Glu Met Ala Leu  Arg Val Ala
    1595                 1600                 1605

Ser Leu  Asp Tyr Leu Gly Thr  Val Ala Ala Arg Leu  Arg Lys Asp
    1610                 1615                 1620

Ala Val  Thr Ser Lys Met Asp  Gln Gly Ser Ile Glu  Arg Ile Leu
    1625                 1630                 1635

Lys Gln  Val Ser Gly Gly Glu  Asp Glu Ile Gln Gln  Leu Gln Lys
    1640                 1645                 1650

Ala Leu  Leu Asp Tyr Leu Asp  Glu Asn Thr Glu Thr  Asp Pro Ser
    1655                 1660                 1665

Leu Val  Phe Ser Arg Lys Phe  Tyr Ile Ala Gln Trp  Phe Arg Asp
    1670                 1675                 1680

Thr Thr  Leu Glu Thr Glu Lys  Ala Met Lys Ser Gln  Lys Asp Glu
    1685                 1690                 1695

Glu Ser  Ser Glu Gly Thr His  His Ala Lys Glu Ile  Glu Thr Thr
    1700                 1705                 1710

Gly Gln  Ile Met His Arg Ala  Glu Asn Arg Lys Lys  Phe Leu Arg
    1715                 1720                 1725

Ser Ile  Ile Lys Thr Thr Pro  Ser Gln Phe Ser Thr  Leu Lys Met
    1730                 1735                 1740

Asn Ser  Asp Thr Val Asp Tyr  Asp Asp Ala Cys Leu  Ile Val Arg
    1745                 1750                 1755

Tyr Leu  Ala Ser Met Arg Pro  Phe Ala Gln Ser Phe  Asp Ile Tyr
    1760                 1765                 1770

Leu Thr  Gln Ile Leu Arg Val  Leu Gly Glu Asn Ala  Ile Ala Val
    1775                 1780                 1785

Arg Thr  Lys Ala Met Lys Cys  Leu Ser Glu Val Val  Ala Val Asp
    1790                 1795                 1800

Pro Ser  Ile Leu Ala Arg Leu  Asp Met Gln Arg Gly  Val His Gly
    1805                 1810                 1815

Arg Leu  Met Asp Asn Ser Thr  Ser Val Arg Glu Ala  Ala Val Glu
    1820                 1825                 1830

Leu Leu  Gly Arg Phe Val Leu  Cys Arg Pro Gln Leu  Ala Glu Gln
    1835                 1840                 1845

Tyr Tyr  Asp Met Leu Ile Glu  Arg Ile Leu Asp Thr  Gly Ile Ser
    1850                 1855                 1860

Val Arg  Lys Arg Val Ile Lys  Ile Leu Arg Asp Ile  Cys Ile Glu
    1865                 1870                 1875

Gln Pro  Thr Phe Pro Lys Ile  Thr Glu Met Cys Val  Lys Met Ile
```

-continued

```
    1880                1885                1890

Arg Arg  Val Asn Asp Glu Glu  Gly Ile Lys Lys Leu  Val Asn Glu
    1895                1900                1905

Thr Phe  Gln Lys Leu Trp Phe  Thr Pro Thr Pro His  Asn Asp Lys
    1910                1915                1920

Glu Ala  Met Thr Arg Lys Ile  Leu Asn Ile Thr Asp  Val Val Ala
    1925                1930                1935

Ala Cys  Arg Asp Thr Gly Tyr  Asp Trp Phe Glu Gln  Leu Leu Gln
    1940                1945                1950

Asn Leu  Leu Lys Ser Glu Glu  Asp Ser Ser Tyr Lys  Pro Val Lys
    1955                1960                1965

Lys Ala  Cys Thr Gln Leu Val  Asp Asn Leu Val Glu  His Ile Leu
    1970                1975                1980

Lys Tyr  Glu Glu Ser Leu Ala  Asp Ser Asp Asn Lys  Gly Val Asn
    1985                1990                1995

Ser Gly  Arg Leu Val Ala Cys  Ile Thr Thr Leu Phe  Leu Phe Ser
    2000                2005                2010

Lys Ile  Arg Pro Gln Leu Met  Val Lys His Ala Met  Thr Met Gln
    2015                2020                2025

Pro Tyr  Leu Thr Thr Lys Cys  Ser Thr Gln Asn Asp  Phe Met Val
    2030                2035                2040

Ile Cys  Asn Val Ala Lys Ile  Leu Glu Leu Val Val  Pro Leu Met
    2045                2050                2055

Glu His  Pro Ser Glu Thr Phe  Leu Ala Thr Ile Glu  Glu Asp Leu
    2060                2065                2070

Met Lys  Leu Ile Ile Lys Tyr  Gly Met Thr Val Val  Gln His Cys
    2075                2080                2085

Val Ser  Cys Leu Gly Ala Val  Val Asn Lys Val Thr  Gln Asn Phe
    2090                2095                2100

Lys Phe  Val Trp Ala Cys Phe  Asn Arg Tyr Tyr Gly  Ala Ile Ser
    2105                2110                2115

Lys Leu  Lys Ser Gln His Gln  Glu Asp Pro Asn Asn  Thr Ser Leu
    2120                2125                2130

Leu Thr  Asn Lys Pro Ala Leu  Leu Arg Ser Leu Phe  Thr Val Gly
    2135                2140                2145

Ala Leu  Cys Arg His Phe Asp  Phe Asp Leu Glu Asp  Phe Lys Gly
    2150                2155                2160

Asn Ser  Lys Val Asn Ile Lys  Asp Lys Val Leu Glu  Leu Leu Met
    2165                2170                2175

Tyr Phe  Thr Lys His Ser Asp  Glu Glu Val Gln Thr  Lys Ala Ile
    2180                2185                2190

Ile Gly  Leu Gly Phe Ala Phe  Ile Gln His Pro Ser  Leu Met Phe
    2195                2200                2205

Glu Gln  Glu Val Lys Asn Leu  Tyr Asn Asn Ile Leu  Ser Asp Lys
    2210                2215                2220

Asn Ser  Ser Val Asn Leu Lys  Ile Gln Val Leu Lys  Asn Leu Gln
    2225                2230                2235

Thr Tyr  Leu Gln Glu Glu Asp  Thr Arg Met Gln Gln  Ala Asp Arg
    2240                2245                2250

Asp Trp  Lys Lys Val Ala Lys  Gln Glu Asp Leu Lys  Glu Met Gly
    2255                2260                2265

Asp Val  Ser Ser Gly Met Ser  Ser Ser Ile Met Gln  Leu Tyr Leu
    2270                2275                2280
```

-continued

```
Lys Gln  Val Leu Glu Ala Phe  Phe His Thr Gln Ser  Ser Val Arg
    2285                 2290                 2295

His Phe  Ala Leu Asn Val Ile  Ala Leu Thr Leu Asn  Gln Gly Leu
    2300                 2305                 2310

Ile His  Pro Val Gln Cys Val  Pro Tyr Leu Ile Ala  Met Gly Thr
    2315                 2320                 2325

Asp Pro  Glu Pro Ala Met Arg  Asn Lys Ala Asp Gln  Gln Leu Val
    2330                 2335                 2340

Glu Ile  Asp Lys Lys Tyr Ala  Gly Phe Ile His Met  Lys Ala Val
    2345                 2350                 2355

Ala Gly  Met Lys Met Ser Tyr  Gln Val Gln Gln Ala  Ile Asn Thr
    2360                 2365                 2370

Cys Leu  Lys Asp Pro Val Arg  Gly Phe Arg Gln Asp  Glu Ser Ser
    2375                 2380                 2385

Ser Ala  Leu Cys Ser His Leu  Tyr Ser Met Ile Arg  Gly Asn Arg
    2390                 2395                 2400

Gln His  Arg Arg Ala Phe Leu  Ile Ser Leu Leu Asn  Leu Phe Asp
    2405                 2410                 2415

Asp Thr  Ala Lys Thr Asp Val  Thr Met Leu Leu Tyr  Ile Ala Asp
    2420                 2425                 2430

Asn Leu  Ala Cys Phe Pro Tyr  Gln Thr Gln Glu Glu  Pro Leu Phe
    2435                 2440                 2445

Ile Met  His His Ile Asp Ile  Thr Leu Ser Val Ser  Gly Ser Asn
    2450                 2455                 2460

Leu Leu  Gln Ser Phe Lys Glu  Ser Met Val Lys Asp  Lys Arg Lys
    2465                 2470                 2475

Glu Arg  Lys Ser Ser Pro Ser  Lys Glu Asn Glu Ser  Ser Asp Ser
    2480                 2485                 2490

Glu Glu  Glu Val Ser Arg Pro  Arg Lys Ser Arg Lys  Arg Val Asp
    2495                 2500                 2505

Ser Asp  Ser Asp Ser Asp Ser  Glu Asp Asp Ile Asn  Ser Val Met
    2510                 2515                 2520

Lys Cys  Leu Pro Glu Asn Ser  Ala Pro Leu Ile Glu  Phe Ala Asn
    2525                 2530                 2535

Val Ser  Gln Gly Ile Leu Leu  Leu Leu Met Leu Lys  Gln His Leu
    2540                 2545                 2550

Lys Asn  Leu Cys Gly Phe Ser  Asp Ser Lys Ile Gln  Lys Tyr Ser
    2555                 2560                 2565

Pro Ser  Glu Ser Ala Lys Val  Tyr Asp Lys Ala Ile  Asn Arg Lys
    2570                 2575                 2580

Thr Gly  Val His Phe His Pro  Lys Gln Thr Leu Asp  Phe Leu Arg
    2585                 2590                 2595

Ser Asp  Met Ala Asn Ser Lys  Ile Thr Glu Glu Val  Lys Arg Ser
    2600                 2605                 2610

Ile Val  Lys Gln Tyr Leu Asp  Phe Lys Leu Leu Met  Glu His Leu
    2615                 2620                 2625

Asp Pro  Asp Glu Glu Glu Glu  Glu Gly Glu Val Ser  Ala Ser Thr
    2630                 2635                 2640

Asn Ala  Arg Asn Lys Ala Ile  Thr Ser Leu Leu Gly  Gly Gly Ser
    2645                 2650                 2655

Pro Lys  Asn Asn Thr Ala Ala  Glu Thr Glu Asp Asp  Glu Ser Asp
    2660                 2665                 2670
```

-continued

```
Gly Glu  Asp Arg Gly Gly Gly  Thr Ser Gly Val Arg  Arg Arg Arg
    2675                 2680                 2685

Ser Gln  Arg Ile Ser Gln Arg  Ile Thr
    2690                 2695


<210> SEQ ID NO 81
<211> LENGTH: 504
<212> TYPE: PRT
<213> ORGANISM: Rattus rattus

<400> SEQUENCE: 81

Met Gln Asp His Gln His Val Pro Ile Asp Ile Gln Thr Ser Lys Leu
1               5                   10                  15

Leu Asp Trp Leu Val Asp Arg Arg His Cys Asn Leu Lys Trp Gln Ser
            20                  25                  30

Leu Val Leu Thr Ile Arg Glu Lys Ile Asn Thr Ala Ile Gln Asp Met
        35                  40                  45

Pro Glu Ser Gln Glu Ile Ala Gln Leu Leu Ser Gly Ser Tyr Ile His
    50                  55                  60

Tyr Phe His Cys Leu Arg Ile Val Asp Leu Leu Lys Gly Thr Glu Ala
65                  70                  75                  80

Ser Thr Lys Asn Ile Phe Gly Arg Tyr Ser Ser Gln Arg Met Lys Asp
                85                  90                  95

Trp Gln Glu Ile Ile Ser Leu Tyr Glu Lys Asp Asn Thr Tyr Leu Val
            100                 105                 110

Glu Leu Ser Ser Leu Leu Val Arg Asn Val Asn Tyr Glu Ile Pro Ser
        115                 120                 125

Leu Lys Lys Gln Ile Ala Lys Cys Gln Gln Leu Gln Gln Asp Tyr Ser
    130                 135                 140

Arg Lys Glu Glu Glu Gly Gln Ala Gly Ala Ala Glu Met Arg Glu Gln
145                 150                 155                 160

Phe Tyr His Ser Cys Lys Gln Tyr Gly Ile Thr Gly Asp Asn Val Arg
                165                 170                 175

Arg Glu Leu Leu Ala Leu Val Lys Asp Leu Pro Ser Gln Leu Ala Glu
            180                 185                 190

Ile Gly Ala Gly Ala Gln Ser Leu Gly Glu Ala Ile Asp Leu Tyr Gln
        195                 200                 205

Ala Cys Val Glu Phe Val Cys Asp Ser Pro Thr Glu Gln Val Leu Pro
    210                 215                 220

Met Leu Arg Tyr Val Gln Lys Lys Gly Asn Ser Thr Val Tyr Glu Trp
225                 230                 235                 240

Arg Thr Gly Thr Glu Pro Ser Val Val Glu Arg Pro Gln Leu Glu Asp
                245                 250                 255

Pro Pro Glu Gln Val Gln Glu Asp Glu Ile Asp Trp Gly Asp Phe Gly
            260                 265                 270

Leu Glu Ala Val Ser Asp Ser Gly Asn Ile Ile Ser Ala Glu Thr Pro
        275                 280                 285

Gly Ile Asp Trp Gly Ile Ser Leu Glu Ser Glu Ser Lys Asp Ala Gly
    290                 295                 300

Ala Asp Lys Ile Asp Trp Gly Asp Asn Ala Val Ala Ser Glu Ile Thr
305                 310                 315                 320

Val Leu Glu Thr Gly Thr Glu Ala Pro Glu Gly Val Ala Arg Gly Ser
                325                 330                 335

Asp Ala Leu Thr Leu Leu Glu Tyr Pro Glu Thr Arg Asn Gln Phe Ile
            340                 345                 350
```

```
Asp Glu Leu Met Glu Leu Glu Ile Phe Leu Ser Gln Arg Ala Val Glu
        355                 360                 365

Met Ser Glu Glu Ala Asp Ile Leu Ser Val Ser Gln Phe Gln Leu Ala
    370                 375                 380

Pro Ala Ile Leu Gln Gly Gln Thr Lys Glu Lys Met Leu Ser Leu Val
385                 390                 395                 400

Ser Thr Leu Gln His Leu Ile Gly Gln Leu Thr Ser Leu Arg Met Gln
                405                 410                 415

His Leu Phe Met Ile Leu Ala Ser Pro Arg Tyr Val Asp Arg Val Thr
            420                 425                 430

Glu Leu Leu Gln Gln Lys Leu Lys Gln Ser Gln Leu Leu Ala Leu Lys
        435                 440                 445

Lys Asp Leu Met Val Glu Lys Gln Gln Glu Ala Leu Gln Glu Gln Ala
    450                 455                 460

Ala Leu Glu Pro Lys Leu Asp Leu Leu Leu Glu Lys Thr Arg Glu Leu
465                 470                 475                 480

Gln Lys Leu Ile Glu Ala Asp Ile Ser Lys Arg Tyr Asn Gly Arg Pro
                485                 490                 495

Val Asn Leu Met Gly Thr Ser Val
            500


<210> SEQ ID NO 82
<211> LENGTH: 507
<212> TYPE: PRT
<213> ORGANISM: Danio rerio

<400> SEQUENCE: 82

Met Glu Asn Ile Gln Asn Leu Pro Ile Asp Ile Gln Thr Ser Lys Leu
1               5                   10                  15

Leu Asp Trp Leu Val Asp Arg Arg His Cys Thr Leu Lys Trp Gln Ser
            20                  25                  30

Ala Val Met Thr Ile Arg Glu Lys Ile Asn Ala Ala Ile Gln Asp Met
        35                  40                  45

Pro Glu Asn Glu Glu Ile Lys Gln Leu Leu Ser Gly Ser Tyr Ile His
    50                  55                  60

His Phe His Cys Leu Gln Ile Ile Glu Val Leu Lys Gly Thr Glu Ala
65                  70                  75                  80

Ser Thr Lys Asn Ile Phe Gly Arg Tyr Ser Ser Gln Arg Met Lys Asp
                85                  90                  95

Trp Gln Glu Ile Val Ser Met Tyr Glu Lys Asp Asn Val Tyr Leu Ala
            100                 105                 110

Glu Met Ala Ser Ile Leu Val Arg Asn Val Ser Tyr Glu Gly Pro Ala
        115                 120                 125

Leu Arg Lys Gln Val Ser Lys Ala Gln Gln Leu Gln Gln Glu Leu Ser
    130                 135                 140

Arg Arg Glu Leu Glu Cys Gln Ser Gly Ser Ala Asp Met Arg Glu Arg
145                 150                 155                 160

Tyr Tyr Ala Ala Cys Lys Gln Tyr Gly Ile Lys Gly Glu Asn Val Ala
                165                 170                 175

Arg Glu Leu Gln Ala Gln Val Lys Asp Leu Pro Val Val Leu Glu Glu
            180                 185                 190

Thr Gly Lys Lys Ala Ala Cys Leu Lys Asp Ala Ile Glu Phe Tyr Thr
        195                 200                 205

Ala Phe Thr Lys Phe Val Ser Asp Trp Ser Glu Glu Val Leu Pro Leu
```

-continued

```
    210                 215                 220

Leu Arg Phe Val Gln Lys Lys Gly Asn Thr Thr Val Tyr Glu Arg Lys
225                 230                 235                 240

Thr Gly Asn Val Pro Lys Val Val Glu Arg Pro Val Met Glu Glu Ala
                245                 250                 255

Pro Pro Asp Val Val Thr Glu Glu Thr Ile Asp Trp Gly Asp Leu Gly
            260                 265                 270

Ser Gly Ala Gly Thr Gly Ser Glu Glu Val Asn Phe Gly Ile Ser Val
        275                 280                 285

Glu Asp Gly Val Asp Trp Gly Ile Gly Leu Glu Ser Gly Thr Glu Glu
    290                 295                 300

Thr Ser Gly Gly Gly Ile Asn Trp Gly Asp Ser Glu Ser Ala Pro Leu
305                 310                 315                 320

Glu Ile Glu Val Val Asp Val Gly Thr Asp Cys Pro Asp Gly Val Ala
                325                 330                 335

Arg Gly Glu Asp Ala Leu Ser Leu Leu Glu Asn Ser Gln Thr Arg Ser
            340                 345                 350

Gln Phe Ile Asn Glu Leu Lys Glu Leu Glu Met Phe Leu Cys Gln Arg
        355                 360                 365

Leu Ser Glu Met Arg Glu Glu Gly Asp Leu Val Ala Met Ser Gln Phe
    370                 375                 380

Gln Leu Ala Pro Ser Val Ile Gln Ala Gln Thr Pro Gln Arg Val Gln
385                 390                 395                 400

Val Met Leu Ala Asp Val Arg Glu Leu Leu Asn Gly Leu Thr Ser Val
                405                 410                 415

Arg Met Gln His Leu Phe Met Ile Gln Ala Ser Pro Arg Tyr Val Glu
            420                 425                 430

Arg Val Ser Glu Leu Leu Arg Gln Lys Leu Lys Gln Ala Asp Ile Met
        435                 440                 445

Val Leu Lys Arg Gly Thr Leu Ala Glu Lys Arg Gln Glu Ala Leu Glu
    450                 455                 460

Glu Gln Ala Lys Leu Glu Pro Arg Ile Asp Leu Leu Ala Ala Arg Thr
465                 470                 475                 480

Lys Glu Leu Gln Lys Leu Ile Glu Ala Asp Ile Ser Lys Arg Tyr Asn
                485                 490                 495

Asn Arg Pro Val Asn Leu Met Gly Val His Val
            500                 505


<210> SEQ ID NO 83
<211> LENGTH: 505
<212> TYPE: PRT
<213> ORGANISM: Tetraodon nigroviridis

<400> SEQUENCE: 83

Met Glu Asn Ile Gln Asn Leu Pro Ile Asp Ile Gln Thr Ser Lys Leu
1               5                   10                  15

Leu Asp Trp Leu Leu Asp Arg Arg His Cys Asn Met Arg Trp Gln Asn
            20                  25                  30

Ala Phe Lys Glu Ile Arg Glu Lys Ile Asn Ala Ala Ile Gln Asp Met
        35                  40                  45

Pro Glu Asn Glu Glu Ile Lys Gln Leu Leu Ser Gly Ser His Ile His
    50                  55                  60

Tyr Phe His Cys Leu Arg Ile Val Glu Ile Leu Lys Arg Thr Glu Ala
65                  70                  75                  80
```

-continued

```
Ser Ser Lys Asn Ile Phe Gly Arg Tyr Ser Ser Gln Arg Met Lys Asp
                85                  90                  95

Trp Gln Asp Ile Val Ser Leu Tyr Glu Ala Asp Asn Val Tyr Leu Ala
            100                 105                 110

Glu Leu Ala Gly Leu Leu Ile Arg Asn Val Thr Tyr Glu Gly Pro Ala
        115                 120                 125

Leu Arg Arg Gln Leu Ala Lys Ala Gln Gln Leu Gln Gln Glu Leu Ser
    130                 135                 140

Arg Arg Glu Val Glu Cys Gln Ser Ser Ala Ala Asp Met Arg Glu Arg
145                 150                 155                 160

Tyr Tyr Ala Ala Cys Arg Gln Tyr Gly Ile Arg Gly Asp Ser Val Thr
                165                 170                 175

Arg Glu Leu Gln Ala Leu Val Lys Asp Leu Pro Val Val Leu Glu Gly
            180                 185                 190

Val Gly Lys Asp Ser Ala Lys Leu Glu Lys Gln Ile Gln Leu Tyr Ser
        195                 200                 205

Ala Phe Thr Asp Phe Val Cys Gly Trp Ser Glu Ala Val Leu Pro Met
    210                 215                 220

Leu Thr Phe Val Gln Lys Arg Gly Asn Thr Thr Phe Tyr Glu Trp Arg
225                 230                 235                 240

Thr Gly Lys Thr Pro Thr Val Val Glu Arg Pro Val Val Glu Ala Ala
                245                 250                 255

Pro Ala Gly Gly Ile Thr Glu Asp Thr Ile Asp Trp Gly Asp Phe Gly
            260                 265                 270

Lys Ser Ala Gly Thr Ser Asp Ile Pro Ala Ala Ile Thr Val Glu Asp
        275                 280                 285

Gly Ile Asp Trp Gly Ile Ser Leu Glu Pro Val Ala Glu Asp Thr Ser
    290                 295                 300

Val Ser Gly Ile Asp Trp Gly Asp Ala Glu Ala Pro Pro Val Glu Ile
305                 310                 315                 320

Glu Val Val Asp Ala Gly Thr Asp Cys Pro Glu Gly Val Ala Arg Gly
                325                 330                 335

Glu Asp Ala Leu Thr Val Leu Glu Lys Pro Thr Ser Arg Ser Gln Phe
            340                 345                 350

Ile Asp Glu Leu Met Glu Leu Glu Ala Phe Leu Arg Gln Arg Leu Ser
        355                 360                 365

Glu Met Gly Glu Glu Gly Asp Val Ile Ala Met Ser Gln Phe Gln Leu
    370                 375                 380

Ala Pro Pro Ile Ile Gln Asp Gln Ser Cys Glu Lys Val Arg Gln Met
385                 390                 395                 400

Leu Ser Glu Val Arg Asp Ile Leu Gly Arg Leu Thr Ser Leu Gln Met
                405                 410                 415

Gln Gln Leu Phe Met Ile Gln Ala Ser Pro Arg Tyr Val Glu Arg Val
            420                 425                 430

Ser Asp Val Leu Arg Gln Lys Met Lys Gln Ala Asp Ile Leu Val Val
        435                 440                 445

Lys Gly Ala Arg Met Ile Glu Lys Arg Gln Glu Ala Leu Glu Glu Gln
    450                 455                 460

Ala Arg Leu Glu Pro Arg Ile Asp Leu Leu Ala Gly His Thr Arg Glu
465                 470                 475                 480

Leu Gln Lys Leu Ile Glu Ala Asp Ile Ser Lys Arg Tyr Ser Lys Arg
                485                 490                 495

Pro Val Asn Leu Met Gly Val Asn Val
```

500 505

<210> SEQ ID NO 84
<211> LENGTH: 508
<212> TYPE: PRT
<213> ORGANISM: Xenopus laevis

<400> SEQUENCE: 84

Met Gln Asp Val Gln Asn Leu Pro Ile Asp Ile Gln Thr Gly Arg Leu
1 5 10 15

Leu Asp Trp Leu Val Asp Arg Arg His Cys Thr Leu Lys Trp Gln Ser
20 25 30

Lys Val Leu Gln Ile Arg Glu Lys Ile Asn Gln Ala Leu Gln Asp Met
35 40 45

Pro Glu His Asp Glu Ile Arg Ser Leu Leu Ser Gly Thr Tyr Ile Asn
50 55 60

Tyr Phe His Cys Leu Lys Ile Val Glu Ile Leu Lys Gly Thr Glu Ala
65 70 75 80

Ala Thr Arg Asn Leu Phe Gly Arg Tyr Ser Ser Gln Arg Met Lys Asp
85 90 95

Trp Gln Glu Val Val Ser Leu Tyr Gln Ala Asp Asn Thr Tyr Leu Gly
100 105 110

Glu Ser Ala Ser Leu Phe Met Arg Ser Val Ser Tyr Glu Ile Pro Ala
115 120 125

Leu Lys Lys Gln Met Thr Arg Cys Glu Gln Leu Ser Leu Glu Ser Glu
130 135 140

Arg Arg Ala Glu Glu Cys Leu His Gly Ala Ala Gln Gln Arg Glu Gln
145 150 155 160

Tyr Tyr Asn Ser Cys Lys Asn Tyr Gly Ile Ser Gly Glu Asp Ile Arg
165 170 175

Lys Glu Leu Val Ala Leu Val Cys Asp Val Pro Ser Val Leu Arg Gln
180 185 190

Ile Gly Ala Asp Ala Ala Gly Leu Leu Ser Ala Ile Gln Leu Tyr Gln
195 200 205

Ala Cys Val Thr Phe Val Cys Asp Ser Ser Pro Glu Glu Ala Leu Pro
210 215 220

Ile Leu Arg His Val Gln Lys Cys Gly Asp Thr Thr Ile Tyr Glu Trp
225 230 235 240

Arg Val Gly Glu Ala Pro Arg Arg Val Glu Arg Pro Asp Lys Glu Lys
245 250 255

Gln Glu Thr Pro Gln Cys Pro Glu Glu Gly Glu Ile Asn Trp Gly Asp
260 265 270

Phe Glu Val Gln Pro Ser Thr Ala Ala Glu Thr Glu Ala Gly Leu Asp
275 280 285

Ser Leu Ala Thr Gly Glu Ile Asp Trp Gly Ile Ser Val Glu Pro Glu
290 295 300

Ala Ala Glu Val Asp Gly Ile Asn Trp Asp Ala Gly Glu Glu Pro Thr
305 310 315 320

Ala Val Ile Thr Val Leu Glu Thr Gly Ser Asn Val Leu Pro Gly Val
325 330 335

Ala Arg Gly Ser Asp Ala Leu Ser Val Leu Glu Asn Thr Asp Thr Arg
340 345 350

Asn Gln Phe Val Asp Glu Leu Met Glu Leu Glu Leu Phe Leu Cys Gln
355 360 365

-continued

```
Trp Gln Gln Ser Met Glu Cys Asp Thr Asp Ile Val Thr Val Thr Gln
    370                 375                 380

Phe Gln Thr Ala Pro Ser Ile Leu Gln Gly Gln Thr Gln Gly Lys Val
385                 390                 395                 400

Leu Ala Met Ile Ser Val Val Arg Gly Leu Ile Ser Arg Leu Thr Asp
                405                 410                 415

Thr Arg Met Arg Gln Leu Phe Leu Ile Leu Ala Ser Pro Arg Tyr Val
            420                 425                 430

Asp Arg Val Thr Asp His Leu Gly Gln Arg Leu Arg Gln Ala Gln Leu
        435                 440                 445

Leu Glu Lys Lys Ser Val Ser Trp Val Glu Arg Gly Arg Ala Ala Gln
    450                 455                 460

Glu Glu Arg Gln Ser Leu Glu Pro Arg Leu Ser Leu Leu Gln Glu Arg
465                 470                 475                 480

Ser Arg Glu Leu Lys Lys Gln Ile Glu Ala Asp Leu Ser Lys Arg Tyr
                485                 490                 495

Asn Asn Arg Pro Val Asn Leu Ile Gly Thr Gly Leu
            500                 505


<210> SEQ ID NO 85
<211> LENGTH: 535
<212> TYPE: PRT
<213> ORGANISM: Anopheles gambiae

<400> SEQUENCE: 85

Thr Leu Phe Cys Phe Cys Ile His Ile Pro Phe Thr Asp Gln Gln Arg
1               5                   10                  15

Thr Ser Val Trp Pro Val Thr Asn Asn Met Asn Glu Ala Glu Ile Pro
            20                  25                  30

Ile Asp Ile Ala Ala Gly Lys Leu Leu Asp Trp Leu Ile Ser Arg Arg
        35                  40                  45

Ile Val Asp Lys Asn Trp His Leu His Ile Arg Asn Ile Arg Asn Lys
    50                  55                  60

Ile Ser Asn Ala Ile Thr Asp Met Pro Glu His Asp Glu Leu Leu Gln
65                  70                  75                  80

Leu Leu Ser Gly Ala His Ile Asn Tyr Phe His Cys Leu Arg Ile Val
                85                  90                  95

Asp Ile Leu Lys Thr Thr Glu Ala Asp Ser Lys Asn Val Phe Gly Arg
            100                 105                 110

Tyr Gly Ser Gln Arg Met Lys Asp Trp Gln Glu Ile Val Lys Met Tyr
        115                 120                 125

Glu Lys Asp Asn Leu Tyr Leu Ala Glu Ala Ala Gln Ile Leu Val Arg
    130                 135                 140

Asn Ile Asn Tyr Glu Ile Pro Gly Ile Arg Lys Gln Ile Lys His Leu
145                 150                 155                 160

Glu Gln Leu Ser Glu Glu Ala Asp Lys Lys Val Glu Asp Leu Glu Arg
                165                 170                 175

Ser Glu Lys Val Val Met Ala Glu Tyr Gln Asn Met Cys Lys Gln Leu
            180                 185                 190

Gly Val Thr Gly Thr Asn Leu Arg Gln Glu Leu Val Asp Lys Val Phe
        195                 200                 205

Asn Asp Leu Pro Gly Met Leu Thr Lys Val Ala Ser Ser Val Ala Pro
    210                 215                 220

Leu Lys Lys Thr Val Glu Leu Tyr Ala Ser Phe Met Asn Asp Ala Glu
225                 230                 235                 240
```

```
Cys Leu Thr Leu Leu Lys His Val Leu Ala Lys Gly Asn Thr Thr Val
                245                 250                 255

Tyr Glu Phe Val Tyr Gly Glu Pro Pro Leu Ser Ile Glu Glu Pro Pro
            260                 265                 270

Val Lys Phe Val Thr Glu Gln Gln Gln Glu Ala Ala Asp Asp Gly Gly
        275                 280                 285

Ala Ile Asp Phe Gly Asp Asp Asp Gly Gly Ala Ile Asp Phe Gly Asp
    290                 295                 300

Gly Ser Gly Leu Asp Leu Asp Ala Pro Val Glu Leu Glu Ile Gly Asp
305                 310                 315                 320

Ile Asp Trp Gly Ala Ala Asp Glu Gly Ala Asp Pro Ala Leu Ala Gly
                325                 330                 335

Ala Asn Asp Gly Asn Val Ile Asp Phe Asn Ile Ser Leu Glu Glu Ser
            340                 345                 350

Gly Ile Val Val Glu Glu Asp Gly Asn Leu Gly Gly Val Ala Lys Gly
        355                 360                 365

Asp Glu Ala Phe Thr Val Leu Asp Ala Gln Gln Tyr Arg Asp Arg Phe
    370                 375                 380

Val Asn Asp Leu Leu Glu Leu Gln Ser Phe Leu Lys Met Arg Leu His
385                 390                 395                 400

Gln Leu Gly Ser Ala Asp Lys Ala Gln Val Leu Ala Phe Ala Ile Met
                405                 410                 415

Asp Asn Phe Lys Asp His Asp Glu Lys Thr Val Ala Ser Met Leu Ala
            420                 425                 430

Glu Val Glu Val Val Tyr Ala Gly Val Thr Asp Glu Leu Leu Gln His
        435                 440                 445

Leu Leu Gln Ile Lys His Ser Pro Val Tyr Val Asp Ile Leu Thr Ser
    450                 455                 460

Asn Val Lys Gln Lys Leu Thr Ser Ile Asp Lys Met Lys Glu Thr Ala
465                 470                 475                 480

Leu Met Lys Arg Glu Lys Ser Val Ser Phe Lys Gln Gln Ser Val Glu
                485                 490                 495

Leu Lys Pro Thr Gln Thr Lys Ile Val Glu Gln Thr Lys Thr Leu Gln
            500                 505                 510

Gly Gln Ile Glu Lys Asp Ile Ser Lys Arg Tyr Lys Asn Arg Pro Val
        515                 520                 525

Asn Leu Tyr Gly Thr Asn Leu
    530                 535
```

<210> SEQ ID NO 86
<211> LENGTH: 486
<212> TYPE: PRT
<213> ORGANISM: Caenorhabditis briggsae

<400> SEQUENCE: 86

```
Met Ser Asp Asp Leu Pro Ile Asp Ile His Ser Ser Lys Leu Leu Asp
1               5                   10                  15

Trp Leu Val Ser Arg Arg His Cys Asn Lys Asp Trp Gln Lys Ser Val
            20                  25                  30

Leu Ala Ile Arg Glu Lys Ile Lys His Ala Ile Leu Asp Met Pro Glu
        35                  40                  45

Ser Gln Lys Ile Val Glu Leu Leu Gln Gly Ala Tyr Ile Asn Tyr Phe
    50                  55                  60

His Cys Cys Gln Ile Ile Glu Val Leu Arg Asp Thr Glu Lys Asp Thr
```

-continued

```
65                  70                  75                  80

Lys Asn Phe Leu Gly Phe Tyr Ser Ser Gln Arg Met Lys Asp Trp Gln
                85                  90                  95

Glu Ile Glu Gly Met Tyr Lys Lys Asp Asn Val Tyr Leu Ala Glu Ala
            100                 105                 110

Ala Gln Thr Leu Gln Arg Leu Ala Gln Tyr Glu Ile Pro Gly Leu Lys
        115                 120                 125

Lys Gln Ile Thr Lys Asn Asp Gln Val Val Ser Asp Ala Ile Lys Lys
    130                 135                 140

Phe Ala Asp Tyr Gly Lys Gln Ser Glu Asp Ala Lys Lys Gln Phe Glu
145                 150                 155                 160

Lys Asn Val Gln Lys Met Gly Leu Lys Gly Val Ser Leu Arg Ala Glu
                165                 170                 175

Leu Leu Ala Leu Ala Ala Asp Leu Pro Ala Phe Phe Glu Gln Thr Ser
            180                 185                 190

Lys Asp Ile Gln Gln Leu Ser Pro Ala Arg Asp Tyr Phe Lys Ala Phe
        195                 200                 205

Arg Ser Tyr Met His Gln Asn Ser Ala Pro Glu Ser Ser Ile Leu Pro
    210                 215                 220

Leu Leu Ala Leu Ile Cys Asp Arg Gly Val Asp Val Thr Thr Tyr Glu
225                 230                 235                 240

Trp Lys Tyr His Gln Lys Pro Asp Arg Ile Glu Gln Pro Asn Phe Glu
                245                 250                 255

Leu Leu Leu Lys Asp Asp Lys Lys Gly Ser Asp Glu Ile Asp Phe Gly
            260                 265                 270

Asp Asp Ile Asp Phe Gly Asp Asp Asp Gly Gly Ile Asp Phe Gly Ala
        275                 280                 285

Asp Ser Val Glu Ile Asp Ile Val Ala Asp Asp Ser Gly Ala Val Gly
    290                 295                 300

Glu Lys Val Ala Ser Gly Gln Asp Ala Leu Ser Leu Leu Glu Asn Ser
305                 310                 315                 320

Glu Ala Gln Lys Ala Leu Lys Leu Glu Leu Asn Glu Leu Leu Ala Phe
                325                 330                 335

Leu Ser Met Arg Leu Asp Asp Glu Thr Arg Glu Thr Gly Ala Asp Ile
            340                 345                 350

Leu Ile Arg Gly Ala Glu Lys Arg Pro Asp Asp Val Ala Lys Val Thr
        355                 360                 365

Asp Lys Asp Leu Lys Ala Trp Ile Ala Glu Ile Glu Arg Val Leu Lys
    370                 375                 380

Glu Phe Glu Asn Pro Gln Lys Ile His Leu Phe Lys Ile Arg Gly Cys
385                 390                 395                 400

Pro Gln Tyr Val Glu Gln Val Val Glu Gln Leu Glu Lys Lys Arg Asp
                405                 410                 415

Met Glu Gln Arg Tyr Lys Arg Leu Gln Ser Leu Met Thr Asp Asn Gln
            420                 425                 430

Glu Ala Ala Arg Val Ala Val Ser Lys Ala Asn Ala Glu Leu Lys Thr
        435                 440                 445

Ile Val Glu Ser Thr Arg Leu Leu Gln Lys Gln Val Glu Ala Glu Ile
    450                 455                 460

Ser Lys Lys Tyr Asn Gly Arg Arg Val Asn Leu Met Gly Gly Ile Asn
465                 470                 475                 480

Gln Ala Leu Gly Gly Val
                485
```

<210> SEQ ID NO 87
<211> LENGTH: 509
<212> TYPE: PRT
<213> ORGANISM: Drosophila melanogaster

<400> SEQUENCE: 87

```
Met Asn Glu Ser Glu Ile Pro Ile Asp Ile His Thr Leu Lys Leu Gln
1               5                   10                  15

Asp Trp Leu Ile Ser Arg Arg Ile Val Pro Lys Asn Val Gln Gln Glu
            20                  25                  30

Leu Arg Glu Ile His Arg Lys Ile Ser Asn Ala Leu Gln Asp Met Pro
        35                  40                  45

Ser Asn Glu Gln Leu Ile Lys Leu Leu Ala Arg Thr Asn Ile Asn Tyr
    50                  55                  60

Tyr His Val Lys Glu Ile Ile Glu Ile Leu Lys Gln Thr Glu Lys Asp
65                  70                  75                  80

Thr Lys Ser Val Phe Gly Thr Tyr Gly Ser Gln Arg Met Lys Asp Trp
                85                  90                  95

Gln Glu Ile Ser Arg Leu Tyr Glu Lys Asn Ala Thr Tyr Leu Ala Glu
            100                 105                 110

Thr Ala Gln Ile Phe Val Arg Asn Val Asn Tyr Glu Ile Pro Gly Val
        115                 120                 125

Arg Lys Gln Met Ala Arg Leu Glu Gln Gln Ala Asp Glu Thr Gln Lys
    130                 135                 140

Arg Ala His Asp Leu Asn Lys Pro Glu Ser Gln Ile Leu Ala Asp His
145                 150                 155                 160

Ser Ala Leu Leu Glu Gln Leu Gly Val Lys Gly Asp Asn Leu His Ala
                165                 170                 175

Glu Phe Val Gln Val Leu Ser Gly Leu Pro Glu Leu Tyr Asp Lys Ser
            180                 185                 190

Leu Val Gly Ile Ala Asn Ile Gln Pro Gly Ile Asp Leu Tyr Ala Glu
        195                 200                 205

Val Ser Gly Asn Lys Gln Val Leu Pro Ile Leu Asn His Leu Val Glu
    210                 215                 220

Phe Gly Asn Thr Thr Val Tyr Gln Tyr Ile His Lys Glu Ala Pro Leu
225                 230                 235                 240

Ala Val Glu Glu Pro Pro Ile Arg Leu Asn Leu Ser Glu Gly Asn Ala
                245                 250                 255

Ser Lys Asp Asp Asn Ala Val Ala Glu Ile Asp Phe Gly Thr Asp Asp
            260                 265                 270

Asn Gly Gly Thr Ser Ser Thr Val Ser Ala Glu Ile Ile Asp Tyr Gly
        275                 280                 285

Asp Phe Gly Ser Gly Asp Leu Pro Glu Ser Asp Gly Gly Asn Ile Asp
    290                 295                 300

Trp Gly Ile Glu Ser Ala Pro Thr Asp Ala Val Glu Ile Asn Phe Asp
305                 310                 315                 320

Ile Pro Val Glu Glu Tyr Gly Ile Val Val Glu Gly Thr Gly Met Asp
                325                 330                 335

Gly Gly Thr Ala Lys Gly Asp Gln Ala Tyr Thr Leu Leu Asp Ser Pro
            340                 345                 350

Asn Tyr Arg Asp Arg Phe Leu Asp Glu Ile Tyr Glu Leu Glu Ser Phe
        355                 360                 365

Leu Arg Met Arg Ile Tyr Glu Leu Lys Gln Leu Glu Ser Ser Ser Asp
```

```
    370                 375                 380

Ile Met Phe Ser Leu Met Asp Asn Ile Ala Thr His Asp Gly Glu Ser
385                 390                 395                 400

Ile Trp Lys Ile Leu Val Ser Val Glu Lys Ile Ile Gln Gln Thr Ser
                405                 410                 415

Asp Lys Gln Thr Gln His Leu Phe Gln Leu Lys His Ser Pro Lys Tyr
            420                 425                 430

Ala Asn Met Leu Ala Thr Lys Leu Gln Gln Met Thr Lys Ala Val Glu
        435                 440                 445

Lys Leu Arg Ala Thr Arg Glu Ala Leu Lys Gln Leu Thr Ile Glu Leu
    450                 455                 460

Arg Glu Gln Arg Gln Asp Leu Asn Pro Val Leu Glu Glu Leu Ile Ala
465                 470                 475                 480

Gln Thr Arg Thr Leu Gln Ser His Ile Glu Lys Asp Ile Ser Lys Arg
                485                 490                 495

Tyr Lys Asn Arg Val Val Asn Leu Met Gly Gly Val Asn
            500                 505


<210> SEQ ID NO 88
<211> LENGTH: 549
<212> TYPE: PRT
<213> ORGANISM: Arabidopsis thaliana

<400> SEQUENCE: 88

Met Pro Ser Gln Asp Asp Val Gln Asn Leu Pro Ile Asp Ile Thr Phe
1               5                   10                  15

Ser Arg Leu Gly Glu Trp Leu Val Asp Arg Lys Arg Ile Pro Ala Asp
            20                  25                  30

Trp Arg Lys Arg Val Ala Val Ile Arg Val Lys Ile Leu Lys Glu Phe
        35                  40                  45

Ser Ser Leu Pro Lys Glu Ile Asp Pro Phe Phe Gln Thr Leu Asp Pro
    50                  55                  60

Glu Val Ile Gly Tyr Leu Glu Val Lys Lys Val Tyr Glu Ile Leu Leu
65                  70                  75                  80

Lys Thr Thr Pro Glu Ser Arg Asn Ile Phe Gly Arg Leu Ser Gly Ala
                85                  90                  95

Ser Gly Val Trp Glu Ala Ile Val Arg Ala Phe Glu Lys Asp His Ile
            100                 105                 110

Tyr Leu Gly Glu Ala Ala Gln Ile Ile Ile Gln Asn Val Asn Tyr Glu
        115                 120                 125

Ile Pro Tyr Leu Lys Lys Gln Val Gln Lys Val Gln Gln Gln Met Thr
    130                 135                 140

Glu Leu Asp Arg Lys Glu Ala Asp Ile Lys Arg Ser Val Ala Leu Ser
145                 150                 155                 160

Ala Thr Lys Tyr Glu Asp Ala Cys Arg Glu Leu Gly Leu Gln Gly Asn
                165                 170                 175

Asn Val Arg Arg Glu Leu Leu Glu Thr Ala Ser Ser Leu Pro Ser Thr
            180                 185                 190

Phe Ser Lys Ile Leu Glu Val Ile Asn Ser Asp Ser Val Thr Gly Ala
        195                 200                 205

Met Glu Tyr Tyr Ser Ala Tyr Val Gln Asp Val His Thr Glu Lys Asp
    210                 215                 220

Lys Pro Leu Arg Ile Val Leu Gln Asn Leu Lys Tyr Ile Arg Glu Asn
225                 230                 235                 240
```

-continued

```
Pro Pro Ser Leu Ser Val Phe Gly Asp Ser Glu Gly Leu Asp Ala Asp
                245                 250                 255

Asn Ile Gln Ser Ser Glu Asn Ala Asn Gly Thr Asp Ala Ala Ala Asp
            260                 265                 270

Ser Ile Asp Trp Asp Ile Thr Val Glu Thr Pro Glu Ile Asp Trp Asp
        275                 280                 285

Val Ser Met Val Glu Glu Val Asp Ser Gly Asn Asp Leu Gly Ser Tyr
    290                 295                 300

Glu Ile Val Asn Ala Ser Asp Ile Pro Glu Asn Ser Pro Phe Lys Val
305                 310                 315                 320

Glu Glu Ser Gln Gly Leu Glu Val Asp Val Ser Glu Ile Ser Trp Asp
                325                 330                 335

Val Ser Val Glu Thr Pro Gln Val Glu Glu Ile Gly Asp Ser Ala Leu
            340                 345                 350

Leu Glu Ser Asn Gln Thr Gln Leu Thr Asp Ser Thr Thr Gln Val Leu
        355                 360                 365

Gly Ser Gly Gly Glu Arg Ser Gln Leu Leu Glu Thr Glu Tyr Arg Asn
    370                 375                 380

Lys Ile Leu Asp Asp Leu Tyr Glu Val Lys Ala Phe Leu Asn Gln Arg
385                 390                 395                 400

Leu Ile Glu Leu Arg Asn Glu Asp Thr Leu Ser Leu Gln His His Val
                405                 410                 415

Gln Ala Val Ser Pro Met Val Leu Gln Gln Tyr Ser Pro Glu Thr Ile
            420                 425                 430

Glu Pro Met Val Val Asp Ile Ser Met Ala Ile Ser Leu Leu Thr Asn
        435                 440                 445

Lys Lys Ser Arg Asp Leu Ile Met Ile Leu Asn Ser Lys Arg Phe Leu
    450                 455                 460

Asp Arg Leu Val Ser Glu Leu Glu Glu Lys Lys His Arg Glu Val Lys
465                 470                 475                 480

Leu Arg Glu Ser Leu Lys Asp Val Gly Arg Arg Arg Met Glu Leu Gln
                485                 490                 495

Asn Ser Leu Ser Ala Ile Trp Pro Lys Gln Glu Ala Ala Leu Ser Lys
            500                 505                 510

Thr Arg Glu Leu Lys Glu Leu Cys Glu Thr Ser Leu Ser Ser Met Phe
        515                 520                 525

Asp Gly Arg Pro Val Asn Ile Arg Gly Glu Ile Asn Thr Leu Leu Asn
    530                 535                 540

Ala Gly Val Ser Ala
545
```

<210> SEQ ID NO 89
<211> LENGTH: 510
<212> TYPE: PRT
<213> ORGANISM: Consensus sequence
<220> FEATURE:
<221> NAME/KEY: MISC_FEATURE
<222> LOCATION: (1)..(510)
<223> OTHER INFORMATION: Each X may be any amino acid

<400> SEQUENCE: 89

```
Met Xaa Xaa Xaa Gln Xaa Xaa Pro Ile Asp Ile Gln Thr Xaa Xaa Leu
1               5                   10                  15

Leu Asp Trp Leu Xaa Asp Arg Arg His Cys Xaa Xaa Xaa Trp Gln Xaa
            20                  25                  30

Xaa Xaa Xaa Xaa Ile Arg Glu Lys Ile Asn Xaa Ala Xaa Gln Asp Met
```

-continued

```
        35                  40                  45

Pro Xaa Xaa Xaa Glu Ile Xaa Gln Leu Leu Ser Gly Xaa Xaa Xaa Xaa
    50                  55                  60

Xaa Phe His Cys Leu Xaa Ile Xaa Xaa Xaa Leu Lys Xaa Thr Glu Ala
65                  70                  75                  80

Xaa Xaa Xaa Xaa Xaa Phe Gly Arg Tyr Ser Ser Gln Arg Met Lys Asp
                85                  90                  95

Trp Gln Xaa Xaa Xaa Xaa Xaa Tyr Xaa Xaa Asp Asn Xaa Tyr Leu Xaa
            100                 105                 110

Glu Xaa Xaa Xaa Xaa Xaa Xaa Xaa Xaa Xaa Xaa Tyr Glu Xaa Xaa Xaa
        115                 120                 125

Xaa Xaa Xaa Gln Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Arg Glu Xaa
145                 150                 155                 160

Xaa Tyr Xaa Xaa Xaa Xaa Xaa Tyr Gly Ile Xaa Gly Xaa Xaa Xaa Xaa
                165                 170                 175

Xaa Glu Leu Xaa Xaa Xaa Xaa Xaa Asp Xaa Pro Xaa Xaa Xaa Xaa Xaa
            180                 185                 190

Xaa Xaa Xaa Xaa Xaa Xaa Xaa Xaa Xaa Leu Xaa Xaa Xaa Xaa Xaa Xaa
        195                 200                 205

Tyr Xaa Xaa Xaa Xaa Xaa Phe Val Xaa Xaa Xaa Xaa Xaa Xaa Xaa Xaa
    210                 215                 220

Xaa Xaa Xaa Leu Pro Xaa Xaa Xaa Xaa Val Gln Lys Xaa Gly Xaa Xaa
225                 230                 235                 240

Thr Xaa Tyr Glu Xaa Xaa Xaa Gly Xaa Xaa Xaa Xaa Xaa Val Glu Xaa
                245                 250                 255

Pro Xaa Xaa Glu Xaa Xaa Xaa Xaa Xaa Xaa Xaa Xaa Xaa Xaa Xaa Xaa
            260                 265                 270

Xaa Xaa Trp Gly Asp Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Asp Trp Gly Ile
    290                 295                 300

Xaa Xaa Glu Xaa Xaa Xaa Xaa Xaa Xaa Xaa Xaa Xaa Xaa Xaa Xaa Xaa
305                 310                 315                 320

Xaa Xaa Xaa Xaa Xaa Xaa Val Xaa Xaa Xaa Gly Xaa Xaa Xaa Xaa Xaa
                325                 330                 335

Gly Val Ala Arg Gly Xaa Asp Ala Leu Xaa Xaa Leu Glu Xaa Xaa Xaa
            340                 345                 350

Xaa Arg Xaa Gln Phe Xaa Xaa Glu Leu Xaa Glu Leu Glu Xaa Phe Leu
        355                 360                 365

Xaa Xaa Xaa Xaa Xaa Xaa Xaa Xaa Xaa Xaa Xaa Asp Xaa Xaa Xaa Xaa
    370                 375                 380

Xaa Gln Phe Gln Xaa Gln Pro Xaa Xaa Xaa Gln Xaa Gln Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Leu Phe Xaa Ile Xaa Ala Ser Pro Arg
            420                 425                 430

Tyr Val Xaa Arg Val Xaa Xaa Xaa Leu Xaa Xaa Xaa Xaa Xaa Gln Xaa
        435                 440                 445

Xaa Xaa Xaa Xaa Xaa Xaa Xaa Xaa Xaa Xaa Xaa Xaa Xaa Xaa Xaa Xaa
    450                 455                 460
```

```
Xaa Xaa Xaa Glu Xaa Xaa Xaa Leu Glu Pro Xaa Xaa Xaa Leu Leu Xaa
465                 470                 475                 480

Xaa Xaa Xaa Xaa Glu Leu Xaa Lys Xaa Ile Glu Ala Asp Xaa Ser Lys
                485                 490                 495

Arg Tyr Xaa Xaa Arg Pro Val Asn Leu Xaa Gly Xaa Xaa Xaa
            500                 505                 510


<210> SEQ ID NO 90
<211> LENGTH: 506
<212> TYPE: PRT
<213> ORGANISM: Consensus sequence
<220> FEATURE:
<221> NAME/KEY: MISC_FEATURE
<222> LOCATION: (1)..(506)
<223> OTHER INFORMATION: Each  X may be any amino acid

<400> SEQUENCE: 90

Met Xaa Asp His Gln His Xaa Pro Ile Asp Ile Gln Thr Ser Lys Leu
1               5                   10                  15

Leu Asp Trp Leu Val Asp Arg Arg His Cys Xaa Leu Lys Trp Gln Ser
            20                  25                  30

Leu Val Leu Thr Ile Arg Glu Lys Ile Asn Xaa Ala Ile Gln Asp Met
        35                  40                  45

Pro Glu Ser Xaa Glu Ile Ala Gln Leu Leu Ser Gly Ser Tyr Ile His
    50                  55                  60

Tyr Phe His Cys Leu Arg Ile Xaa Asp Leu Leu Lys Gly Thr Glu Ala
65                  70                  75                  80

Ser Thr Lys Asn Ile Phe Gly Arg Tyr Ser Ser Gln Arg Met Lys Asp
                85                  90                  95

Trp Gln Glu Ile Xaa Xaa Leu Tyr Glu Lys Asp Asn Thr Tyr Leu Val
            100                 105                 110

Glu Leu Xaa Ser Leu Leu Val Arg Asn Val Xaa Tyr Glu Ile Pro Ser
        115                 120                 125

Leu Lys Lys Gln Ile Ala Lys Cys Gln Gln Leu Gln Gln Xaa Tyr Ser
    130                 135                 140

Arg Lys Glu Glu Glu Xaa Gln Ala Gly Ala Ala Glu Met Arg Glu Gln
145                 150                 155                 160

Phe Tyr His Ser Cys Lys Gln Tyr Gly Ile Thr Gly Xaa Asn Val Arg
                165                 170                 175

Xaa Glu Leu Leu Ala Leu Val Lys Asp Leu Pro Ser Gln Leu Ala Glu
            180                 185                 190

Ile Gly Ala Xaa Ala Gln Xaa Xaa Leu Gly Glu Ala Ile Asp Xaa Tyr
        195                 200                 205

Gln Ala Xaa Val Xaa Phe Val Cys Xaa Ser Xaa Xaa Xaa Pro Thr Glu
    210                 215                 220

Gln Val Leu Pro Met Leu Arg Xaa Val Gln Lys Xaa Gly Asn Ser Thr
225                 230                 235                 240

Val Tyr Glu Trp Arg Thr Gly Thr Glu Pro Ser Val Val Glu Arg Pro
                245                 250                 255

Xaa Leu Glu Xaa Xaa Pro Glu Xaa Xaa Gln Val Xaa Glu Asp Xaa Ile
            260                 265                 270

Asp Trp Gly Asp Phe Gly Xaa Glu Ala Val Ser Xaa Xaa Xaa Xaa Xaa
        275                 280                 285

Xaa Ile Xaa Ala Glu Xaa Xaa Xaa Ile Asp Trp Gly Ile Xaa Xaa Glu
    290                 295                 300
```

-continued

```
Ser Xaa Xaa Lys Ile Asp Trp Gly Asp Xaa Ala Xaa Ala Xaa Xaa Xaa
305                 310                 315                 320

Ile Thr Val Leu Glu Xaa Gly Thr Xaa Ala Pro Glu Gly Val Ala Arg
                325                 330                 335

Gly Xaa Asp Ala Leu Thr Leu Leu Glu Tyr Xaa Glu Thr Arg Asn Gln
            340                 345                 350

Phe Xaa Asp Glu Leu Met Glu Leu Glu Ile Phe Leu Xaa Gln Arg Ala
        355                 360                 365

Val Glu Xaa Ser Glu Glu Ala Asp Xaa Leu Ser Val Ser Gln Phe Gln
    370                 375                 380

Leu Ala Pro Ala Ile Leu Gln Gly Gln Thr Lys Glu Lys Met Xaa Xaa
385                 390                 395                 400

Xaa Val Ser Xaa Leu Xaa Xaa Leu Ile Gly Xaa Leu Thr Ser Leu Xaa
                405                 410                 415

Xaa Gln His Leu Phe Met Ile Leu Ala Ser Pro Arg Tyr Val Asp Arg
            420                 425                 430

Val Thr Glu Xaa Leu Gln Gln Lys Leu Lys Gln Ser Gln Leu Leu Ala
        435                 440                 445

Leu Lys Lys Xaa Leu Met Val Xaa Lys Gln Gln Glu Ala Leu Xaa Glu
    450                 455                 460

Gln Ala Ala Leu Glu Pro Lys Leu Asp Leu Leu Leu Glu Lys Thr Xaa
465                 470                 475                 480

Glu Leu Gln Lys Leu Ile Glu Ala Asp Ile Ser Lys Arg Tyr Xaa Gly
                485                 490                 495

Arg Pro Val Asn Leu Met Gly Thr Ser Xaa
            500                 505


<210> SEQ ID NO 91
<211> LENGTH: 6
<212> TYPE: PRT
<213> ORGANISM: Consensus sequence

<400> SEQUENCE: 91

Pro Ile Asp Ile Gln Thr
1               5


<210> SEQ ID NO 92
<211> LENGTH: 5
<212> TYPE: PRT
<213> ORGANISM: Motif sequence

<400> SEQUENCE: 92

Leu Leu Asp Trp Leu
1               5


<210> SEQ ID NO 93
<211> LENGTH: 5
<212> TYPE: PRT
<213> ORGANISM: Motif sequence

<400> SEQUENCE: 93

Asp Arg Arg His Cys
1               5


<210> SEQ ID NO 94
<211> LENGTH: 6
<212> TYPE: PRT
<213> ORGANISM: Motif sequence

<400> SEQUENCE: 94
```

Ile Arg Glu Lys Ile Asn
1 5

<210> SEQ ID NO 95
<211> LENGTH: 5
<212> TYPE: PRT
<213> ORGANISM: Motif sequence

<400> SEQUENCE: 95

Gln Leu Leu Ser Gly
1 5

<210> SEQ ID NO 96
<211> LENGTH: 13
<212> TYPE: PRT
<213> ORGANISM: Motif sequence

<400> SEQUENCE: 96

Phe Gly Arg Tyr Ser Ser Gln Arg Met Lys Asp Trp Gln
1 5 10

<210> SEQ ID NO 97
<211> LENGTH: 4
<212> TYPE: PRT
<213> ORGANISM: Motif sequence

<400> SEQUENCE: 97

Asp Trp Gly Ile
1

<210> SEQ ID NO 98
<211> LENGTH: 4
<212> TYPE: PRT
<213> ORGANISM: Motif sequence

<400> SEQUENCE: 98

Ile Asp Trp Gly
1

<210> SEQ ID NO 99
<211> LENGTH: 9
<212> TYPE: PRT
<213> ORGANISM: Motif sequence
<220> FEATURE:
<221> NAME/KEY: MISC_FEATURE
<222> LOCATION: (6)..(6)
<223> OTHER INFORMATION: X may be any amino acid

<400> SEQUENCE: 99

Gly Val Ala Arg Gly Xaa Asp Ala Leu
1 5

<210> SEQ ID NO 100
<211> LENGTH: 9
<212> TYPE: PRT
<213> ORGANISM: Motif sequence
<220> FEATURE:
<221> NAME/KEY: MISC_FEATURE
<222> LOCATION: (7)..(7)
<223> OTHER INFORMATION: X may be any amino acid

<400> SEQUENCE: 100

Ala Ser Pro Arg Tyr Val Xaa Arg Val
1 5

-continued

```
<210> SEQ ID NO 101
<211> LENGTH: 9
<212> TYPE: PRT
<213> ORGANISM: Motif sequence
<220> FEATURE:
<221> NAME/KEY: MISC_FEATURE
<222> LOCATION: (5)..(5)
<223> OTHER INFORMATION: X may be any amino acid

<400> SEQUENCE: 101

Ile Glu Ala Asp Xaa Ser Lys Arg Tyr
1               5


<210> SEQ ID NO 102
<211> LENGTH: 5
<212> TYPE: PRT
<213> ORGANISM: Motif sequence

<400> SEQUENCE: 102

Arg Pro Val Asn Leu
1               5
```